United States Patent
Nordgren et al.

(10) Patent No.: US 7,527,960 B2
(45) Date of Patent: May 5, 2009

(54) AVIPOX RECOMBINANTS EXPRESSING FOOT AND MOUTH DISEASE VIRUS GENES

(75) Inventors: Robert Nordgren, Athens, GA (US); Sheena May Loosmore, Aurora (CA); Jean-Christophe Francis Audonnet, Lyons (FR); Marvin J. Grubman, Southold, NY (US)

(73) Assignee: Merial Limited, Duluth, GA (US)

( * ) Notice: Subject to any disclaimer, the term of this patent is extended or adjusted under 35 U.S.C. 154(b) by 519 days.

(21) Appl. No.: 11/110,480

(22) Filed: Apr. 20, 2005

(65) Prior Publication Data

US 2005/0287672 A1     Dec. 29, 2005

Related U.S. Application Data

(60) Provisional application No. 60/563,786, filed on Jun. 25, 2004.

(51) Int. Cl.
*C12N 7/01* (2006.01)

(52) U.S. Cl. ................. 435/235.1; 435/320.1

(58) Field of Classification Search ............ None
See application file for complete search history.

(56) References Cited

U.S. PATENT DOCUMENTS

| | | | | |
|---|---|---|---|---|
| 5,494,807 A | * | 2/1996 | Paoletti et al. | 435/69.3 |
| 5,756,103 A | | 5/1998 | Paoletti et al. | |
| 2005/0255127 A1 | * | 11/2005 | Loosmore et al. | 424/199.1 |

FOREIGN PATENT DOCUMENTS

| | | |
|---|---|---|
| WO | WO 96/40880 | 12/1996 |
| WO | WO 01/89559 | 11/2001 |
| WO | WO 0200251 | * 1/2002 |

OTHER PUBLICATIONS

Sanz-Parra A et al: "Recombinant viruses expressing the foot-and-mouth disease virus capsid precursor polypeptide (P1) induce cellular but not humoral antiviral immunity and partial protection in pigs" Virology, Academic Press, Orlando, US, vol. 259, No. 1, Jun. 20, 1999, pp. 129-134, XP002208694.

Mayr G A et al: "Immune responses and protection against foot-and-mouth disease virus (FMDV) challenge in swine vaccinated with adenovirus-FMDV constructs" Vaccine, Butterworth Scientific. Guildford, GB, vol. 19, No. 15-16, Feb. 28, 2001, pp. 2152-2162, XP004316957.

Fries L F et al: "Human safety and immunogenicity of a canarypox-rabies glycoprotein recombinant vaccine: an alternative poxvirus vector system" Vaccine, Butterworth Scientific, Guildford, GB, vol. 14, No. 5, Apr. 1996, pp. 428-434, XP004057299.

Zheng et al: "Construction and immunogenicity of recombinant fowlpox virus containing the capsid and 3C protease coding regions of foot-and-mouth disease virus" Journal of Virological Methods, Amsterdam, NL, vol. 136, No. 1-2, Sep. 2006, pp. 230-237, XP005561480.

* cited by examiner

*Primary Examiner*—James S Ketter
(74) *Attorney, Agent, or Firm*—Judy Jarecki-Black; Thomas Kowalski

(57) ABSTRACT

The present invention relates to modified poxviral vectors and to methods of making and using the same. In particular, the invention relates to recombinant avipox that expresses gene products of foot and mouth disease virus (FMDV), and to compositions or vaccines that elicit immune responses directed to FMDV gene products and which can confer protective immunity against infection by FMDV.

22 Claims, 78 Drawing Sheets

Fig 1
FMDV Genes Present In Avipox Recombinants

FMDV genome

- deleted in pAd5-A24
- P1 from A24
- deleted in pAd5-A24
- deleted in pAd5-A24

FMDV genes in pAd5-A24

P1 from A24 — VP4, VP2, VP3, VP1, 2A, 3C from A12

Fig 2
Oligonucleotide Primers To PCR Amplify H6p FMDV P1+3C

```
                        H6p                 FMDV A24
              Nru I                   M   G   A   G   Q   S   S   P
11277.SL  5'  TA TCGCGA TATCCGTTAAGTTTGTATCGTAATGGGAGCTGGGCAATCCAGCCCA

FMDV A12
              V   D   P   E   P   Q   H   E   *   *    T5NT    BamH I
              GTTGACCCTGAACCACAACACGAGTAGTAATTTTTCTAGA GGATCC
11282.SL  3'  CAACTGGGACTTGGTGTTGTGCTCATCATTAAAA AGATCT CCTAGG
                                                 Xba I
```

Fig 3A
Construction Of pC5 H6p FMDV P1+3C, pHM-1175-1

Fig 3B
Construction Of pC5 H6p FMDV P1+3C, pHM-1175-1

Fig 4A
Sequence Of The C5 H6p FMDV P1+3C Gene cassette In pHM-1175-1, pC5 H6p FMDV P1+3C

```
      ⇒ C5R
   1  TGAATGTTAA ATGTTATACT TTGGATGAAG CTATAAATAT GCATTGGAAA AATAATCCAT
  61  TTAAAGAAAG GATTCAAATA CTACAAAACC TAAGCGATAA TATGTTAACT AAGCTTATTC
 121  TTAACGACGC TTTAAATATA CACAAATAAA CATAATTTTT GTATAACCTA ACAAATAACT
 181  AAAACATAAA AATAATAAAA GGAAATGTAA TATCGTAATT ATTTTACTCA GGAATGGGGT
 241  TAAATATTTA TATCACGTGT ATATCTATAC TGTTATCGTA TACTCTTTAC AATTACTATT
 301  ACGAATATGC AAGAGATAAT AAGATTACGT ATTTAAGAGA ATCTTGTCAT GATAATTGGG
 361  TACGACATAG TGATAAATGC TATTTCGCAT CGTTACATAA AGTCAGTTGG AAAGATGGAT
 421  TTGACAGATG TAACTTAATA GGTGCAAAAA TGTTAAATAA CAGCATTCTA TCGGAAGATA
 481  GGATACCAGT TATATTATAC AAAAATCACT GGTTGGATAA AACAGATTCT GCAATATTCG
 541  TAAAAGATGA AGATTACTGC GAATTTGTAA ACTATGACAA TAAAAAGCCA TTTATCTCAA
 601  CGACATCGTG TAATTCTTCC ATGTTTTATG TATGTGTTTC AGATATTATG AGATTACTAT
 661  AAACTTTTTG TATACTTATA TTCCGTAAAC TATATTAATC ATGAAGAAAA TGAAAAAGTA
 721  TAGAAGCTGT TCACGAGCGG TTGTTGAAAA CAACAAAATT ATACATTCAA GATGGCTTAC
 781  ATATACGTCT GTGAGGCTAT CATGGATAAT GACAATGCAT CTCTAAATAG GTTTTTGGAC
 841  AATGGATTCG ACCCTAACAC GGAATATGGT ACTCTACAAT CTCCTCTTGA AATGGCTGTA
 901  ATGTTCAAGA ATACCGAGGC TATAAAAATC TTGATGAGGT ATGGAGCTAA ACCTGTAGTT
 961  ACTGAATGCA CAACTTCTTG TCTGCATGAT GCGGTGTTGA GAGACGACTA CAAAATAGTG
1021  AAAGATCTGT TGAAGAATAA CTATGTAAAC AATGTTCTTT ACAGCGGAGG CTTTACTCCT
1081  TTGTGTTTGG CAGCTTACCT TAACAAAGTT AATTTGGTTA AACTTCTATT GGCTCATTCG
1141  GCGGATGTAG ATATTTCAAA CACGGATCGG TTAACTCCTC TACATATAGC CGTATCAAAT
1201  AAAAATTTAA CAATGGTTAA ACTTCTATTG AACAAAGGTG CTGATACTGA CTTGCTGGAT
1261  AACATGGGAC GTACTCCTTT AATGATCGCT GTACAATCTG GAAATATTGA AATATGTAGC
1321  ACACTACTTA AAAAAAATAA AATGTCCAGA ACTGGGAAAA ATTGATCTTG CCAGCTGTAA
1381  TTCATGGTAG AAAAGAAGTG CTCAGGCTAC TTTTCAACAA AGGAGCAGAT GTAAACTACA
1441  TCTTTGAAAG AAATGGAAAA TCATATACTG TTTTGGAATT GATTAAAGAA AGTTACTCTG
1501  AGACACAAAA GAGGTAGCTG AAGTGGTACT CTCAAAGGTA CGTGACTAAT TAGCTATAAA
```

Fig 4B
Sequence Of The C5 H6p FMDV P1+3C Gene Cassette In pHM-1175-1, pC5 H6p FMDV P1+3C

```
1561    AAGGATCCGG GTTAATTAAT TAGTCATCAG GCAGGGCGAG AACGAGACTA TCTGCTCGTT

⇒ H6p
1621    AATTAATTAG AGCTTCTTTA TTCTATACTT AAAAAGTGAA AATAAATACA AAGGTTCTTG

1681    AGGGTTGTGT TAAATTGAAA GCGAGAAATA ATCATAAATT ATTTCATTAT CGCGATATCC
                           ⇒ A24 VP4
                     M   G   A   G   Q   S   S   P   A   T   G   S   Q   N   Q ·
1741    GTTAAGTTTG TATCGTAATG GGAGCTGGGC AATCCAGCCC AGCAACCGGC TCGCAGAACC

.. S   G   N   T   G   S   I   I   N   N   Y   Y   M   Q   Q   Y   Q   N   S   M ·
1801    AGTCTGGCAA CACTGGCAGC ATAATCAACA ACTACTACAT GCAACAGTAC CAGAACTCCA

.. D   T   Q   L   G   D   N   A   I   S   G   G   S   N   E   G   S   T   D   T ·
1861    TGGACACACA GTTGGGAGAC AATGCCATCA GTGGAGGCTC CAACGAGGGC TCCACGGACA

.. T   S   T   H   T   T   N   T   Q   N   N   D   W   F   S   K   L   A   S   S ·
1921    CAACTTCAAC ACACACAACC AACACTCAAA ACAATGACTG GTTCTGAAAG CTCGCCAGTT

⇒ A24 VP2
          .. A   F   T   G   L   F   G   A   L   L   A   D   K   K   T   E   E   T   T   L ·
1981    CAGCTTTTAC CGGTCTGTTC GGTGCACTGC TCGCCGACAA GAAGACAGAG GAAACGACAC

.. L   E   D   R   I   L   T   T   R   N   G   H   T   T   S   T   T   Q   S   S ·
2041    TTCTTGAGGA CCGCATCCTC ACCACCCGCA ACGGGCACAC CACCTCGACG ACCCAATCGA

.. V   G   V   T   H   G   Y   S   T   E   E   D   H   V   A   G   P   N   T   S ·
2101    GTGTGGGTGT CACACACGGG TACTCCACAG AGGAGGACCA CGTTGCTGGG CCCAACACAT

.. G   L   E   T   R   V   V   Q   A   E   R   F   Y   K   K   Y   L   F   D   W ·
2161    CGGGCCTGGA GACGCGAGTG GTGCAGGCAG AGAGATTCTA CAAAAAGTAC TTGTTTGACT

.. T   T   D   K   A   F   G   H   L   E   K   L   E   L   P   S   D   H   H   G ·
2221    GGACAACGGA CAAGGCATTT GGACACCTGG AAAAGCTGGA GCTCCCGTCC GACCACCACG

.. V   F   G   H   L   V   D   S   Y   A   Y   M   R   N   G   W   D   V   E   V ·
2281    GTGTCTTTGG ACACTTGGTG GACTCGTACG CCTATATGAG AAATGGCTGG GATGTTGAGG

.. S   A   V   G   N   Q   F   N   G   G   C   L   L   V   A   M   V   P   E   W ·
2341    TGTCCGCTGT TGGCAACCAG TTCAACGGCG GGTGCCTCCT GGTGGCCATG GTACCTGAAT

.. K   E   F   D   T   R   E   K   Y   Q   L   T   L   F   P   H   Q   F   I   S ·
2401    GGAAGGAATT TGACACACGG GAGAAATACC AACTCACCCT TTTCCCGCAC CAGTTTATTA

.. P   R   T   N   M   T   A   H   I   T   V   P   Y   L   G   V   N   R   Y   D ·
2461    GCCCCAGAAC TAACATGACT GCCCACATCA CGGTCCCCTA CCTTGGTGTG AACAGGTATG

.. Q   Y   K   K   H   K   P   W   T   L   V   V   M   V   V   S   P   L   T   V ·
2521    ATCAGTACAA GAAGCATAAG CCCTGGACAT TGGTTGTCAT GGTCGTGTCG CCACTTACGG

.. N   N   T   S   A   A   Q   I   K   V   Y   A   N   I   A   P   T   Y   V   H ·
2581    TCAACAACAC TAGTGCGGCA CAAATCAAGG TCTACGCCAA CATAGCTCCG ACCTATGTTC
```

Fig 4C
Sequence Of The C5 H6p FMDV P1+3C Gene Cassette In pHM-1175-1, pC5 H6p FMDV P1+3C

```
                ⇒ A24 VP3
       .. V  A  G   E  L  P   S  K  E   G  I  F   P  V  A   C  A  D  G  Y ·
2641   ACGTGGCCGG TGAACTCCCC TCGAAAGAGG GGATTTTCCC GGTTGCATGT GCGGACGGTT

.. G  G  L   V  T  T   D  P  K   T  A  D   P  A  Y   G  K  V  Y  N ·
2701   ACGGAGGATT GGTGACGACA GACCCGAAGA CAGCTGACCC TGCTTATGGC AAGGTGTACA

.. P  P  R   T  N  Y   P  G  R   F  T  N   L  D  V   A  E  A  C ·
2761   ACCCGCCTAG GACTAACTAC CCTGGGCGCT TCACCAACCT GTTGGACGTG GCCGAAGCGT

.. P  T  F   L  C  F   D  D  G   K  P  Y   V  T  T   R  T  D  D  T ·
2821   GTCCCACTTT CCTCTGCTTT GACGACGGGA AACCGTACGT CACCACGCGG ACGGATGACA

.. R  L  L   A  K  F   D  L  S   L  A  A   K  H  M   S  N  T  Y  L ·
2881   CCCGACTTTT GGCCAAGTTT GACCTTTCCC TTGCCGCAAA ACATATGTCC AACACATACC

.. S  G  I   A  Q  Y   Y  T  Q   Y  S  G   T  I  N   L  H  F  M  F ·
2941   TGTCAGGGAT TGCTCAGTAC TACACACAGT ACTCTGGCAC CATCAATTTG CATTTCATGT

.. T  G  S   T  D  S   K  A  R   Y  M  V   A  Y  I   P  P  G  V  E ·
3001   TTACAGGTTC CACTGATTCA AAGGCCCGAT ACATGGTGGC CTACATCCCA CCTGGGGTGG

.. T  P  P   D  T  P   E  R  A   A  H  C   I  H  A   E  W  D  T  G ·
3061   AGACACCACC GGACACACCT GAAAGGGCTG CCCACTGCAT TCACGCTGAA TGGGACACTG

.. L  N  S   K  F  T   F  S  I   P  Y  V   S  A  A   D  Y  A  Y  T ·
3121   GACTAAACTC CAAATTCACT TTCTCAATCC CGTACGTATC CGCCGCGGAT TACGCGTACA

.. A  S  D   T  A  E   T  I  N   V  Q  G   W  V  C   I  Y  Q  I  T ·
3181   CAGCGTCTGA CACGGCAGAA ACAATCAACG TACAGGGATG GGTCTGCATC TACCAAATTA

.. H  G  K   A  E  N   D  T  L   V  V  S   V  S  A   G  K  D  F  E ·
3241   CACACGGGAA GGCTGAAAAT GACACCTTGG TCGTGTCGGT TAGCGCCGGC AAAGACTTTG

⇒ A24 VP1
       .. L  R  L   P  I  D   P  R  Q   Q  T  T   A  T  G   E  S  A  D  P ·
3301   AGTTGCGCCT CCCGATTGAC CCCCGCCAGC AGACCACCGC TACCGGGGAA TCAGCAGACC

.. V  T  T   T  V  E   N  Y  G   G  E  T   Q  I  Q   R  R  H  H  T ·
3361   CGGTCACCAC CACCGTGGAG AACTACGGCG GTGAGACACA AATCCAGAGA CGTCACCACA

.. D  I  G   F  I  M   D  R  F   V  K  I   Q  S  L   S  P  T  H  V ·
3421   CGGACATTGG TTTCATCATG GACAGATTTG TGAAGATCCA AAGCTTGAGC CCAACACATG

.. I  D  L   M  Q  A   H  Q  H   G  L  V   G  A  L   L  R  A  A  T ·
3481   TCATTGACCT CATGCAGGCT CACCAACACG GTCTGGTGGG TGCCTTGCTG CGTGCAGCCA

.. Y  Y  F   S  D  L   E  I  V   V  R  H   E  G  N   L  T  W  V  P ·
3541   CGTACTACTT TTCTGACCTG GAAATTGTTG TACGGCACGA AGGCAATCTG ACCTGGGTGC

.. N  G  A   P  E  S   A  L  L   N  T  S   N  P  T   A  Y  N  K  A ·
```

Fig 4D
Sequence Of The C5 H6p FMDV P1+3C Gene Cassette In pHM-1175-1, pC5 H6p FMDV P1+3C

```
3601   CCAACGGCGC CCCTGAATCA GCCCTGTTGA ACACCAGCAA CCCCACTGCC TACAACAAGG

.. P  F  T   R  L  A   L  P  Y   T  A  P   H  R  V   L  A  T  V  Y  ·
3661   CACCATTCAC GAGACTCGCT CTCCCCTACA CTGCGCCGCA CCGTGTGCTG GCAACAGTGT

.. N  G  T   S  K  Y   A  V  G   G  S  G   R  R  G   D  M  G  S  L  ·
3721   ACAACGGGAC GAGTAAGTAT GCTGTGGGTG GTTCAGGCAG AAGAGGCGAC ATGGGGTCTC

.. A  A  R   V  V  K   Q  L  P   A  S  F   N  Y  G   A  I  K  A  D  ·
3781   TCGCGGCGCG AGTCGTGAAA CAGCTTCCTG CTTCATTTAA CTACGGTGCA ATCAAGGCCG

.. A  I  H   E  L  L   V  R  M   K  R  A   E  L  Y   C  P  R  P  L  ·
3841   ACGCCATCCA CGAACTTCTC GTGCGCATGA AACGGGCCGA GCTCTACTGC CCCAGACCGC

.. L  A  I   E  V  S   S  Q  D   R  H  K   Q  K  I   I  A  P  A  K  ·
3901   TGTTGGCAAT AGAGGTGTCT TCGCAAGACA GGCACAAGCA AAAGATCATT GCACCAGCAA

⇒ A24 2A                                                  ⇒ 2B
         .. Q  L  L   N  F  D   L  L  K   L  A  G   D  V  E   S  N  P  G  P  ·
3961   AGCAGCTTCT GAATTTTGAC CTGCTCAAGT TGGCCGGAGA CGTTGAGTCC AACCCCGGGC

.. F  F  F   A  D  V   R  S  N   F  S  K   L  V  D   T  I  N  Q  M  ·
4021   CATTCTTCTT TGCTGACGTT AGGTCAAACT TTTCAAAGTT GGTAGACACA ATCAACCAGA

.. Q  E  D   M  S  T   K  H  G   P  D  F   N  R  L   V  S  A  F  E  ·
4081   TGCAGGAGGA CATGTCCACA AAACACGGGC CCGACTTCAA CCGGTTGGTG TCCGCATTTG

.. E  L  A   T  G  V   K  A  I   R  T  G   L  D  E   A  K  P  W  Y  ·
4141   AGGAATTGGC CACTGGAGTT AAAGCTATCA GGACCGGTCT CGACGAGGCC AAACCCTGGT

.. K  L  I   K  L  L   S  R  L  S   C  M  A   A  V  A   A  R  S  K  ·
4201   ACAAGCTTAT CAAACTCCTA AGCCGCCTGT CGTGCATGGC CGCTGTGGCA GCACGGTCCA

A24/A12 junction ⇒ A12 3B
         .. D  P  V   L  V  A   I  M  L  A   D  T  G   L  E  R   Q  R  P  L  ·
4261   AGGACCCAGT CCTTGTGGCC ATCATGCTGG CCGACACCGG TCTCGAGCGT CAGAGACCTC .. K  V  R   A  K  L   P  Q  Q   E  G  P   Y  A  G   P  L  E  R  Q  ·
4321   TGAAAGTGAG AGCTAAGCTC CCACAGCAGG AAGGACCTTA CGCTGGCCCG TTGGAGAGAC .. K  P  L   K  V  K   A  K  P   V  V  K   E  G  P   Y  E  G  P  ·
4381   AGAAACCGCT GAAAGTGAAA GCAAAAGCCC CGGTCGTCAA GGAAGGACCT TACGAGGGAC ⇒ A12 3C
         .. V  K  K   P  V  A   L  K  V  K   A  K  N   L  I  V   T  E  S  G  ·
4441   CGGTGAAGAA GCCTGTCGCT TTGAAAGTGA AAGCTAAGAA CTTGATAGTC ACTGAGAGTG .. A  P  P   T  D  L   Q  K  M   V  M  G  N   T  K  P   V  E  L  I  ·
4501   GTGCCCCACC GACCGACTTG CAAAAGATGG TCATGGGCAA CACAAAGCCT GTTGAGCTCA .. L  D  G   K  T  V   A  I  C   C  A  T  G   V  F  G   T  A  Y  L  ·
4561   TCCTTGACGG GAAGACAGTA GCCATCTGTT GTGCTACTGG AGTGTTTGGC ACTGCTTACC
```

Fig 4E
Sequence Of The C5 H6p FMDV P1+3C Gene Cassette In pHM-1175-1, pC5 H6p FMDV P1+3C

```
          .. V   P   R     H   L   F     A   E   K   Y     D   K   I     M   L   D     G   R   A   M ·
     4621    TCGTGCCTCG TCATCTTTTC GCAGAGAAGT ATGACAAGAT CATGCTGGAT GGCAGAGCCA

.. T   D   S     D   Y   R     V   F   E   F     E   I   K     V   K   G     Q   D   M   L ·
     4681    TGACAGACAG TGACTACAGA GTGTTTGAGT TTGAGATTAA AGTAAAAGGA CAGGACATGC

.. S   D   A     L   M     V   L   H   R     G   N   R     V   R   D     I   T   K   H ·
     4741    TCTCAGACGC TGCGCTCATG GTGCTCCACC GTGGGAACCG CGTGAGAGAT ATCACGAAAC

.. F   R   D     T   A   R     M   K   K   G     T   P   V     V   G   V     V   N   N   A ·
     4801    ACTTTCGTGA TACAGCAAGA ATGAAGAAAG CACCCCCGT CGTCGGTGTG GTCAACAACG

.. D   V   G     R   L   I     F   S   G   E     A   L   T     Y   K   D     I   V   V   C ·
     4861    CCGACGTTGG GAGACTGATT TTCTCTGGTG AGGCCCTCAC CTACAAGGAT ATTGTAGTGT

.. M   D   G     D   T   M     P   G   L   F     A   Y   K     A   A   T     K   A   G   Y ·
     4921    GCATGGACGG AGACACCATG CCTGGCCTCT TTGCCTACAA AGCCGCCACC AAGGCAGGCT

.. C   G   G     A   V   L     A   K   D   G     A   D   T     F   I   V     G   T   H   S ·
     4981    ACTGTGGAGG AGCCGTTCTC GCCAAGGACG GGGCCGACAC TTTCATCGTC GGCACTCACT

.. A   G   G     N   G   V     G   Y   C   S     C   V   S     R   S   M     L   L   R   M ·
     5041    CCGCAGGAGG CAATGGAGTT GGATACTGCT CATGCGTTTC CAGGTCCATG CTTCTCAGAA

.. K   A   H     V   D   P     E   P   Q   H     E   *   *
     5101    TGAAGGCACA CGTTGACCCT GAACCACAAC ACGAGTAGTA ATTTTTCTAG AATCGATCCC
                                                                    ─────────
                                               ⇒ C5L
     5161    GGGTTTTTAT GACTAGTTAA TCACGGCCGC TTATAAAGAT CTAAAATGCA TAATTTCTAA

5221    ATAATGAAAA AAAGTACATC ATGAGCAACG CGTTAGTATA TTTTACAATG GAGATTAACG

5281    CTCTATACCG TTCTATGTTT ATTGATTCAG ATGATGTTTT AGAAAGAAA GTTATTGAAT

5341    ATGAAAACTT TAATGAAGAT GAAGATGACG ACGATGATTA TTGTTGTAAA TCTGTTTTAG

5401    ATGAAGAAGA TGACGCGCTA AAGTATACTA TGGTTACAAA GTATAAGTCT ATACTACTAA

5461    TGGCGACTTG TGCAAGAAGG TATAGTATAG TGAAAATGTT GTTAGATTAT GATTATGAAA

5521    AACCAAATAA ATCAGATCCA TATCTAAAGG TATCTCCTTT GCACATAATT TCATCTATTC

5581    CTAGTTTAGA ATAC
```

Fig 5A
Construction Of pF8 H6p FMDV P1+3C, pHM-1180-11

Figure 5B
Construction Of pF8 H6p FMDV P1+3C, pHM-1180-11

Fig 6A
Sequence Of The F8 H6p FMDV Gene Cassette in pF8 H6p FMDV P1+3C, pHM-1180-11

```
       ⇒ F8R
   1   GACCCTTTAC AAGAATAAAA GAAGAAACAA CTGTGAAATA GTTTATAAAT GTAATTCGTA
  61   TGCAGAAAAC GATAATATAT TTTGGTATGA GAAATCTAAA GGAGACATAG TTTGTATAGA
 121   CATGCGCTCT TCCGATGAGA TATTCGATGC TTTTCTAATG TATCATATAG CTACAAGATA
 181   TGCCTATCAT GATGATGATA TATATCTACA AATAGTGTTA TATTATTCTA ATAATCAAAA
 241   TGTTATATCT TATATTACGA AAAATAAATA CGTTAAGTAT ATAAGAAATA AACTAGAGA
 301   CGATATTCAT AAAGTAAAAA TATTAGCTCT AGAAGACTTT ACAACGGAAG AAATATATTG
 361   TTGGATTAGT AATATATAAC AGCGTAGCTG CACGGTTTTG ATCATTTTCC AACAATATAA
 421   ACCAATGAAG GAGGACGACT CATCAAACAT AAATAACATT CACGGAAAAT ATTCAGTATC
 481   AGATTTATCA CAAGATGATT ATGTTATTGA ATGTATAGAC GGATCTTTTG ATTCGATCAA
 541   GTATAGAGAT ATAAAGGTTA TAATAATGAA GAATAACGGT TACGTTAATT GTAGTAAATT
 601   ATGTAAAATG CGGAATAAAT ACTTTTCTAG ATGGTTGCGT CTTTCTACTT CTAAAGCATT
 661   ATTAGACATT TACAATAATA AGTCAGTAGA TAATGCTATT GTTAAAGTCT ATGGTAAAGG
 721   TAAGAAACTT ATTATAACAG GATTTATCT CAAACAAAAT ATGATACGTT ATGTTATTGA
 781   GTGGATAGGG GATGATTTTA CAAACGATAT ATACAAAATG ATTAATTTCT ATAATGCGTT
 841   ATTCGGTAAC GATGAATTAA AAATAGTATC CTGTGAAAAC ACTCTATGCC CGTTTATAGA
 901   ACTTGGTAGA TGCTATTATG GTAAAAAATG TAAGTATATA CACGGAGATC AATGTGATAT
 961   CTGTGGTCTA TATATACTAC ACCCTACCGA TATTAACCAA CGAGTTTCTC ACAAGAAAAC
1021   TTGTTTAGTA GATAGAGATT CTTTGATTGT GTTTAAAAGA AGTACCAGTA AAAAGTGTGG
1081   CATATGCATA GAAGAAATAA ACAAAAAACA TATTTCCGAA CAGTATTTTG GAATTCTCCC
1141   AAGTTGTAAA CATATTTTTT GCCTATCATG TATAAGACGT TGGGCAGATA CTACCAGAAA
1201   TACAGATACT GAAAATACGT GTCCTGAATG TAGAATAGTT TTTCCTTTCA TAATACCCAG
1261   TAGGTATTGG ATAGATAATA AATATGATAA AAAAATATTA TATAATAGAT ATAAGAAAAT
1321   GATTTTTACA AAAATACCTA TAAGAACAAT AAAAATATAA TTACATTTAC GGAAAATAGC
1381   TGGTTTTAGT TTACCAACTT AGAGTAATTA TCATATTGAA TCTATATTGC TAATTAGCTA
1441   ATAAAACCC GGGTTAATTA ATTAGTCATC AGGCAGGGCG AGAACGAGAC TATCTGCTCG
                          ⇒ H6p
1501   TTAATTAATT AGAGCTTCTT TATTCTATAC TTAAAAAGTG AAAATAAATA CAAAGGTTCT
```

Fig 6B
Sequence Of The F8 H6p FMDV Gene Cassette in pF8 H6p FMDV P1+3C, pHM-1180-11

```
1561   TGAGGGTTGT GTTAAATTGA AAGCGAGAAA TAATCATAAA TTATTTCATT ATCGCGATAT

⇒ FMDV VP4
                       M   G   A   G   Q   S   S   P   A   T   G   S   Q   N  ·
1621   CCGTTAAGTT TGTATCGTAA TGGGAGCTGG GCAATCCAGC CCAGCAACCG GCTCGCAGAA

· Q   S   G   N   T   G   S   I   I   N   N   Y   Y   M   Q   Q   Y   Q   N   S  ·
1681   CCAGTCTGGC AACACTGGCA GCATAATCAA CAACTACTAC ATGCAACAGT ACCAGAACTC

· M   D   T   Q   L   G   D   N   A   I   S   G   G   S   N   E   G   S   T   D  ·
1741   CATGGACACA CAGTTGGGAG ACAATGCCAT CAGTGGAGGC TCCAACGAGG GCTCCACGGA

· T   T   S   T   H   T   T   N   T   Q   N   N   D   W   F   S   K   L   A   S  ·
1801   CACAACTTCA ACACACACAA CCAACACTCA AAACAATGAC TGGTTCTCGA AGCTCGCCAG

⇒ VP2
       · S   A   F   T   G   L   F   G   A   L   L   A   D   K   K   T   E   E   T   T  ·
1861   TTCAGCTTTT ACCGGTCTGT TCGGTGCACT GCTCGCCGAC AAGAAGACAG AGGAAACGAC

· L   L   E   D   R   I   L   T   T   R   N   G   H   T   T   S   T   T   Q   S  ·
1921   ACTTCTTGAG GACCGCATCC TCACCACCCG CAACGGGCAC ACCACCTCGA CGACCCAATC

· S   V   G   V   T   H   G   Y   S   T   E   E   D   H   V   A   G   P   N   T  ·
1981   GAGTGTGGGT GTCACACACG GGTACTCCAC AGAGGAGGAC CACGTTGCTG GGCCCAACAC

· S   G   L   E   T   R   V   Q   A   E   R   F   Y   K   K   Y   L   F   D  ·
2041   ATCGGGCCTG GAGACGCGAG TGGTGCAGGC AGAGAGATTC TACAAAAAGT ACTTGTTTGA

· W   T   T   D   K   A   F   G   H   L   E   K   L   E   L   P   S   D   H   H  ·
2101   CTGGACAACG GACAAGGCAT TTGGACACCT GGAAAAGCTG GAGCTCCCGT CCGACCACCA

· G   V   F   G   H   L   V   D   S   Y   A   Y   M   R   N   G   W   D   V   E  ·
2161   CGGTGTCTTT GGACACTTGG TGGACTCGTA CGCCTATATG AGAAATGGCT GGGATGTTGA

· V   S   A   V   G   N   Q   F   N   G   G   C   L   L   V   A   M   V   P   E  ·
2221   GGTGTCCGCT GTTGGCAACC AGTTCAACGG CGGGTGCCTC CTGGTGGCCA TGGTACCTGA

· W   K   E   F   D   T   R   E   K   Y   Q   L   T   L   F   P   H   Q   F   I  ·
2281   ATGGAAGGAA TTTGACACAC GGGAGAAATA CCAACTCACC CTTTTCCCGC ACCAGTTTAT

· S   P   R   T   N   M   T   A   H   I   T   V   P   Y   L   G   V   N   R   Y  ·
2341   TAGCCCCAGA ACTAACATGA CTGCCCACAT CACGGTCCCC TACCTTGGTG TGAACAGGTA

· D   Q   Y   K   K   H   K   P   W   T   L   V   V   M   V   V   S   P   L   T  ·
2401   TGATCAGTAC AAGAAGCATA AGCCCTGGAC ATTGGTTGTC ATGGTCGTGT CGCCACTTAC

· V   N   N   T   S   A   A   Q   I   K   V   Y   A   N   I   A   P   T   Y   V  ·
2461   GGTCAACAAC ACTAGTGCGG CACAAATCAA GGTCTACGCC AACATAGCTC CGACCTATGT

⇒ VP3
       · H   V   A   G   E   L   P   S   K   E   G   I   F   P   V   A   C   A   D   G  ·
2521   TCACGTGGCC GGTGAACTCC CCTCGAAAGA GGGGATTTTC CCGGTTGCAT GTGCGGACGG
```

Fig 6C
Sequence Of The F8 H6p FMDV Gene Cassette in pF8 H6p FMDV P1+3C, pHM-1180-11

```
            . Y  G  G    L  V  T  T    D  P  K    T  A  D    P  A  Y  G    K  V  Y  .
2581        TTACGGAGGA   TTGGTGACGA   CAGACCCGAA  GACAGCTGAC  CCTGCTTATG   GCAAGGTGTA

. N  P  P    R  T  N  Y    P  G  R    F  T  N    L  L  D  V    A  E  A  .
2641        CAACCCGCCT   AGGACTAACT   ACCCTGGGCG  CTTCACCAAC  CTGTTGGACG   TGGCCGAAGC

. C  P  T    F  L  C  F    D  D  G    K  P  Y    V  T  T  R    T  D  D  .
2701        GTGTCCCACT   TTCCTCTGCT   TTGACGACGG  GAAACCGTAC  GTCACCACGC   GGACGGATGA

. T  R  L    A  K  F  D    L  S  L    A  A  K    H  M  S  N    T  Y  .
2761        CACCCGACTT   TTGGCCAAGT   TTGACCTTTC  CCTGCCGCA   AAACATATGT   CCAACACATA

. L  S  G    I  A  Q  Y    Y  T  Q    Y  S  G    T  I  N  L    H  F  M  .
2821        CCTGTCAGGG   ATTGCTCAGT   ACTACACACA  GTACTCTGGC  ACCATCAATT   TGCATTTCAT

. F  T  G    S  T  D  S    K  A  R    Y  M  V    A  Y  I  P    P  G  V  .
2881        GTTTACAGGT   TCCACTGATT   CAAAGGCCCG  ATACATGGTG  GCCTACATCC   CACCTGGGGT

. E  T  P    P  D  T  P    E  R  A    A  H  C    I  H  A  E    W  D  T  .
2941        GGAGACACCA   CCGGACACAC   CTGAAAGGGC  TGCCCACTGC  ATTCACGCTG   AATGGGACAC

. G  L  N    S  K  F  T    F  S  I    P  Y  V    S  A  A  D    Y  A  Y  .
3001        TGGACTAAAC   TCCAAATTCA   CTTTCTCAAT  CCCGTACGTA  TCCGCCGCGG   ATTACGCGTA

. T  A  S    D  T  A  E    T  I  N    V  Q  G    W  V  C  I    Y  Q  I  .
3061        CACAGCGTCT   GACACGGCAG   AAACAATCAA  CGTACAGGGA  TGGGTCTGCA   TCTACCAAAT

. T  H  G    K  A  E  N    D  T  L    V  V  S    V  S  A  G    K  D  F  .
3121        TACACACGGG   AAGGCTGAAA   ATGACACCTT  GGTCGTGTCG  GTTAGCGCCG   GCAAAGACTT
                                                                    ⇒ VP1
            . E  L  R    L  P  I  D    P  R  Q    Q  T  T    A  T  G  E    S  A  D  .
3181        TGAGTTGCGC   CTCCCGATTG   ACCCCCGCCA  GCAGACCACC  GCTACCGGGG   AATCAGCAGA

. P  V  T    T  T  V  E    N  Y  G    E  T  Q    I  Q  R  H    H  .
3241        CCCGGTCACC   ACCACCGTGG   AGAACTACGG  CGGTGAGACA  CAAATCCAGA   GACGTCACCA

. T  D  I    G  F  I  M    D  R  F    V  K  I    Q  S  L  S    P  T  H  .
3301        CACGGACATT   GGTTTCATCA   TGGACAGATT  TGTGAAGATC  CAAAGCTTGA   GCCCAACACA

. V  I  D    L  M  Q  A    H  Q  H    G  L  V    G  A  L  L    R  A  A  .
3361        TGTCATTGAC   CTCATGCAGG   CTCACCAACA  CGGTCTGGTG  GGTGCCTTGC   TGCGTGCAGC

. T  Y  Y    F  S  D  L    E  I  V    R  H  E    G  N  L  T    W  V  .
3421        CACGTACTAC   TTTTCTGACC   TGGAAATTGT  TGTACGGCAC  GAAGGCAATC   TGACCTGGGT

. P  N  G    A  P  E  S    A  L  L    N  T  S    N  P  T  A    Y  N  K  .
3481        GCCCAACGGC   GCCCCTGAAT   CAGCCCTGTT  GAACACCAGC  AACCCCACTG   CCTACAACAA

. A  P  F    T  R  L  A    L  P  Y    T  A  P    H  R  V  L    A  T  V  .
3541        GGCACCATTC   ACGAGACTCG   CTCTCCCCTA  CACTGCGCCG  CACCGTGTGC   TGGCAACAGT
```

Fig 6D
Sequence Of The F8 H6p FMDV Gene Cassette in pF8 H6p FMDV P1+3C, pHM-1180-11

```
         . Y  N  G    T  S  K  Y    A  V  G    S  G    R  R  G    D    M  G  S  .
3601     GTACAACGGG  ACGAGTAAGT  ATGCTGTGGG  TGGTTCAGGC  AGAAGAGGCG  ACATGGGTC

. L  A  A    R  V  V  K    Q  L  P    A  S  F    N  Y  G    A  I  K  A  .
3661     TCTCGCGGCG  CGAGTCGTGA  AACAGCTTCC  TGCTTCATTT  AACTACGGTG  CAATCAAGGC

. D  A  I    H  E  L  L    V  R  M    K  R  A    E  L  Y    C    P  R  P  .
3721     CGACGCCATC  CACGAACTTC  TCGTGCGCAT  GAAACGGGCC  GAGCTCTACT  GCCCCAGACC

. L  L  A    I  E  V  S    S  Q  D    R  H  K    Q  K  I  I    A  P  A  .
3781     GCTGTTGGCA  ATAGAGGTGT  CTTCGCAAGA  CAGGCACAAG  CAAAAGATCA  TTGCACCAGC

⇒ A24 2A
         . K  Q  L    L  N  F  D    L  L  K    L  A  G    D  V  E  S    N  P  G  .
3841     AAAGCAGCTT  CTGAATTTTG  ACCTGCTCAA  GTTGGCCGGA  GACGTTGAGT  CCAACCCCGG

⇒ A24 2B
         . P  F  F    F  A  D  V    R  S  N    P  S  K    L  V  D  T    I  N  Q  .
3901     GCCATTCTTC  TTTGCTGACG  TTAGGTCAAA  CTTTTCAAAG  TTGGTAGACA  CAATCAACCA

. M  Q  E    D  M  S  T    K  H  G    P  D  F    N  R  L  V    S  A  F  .
3961     GATGCAGGAG  GACATGTCCA  CAAAACACGG  GCCCGACTTC  AACCGGTTGG  TGTCCGCATT

. E  E  L    A  T  G  V    K  A  I    R  T  G    L  D  E  A    K  P  W  .
4021     TGAGGAATTG  GCCACTGGAG  TTAAAGCTAT  CAGGACCGGT  CTCGACGAGG  CCAAACCCTG

. Y  K  L    I  K  L  L    S  R  L    S  C  M    A  A  V  A    A  R  S  .
4081     GTACAAGCTT  ATCAAACTCC  TAAGCCGCCT  GTCGTGCATG  GCCGCTGTGG  CAGCACGGTC

A24/A12 junction ⇒ A12 3B
         . K  D  P    V  L  V  A    I  M  L    A  D  T    G  L  E  R    Q  R  P  .
4141     CAAGGACCCA  GTCCTTGTGG  CCATCATGCT  GGCCGACACC  GGTCTCGAGC  GTCAGAGACC . L  K  V    R  A  K  L    P  Q  Q    E  G  P    Y  A  G  P    L  E  R  .
4201     TCTGAAAGTG  AGAGCTAAGC  TCCCACAGCA  GGAAGGACCT  TACGCTGGCC  CGTTGGAGAG . Q  K  P    L  K  V  K    A  K  A    P  V  V    K  E  G  P    Y  E  G  .
4261     ACAGAAACCG  CTGAAAGTGA  AGCAAAAGC   CCCGGTCGTC  AAGGAAGGAC  CTTACGAGGG ⇒ 3C
         . P  V  K    K  P  V  A    L  K  V    K  A  K    N  L  I  V    T  E  S  .
4321     ACCGGTGAAG  AAGCCTGTCG  CTTTGAAAGT  GAAAGCTAAG  AACTTGATAG  TCACTGAGAG . G  A  P    P  T  D  L    Q  K  M    V  M  G    N  T  K  P    V  E  L  .
4381     TGGTGCCCCA  CCGACCGACT  TGCAAAAGAT  GGTCATGGGC  AACACAAAGC  CTGTTGAGCT . I  L  D    G  K  T  V    A  I  C    C  A  T    G  V  F  G    T  A  Y  .
4441     CATCCTTGAC  GGGAAGACAG  TAGCCATCTG  TTGTGCTACT  GGAGTGTTTG  GCACTGCTTA . L  V  P    R  H  L  F    A  E  K    Y  D  K    I  M  L  D    G  R  A  .
4501     CCTCGTGCCT  CGTCATCTTT  TCGCAGAGAA  GTATGACAAG  ATCATGCTGG  ATGGCAGAGC
```

Fig 6E
Sequence Of The F8 H6p FMDV Gene Cassette in pF8 H6p FMDV P1+3C, pHM-1180-11

```
      . M   T   D   S   Y   R   V   F   E   F   E   I   K   V   K   G   Q   D   M   ·
4561  CATGACAGAC AGTGACTACA GAGTGTTTGA GTTTGAGATT AAAGTAAAAG GACAGGACAT

. L   S   D   A   A   L   M   V   L   H   R   G   N   R   V   R   D   I   T   K   ·
4621  GCTCTCAGAC GCTGCGCTCA TGGTGCTCCA CCGTGGGAAC CGCGTGAGAG ATATCACGAA

. H   F   R   D   T   A   R   M   K   K   G   T   P   V   V   G   V   N   N   ·
4681  ACACTTTCGT GATACAGCAA GAATGAAGAA AGGCACCCCC GTCGTCGGTG TGGTCAACAA

. A   D   V   G   R   L   I   F   S   G   E   A   L   T   Y   K   D   I   V   V   ·
4741  CGCCGACGTT GGGAGACTGA TTTTCTCTGG TGAGGCCCTC ACCTACAAGG ATATTGTAGT

. C   M   D   G   D   T   M   P   G   L   F   A   Y   K   A   A   T   K   A   G   ·
4801  GTGCATGGAC GGAGACACCA TGCCTGGCCT CTTTGCCTAC AAAGCCGCCA CCAAGGCAGG

. Y   C   G   G   A   V   L   A   K   D   G   A   D   T   F   I   V   G   T   H   ·
4861  CTACTGTGGA GGAGCCGTTC TCGCCAAGGA CGGGGCCGAC ACTTTCATCG TCGGCACTCA

. S   A   G   G   N   G   V   G   Y   C   S   C   V   S   R   S   M   L   L   R   ·
4921  CTCCGCAGGA GGCAATGGAG TTGGATACTG CTCATGCGTT TCCAGGTCCA TGCTTCTCAG

. M   K   A   H   V   D   P   E   P   Q   H   E
4981  AATGAAGGCA CACGTTGACC CTGAACCACA ACACGAGTAG TAATTTTTCT AGAGGATCCC

⇒ F8L
5041  TCGAGTTTTT ATTGACTAGT TAATCATAAG ATAAATAATA TACAGCATTG TAACCATCGT
5101  CATCCGTTAT ACGGGGAATA ATATTACCAT ACAGTATTAT TAAATTTTCT TACGAAGAAT
5161  ATAGATCGGT ATTTATCGTT AGTTTATTTT ACATTTATTA ATTAAACATG TCTACTATTA
5221  CCTGTTATGG AAATGACAAA TTTAGTTATA TAATTTATGA TAAAATTAAG ATAATAATAA
5281  TGAAATCAAA TAATTATGTA AATGCTACTA GATTATGTGA ATTACGAGGA AGAAAGTTTA
5341  CGAACTGGAA AAAATTAAGT GAATCTAAAA TATTAGTCGA TAATGTAAAA AAAATAAATG
5401  ATAAAACTAA CCAGTTAAAA ACGGATATGA TTATATACGT TAAGGATATT GATCATAAAG
5461  GAAGAGATAC TTGCGGTTAC TATGTACACC AAGATCTGGT ATCTTCTATA TCAAATTGGA
5521  TATCTCCGTT ATTCGCCGTT AAGGTAAATA AAATTATTAA CTATTATATA TGTAATGAAT
5581  ATGATATACG ACTTAGCGAA ATGGAATCTG ATATGACAGA AGTAATAGAT GTAGTTGATA
5641  AATTAGTAGG AGGATACAAT GATGAAATAG CAGAAATAAT ATATTTGTTT AATAAATTTA
5701  TAGAAAAATA TATTGCTAAC ATATCGTTAT CAACTGAATT ATCTAGTATA TTAAATAATT
5761  TTATAAATTT TAATAAAAAA TACAATAACG ACATAAAAGA TATTAAATCT TTAATTCTTG
```

Fig 6F
Sequence Of The F8 H6p FMDV Gene Cassette in pF8 H6p FMDV P1+3C, pHM-1180-11

```
5821   ATCTGAAAAA CACATCTATA AAACTAGATA AAAAGTTATT CGATAAAGAT AATAATGAAT
5881   CGAACGATGA AAAATTGGAA ACAGAAGTTG ATAAGCTAAT TTTTTTCATC TAAATAGTAT
5941   TATTTTATTG AAGTACGAAG TTTTACGTTA GATAAATAAT AAAGGTCGAT TTTTATTTTG
6001   TTAAATATCA AATATGTCAT TATCTGATAA AGATACAAAA ACACACGGTG ATTATCAACC
6061   ATCTAACGAA CAGATATTAC AAAAAATACG TCGGACTATG GAAAACGAAG CTGATAGCCT
6121   CAATAGAAGA AGCATTAAAG AAATTGTTGT AGATGTTATG AAGAATTGGG ATCATCCTCT
6181   CAACGAAGAA ATAGATAAAG TTCTAAACTG GAAAAATGAT ACATTAAACG ATTTAGATCA
6241   TCTAAATACA GATGATAATA TTAAGGAAAT CATACAATGT CTGATTAGAG AATTTGCGTT
6301   TAAAAGATC AATTCTATTA TGTATAGTTA TGCTATGGTA AAACTCAATT CAGATAACGA
6361   AACATTGAAA GATAAAATTA AGGATTATTT TATAGAAACT ATTCTTAAAG ACAAACGTGG
6421   TTATAAACAA AAGCCATTAC CC
```

Fig 7
PCR Primers For Amplification Of 3'-FMDV

```
            A24 2B           A12 3B
           D  T  G  L  E  R  Q  R
11280.SL  5' CGACACCGGT[CTCGAG]CGTCAGAG
                       Xho I = A24/A12 junction
```

```
           V  D  P  E  P  Q  H  E  *  *  T5NT
           GTTGACCCTGAACCACAACACGAGTAGTAATTTTTCTGCAG
11352.CXL 3' CAACTGGGACTTGGTGTTGTGCTCATCATTAAAAA[GACGTC]
                                                 Pst I
```

Fig 8
Construction of pC6 FMDV P1+3C, pCXL-1013-2

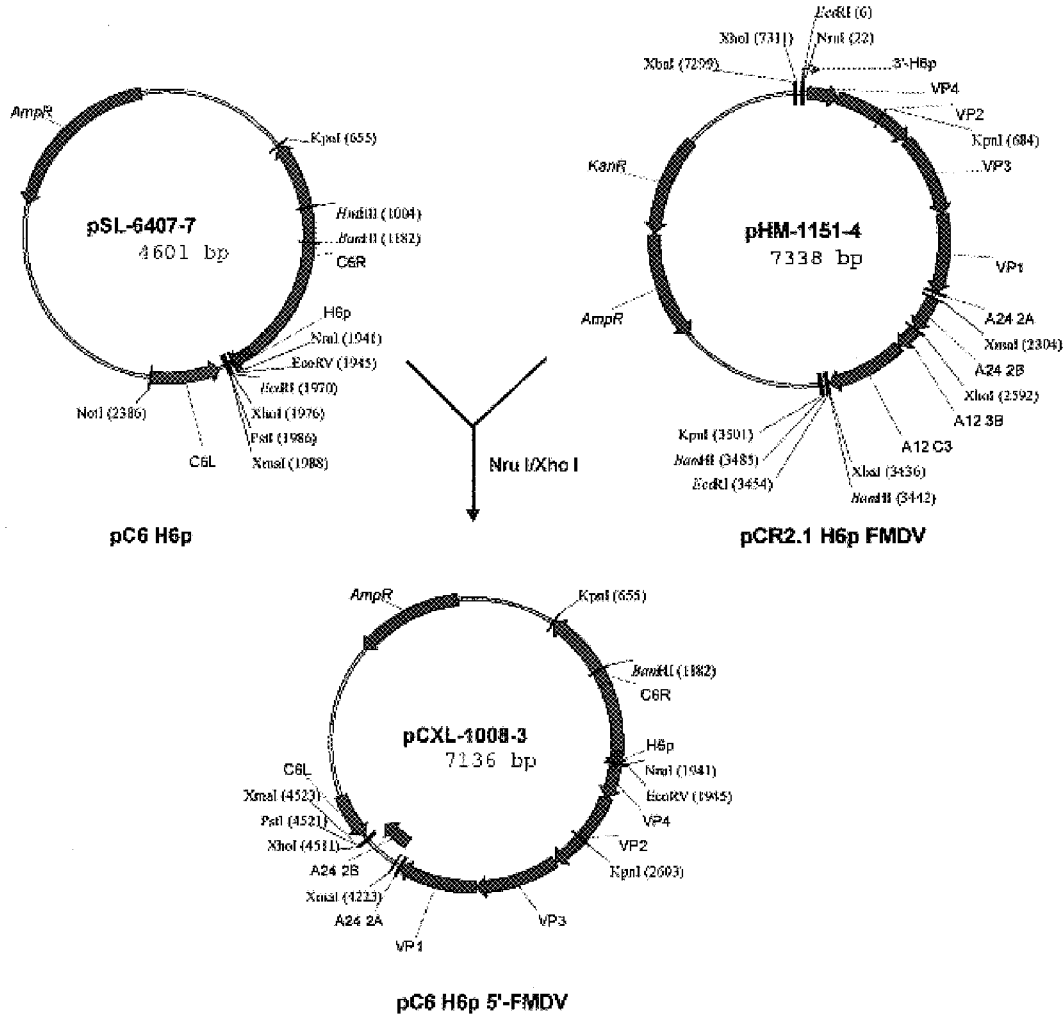

Fig 9B
Construction of pC6 H6p FMDV P1+3C, pCXL-1013-4.

Fig 10A
Sequence of the C6 H6p FMDV gene cassette in pC6 H6p FMDV P1+3C, pCXL-1013-4

```
   1  TTCATAAATA CAAGTTTGAT TAAACTTAAG TTGTTCTAAA GTTCTTTCCT CCGAAGGTAT
  61  AGAACAAAGT ATTTCTTCTA CATCCTTACT ATTTATTGCA GCTTTTAACA GCCTATCACG
 121  TATCCTATTT TTAGTATTGG TAGAACGTTT TAGTTCTAAA GTTAAAATAT TAGACATAAT
 181  TGGCATATTG CTTATTCCTT GCATAGTTGA GTCTGTAGAT CGTTTCAGTA TATCACTGAT
 241  TAATGTACTA CTGTTATGAT GAAATATAGA ATCGATATTG GCATTTAACT GTTTTGTTAT
 301  ACTAAGTCTA GATTTTAAAT CTTCTAGTAA TATGCTATTT AATATAAAAG CTTCCACGTT
 361  TTTGTATACA TTTCTTTCCA TATTAGTAGC TACTACTAAA TGATTATCTT CTTTCATATC
 421  TTGTAGATAA GATAGACTAT CTTTATCTTT ATTAGTAGAA AATACTTCTG GCCATACATC
 481  GTTAAATTTT TTTGTTGTTG TTAGATATAA TATTAAATAT CTAGAGGATC CTATTATTTG
 541  TGGTAAAATG TTTATAGAGT AAAATGATCT GGCTATTAAA CATAGGCCAG TTACCATAGA
 601  ATGCTGCTTC CCGTTACAGT GTTTTACCAT AACCATAGAT CTGCCTGTAT TGTTGATACA
 661  TATAACAGCT GTAAATCCTA AAAAATTCCT ATCATAATTA TTAATATTAG GTAATTCATT
 721  TCCATGTGAA AGATAGACTA ATTTTATATC CTTTACCTCC AAATAATTAT TTACATCTCT
 781  TAAACAATCT ATTTTAATAT CATTAACTGG TATTTTATAA TATCCAGAAA GGTTTGAAGG
 841  GGTTGATGGA ATAAGTCTAT TAACATCGTT AAGTAAATTA TTAATATCAT GAATCTTTAT
 901  TATATTATAC CCATAAGTTA AATTTATATT TACTTTCTCA TCATCTGACT TAGTTAGTTT
 961  GTAATAAGGT GTGTCTGAAA AAATTAAAAG GTAATTCGTT GAATGAAGCT GTATTTGCTG
1021  TATCATTTTT ATCTAATTTT GGAGATTTAG CAGTACTTAC TTCATTAGAA GAAGAATCTG
1081  CCAGTTCCTG TCTATTACTG ATATTTCGTT TCATTATTAT ATGATTTATA TTTTACTTTT
                 C6R ⇐                                    ⇒ H6p
1141  TCAATTATAT ATACTCATTT GACTAGTTAA TCAATAAAAA GAATTGTTCT TTATTCTATA
1201  CTTAAAAAGT GAAAATAAAT ACAAGGTTC TTGAGGGTTG TGTTAAATTG AAAGCGAGAA
                                                             ⇒ VP4
                                                             M G A G ·
1261  ATAATCATAA ATTATTTCAT TATCGCGATA TCCGTTAAGT TTGTATCGTA ATGGGAGCTG

.. Q  S  S    P  A  T    G  S  Q  N  Q  S  G    N  T  G    S  I  I  N ·
1321  GGCAATCCAG CCCAGCAACC GGCTCGCAGA ACCAGTCTGG CAACACTGGC AGCATAATCA

.. N  Y  Y    M  Q  Q    Y  Q  N  S  M  D  T    Q  L  G    D  N  A  I ·
1381  ACAACTACTA CATGCAACAG TACCAGAACT CCATGGACAC ACAGTTGGGA GACAATGCCA
```

Fig 10B
Sequence of the C6 H6p FMDV gene cassette in pC6 H6p FMDV P1+3C, pCXL-1013-4

```
      .. S    G    G     S    N    E    G    S    T    D    T    T    S    T    H    T    T    N    T    Q   .
     1441    TCAGTGGAGG  CTCCAACGAG  GGCTCCACGG  ACACAACTTC  AACACACACA  ACCAACACTC

.. N    N    D     W    F    S    K    L    A    S    S    A    F    T    G    L    F    G    A    L   .
     1501    AAAACAATGA  CTGGTTCTCG  AAGCTCGCCA  GTTCAGCTTT  TACCGGTCTG  TTCGGTGCAC
                   ⇒ VP2
             .. L    A    D     K    K    T    E    E    T    T    L    L    E    D    R    I    L    T    T    R   .
     1561    TGCTCGCCGA  CAAGAAGACA  GAGGAAACGA  CACTTCTTGA  GGACCGCATC  CTCACCACCC

.. N    G    H     T    T    S    T    T    Q    S    S    V    G    V    T    H    G    Y    S    T   .
     1621    GCAACGGGCA  CACCACCTCG  ACGACCCAAT  CGAGTGTGGG  TGTCACACAC  GGGTACTCCA

.. E    E    D     H    V    A    G    P    N    T    S    G    L    E    T    R    V    V    Q    A   .
     1681    CAGAGGAGGA  CCACGTTGCT  GGGCCCAACA  CATCGGGCCT  GGAGACGCGA  GTGGTGCAGG

.. E    R    F     Y    K    K    Y    L    F    D    W    T    T    D    K    A    F    G    H    L   .
     1741    CAGAGAGATT  CTACAAAAAG  TACTTGTTTG  ACTGGACAAC  GGACAAGGCA  TTTGGACACC

.. E    K    L     E    L    P    S    D    H    H    G    V    F    G    H    L    V    D    S    Y   .
     1801    TGGAAAAGCT  GGAGCTCCCG  TCCGACCACC  ACGGTGTCTT  TGGACACTTG  GTGGACTCGT

.. A    Y    M     R    N    G    W    D    V    E    V    S    A    V    G    N    Q    F    N    G   .
     1861    ACGCCTATAT  GAGAAATGGC  TGGGATGTTG  AGGTGTCCGC  TGTTGGCAAC  CAGTTCAACG

.. G    C    L     V    A    M    V    P    E    W    K    E    F    D    T    R    E    K    Y   .
     1921    GCGGGTGCCT  CCTGGTGGCC  ATGGTACCTG  AATGGAAGGA  ATTTGACACA  CGGGAGAAAT

.. Q    L    T     L    F    P    H    Q    F    I    S    P    R    T    N    M    T    A    H    I   .
     1981    ACCAACTCAC  CCTTTTCCCG  CACCAGTTTA  TTAGCCCCAG  AACTAACATG  ACTGCCCACA

.. T    V    P     Y    L    G    V    N    R    Y    D    Q    Y    K    K    H    K    P    W    T   .
     2041    TCACGGTCCC  CTACCTTGGT  GTGAACAGGT  ATGATCAGTA  CAAGAAGCAT  AAGCCCTGGA

.. L    V    V     M    V    V    S    P    L    T    V    N    N    T    S    A    A    Q    I    K   .
     2101    CATTGGTTGT  CATGGTCGTG  TCGCCACTTA  CGGTCAACAA  CACTAGTGCG  GCACAAATCA

.. V    Y    A     N    I    A    P    T    Y    V    H    V    A    G    E    L    P    S    K    E   .
     2161    AGGTCTACGC  CAACATAGCT  CCGACCTATG  TTCACGTGGC  CGGTGAACTC  CCCTCGAAAG
                   ⇒ VP3
             .. G    I    F     P    V    A    C    A    D    G    Y    G    G    L    V    T    T    D    P    K   .
     2221    AGGGGATTTT  CCCGGTTGCA  TGTGCGGACG  GTTACGGAGG  ATTGGTGACG  ACAGACCCGA

.. T    A    D     P    A    Y    G    K    V    Y    N    P    P    R    T    N    Y    P    G    R   .
     2281    AGACAGCTGA  CCCTGCTTAT  GGCAAGGTGT  ACAACCCGCC  TAGGACTAAC  TACCCTGGGC

.. F    T    N     L    L    D    V    A    E    A    C    P    T    F    L    C    F    D    D    G   .
     2341    GCTTCACCAA  CCTGTTGGAC  GTGGCCGAAG  CGTGTCCCAC  TTTCCTCTGC  TTTGACGACG

.. K    P    Y     V    T    T    R    T    D    D    T    R    L    L    A    K    F    D    L    S   .
     2401    GGAAACCGTA  CGTCACCACG  CGGACGGATG  ACACCCGACT  TTTGGCCAAG  TTTGACCTTT
```

Fig 10C
Sequence of the C6 H6p FMDV gene cassette in pC6 H6p FMDV P1+3C, pCXL-1013-4

```
            .. L   A   A     K   H   M     S   N   T     Y   L   S     G   I   A   Q     Y   Y   T   Q ·
      2461  CCCTTGCCGC      AAAACATATG    TCCAACACAT    ACCTGTCAGG    GATTGCTCAG    TACTACACAC
            .. Y   S   G     T   I   N     L   H   F   M     F   T   G     S   T   D     S   K   A   R ·
      2521  AGTACTCTGG      CACCATCAAT    TTGCATTTCA    TGTTTACAGG    TTCCACTGAT    TCAAAGGCCC

.. Y   M   V     A   Y   I     P   P   G   V     E   T   P     P   D   T     P   E   R   A ·
      2581  GATACATGGT      GGCCTACATC    CCACCTGGGG    TGGAGACACC    ACCGGACACA    CCTGAAAGGG
            .. A   H   C     I   H   A     E   W   D     T   G   L   N     S   K   F     T   F   S   I ·
      2641  CTGCCCACTG      CATTCACGCT    GAATGGACA     CTGGACTAAA    CTCCAAATTC    ACTTTCTCAA

.. P   Y   V     S   A   A     D   Y   A   Y     T   A   S     D   T   A     E   T   I   N ·
      2701  TCCCGTACGT      ATCCGCCGCG    GATTACGCGT    ACACAGCGTC    TGACACGGCA    GAAACAATCA
            .. V   Q   G     W   V   C     I   Y   Q   I     T   H   G     K   A   E     N   D   T   L ·
      2761  ACGTACAGGG      ATGGGTCTGC    ATCTACCAAA    TTACACACGG    GAAGGCTGAA    AATGACACCT

.. V   V   S     V   S   A     G   K   D   F     E   L   R     L   P   I     D   P   R   Q ·
      2821  TGGTCGTGTC      GGTTAGCGCC    GGCAAAGACT    TTGAGTTGCG    CCTCCCGATT    GACCCCCGCC

⇒ VP1
            .. Q   T   T     A   T   G     E   S   A   D     P   V   T     T   T   V     E   N   Y   G ·
      2881  AGCAGACCAC      CGCTACCGGG    GAATCAGCAG    ACCCGGTCAC    CACCACCGTG    GAGAACTACG

.. G   E   T     Q   I   Q     R   R   H     H   T   D   I     G   F   I     M   D   R   F ·
      2941  GCGGTGAGAC      ACAAATCCAG    AGACGTCACC    ACACGGACAT    TGGTTTCATC    ATGGACAGAT

.. V   K   I     Q   S   L     S   P   T   H     V   I   D     L   M   Q     A   H   Q   H ·
      3001  TTGTGAAGAT      CCAAAGCTTG    AGCCCAACAC    ATGTCATTGA    CCTCATGCAG    GCTCACCAAC

.. G   L   V     G   A   L     L   R   A   A     T   Y   Y     F   S   D     L   E   I   V ·
      3061  ACGGTCTGGT      GGGTGCCTTG    CTGCGTGCAG    CCACGTACTA    CTTTTCTGAC    CTGGAAATTG

.. V   R   H     E   G   N     L   T   W   V     P   N   G     A   P   E     S   A   L   L ·
      3121  TTGTACGGCA      CGAAGGCAAT    CTGACCTGGG    TGCCCAACGG    CGCCCCTGAA    TCAGCCCTGT

.. N   T   S     N   P   T     A   Y   N   K     A   P   F     T   R   L     A   L   P   Y ·
      3181  TGAACACCAG      CAACCCCACT    GCCTACAACA    AGGCACCATT    CACGAGACTC    GCTCTCCCCT

.. T   A   P     H   R   V     L   A   T   V     Y   N   G     T   S   K     Y   A   V   G ·
      3241  ACACTGCGCC      GCACCGTGTG    CTGGCAACAG    TGTACAACGG    GACGAGTAAG    TATGCTGTGG

.. G   S   G     R   R   G     D   M   G   S     L   A   A     R   V   V     K   Q   L   P ·
      3301  GTGGTTCAGG      CAGAAGAGGC    GACATGGGGT    CTCTCGCGGC    GCGAGTCGTG    AAACAGCTTC

.. A   S   F     N   Y   G     A   I   K   A     D   A   I     H   E   L     L   V   R   M ·
      3361  CTGCTTCATT      TAACTACGGT    GCAATCAAGG    CCGACGCCAT    CCACGAACTT    CTCGTGCGCA

.. K   R   A     E   L   Y     C   P   R   P     L   L   A     I   E   V     S   S   Q   D ·
      3421  TGAAACGGGC      CGAGCTCTAC    TGCCCCAGAC    CGCTGTTGGC    AATAGAGGTG    TCTTCGCAAG

⇒ A24 2A
            .. R   H   K     Q   K   I     I   A   P   A     K   Q   L     L   N   F     D   L   L   K ·
      3481  ACAGGCACAA      GCAAAAGATC    ATTGCACCAG    CAAAGCAGCT    TCTGAATTTT    GACCTGCTCA
```

Fig 10D
Sequence of the C6 H6p FMDV gene cassette in pC6 H6p FMDV P1+3C, pCXL-1013-4

```
                              ⇒ A24 2B
       .. L   A   G     D   V   E     S   N   P     G   P   F   F     F   A   D     V   R   S   N ·
3541   AGTTGGCCGG   AGACGTTGAG   TCCAACCCCG   GGCCATTCTT   CTTTGCTGAC   GTTAGGTCAA

.. F   S   K     L   V   D     T   I   N   Q   M   Q   E     D   M   S     T   K   H   G ·
3601   ACTTTTCAAA   GTTGGTAGAC   ACAATCAACC   AGATGCAGGA   GGACATGTCC   ACAAAACACG

.. P   D   F     N   R   L     V   S   A   F     E   E   L     A   T   G     V   K   A   I ·
3661   GGCCCGACTT   CAACCGGTTG   GTGTCCGCAT   TTGAGGAATT   GGCCACTGGA   GTTAAAGCTA

.. R   T   G     L   D   E     A   K   P   W   Y   K   L     I   K   L     L   S   R   L ·
3721   TCAGGACCGG   TCTCGACGAG   GCCAAACCCT   GGTACAAGCT   TATCAAACTC   CTAAGCCGCC

.. S   C   M     A   A   V     A   A   R   S     K   D   P     V   L   V     A   I   M   L ·
3781   TGTCGTGCAT   GGCCGCTGTG   GCAGCACGGT   CCAAGGACCC   AGTCCTTGTG   GCCATCATGC

A24/A12 junction   ⇒ A12 3B
       .. A   D   T     G   L   E     R   Q   R   P     L   K   V     R   A   K     L   P   Q   Q ·
3841   TGGCCGACAC   CGGTCTCGAG   CGTCAGAGAC   CTCTGAAAGT   GAGAGCTAAG   CTCCCACAGC .. E   G   P     Y   A   G     P   L   E   R     Q   K   P     L   K   V     K   A   K   A ·
3901   AGGAAGGACC   TTACGCTGGC   CCGTTGGAGA   GACAGAAACC   GCTGAAAGTG   AAAGCAAAAG .. P   V   V     K   E   G     P   Y   E   G     P   V   K     K   P   V     A   L   K   V ·
3961   CCCCGGTCGT   CAAGGAAGGA   CCTTACGAGG   GACCGGTGAA   GAAGCCTGTC   GCTTTGAAAG ⇒ A12 3C
       .. K   A   K     N   L   I     V   T   E   S     G   A   P     P   T   D     L   Q   K   M ·
4021   TGAAAGCTAA   GAACTTGATA   GTCACTGAGA   GTGGTGCCCC   ACCGACCGAC   TTGCAAAAGA .. V   M   G     N   T   K     P   V   E   L     I   L   D     G   K   T     V   A   I   C ·
4081   TGGTCATGGG   CAACACAAAG   CCTGTTGAGC   TCATCCTTGA   CGGGAAGACA   GTAGCCATCT .. C   A   T     G   V   F     G   T   A   Y     L   V   P     R   H   L     F   A   E   K ·
4141   GTTGTGCTAC   TGGAGTGTTT   GGCACTGCTT   ACCTCGTGCC   TCGTCATCTT   TTCGCAGAGA .. Y   D   K     I   M   L     D   G   R     A   M   T   D     S   D   Y     R   V   F   E ·
4201   AGTATGACAA   GATCATGCTG   GATGGCAGAG   CCATGACAGA   CAGTGACTAC   AGAGTGTTTG .. F   E   I     K   V   K     G   Q   D   M     L   S   D     A   A   L     M   V   L   H ·
4261   AGTTTGAGAT   TAAAGTAAAA   GGACAGGACA   TGCTCTCAGA   CGCTGCGCTC   ATGGTGCTCC .. R   G   N     R   V   R     D   I   T   K     H   F   R     D   T   A     R   M   K   K ·
4321   ACCGTGGGAA   CCGCGTGAGA   GATATCACGA   AACACTTTCG   TGATACAGCA   AGAATGAAGA .. G   T   P     V   V   G     V   V   N   N     A   D   V     G   R   L     I   F   S   G ·
4381   AAGGCACCCC   CGTCGTCGGT   GTGGTCAACA   ACGCCGACGT   TGGGAGACTG   ATTTTCTCTG .. E   A   L     T   Y   K     D   I   V   V     C   M   D     G   D   T     M   P   G   L ·
4441   GTGAGGCCCT   CACCTACAAG   GATATTGTAG   TGTGCATGGA   CGGAGACACC   ATGCCTGGCC .. F   A   Y     K   A   A     T   K   A   G     Y   C   G     G   A   V     L   A   K   D ·
4501   TCTTTGCCTA   CAAAGCCGCC   ACCAAGGCAG   GCTACTGTGG   AGGAGCCGTT   CTCGCCAAGG
```

Fig 10E
Sequence of the C6 H6p FMDV gene cassette in pC6 H6p FMDV P1+3C, pCXL-1013-4

```
         .. G   A   D      T   F   I      V   G   T      H   S   A      G   N   G      V   G   Y   C  ·
4561     ACGGGGCCGA     CACTTTCATC     GTCGGCACTC     ACTCCGCAGG     AGGCAATGGA     GTTGGATACT

.. S   C   V      S   R   S      M   L   L      R   M   K      A   H   V      D   P   E   P   Q  ·
4621     GCTCATGCGT     TTCCAGGTCC     ATGCTTCTCA     GAATGAAGGC     ACACGTTGAC     CCTGAACCAC

.. H   E   *      *
4681     AACACGAGTA     GTAATTTTTC     TGCAGCCCGG     GTTTTTATAG     CTAATTAGTC     ATTTTTTCGT

4741     AAGTAAGTAT     TTTTATTTAA     TACTTTTTAT     TGTACTTATG     TTAAATATAA     CTGATGATAA

4801     CAAAATCCAT     TATGTATTAT     TTATAACTGT     AATTTCTTTA     GCGTAGTTAG     ATGTCCAATC

4861     TCTCTCAAAT     ACATCGGCTA     TCTTTTTAGT     GAGATTTTGA     TCTATGCAGT     TGAAACTTAT

4921     GAACGCGTGA     TGATTAAAAT     GTGAACCGTC     CAAATTTGCA     GTCATTATAT     GAGCGTATCT

4981     ATTATCTACT     ATCATCATCT     TTGAGTTATT     AATATCATCT     ACTTTAGAAT     TGATAGGAAA

5041     TATGAATACC     TTTGTAGTAA     TATCTATACT     ATCTACACCT     AACTCATTAA     GACTTTTGAT

5101     AG
           ⇐ C6L
```

Fig 11
Comparison of the sequences of the wild-type and mutant vaccinia virus H6 promoters.

H6p  TTCTTTATTCTATACTTAAAAGTGAAAATAAATACAAAGGTTCTTGAGGGTTGTGTTAAATTGAAAGCGAGAAATAATCATAAATTATTTCATTATCGCGATATCCGTTAAGTTTGTATCGTA

H6p* TTCTTTATTCTATACTTAAAAGTGAAATAAATACAAAGGTTCTTG

H6p = wild-type early/late H6 promoter

H6p* = early H6 promoter with a single nucleotide mutation

Fig 12A
PCR primers to amplify H6p* 5'-FMDV

```
                  Eco RI ⇒ H6p*                                          ⇒VP4
                                                                        M   G
11353.CXL  5'  GAATTCTTCTTTATTCTATACTTAAAAAGTGCAAATAAATACAAAGGTTCTTGATGGGAG

L  A  A  K  H  M  S
               CTTGCCGCAAAACATATGTCCA
11358.CXL  3'  GAACGGCGTTTTGTATACAGGT
                                Nde I
```

Fig 12B
PCR primers for site-directed mutagenesis in VP4

```
               H6p* VP4
                 M  G  A  G  Q  S  S
11410.HM  5'  CTTGATGGGAGCTGGGCAATCCAGC
11411.HM  3'  GAACTACCCTCGACCCGTTAGGTCG
```

Fig 13A
Construction of pC6 H6p* FMDV P1+3C, pHM-1273-1

Fig 13B
Construction of pC6 H6p* FMDV P1+3C, pHM-1273-1.

Fig 14A
Sequence of the C6 H6p* FMDV gene cassette in pC6 H6p* FMDV P1+3C, pHM-1273-1

```
   1  TTCATAAATA CAAGTTTGAT TAAACTTAAG TTGTTCTAAA GTTCTTTCCT CCGAAGGTAT
  61  AGAACAAAGT ATTTCTTCTA CATCCTTACT ATTTATTGCA GCTTTTAACA GCCTATCACG
 121  TATCCTATTT TTAGTATTGG TAGAACGTTT TAGTTCTAAA GTTAAAATAT TAGACATAAT
 181  TGGCATATTG CTTATTCCTT GCATAGTTGA GTCTGTAGAT CGTTTCAGTA TATCACTGAT
 241  TAATGTACTA CTGTTATGAT GAAATATAGA ATCGATATTG GCATTTAACT GTTTTGTTAT
 301  ACTAAGTCTA GATTTTAAAT CTTCTAGTAA TATGCTATTT AATATAAAAG CTTCCACGTT
 361  TTTGTATACA TTTCTTTCCA TATTAGTAGC TACTACTAAA TGATTATCTT CTTTCATATC
 421  TTGTAGATAA GATAGACTAT CTTTATCTTT ATTAGTAGAA AATACTTCTG GCCATACATC
 481  GTTAAATTTT TTTGTTGTTG TTAGATATAA TATTAAATAT CTAGAGGATC CTATTATTTG
 541  TGGTAAAATG TTTATAGAGT AAAATGATCT GGCTATTAAA CATAGGCCAG TTACCATAGA
 601  ATGCTGCTTC CCGTTACAGT GTTTTACCAT AACCATAGAT CTGCCTGTAT TGTTGATACA
 661  TATAACAGCT GTAAATCCTA AAAAATTCCT ATCATAATTA TTAATATTAG GTAATTCATT
 721  TCCATGTGAA AGATAGACTA ATTTTATATC CTTTACCTCC AAATAATTAT TTACATCTCT
 781  TAAACAATCT ATTTTAATAT CATTAACTGG TATTTATAA TATCCAGAAA GGTTTGAAGG
 841  GGTTGATGGA ATAAGTCTAT TAACATCGTT AAGTAAATTA TTAATATCAT GAATCTTTAT
 901  TATATTATAC CCATAAGTTA AATTTATATT TACTTTCTCA TCATCTGACT TAGTTAGTTT
 961  GTAATAAGGT GTGTCTGAAA AAATTAAAAG GTAATTCGTT GAATGAAGCT GTATTTGCTG
1021  TATCATTTTT ATCTAATTTT GGAGATTTAG CAGTACTTAC TTCATTAGAA GAAGAATCTG
1081  CCAGTTCCTG TCTATTACTG ATATTTCGTT TCATTATTAT ATGATTTATA TTTTACTTTT
              C6R ⇐                                    ⇒ H6p*
1141  TCAATTATAT ATACTCATTT GACTAGTTAA TCAATAAAAA GAATTCTTCT TTATTCTATA
                                                ⇒ VP4
                                                M  G  A  G  Q  S   S  P  A
1201  CTTAAAAAGT GCAAATAAAT ACAAAGGTTC TTGATGGGAG CTGGCAATC CAGCCCAGCA

T  G  S  Q   N  Q  S   G  N  T   G  S  I  I   N  N  Y   Y  M  Q
1261  ACCGGCTCGC AGAACCAGTC TGGCAACACT GGCAGCATAA TCAACAACTA CTACATGCAA

Q  Y  Q   N  S  M  D   T  Q  L   G  D  N  A   I  S  G   G  S  N
1321  CAGTACCAGA ACTCCATGGA CACACAGTTG GGAGACAATG CCATCAGTGG AGGCTCCAAC
```

Fig 14B
Sequence of the C6 H6p* FMDV gene cassette in pC6 H6p* FMDV P1+3C, pHM-1273-1

```
           E  G  S  T     D  T  T     S  T  H     T  T  N  T     Q  N  N     D  W  F
     1381  GAGGGCTCCA CGGACACAAC TTCAACACAC ACAACCAACA CTCAAAACAA TGACTGGTTC

⇒ VP2
           S  K  L  A     S  S  A     F  T  G     L  F  G  A     L  L  A     D  K  K
     1441  TCGAAGCTCG CCAGTTCAGC TTTTACCGGT CTGTTCGGTG CACTGCTCGC CGACAAGAAG

T  E  E  T     T  L  L     E  D  R     I  L  T  T     R  N  G     H  T  T
     1501  ACAGAGGAAA CGACACTTCT TGAGGACCGC ATCCTCACCA CCCGCAACGG GCACACCACC

S  T  T  Q     S  S  V     G  V  T     H  G  Y  S     T  E  E     D  H  V
     1561  TCGACGACCC AATCGAGTGT GGGTGTCACA CACGGGTACT CCACAGAGGA GGACCACGTT

A  G  P  N     T  S  G     L  E  T     R  V  V  Q     A  E  R     F  Y  K
     1621  GCTGGGCCCA ACACATCGGG CCTGGAGACG CGAGTGGTGC AGGCAGAGAG ATTCTACAAA

K  Y  L  F     D  W  T     T  D  K     A  F  G  H     L  E  K     L  E  L
     1681  AAGTACTTGT TTGACTGGAC AACGGACAAG GCATTTGGAC ACCTGGAAAA GCTGGAGCTC

P  S  D  H     H  G  V     F  G  H     L  V  D  S     Y  A  Y     M  R  N
     1741  CCGTCCGACC ACCACGGTGT CTTTGGACAC TTGGTGGACT CGTACGCCTA TATGAGAAAT

G  W  D  V     E  V  S     A  V  G     N  Q  F  N     G  G  C     L  L  V
     1801  GGCTGGGATG TTGAGGTGTC CGCTGTTGGC AACCAGTTCA ACGGCGGGTG CCTCCTGGTG

A  M  V  P     E  W  K     E  F  D     T  R  E  K     Y  Q  L     T  L  F
     1861  GCCATGGTAC CTGAATGGAA GGAATTTGAC ACACGGGAGA AATACCAACT CACCCTTTTC

P  H  Q  F     I  S  P     R  T  N     M  T  A  H     I  T  V     P  Y  L
     1921  CCGCACCAGT TTATTAGCCC CAGAACTAAC ATGACTGCCC ACATCACGGT CCCCTACCTT

G  V  N  R     Y  D  Q     Y  K  K     H  K  P  W     T  L  V     V  M  V
     1981  GGTGTGAACA GGTATGATCA GTACAAGAAG CATAAGCCCT GGACATTGGT TGTCATGGTC

V  S  P  L     T  V  N     N  T  S     A  A  Q  I     K  V  Y     A  N  I
     2041  GTGTCGCCAC TTACGGTCAA CAACACTAGT GCGGCACAAA TCAAGGTCTA CGCCAACATA

⇒ VP3
           A  P  T  Y     V  H  V     A  G  E     L  P  S  K     E  G  I     F  P  V
     2101  GCTCCGACCT ATGTTCACGT GGCCGGTGAA CTCCCCTCGA AGAGGGGAT TTTCCCGGTT

A  C  A  D     G  Y  G     G  L  V     T  T  D  P     K  T  A     D  P  A
     2161  GCATGTGCGG ACGGTTACGG AGGATTGGTG ACGACAGACC CGAAGACAGC TGACCCTGCT

Y  G  K  V     Y  N  P     P  R  T     N  Y  P  G     R  F  T     N  L  L
     2221  TATGGCAAGG TGTACAACCC GCCTAGGACT AACTACCCTG GGCGCTTCAC CAACCTGTTG

D  V  A  E     A  C  P     T  F  L     C  F  D  D     G  K  P     Y  V  T
     2281  GACGTGGCCG AAGCGTGTCC CACTTTCCTC TGCTTTGACG ACGGGAAACC GTACGTCACC

T  R  T  D     D  T  R     L  A     K  F  D  L     S  L  A     K  H
     2341  ACGCGGACGG ATGACACCCG ACTTTTGGCC AAGTTTGACC TTTCCCTTGC CGCAAAACAT
```

Fig 14C
Sequence of the C6 H6p* FMDV gene cassette in pC6 H6p* FMDV P1+3C, pHM-1273-1

```
     M  S  N  T  Y  L  S  G  I  A  Q  Y  Y  T  Q  Y  S  G  T  I
2401 ATGTCCAACA CATACCTGTC AGGGATTGCT CAGTACTACA CACAGTACTC TGGCACCATC

N  L  H  F  M  F  T  G  S  T  D  S  K  A  R  Y  M  V  A  Y
2461 AATTTGCATT TCATGTTTAC AGGTTCCACT GATTCAAAGG CCCGATACAT GGTGGCCTAC

I  P  P  G  V  E  T  P  P  D  T  P  E  R  A  A  H  C  I  H
2521 ATCCCACCTG GGTGGAGAC ACCACCGGAC ACACCTGAAA GGGCTGCCCA CTGCATTCAC

A  E  W  D  T  G  L  N  S  K  F  T  F  S  I  P  Y  V  S  A
2581 GCTGAATGGG ACACTGGACT AAACTCCAAA TTCACTTTCT CAATCCCGTA CGTATCCGCC

A  D  Y  A  Y  T  A  S  D  T  A  E  T  I  N  V  Q  G  W  V
2641 GCGGATTACG CGTACACAGC GTCTGACACG GCAGAAACAA TCAACGTACA GGGATGGGTC

C  I  Y  Q  I  T  H  G  K  A  E  N  D  T  L  V  V  S  V  S
2701 TGCATCTACC AAATTACACA CGGGAAGGCT GAAAATGACA CCTTGGTCGT GTCGGTTAGC

⇒ VP1
     A  G  K  D  F  E  L  R  L  P  I  D  P  R  Q  Q  T  T  A  T
2761 GCCGGCAAAG ACTTTGAGTT GCGCCTCCCG ATTGACCCCC GCCAGCAGAC CACCGCTACC

G  E  S  A  D  P  V  T  T  T  V  E  N  Y  G  G  E  T  Q  I
2821 GGGGAATCAG CAGACCCGGT CACCACCACC GTGGAGAACT ACGGCGGTGA GACACAAATC

Q  R  R  H  H  T  D  I  G  F  I  M  D  R  F  V  K  I  Q  S
2881 CAGAGACGTC ACCACACGGA CATTGGTTTC ATCATGGACA GATTTGTGAA GATCCAAAGC

L  S  P  T  H  V  I  D  L  M  Q  A  H  Q  H  G  L  V  G  A
2941 TTGAGCCCAA CACATGTCAT TGACCTCATG CAGGCTCACC AACACGGTCT GGTGGGTGCC

L  L  R  A  A  T  Y  Y  F  S  D  L  E  I  V  V  R  H  E  G
3001 TTGCTGCGTG CAGCCACGTA CTACTTTTCT GACCTGGAAA TTGTTGTACG GCACGAAGGC

N  L  T  W  V  P  N  G  A  P  E  S  A  L  L  N  T  S  N  P
3061 AATCTGACCT GGGTGCCCAA CGGCGCCCCT GAATCAGCCC TGTTGAACAC CAGCAACCCC

T  A  Y  N  K  A  P  F  T  R  L  A  L  P  Y  T  A  P  H  R
3121 ACTGCCTACA ACAAGGCACC ATTCACGAGA CTCGCTCTCC CCTACACTGC GCCGCACCGT

V  L  A  T  V  Y  N  G  T  S  K  Y  A  V  G  G  S  G  R  R
3181 GTGCTGGCAA CAGTGTACAA CGGGACGAGT AAGTATGCTG TGGGTGGTTC AGGCAGAAGA

G  D  M  G  S  L  A  A  R  V  V  K  Q  L  P  A  S  F  N  Y
3241 GGCGACATGG GGTCTCTCGC GGCGCGAGTC GTGAAACAGC TTCCTGCTTC ATTTAACTAC

G  A  I  K  A  D  A  I  H  E  L  L  V  R  M  K  R  A  E  L
3301 GGTGCAATCA AGGCCGACGC CATCCACGAA CTTCTCGTGC GCATGAAACG GGCCGAGCTC

Y  C  P  R  P  L  L  A  I  E  V  S  S  Q  D  R  H  K  Q  K
3361 TACTGCCCCA GACCGCTGTT GGCAATAGAG GTGTCTTCGC AAGACAGGCA CAAGCAAAAG
```

Fig 14D
Sequence of the C6 H6p* FMDV gene cassette in pC6 H6p* FMDV P1+3C, pHM-1273-1

```
                            ⇒ A24 2A
              I   I   A   P   A   K   Q   L   L   N   F   D   L   L   K   L   A   G   D   V
       3421   ATCATTGCAC CAGCAAAGCA GCTTCTGAAT TTTGACCTGC TCAAGTTGGC CGGAGACGTT

⇒ A24 2B
              E   S   N   P   G   P   F   F   F   A   D   V   R   S   N   F   S   K   L   V
       3481   GAGTCCAACC CCGGGCCATT CTTCTTTGCT GACGTTAGGT CAAACTTTTC AAAGTTGGTA

D   T   I   N   Q   M   Q   E   D   M   S   T   K   H   G   P   D   F   N   R
       3541   GACACAATCA ACCAGATGCA GGAGGACATG TCCACAAAAC ACGGGCCCGA CTTCAACCGG

L   V   S   A   F   E   E   L   A   T   G   V   K   A   I   R   T   G   L   D
       3601   TTGGTGTCCG CATTTGAGGA ATTGGCCACT GGAGTTAAAG CTATCAGGAC CGGTCTCGAC

E   A   K   P   W   Y   K   L   I   K   L   L   S   R   L   S   C   M   A   A
       3661   GAGGCCAAAC CCTGGTACAA GCTTATCAAA CTCCTAAGCC GCCTGTCGTG CATGGCCGCT

A24/A12 junction
              V   A   A   R   S   K   D   P   V   L   V   A   I   M   L   A   D   T   G   L
       3721   GTGGCAGCAC GGTCCAAGGA CCCAGTCCTT GTGGCCATCA TGCTGGCCGA CACCGGT CTC ⇒ A12 3B
              E   R   Q   R   P   L   K   V   R   A   K   L   P   Q   Q   E   G   P   Y   A
       3781   GAG CGTCAGA GACCTCTGAA AGTGAGAGCT AAGCTCCCAC AGCAGGAAGG ACCTTACGCT G   P   L   E   R   Q   K   P   L   K   V   K   A   P   V   K   E
       3841   GGCCCGTTGG AGAGACAGAA ACCGCTGAAA GTGAAAGCAA AGCCCCGGT CGTCAAGGAA G   P   Y   E   G   P   V   K   K   P   V   A   L   K   V   K   A   K   N   L
       3901   GGACCTTACG AGGGACCGGT GAAGAAGCCT GTCGCTTTGA AAGTGAAAGC TAAGAACTTG ⇒ A12 3C
              I   V   T   E   S   G   A   P   P   T   D   L   Q   K   M   V   M   G   N   T
       3961   ATAGTCACTG AGAGTGGTGC CCCACCGACC GACTTGCAAA AGATGGTCAT GGGCAACACA K   P   V   E   L   I   L   D   G   K   T   V   A   I   C   C   A   T   G   V
       4021   AAGCCTGTTG AGCTCATCCT TGACGGGAAG ACAGTAGCCA TCTGTTGTGC TACTGGAGTG F   G   T   A   Y   L   V   P   R   H   L   F   A   E   K   Y   D   K   I   M
       4081   TTTGGCACTG CTTACCTCGT GCCTCGTCAT CTTTTCGCAG AGAAGTATGA CAAGATCATG L   D   G   R   A   M   T   D   S   D   Y   R   V   F   E   F   E   I   K   V
       4141   CTGGATGGCA GAGCCATGAC AGACAGTGAC TACAGAGTGT TTGAGTTTGA GATTAAAGTA K   G   Q   D   M   L   S   D   A   A   L   M   V   L   H   R   G   N   R   V
       4201   AAAGGACAGG ACATGCTCTC AGACGCTGCG CTCATGGTGC TCCACCGTGG GAACCGCGTG R   D   I   T   K   H   F   R   D   T   A   R   M   K   K   G   T   P   V   V
       4261   AGAGATATCA CGAAACACTT TCGTGATACA GCAAGAATGA AGAAAGGCAC CCCCGTCGTC G   V   V   N   N   A   D   V   G   R   L   I   F   S   G   E   A   L   T   Y
       4321   GGTGTGGTCA ACAACGCCGA CGTTGGGAGA CTGATTTTCT CTGGTGAGGC CCTCACCTAC
```

Fig 14E
Sequence of the C6 H6p* FMDV gene cassette in pC6 H6p* FMDV P1+3C, pHM-1273-1

```
             K  D  I     V  V  C  M     D  G  D     T  M  P  G     L  F  A     Y  K  A
      4381   AAGGATATTG TAGTGTGCAT GGACGGAGAC ACCATGCCTG GCCTCTTTGC CTACAAAGCC

A  T  K  A     G  Y  C     G  G  A     V  L  A  K     D  G  A     D  T  F
      4441   GCCACCAAGG CAGGCTACTG TGGAGGAGCC GTTCTCGCCA AGGACGGGGC CGACACTTTC

I  V  G  T     H  S  A     G  G  N     G  V  G  Y     C  S     V  S  R
      4501   ATCGTCGGCA CTCACTCCGC AGGAGGCAAT GGAGTTGGAT ACTGCTCATG CGTTTCCAGG

S  M  L     R  M  K     A  H  V     D  P  E  P     Q  H  E     *  *
      4561   TCCATGCTTC TCAGAATGAA GGCACACGTT GACCCTGAAC CACAACACGA GTAGTAATTT

4621   TTCTGCAGCC CGGGTTTTTA TAGCTAATTA GTCATTTTTT CGTAAGTAAG TATTTTTATT

4681   TAATACTTTT TATTGTACTT ATGTTAAATA TAACTGATGA TAACAAAATC CATTATGTAT

4741   TATTTATAAC TGTAATTTCT TTAGCGTAGT TAGATGTCCA ATCTCTCTCA AATACATCGG

4801   CTATCTTTTT AGTGAGATTT TGATCTATGC AGTTGAAACT TATGAACGCG TGATGATTAA

4861   AATGTGAACC GTCCAAATTT GCAGTCATTA TATGAGCGTA TCTATTATCT ACTATCATCA

4921   TCTTTGAGTT ATTAATATCA TCTACTTTAG AATTGATAGG AAATATGAAT ACCTTTGTAG

4981   TAATATCTAT ACTATCTACA CCTAACTCAT TAAGACTTTT GATAG
                                                                  C6L  ⇐
```

Figure 15A
PCR primers to amplify the 75 bp I3Lp 5'-FMDV fragment.

```
            EcoRI ⇒  I3Lp
11423.CXL 5' GAATTCTGAGATAAAGTGAAAATATAT 3'
```

```
                                    VP4
            I3Lp                  M   G   A
            ACAATTATTTAGGTTTAATCATGGGAGCTG
11424.CXL 3' TGTTAATAAATCCAAATTAGTACCCTCGAC 5'
```

Figure 15B
PCR primers to amplify the 648 bp 5'-FMDV fragment.

```
            I3Lp      M  G  A  G  Q  S
11425.CXL 5' AGGTTTAATCATGGGAGCTGGGCAATCCA 3'
```

```
                      VP2
              C  L  L  V  A  M  V  P
              TGCCTCCTGGTGGCCATGGTACC
11407.CXL 3'  ACGGAGGACCACCGGTACCATGG 5'
                              Kpn I
```

Fig 16A
Construction of pC6 I3Lp FMDV P1+3C, pCXL-1079-1

Fig 16B
Construction of pC6 I3Lp FMDV P1+3C, pCXL-1079-1

Fig 17A
Sequence of the C6 I3Lp FMDV gene cassette in pC6 I3Lp FMDV P1+3C, pCXL-1079-1

```
   1   TTCATAAATA CAAGTTTGAT TAAACTTAAG TTGTTCTAAA GTTCTTTCCT CCGAAGGTAT
  61   AGAACAAAGT ATTTCTTCTA CATCCTTACT ATTTATTGCA GCTTTTAACA GCCTATCACG
 121   TATCCTATTT TTAGTATTGG TAGAACGTTT TAGTTCTAAA GTTAAAATAT TAGACATAAT
 181   TGGCATATTG CTTATTCCTT GCATAGTTGA GTCTGTAGAT CGTTTCAGTA TATCACTGAT
 241   TAATGTACTA CTGTTATGAT GAAATATAGA ATCGATATTG GCATTTAACT GTTTTGTTAT
 301   ACTAAGTCTA GATTTAAAT CTTCTAGTAA TATGCTATTT AATATAAAAG CTTCCACGTT
 361   TTTGTATACA TTTCTTTCCA TATTAGTAGC TACTACTAAA TGATTATCTT CTTTCATATC
 421   TTGTAGATAA GATAGACTAT CTTTATCTTT ATTAGTAGAA AATACTTCTG GCCATACATC
 481   GTTAAATTTT TTTGTTGTTG TTAGATATAA TATTAAATAT CTAGAGGATC CTATTATTTG
 541   TGGTAAAATG TTTATAGAGT AAAATGATCT GGCTATTAAA CATAGGCCAG TTACCATAGA
 601   ATGCTGCTTC CCGTTACAGT GTTTTACCAT AACCATAGAT CTGCCTGTAT TGTTGATACA
 661   TATAACAGCT GTAAATCCTA AAAAATTCCT ATCATAATTA TTAATATTAG GTAATTCATT
 721   TCCATGTGAA AGATAGACTA ATTTTATATC CTTTACCTCC AAATAATTAT TTACATCTCT
 781   TAAACAATCT ATTTTAATAT CATTAACTGG TATTTTATAA TATCCAGAAA GGTTTGAAGG
 841   GGTTGATGGA ATAAGTCTAT TAACATCGTT AAGTAAATTA TTAATATCAT GAATCTTTAT
 901   TATATTATAC CCATAAGTTA AATTTATATT TACTTTCTCA TCATCTGACT TAGTTAGTTT
 961   GTAATAAGGT GTGTCTGAAA AAATTAAAAG GTAATTCGTT GAATGAAGCT GTATTTGCTG
1021   TATCATTTTT ATCTAATTTT GGAGATTTAG CAGTACTTAC TTCATTAGAA GAAGAATCTG
1081   CCAGTTCCTG TCTATTACTG ATATTTCGTT TCATTATTAT ATGATTTATA TTTTACTTTT
                   C6R ⇐                                    ⇒ I3Lp
1141   TCAATTATAT ATACTCATTT GACTAGTTAA TCAATAAAAA GAATTCTGAG ATAAAGTGAA
                                                    ⇒ VP4
                                                 M  G   A  G   Q
1201   AATATATATC ATTATATTAC AAAGTACAAT TATTTAGGTT TAATCATGGG AGCTGGGCAA
          S  S  P   A  T   G  S   Q  N   Q  S   G  N   T  G   S  I   I  N  N
1261   TCCAGCCCAG CAACCGGCTC GCAGAACCAG TCTGGCAACA CTGGCAGCAT AATCAACAAC
          Y  Y  M   Q  Q   Y  Q   N  S   M  D   T  Q   L  G   D  N   A  I  S
1321   TACTACATGC AACAGTACCA GAACTCCATG GACACACAGT TGGGAGACAA TGCCATCAGT
```

Fig 17B
Sequence of the C6 I3Lp FMDV gene cassette in pC6 I3Lp FMDV P1+3C, pCXL-1079-1

```
             G   G   S   N   E   G   S   T   D   T   T   S   T   H   T   T   N   T   Q   N
1381         GGAGGCTCCA ACGAGGGCTC CACGGACACA ACTTCAACAC ACACAACCAA CACTCAAAAC

N   D   W   F   S   K   L   A   S   S   A   F   T   G   L   F   G   A   L   L
1441         AATGACTGGT TCTCGAAGCT CGCCAGTTCA GCTTTTACCG GTCTGTTCGG TGCACTGCTC

⇒ VP2
             A   D   K   K   T   E   E   T   T   L   L   E   D   R   I   L   T   T   R   N
1501         GCCGACAAGA AGACAGAGGA AACGACACTT CTTGAGGACC GCATCCTCAC CACCCGCAAC

G   H   T   T   S   T   T   Q   S   S   V   G   V   T   H   G   Y   S   T   E
1561         GGGCACACCA CCTCGACGAC CCAATCGAGT GTGGGTGTCA CACACGGGTA CTCCACAGAG

E   D   H   V   A   G   P   N   T   S   G   L   E   T   R   V   V   Q   A   E
1621         GAGGACCACG TTGCTGGGCC CAACACATCG GGCCTGGAGA CGCGAGTGGT GCAGGCAGAG

R   F   Y   K   K   Y   L   F   D   W   T   T   D   K   A   F   G   H   L   E
1681         AGATTCTACA AAAAGTACTT GTTTGACTGG ACAACGGACA AGGCATTTGG ACACCTGGAA

K   L   E   L   P   S   D   H   H   G   V   F   G   H   L   V   D   S   Y   A
1741         AAGCTGGAGC TCCCGTCCGA CCACCACGGT GTCTTTGGAC ACTTGGTGGA CTCGTACGCC

Y   M   R   N   G   W   D   V   E   V   S   A   V   G   N   Q   F   N   G   G
1801         TATATGAGAA ATGGCTGGGA TGTTGAGGTG TCCGCTGTTG GCAACCAGTT CAACGGCGGG

C   L   L   V   A   M   V   P   E   W   K   E   F   D   T   R   E   K   Y   Q
1861         TGCCTCCTGG TGGCCATGGT ACCTGAATGG AAGGAATTTG ACACACGGGA GAAATACCAA

L   T   L   F   P   H   Q   F   I   S   P   R   T   N   M   T   A   H   I   T
1921         CTCACCCTTT TCCCGCACCA GTTTATTAGC CCCAGAACTA ACATGACTGC CCACATCACG

V   P   Y   L   G   V   N   R   Y   D   Q   Y   K   K   H   K   P   W   T   L
1981         GTCCCCTACC TTGGTGTGAA CAGGTATGAT CAGTACAAGA AGCATAAGCC CTGGACATTG

V   V   M   V   V   S   P   L   T   V   N   N   T   S   A   A   Q   I   K   V
2041         GTTGTCATGG TCGTGTCGCC ACTTACGGTC AACAACACTA GTGCGGCACA AATCAAGGTC

⇒ VP3
             Y   A   N   I   A   P   T   Y   V   H   V   A   G   E   L   P   S   K   E   G
2101         TACGCCAACA TAGCTCCGAC CTATGTTCAC GTGGCCGGTG AACTCCCCTC GAAAGAGGGG

I   F   P   V   A   C   A   D   G   Y   G   G   L   V   T   T   D   P   K   T
2161         ATTTTCCCGG TTGCATGTGC GGACGGTTAC GGAGGATTGG TGACGACAGA CCCGAAGACA

A   D   P   A   Y   G   K   V   Y   N   P   P   R   T   N   Y   P   G   R   F
2221         GCTGACCCTG CTTATGGCAA GGTGTACAAC CCGCCTAGGA CTAACTACCC TGGGCGCTTC

T   N   L   L   D   V   A   E   A   C   P   T   F   L   C   F   D   D   G   K
2281         ACCAACCTGT TGGACGTGGC CGAAGCGTGT CCCACTTTCC TCTGCTTTGA CGACGGGAAA

P   Y   V   T   T   R   T   D   D   T   R   L   L   A   K   F   D   L   S   L
2341         CCGTACGTCA CCACGCGGAC GGATGACACC CGACTTTTGG CCAAGTTTGA CCTTTCCCTT
```

Fig 17C
Sequence of the C6 I3Lp FMDV gene cassette in pC6 I3Lp FMDV P1+3C, pCXL-1079-1

```
         A   A   K   H   M   S   N   T   Y   L   S   G   I   A   Q   Y   Y   T   Q   Y
2401   GCCGCAAAAC ATATGTCCAA CACATACCTG TCAGGGATTG CTCAGTACTA CACACAGTAC

S   G   T   I   N   L   H   F   M   F   T   G   S   T   D   S   K   A   R   Y
2461   TCTGGCACCA TCAATTTGCA TTTCATGTTT ACAGGTTCCA CTGATTCAAA GGCCCGATAC

M   V   A   Y   I   P   P   G   V   E   T   P   P   D   T   P   E   R   A   A
2521   ATGGTGGCCT ACATCCCACC TGGGGTGGAG ACACCACCGG ACACACCTGA AAGGGCTGCC

H   C   I   H   A   E   W   D   T   G   L   N   S   K   F   T   F   S   I   P
2581   CACTGCATTC ACGCTGAATG GGACACTGGA CTAAACTCCA AATTCACTTT CTCAATCCCG

Y   V   S   A   A   D   Y   A   Y   T   A   S   D   T   A   E   T   I   N   V
2641   TACGTATCCG CCGCGGATTA CGCGTACACA GCGTCTGACA CGGCAGAAAC AATCAACGTA

Q   G   W   V   C   I   Y   Q   I   T   H   G   K   A   E   N   D   T   L   V
2701   CAGGGATGGG TCTGCATCTA CCAAATTACA CACGGGAAGG CTGAAAATGA CACCTTGGTC

V   S   V   S   A   G   K   D   F   E   L   R   L   P   I   D   P   R   Q   Q
2761   GTGTCGGTTA GCGCCGGCAA AGACTTTGAG TTGCGCCTCC CGATTGACCC CCGCCAGCAG

⇒ VP1
         T   T   A   T   G   E   S   A   D   P   V   T   T   T   V   E   N   Y   G   G
2821   ACCACCGCTA CCGGGGAATC AGCAGACCCG GTCACCACCA CCGTGGAGAA CTACGGCGGT

E   T   Q   I   Q   R   R   H   H   T   D   I   G   F   I   M   D   R   F   V
2881   GAGACACAAA TCCAGAGACG TCACCACACG GACATTGGTT TCATCATGGA CAGATTTGTG

K   I   Q   S   L   S   P   T   H   V   I   D   L   M   Q   A   H   Q   H   G
2941   AAGATCCAAA GCTTGAGCCC AACACATGTC ATTGACCTCA TGCAGGCTCA CCAACACGGT

L   V   G   A   L   L   R   A   A   T   Y   Y   F   S   D   L   E   I   V   V
3001   CTGGTGGGTG CCTTGCTGCG TGCAGCCACG TACTACTTTT CTGACCTGGA AATTGTTGTA

R   H   E   G   N   L   T   W   V   P   N   G   A   P   E   S   A   L   L   N
3061   CGGCACGAAG GCAATCTGAC CTGGGTGCCC AACGGCGCCC CTGAATCAGC CCTGTTGAAC

T   S   N   P   T   A   Y   N   K   A   P   F   T   R   L   A   L   P   Y   T
3121   ACCAGCAACC CCACTGCCTA CAACAAGGCA CCATTCACGA GACTCGCTCT CCCCTACACT

A   P   H   R   V   L   A   T   V   Y   N   G   T   S   K   Y   A   V   G   G
3181   GCGCCGCACC GTGTGCTGGC AACAGTGTAC AACGGGACGA GTAAGTATGC TGTGGGTGGT

S   G   R   R   G   D   M   G   S   L   A   A   R   V   K   Q   L   P   A
3241   TCAGGCAGAA GAGGCGACAT GGGGTCTCTC GCGGCGCGAG TCGTGAAACA GCTTCCTGCT

S   F   N   Y   G   A   I   K   A   D   A   I   H   E   L   L   V   R   M   K
3301   TCATTTAACT ACGGTGCAAT CAAGGCCGAC GCCATCCACG AACTTCTCGT GCGCATGAAA

R   A   E   L   Y   C   P   R   P   L   L   A   I   E   V   S   S   Q   D   R
3361   CGGGCCGAGC TCTACTGCCC CAGACCGCTG TTGGCAATAG AGGTGTCTTC GCAAGACAGG
```

Fig 17D
Sequence of the C6 I3Lp FMDV gene cassette in pC6 I3Lp FMDV P1+3C, pCXL-1079-1

```
                              ⇒ A24 2A
         H   K   Q   K   I   I   A   P   A   K   Q   L   L   N   F   D   L   L   K   L
3421    CACAAGCAAA AGATCATTGC ACCAGCAAAG CAGCTTCTGA ATTTTGACCT GCTCAAGTTG

⇒ A24 2B
         A   G   D   V   E   S   N   P   G   P   F   F   F   A   D   V   R   S   N   F
3481    GCCGGAGACG TTGAGTCCAA CCCCGGGCCA TTCTTCTTTG CTGACGTTAG GTCAAACTTT

S   K   L   V   D   T   I   N   Q   M   Q   E   D   M   S   T   K   H   G   P
3541    TCAAAGTTGG TAGACACAAT CAACCAGATG CAGGAGGACA TGTCCACAAA ACACGGGCCC

D   F   N   R   L   V   S   A   F   E   E   L   A   T   G   V   K   A   I   R
3601    GACTTCAACC GGTTGGTGTC CGCATTTGAG GAATTGGCCA CTGGAGTTAA AGCTATCAGG

T   G   L   D   E   A   K   P   W   Y   K   L   I   K   L   L   S   R   L   S
3661    ACCGGTCTCG ACGAGGCCAA ACCCTGGTAC AAGCTTATCA AACTCCTAAG CCGCCTGTCG

C   M   A   A   V   A   A   R   S   K   D   P   V   L   V   A   I   M   L   A
3721    TGCATGGCCG CTGTGGCAGC ACGGTCCAAG GACCCAGTCC TTGTGGCCAT CATGCTGGCC

A24/A12 junction  ⇒ A12 3B
         D   T   G   L   E   R   Q   R   P   L   K   V   R   A   K   L   P   Q   Q   E
3781    GACACCGGTC TCGAG CGTCA GAGACCTCTG AAAGTGAGAG CTAAGCTCCC ACAGCAGGAA G   P   Y   A   G   P   L   E   R   Q   K   P   L   K   V   K   A   K   A   P
3841    GGACCTTACG CTGGCCCGTT GGAGAGACAG AAACCGCTGA AGTGAAAGC AAAAGCCCCG V   V   K   E   G   P   Y   E   G   P   V   K   K   P   V   A   L   K   V   K
3901    GTCGTCAAGG AAGGACCTTA CGAGGGACCG GTGAAGAAGC CTGTCGCTTT GAAAGTGAAA ⇒ A12 3C
         A   K   N   L   I   V   T   E   S   G   A   P   P   T   D   L   Q   K   M   V
3961    GCTAAGAACT TGATAGTCAC TGAGAGTGGT GCCCCACCGA CCGACTTGCA AAAGATGGTC M   G   N   T   K   P   V   E   L   I   L   D   G   K   T   V   A   I   C   C
4021    ATGGGCAACA CAAAGCCTGT TGAGCTCATC CTTGACGGGA AGACAGTAGC CATCTGTTGT A   T   G   V   F   G   T   A   Y   L   V   P   R   H   L   F   A   E   K   Y
4081    GCTACTGGAG TGTTTGGCAC TGCTTACCTC GTGCCTCGTC ATCTTTTCGC AGAGAAGTAT D   K   I   M   L   D   G   R   A   M   T   D   S   D   Y   R   V   F   E   F
4141    GACAAGATCA TGCTGGATGG CAGAGCCATG ACAGACAGTG ACTACAGAGT GTTTGAGTTT E   I   K   V   K   G   Q   D   M   L   S   D   A   A   L   M   V   L   H   R
4201    GAGATTAAAG TAAAAGGACA GGACATGCTC TCAGACGCTG CGCTCATGGT GCTCCACCGT G   N   R   V   R   D   I   T   K   H   F   R   D   T   A   R   M   K   K   G
4261    GGGAACCGCG TGAGAGATAT CACGAAACAC TTTCGTGATA CAGCAAGAAT GAAGAAAGGC T   P   V   V   G   V   V   N   N   A   D   V   G   R   L   I   F   S   G   E
4321    ACCCCCGTCG TCGGTGTGGT CAACAACGCC GACGTTGGGA GACTGATTTT CTCTGGTGAG
```

Fig 17E
Sequence of the C6 I3Lp FMDV gene cassette in pC6 I3Lp FMDV P1+3C, pCXL-1079-1

```
        A  L  T  Y   K  D  I     V  V  C    M  D  G  D    T  M  P    G  L  F
4381    GCCCTCACCT ACAAGGATAT TGTAGTGTGC ATGGACGGAG ACACCATGCC TGGCCTCTTT
        A  Y  K  A    A  T  K    A  G  Y    C  G  G  A    V  L  A    K  D  G
4441    GCCTACAAAG CCGCCACCAA GGCAGGCTAC TGTGGAGGAG CCGTTCTCGC CAAGGACGGG

A  D  T  F    I  V  G    T  H  S    A  G  G  N    G  V  G    Y  C  S
4501    GCCGACACTT TCATCGTCGG CACTCACTCC GCAGGAGGCA ATGGAGTTGG ATACTGCTCA

C  V  S  R    S  M  L    L  R  M    K  A  H  V    D  P  E    P  Q  H
4561    TGCGTTTCCA GGTCCATGCT TCTCAGAATG AAGGCACACG TTGACCCTGA ACCACAACAC

E  *
4621    GAGTAGTAAT TTTTCTGCAG CCCGGGTTTT TATAGCTAAT TAGTCATTTT TTCGTAAGTA

4681    AGTATTTTTA TTTAATACTT TTTATTGTAC TTATGTTAAA TATAACTGAT GATAACAAAA

4741    TCCATTATGT ATTATTTATA ACTGTAATTT CTTTAGCGTA GTTAGATGTC AATCTCTCT

4801    CAAATACATC GGCTATCTTT TTAGTGAGAT TTTGATCTAT GCAGTTGAAA CTTATGAACG

4861    CGTGATGATT AAAATGTGAA CCGTCCAAAT TGCAGTCAT TATATGAGCG TATCTATTAT

4921    CTACTATCAT CATCTTTGAG TTATTAATAT CATCTACTTT AGAATTGATA GGAAATATGA

4981    ATACCTTTGT AGTAATATCT ATACTATCTA CACCTAACTC ATTAAGACTT TTGATAG
                                                                    C6R ⇐
```

Fig 18A
PCR primers to amplify the 48 bp 42Kp 5'-FMDV fragment

```
              EcoR I⇒ 42Kp
11426.CXL 5'  GAATTCTCAAAATTGAAAATATAT 3'
                                   VP4
              42Kp               M   G   A
              ATATATAATTACAATATAAAATGGGAGCTG
11427.CXL 3'  TATATATTAATGTTATATTTTACCCTCGAC 5'
```

Figure 18B
PCR primers to amplify 5'-FMDV

```
                        VP4
              42Kp    M  G  A  G  Q  S
11428.CXL 5'  CAATATAAAATGGGAGCTGGGCAATCCA 3'

VP2
                 C  L  L  V  A  M  V  P
                 TGCCTCCTGGTGGCCATGGTACC
11407.CXL 3'     ACGGAGGACCACCGGTACCATGG 5'
                                 Kpn I
```

Fig 19A
Construction of pC6 42Kp FMDV P1+3C, pCXL-1095-1

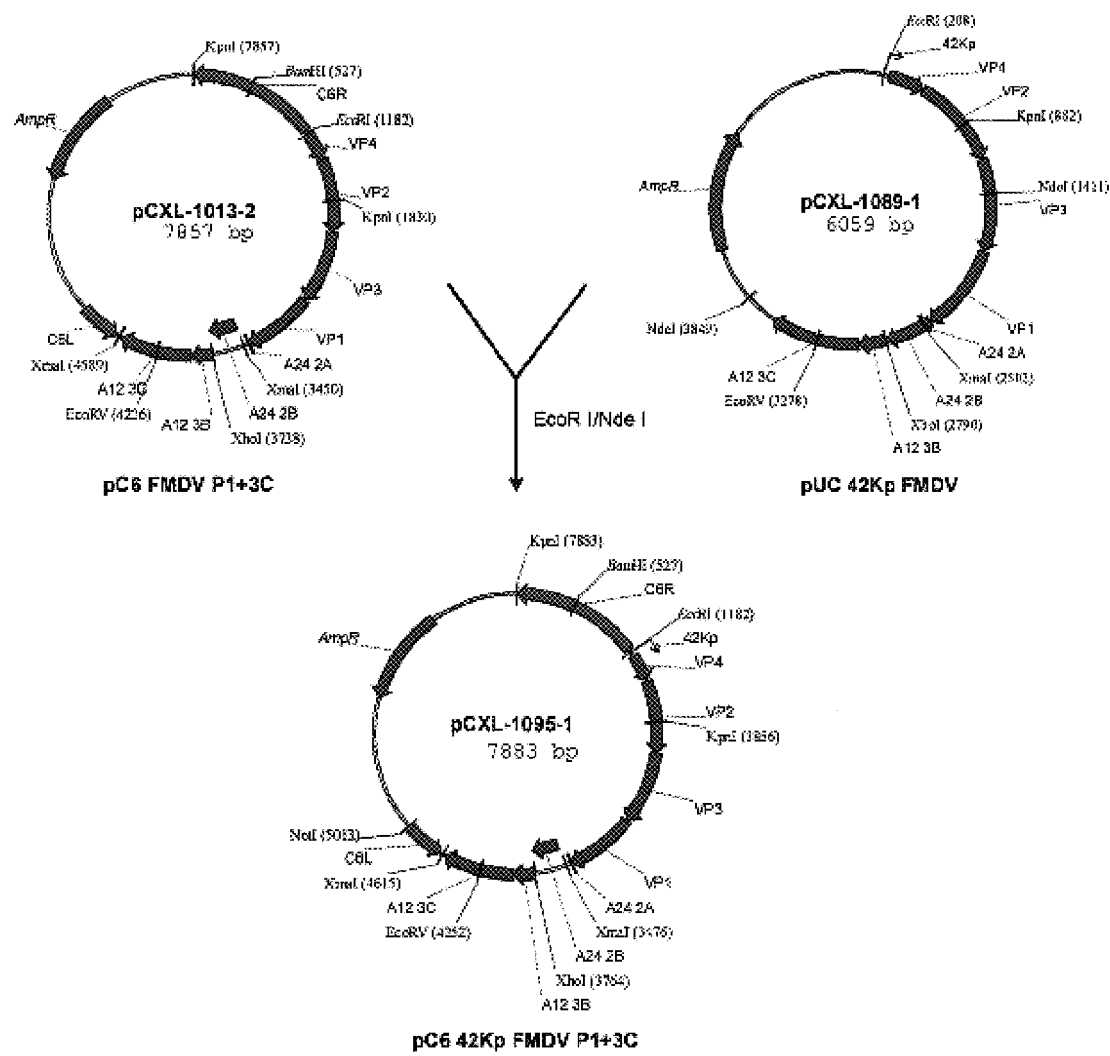

Fig 20A
Sequence of the C6 42Kp FMDV gene cassette in pC6 42Kp FMDV P1+3C, pCXL-1095-1

```
   1  TTCATAAATA CAAGTTTGAT TAAACTTAAG TTGTTCTAAA GTTCTTTCCT CCGAAGGTAT
  61  AGAACAAAGT ATTTCTTCTA CATCCTTACT ATTTATTGCA GCTTTTAACA GCCTATCACG
 121  TATCCTATTT TTAGTATTGG TAGAACGTTT TAGTTCTAAA GTTAAAATAT TAGACATAAT
 181  TGGCATATTG CTTATTCCTT GCATAGTTGA GTCTGTAGAT CGTTTCAGTA TATCACTGAT
 241  TAATGTACTA CTGTTATGAT GAAATATAGA ATCGATATTG GCATTTAACT GTTTTGTTAT
 301  ACTAAGTCTA GATTTTAAAT CTTCTAGTAA TATGCTATTT AATATAAAAG CTTCCACGTT
 361  TTTGTATACA TTTCTTTCCA TATTAGTAGC TACTACTAAA TGATTATCTT CTTTCATATC
 421  TTGTAGATAA GATAGACTAT CTTTATCTTT ATTAGTAGAA AATACTTCTG GCCATACATC
 481  GTTAAATTTT TTTGTTGTTG TTAGATATAA TATTAAATAT CTAGAGGATC CTATTATTTG
 541  TGGTAAAATG TTTATAGAGT AAAATGATCT GGCTATTAAA CATAGGCCAG TTACCATAGA
 601  ATGCTGCTTC CCGTTACAGT GTTTTACCAT AACCATAGAT CTGCCTGTAT TGTTGATACA
 661  TATAACAGCT GTAAATCCTA AAAAATTCCT ATCATAATTA TTAATATTAG GTAATTCATT
 721  TCCATGTGAA AGATAGACTA ATTTATATC  CTTTACCTCC AAATAATTAT TTACATCTCT
 781  TAAACAATCT ATTTTAATAT CATTAACTGG TATTTTATAA TATCCAGAAA GGTTTGAAGG
 841  GGTTGATGGA ATAAGTCTAT TAACATCGTT AAGTAAATTA TTAATATCAT GAATCTTTAT
 901  TATATTATAC CCATAAGTTA AATTTATATT TACTTTCTCA TCATCTGACT TAGTTAGTTT
 961  GTAATAAGGT GTGTCTGAAA AAATTAAAAG GTAATTCGTT GAATGAAGCT GTATTTGCTG
1021  TATCATTTTT ATCTAATTTT GGAGATTTAG CAGTACTTAC TTCATTAGAA GAAGAATCTG
1081  CCAGTTCCTG TCTATTACTG ATATTTCGTT TCATTATTAT ATGATTTATA TTTTACTTTT
              C6R ⇐                                    ⇒ 42Kp
1141  TCAATTATAT ATACTCATTT GACTAGTTAA TCAATAAAAA GAATTCTCAA AATTGAAAAT
                                   ⇒ VP4
                              M   G   A   G   Q   S   S   P   A   T   G   S   Q   N
1201  ATATAATTAC AATATAAAAT GGGAGCTGGG CAATCCAGCC CAGCAACCGG CTCGCAGAAC

Q   S   G   N   T   G   S   I   I   N   N   Y   Y   M   Q   Q   Y   Q   N   S
1261  CAGTCTGGCA ACACTGGCAG CATAATCAAC AACTACTACA TGCAACAGTA CCAGAACTCC

M   D   T   Q   L   G   D   N   A   I   S   G   G   S   N   E   G   S   T   D
1321  ATGGACACAC AGTTGGGAGA CAATGCCATC AGTGGAGGCT CCAACGAGGG CTCCACGGAC
```

Fig 20B
Sequence of the C6 42Kp FMDV gene cassette in pC6 42Kp FMDV P1+3C, pCXL-1095-1

```
            T  T  S  T     H  T  T     N  T  Q     N  N  D     W  F  S  K     L  A  S
1381        ACAACTTCAA CACACACAAC CAACACTCAA AACAATGACT GGTTCTCGAA GCTCGCCAGT

⇒ VP2
            S  A  F  T     G  L  F     G  A  L     L  A  D  K  K  T  E     E  T  T
1441        TCAGCTTTTA CCGGTCTGTT CGGTGCACTG CTCGCCGACA AGAAGACAGA GGAAACGACA

L  L  E  D     R  I  L     T  T  R     N  G  H     T  S  T     T  Q  S
1501        CTTCTTGAGG ACCGCATCCT CACCACCCGC AACGGGCACA CCACCTCGAC GACCCAATCG

S  V  G  V     T  H  G     Y  S  T     E  E  D     H  V  A  G  P  N  T
1561        AGTGTGGGTG TCACACACGG GTACTCCACA GAGGAGGACC ACGTTGCTGG GCCCAACACA

S  G  L  E     T  R  V     V  Q  A     E  R  F     Y  K  K  Y  L  F  D
1621        TCGGGCCTGG AGACGCGAGT GGTGCAGGCA GAGAGATTCT ACAAAAAGTA CTTGTTTGAC

W  T  T  D     K  A  F     G  H  L     E  K  L     E  L  P  S     D  H  H
1681        TGGACAACGG ACAAGGCATT TGGACACCTG GAAAAGCTGG AGCTCCCGTC CGACCACCAC

G  V  F  G     H  L  V     D  S  Y     A  Y  M     R  N  G  W  D  V  E
1741        GGTGTCTTTG GACACTTGGT GGACTCGTAC GCCTATATGA GAAATGGCTG GGATGTTGAG

V  S  A  V     G  N  Q     F  N  G     G  C  L     L  V  A  M     V  P  E
1801        GTGTCCGCTG TTGGCAACCA GTTCAACGGC GGGTGCCTCC TGGTGGCCAT GGTACCTGAA

W  K  E  F     D  T  R     E  K  Y     Q  L  T     L  F  P  H  Q  F  I
1861        TGGAAGGAAT TTGACACACG GGAGAAATAC CAACTCACCC TTTTCCCGCA CCAGTTTATT

S  P  R  T     N  M  T     A  H  I     T  V  P     Y  L  G  V     N  R  Y
1921        AGCCCCAGAA CTAACATGAC TGCCCACATC ACGGTCCCCT ACCTTGGTGT GAACAGGTAT

D  Q  Y  K     K  H  K     P  W  T     L  V  V  M  V  V  S     P  L  T
1981        GATCAGTACA AGAAGCATAA GCCCTGGACA TTGGTTGTCA TGGTCGTGTC GCCACTTACG

V  N  N  T     S  A  A     Q  I  K     V  Y  A  N     I  A  P     T  Y  V
2041        GTCAACAACA CTAGTGCGGC ACAAATCAAG GTCTACGCCA ACATAGCTCC GACCTATGTT

⇒ VP3
            H  V  A  G     E  L  P     S  K  E     G  I  F     P  V  A  C     A  D  G
2101        CACGTGGCCG GTGAACTCCC CTCGAAAGAG GGGATTTTCC CGGTTGCATG TGCGGACGGT

Y  G  G  L     V  T  T     D  P  K     T  A  D  P     A  Y  G     K  V  Y
2161        TACGGAGGAT TGGTGACGAC AGACCCGAAG ACAGCTGACC CTGCTTATGG CAAGGTGTAC

N  P  P  R     T  N  Y     P  G  R     F  T  N  L     L  D  V     A  E  A
2221        AACCCGCCTA GGACTAACTA CCCTGGGCGC TTCACCAACC TGTTGGACGT GGCCGAAGCG

C  P  T  F     L  C  F     D  D  G     K  P  Y  V     T  T  R     T  D  D
2281        TGTCCCACTT TCCTCTGCTT TGACGACGGG AAACCGTACG TCACCACGCG GACGGATGAC

T  R  L  L     A  K  F     D  L  S     L  A  A  K     H  M  S     N  T  Y
2341        ACCCGACTTT TGGCCAAGTT TGACCTTTCC CTTGCCGCAA ACATATGTC CAACACATAC
```

Fig 20C
Sequence of the C6 42Kp FMDV gene cassette in pC6 42Kp FMDV P1+3C, pCXL-1095-1

```
              L   S   G   I       A   Q   Y       Y   T   Q       Y   S   G   T       I   N   L       H   F   M
2401     CTGTCAGGGA  TTGCTCAGTA  CTACACACAG  TACTCTGGCA  CCATCAATTT  GCATTTCATG

F   T   G   S       T   D   S       K   A   R       Y   M   V   A       Y   I   P       P   G   V
2461     TTTACAGGTT  CCACTGATTC  AAAGGCCCGA  TACATGGTGG  CCTACATCCC  ACCTGGGGTG

E   T   P   P       D   T   P       E   R   A       A   H   C   I       H   A   E       W   D   T
2521     GAGACACCAC  CGGACACACC  TGAAAGGGCT  GCCCACTGCA  TTCACGCTGA  ATGGACACT

G   L   N   S       K   F   T       F   S   I       P   Y   V   S       A   A   D       Y   A   Y
2581     GGACTAAACT  CCAAATTCAC  TTTCTCAATC  CCGTACGTAT  CCGCCGCGGA  TTACGCGTAC

T   A   S   D       T   A   E       T   I   N       V   Q   G   W       V   C   I       Y   Q   I
2641     ACAGCGTCTG  ACACGGCAGA  AACAATCAAC  GTACAGGGAT  GGGTCTGCAT  CTACCAAATT

T   H   G   K       A   E   N       D   T   L       V   V   S   V       S   A   G       K   D   F
2701     ACACACGGGA  AGGCTGAAAA  TGACACCTTG  GTCGTGTCGG  TTAGCGCCGG  CAAAGACTTT

⇒ VP1
              E   L   R   L       P   I   D       P   R   Q       Q   T   T   A       T   G   E       S   A   D
2761     GAGTTGCGCC  TCCCGATTGA  CCCCCGCCAG  CAGACCACCG  CTACCGGGGA  ATCAGCAGAC

P   V   T   T       T   V   E       N   Y   G       G   E   T   Q       I   Q   R       R   H   H
2821     CCGGTCACCA  CCACCGTGGA  GAACTACGGC  GGTGAGACAC  AAATCCAGAG  ACGTCACCAC

T   D   I   G       F   I   M       D   R   F       V   K   I   Q       S   L   S       P   T   H
2881     ACGGACATTG  GTTTCATCAT  GGACAGATTT  GTGAAGATCC  AAAGCTTGAG  CCCAACACAT

V   I   D   L       M   Q   A       H   Q   H       G   L   V   G       A   L   L       R   A   A
2941     GTCATTGACC  TCATGCAGGC  TCACCAACAC  GGTCTGGTGG  GTGCCTTGCT  GCGTGCAGCC

T   Y   Y   F       S   D   L       E   I   V       V   R   H   E       G   N   L       T   W   V
3001     ACGTACTACT  TTCTGACCT   GGAAATTGTT  GTACGGCACG  AAGGCAATCT  GACCTGGGTG

P   N   G   A       P   E   S       A   L   L       N   T   S   N       P   T   A       Y   N   K
3061     CCCAACGGCG  CCCCTGAATC  AGCCCTGTTG  AACACCAGCA  ACCCCACTGC  CTACAACAAG

A   P   F   T       R   L   A       L   P   Y       T   A   P   H       R   V   L       A   T   V
3121     GCACCATTCA  CGAGACTCGC  TCTCCCCTAC  ACTGCGCCGC  ACCGTGTGCT  GGCAACAGTG

Y   N   G   T       S   K   Y       A   V   G       G   S   G   R       R   G   D       M   G   S
3181     TACAACGGGA  CGAGTAAGTA  TGCTGTGGGT  GGTTCAGGCA  GAAGAGGCGA  CATGGGGTCT

L   A   A   R       V   V   K       Q   L   P       A   S   F   N       Y   G   A       I   K   A
3241     CTCGCGGCGC  GAGTCGTGAA  ACAGCTTCCT  GCTTCATTTA  ACTACGGTGC  AATCAAGGCC

D   A   I   H       E   L   L       V   R   M       K   R   A   E       L   Y   C       P   R   P
3301     GACGCCATCC  ACGAACTTCT  CGTGCGCATG  AAACGGGCCG  AGCTCTACTG  CCCCAGACCG

L   L   A   I       E   V   S       S   Q   D       R   H   K   Q       K   I   I       A   P   A
3361     CTGTTGGCAA  TAGAGGTGTC  TTCGCAAGAC  AGGCACAAGC  AAAAGATCAT  TGCACCAGCA
```

Fig 20D
Sequence of the C6 42Kp FMDV gene cassette in pC6 42Kp FMDV P1+3C, pCXL-1095-1

⇒ A24 2A

```
           K  Q  L  L   N  F  D   L  L  K   L  A  G  D   V  E  S   N  P  G
     3421  AAGCAGCTTC TGAATTTTGA CCTGCTCAAG TTGGCCGGAG ACGTTGAGTC AACCCCGGG
```

⇒ A24 2B

```
           P  F  F  F   A  D  V   R  S  N   F  S  K  L   V  D  T   I  N  Q
     3481  CCATTCTTCT TTGCTGACGT TAGGTCAAAC TTTTCAAAGT TGGTAGACAC AATCAACCAG

M  Q  E  D   M  S  T   K  H  G   P  D  F  N   R  L  V   S  A  F
     3541  ATGCAGGAGG ACATGTCCAC AAAACACGGG CCCGACTTCA ACCGGTTGGT GTCCGCATTT

E  E  L  A   T  G  V   K  A  I   R  T  G  L   D  E  A   K  P  W
     3601  GAGGAATTGG CCACTGGAGT TAAAGCTATC AGGACCGGTC TCGACGAGGC CAAACCCTGG

Y  K  L  I   K  L  L   S  R  L   S  C  M  A   A  V  A   A  R  S
     3661  TACAAGCTTA TCAAACTCCT AAGCCGCCTG TCGTGCATGG CCGCTGTGGC AGCACGGTCC
```

A24/A12 junction ⇒ A12 3B

```
           K  D  P  V   L  V  A   I  M  L   A  D  T  G   L  E  R   Q  R  P
     3721  AAGGACCCAG TCCTTGTGGC CATCATGCTG GCCGACACCG GTCTCGAGCG TCAGAGACCT

L  K  V  R   A  K  L   P  Q  Q   E  G  P  Y   A  G  P   L  E  R
     3781  CTGAAAGTGA GAGCTAAGCT CCCACAGCAG GAAGGACCTT ACGCTGGCCC GTTGGAGAGA

Q  K  P  L   K  V  K   A  K  A   P  V  V  K   E  G  P   Y  E  G
     3841  CAGAAACCGC TGAAAGTGAA AGCAAAAGCC CCGGTCGTCA AGGAAGGACC TTACGAGGGA
```

⇒ 3C

```
           P  V  K  K   P  V  A   L  K  V   K  A  K  N   L  I  V   T  E  S
     3901  CCGGTGAAGA AGCCTGTCGC TTTGAAAGTG AAAGCTAAGA ACTTGATAGT CACTGAGAGT

G  A  P  P   T  D  L   Q  K  M   V  M  G  N   T  K  P   V  E  L
     3961  GGTGCCCCAC CGACCGACTT GCAAAAGATG GTCATGGGCA ACACAAAGCC TGTTGAGCTC

I  L  D  G   K  T  V   A  I  C   C  A  T  G   V  F  G   T  A  Y
     4021  ATCCTTGACG GGAAGACAGT AGCCATCTGT TGTGCTACTG GAGTGTTTGG CACTGCTTAC

L  V  P  R   H  L  F   A  E  K   Y  D  K  I   M  L  D   G  R  A
     4081  CTCGTGCCTC GTCATCTTTT CGCAGAGAAG TATGACAAGA TCATGCTGGA TGGCAGAGCC

M  T  D  S   D  Y  R   V  F  E   F  E  I  K   V  K  G   Q  D  M
     4141  ATGACAGACA GTGACTACAG AGTGTTTGAG TTTGAGATTA AAGTAAAAGG ACAGGACATG

L  S  D  A   A  L  M   V  L  H   R  G  N  R   V  R  D   I  T  K
     4201  CTCTCAGACG CTGCGCTCAT GGTGCTCCAC CGTGGGAACC GCGTGAGAGA TATCACGAAA

H  F  R  D   T  A  R   M  K  K   G  T  P  V   V  G  V   V  N  N
     4261  CACTTTCGTG ATACAGCAAG AATGAAGAAA GGCACCCCCG TCGTCGGTGT GGTCAACAAC
```

Fig 20E
Sequence of the C6 42Kp FMDV gene cassette in pC6 42Kp FMDV P1+3C, pCXL-1095-1

```
           A   D   V   G    R   L   I    F   S   G    E   A   L   T    Y   K   D    I   V   V
4321   GCCGACGTTG GGAGACTGAT TTTCTCTGGT GAGGCCCTCA CCTACAAGGA TATTGTAGTG

C   M   D    G   D   T   M    P   G   L    F   A   Y   K    A   A   T    K   A   G
4381   TGCATGGACG GAGACACCAT GCCTGGCCTC TTTGCCTACA AAGCCGCCAC CAAGGCAGGC

Y   C   G    G   A   V   L    A   K   D    G   A   D   T    F   I   V    G   T   H
4441   TACTGTGGAG GAGCCGTTCT CGCCAAGGAC GGGGCCGACA CTTTCATCGT CGGCACTCAC

S   A   G   G    N   G   V    G   Y   C    S   C   V   S    R   S   M    L   L   R
4501   TCCGCAGGAG GCAATGGAGT TGGATACTGC TCATGCGTTT CCAGGTCCAT GCTTCTCAGA

M   K   A   H    V   D   P    E   P   Q    H   E   *
4561   ATGAAGGCAC ACGTTGACCC TGAACCACAA CACGAGTAGT AATTTTTCTG CAGCCCGGGT

4621   TTTTATAGCT AATTAGTCAT TTTTTCGTAA GTAAGTATTT TTATTTAATA CTTTTTATTG

4681   TACTTATGTT AAATATAACT GATGATAACA AAATCCATTA TGTATTATTT ATAACTGTAA

4741   TTTCTTTAGC GTAGTTAGAT GTCCAATCTC TCTCAAATAC ATCGGCTATC TTTTTAGTGA

4801   GATTTGATC TATGCAGTTG AAACTTATGA ACGCGTGATG ATTAAAATGT GAACCGTCCA

4861   AATTTGCAGT CATTATATGA GCGTATCTAT TATCTACTAT CATCATCTTT GAGTTATTAA

4921   TATCATCTAC TTTAGAATTG ATAGGAAATA TGAATACCTT TGTAGTAATA TCTATACTAT

4981   CTACACCTAA CTCATTAAGA CTTTTGATAG
                                    C6L  ⇐
```

Fig 21A
Oligonucleotide primers to PCR amplify 7.5Kp 5'-FMDV

```
                ⇒ 7.5Kp                              ⇒ VP4
           EcoR I                                M   G   A   G   Q   S   S   P
11357.CXL 5' GAATTCAAAAGTAGAAAATATATTCTAATTTATTGCACGGATGGGAGCTGGGCAATCCAGCCCA
```

```
                  VP3
             L  A  A  K  H  M  S
             CTTGCCGCAAAACATATGTCCA
11358.CXL 3' GAACGGCGTTTTGTATACAGGT
                           Nde I
```

Fig 21B
Oligonucleotide primers for site-directed mutagenesis
(boxed nucleotides are to be re-introduced)

```
           7.5Kp         ⇒ VP4
                      M  G  A  G  Q  S  S
11429.HM 5' CT[A]ATTTATTGCACGGA[T]GGGAGCTGGG[C]AATCCA
11430.HM 3' AGA[T]TAAATAACGTGCCT[A]CCCTCGACCC[G]TTAGGTC 5'
```

Fig 21C
Oligonucleotide primers for additional site-directed mutagenesis
(boxed nucleotides are to be re-introduced)

```
                 7.5Kp           ⇒ VP4
11445.HM 5' GAAAATATATTCT[A]ATTTATTGCACGGA
11446.HM 3' CTTTTATATAAGA[T]TAAATAACGTGCCT 5'
```

Fig 22A
Construction of pC6 7.5Kp FMDV P1+3C, pHM-1310-4

Fig 22B
Construction of pC6 7.5Kp FMDV P1+3C, pHM-1310-4

Fig 23A
Sequence of the C6 7.5Kp FMDV gene cassette from the pC6 7.5Kp FMDV P1+3C donor plasmid, pHM-1310-4

```
   1  TTCATAAATA CAAGTTTGAT TAAACTTAAG TTGTTCTAAA GTTCTTTCCT CCGAAGGTAT
  61  AGAACAAAGT ATTTCTTCTA CATCCTTACT ATTTATTGCA GCTTTTAACA GCCTATCACG
 121  TATCCTATTT TTAGTATTGG TAGAACGTTT TAGTTCTAAA GTTAAAATAT TAGACATAAT
 181  TGGCATATTG CTTATTCCTT GCATAGTTGA GTCTGTAGAT CGTTTCAGTA TATCACTGAT
 241  TAATGTACTA CTGTTATGAT GAAATATAGA ATCGATATTG GCATTTAACT GTTTTGTTAT
 301  ACTAAGTCTA GATTTTAAAT CTTCTAGTAA TATGCTATTT AATATAAAAG CTTCCACGTT
 361  TTTGTATACA TTTCTTTCCA TATTAGTAGC TACTACTAAA TGATTATCTT CTTTCATATC
 421  TTGTAGATAA GATAGACTAT CTTTATCTTT ATTAGTAGAA AATACTTCTG GCCATACATC
 481  GTTAAATTTT TTGTTGTTG TTAGATATAA TATTAAATAT CTAGAGGATC CTATTATTTG
 541  TGGTAAAATG TTTATAGAGT AAAATGATCT GGCTATTAAA CATAGGCCAG TTACCATAGA
 601  ATGCTGCTTC CCGTTACAGT GTTTTACCAT AACCATAGAT CTGCCTGTAT TGTTGATACA
 661  TATAACAGCT GTAAATCCTA AAAAATTCCT ATCATAATTA TTAATATTAG GTAATTCATT
 721  TCCATGTGAA AGATAGACTA ATTTTATATC CTTTACCTCC AAATAATTAT TTACATCTCT
 781  TAAACAATCT ATTTTAATAT CATTAACTGG TATTTTATAA TATCCAGAAA GGTTTGAAGG
 841  GGTTGATGGA ATAAGTCTAT TAACATCGTT AAGTAAATTA TTAATATCAT GAATCTTTAT
 901  TATATTATAC CCATAAGTTA AATTTATATT TACTTTCTCA TCATCTGACT TAGTTAGTTT
 961  GTAATAAGGT GTGTCTGAAA AAATTAAAAG GTAATTCGTT GAATGAAGCT GTATTTGCTG
1021  TATCATTTTT ATCTAATTTT GGAGATTTAG CAGTACTTAC TTCATTAGAA GAAGAATCTG
1081  CCAGTTCCTG TCTATTACTG ATATTTCGTT TCATTATTAT ATGATTTATA TTTTACTTTT
                C6R ⇐                                          ⇒ 7.5Kp
1141  TCAATTATAT ATACTCATTT GACTAGTTAA TCAATAAAAA GAATTCAAAA GTAGAAAATA
                     ⇒ VP4
                       M   G   A   G   Q   S   S   P   A   T   G   S   Q   N ·
1201  TATTCTAATT TATTGCACGG ATGGGAGCTG GGCAATCCAG CCCAGCAACC GGCTCGCAGA
         · · Q   S   G   N   T   G   S   I   I   N   N   Y   Y   M   Q   Q   Y   Q   N   S ·
1261  ACCAGTCTGG CAACACTGGC AGCATAATCA ACAACTACTA CATGCAACAG TACCAGAACT
```

Fig 23B
Sequence of the C6 7.5Kp FMDV gene cassette from the pC6 7.5Kp FMDV P1+3C donor plasmid, pHM-1310-4

```
              .. M   D   T     Q   L   G     D   N   A     I   S   G     G   S   N     E   G   S   T   D  ·
       1321   CCATGGACAC  ACAGTTGGGA  GACAATGCCA  TCAGTGGAGG  CTCCAACGAG  GGCTCCACGG

.. T   T   S     T   H   T     T   N   T     Q   N   N     D   W   F     S   K   L   A   S  ·
       1381   ACACAACTTC  AACACACACA  ACCAACACTC  AAAACAATGA  CTGGTTCTCG  AAGCTCGCCA
                                                                    ⇒ VP2
              .. S   A   F     T   G   L     F   G   A   L     L   A   D     K   K     E   E   T   T  ·
       1441   GTTCAGCTTT  TACCGGTCTG  TTCGGTGCAC  TGCTCGCCGA  CAAGAAGACA  GAGGAAACGA

.. L   L   E     D   R   I     L   T   T     R   N   G   H     T   T   S     T   T   Q   S  ·
       1501   CACTTCTTGA  GGACCGCATC  CTCACCACCC  GCAACGGGCA  CACCACCTCG  ACGACCCAAT

.. S   V   G     V   T   H     G   Y   S     T   E   E   D     H   V   A     G   P   N   T  ·
       1561   CGAGTGTGGG  TGTCACACAC  GGGTACTCCA  CAGAGGAGGA  CCACGTTGCT  GGGCCCAACA

.. S   G   L     E   T   R     V   V   Q     A   E   R   F     Y   K   K     Y   L   F   D  ·
       1621   CATCGGGCCT  GGAGACGCGA  GTGGTGCAGG  CAGAGAGATT  CTACAAAAAG  TACTTGTTTG

.. W   T   T     D   K   A     F   G   H   L     E   K   L     E   L   P     S   D   H   H  ·
       1681   ACTGGACAAC  GGACAAGGCA  TTTGGACACC  TGGAAAAGCT  GGAGCTCCCG  TCCGACCACC

.. G   V   F     G   H   L     V   D   S   Y     A   Y   M     R   N   G     W   D   V   E  ·
       1741   ACGGTGTCTT  TGGACACTTG  GTGGACTCGT  ACGCCTATAT  GAGAAATGGC  TGGGATGTTG

.. V   S   A     V   G   N     Q   F   N   G     G   C   L     L   V   A     M   V   P   E  ·
       1801   AGGTGTCCGC  TGTTGGCAAC  CAGTTCAACG  GCGGGTGCCT  CCTGGTGGCC  ATGGTACCTG

.. W   K   E     F   D   T     R   E   K   Y     Q   L   T     L   F   P     H   Q   F   I  ·
       1861   AATGGAAGGA  ATTTGACACA  CGGGAGAAAT  ACCAACTCAC  CCTTTTCCCG  CACCAGTTTA

.. S   P   R     T   N   M     T   A   H   I     T   V   P     Y   L   G     V   N   R   Y  ·
       1921   TTAGCCCCAG  AACTAACATG  ACTGCCCACA  TCACGGTCCC  CTACCTTGGT  GTGAACAGGT

.. D   Q   Y     K   K   H     K   P   W   T     L   V   V     M   V   V     S   P   L   T  ·
       1981   ATGATCAGTA  CAAGAAGCAT  AAGCCCTGGA  CATTGGTTGT  CATGGTCGTG  TCGCCACTTA

.. V   N   N     T   S   A     A   Q   I   K     V   Y   A     N   I   A     P   T   Y   V  ·
       2041   CGGTCAACAA  CACTAGTGCG  GCACAAATCA  AGGTCTACGC  CAACATAGCT  CCGACCTATG
                                                       ⇒ VP3
              .. H   V   A     G   E   L     P   S   K   E     G   I   F     P   V   A     C   A   D   G  ·
       2101   TTCACGTGGC  CGGTGAACTC  CCCTCGAAAG  AGGGGATTTT  CCCGGTTGCA  TGTGCGGACG

.. Y   G     L   V   T     T   D   P   K     T   A   D     P   A   Y     G   K   V   Y  ·
       2161   GTTACGGAGG  ATTGGTGACG  ACAGACCCGA  AGACAGCTGA  CCCTGCTTAT  GGCAAGGTGT

.. N   P   P     R   T   N     Y   P   G   R     F   T   N     L   L   D     V   A   E   A  ·
       2221   ACAACCCGCC  TAGGACTAAC  TACCCTGGGC  GCTTCACCAA  CCTGTTGGAC  GTGGCCGAAG

.. C   P   T     F   L   C     F   D   D   G     K   P   Y     V   T   T     R   T   D   D  ·
       2281   CGTGTCCCAC  TTTCCTCTGC  TTTGACGACG  GGAAACCGTA  CGTCACCACG  CGGACGGATG
```

Fig 23C
Sequence of the C6 7.5Kp FMDV gene cassette from the pC6 7.5Kp FMDV P1+3C donor plasmid, pHM-1310-4

```
         .. T  R  L   L  A  K   F  D  L   S  L  A  A   K  H  M   S  N  T  Y  ·
2341     ACACCCGACT  TTTGGCCAAG  TTTGACCTTT  CCCTTGCCGC  AAAACATATG  TCCAACACAT

.. L  S  G   I  A  Q   Y  Y  T  Q   Y  S  G   T  I  N   L  H  F  M  ·
2401     ACCTGTCAGG  GATTGCTCAG  TACTACACAC  AGTACTCTGG  CACCATCAAT  TTGCATTTCA

.. F  T  G   S  T  D   S  K  A  R   Y  M  V   A  Y  I   P  P  G  V  ·
2461     TGTTTACAGG  TTCCACTGAT  TCAAAGGCCC  GATACATGGT  GGCCTACATC  CCACCTGGGG

.. E  T  P   P  D  T   P  E  R  A   A  H  C   I  H  A   E  W  D  T  ·
2521     TGGAGACACC  ACCGGACACA  CCTGAAAGGG  CTGCCCACTG  CATTCACGCT  GAATGGGACA

.. G  L  N   S  K  F   T  F  S  I   P  Y  V   S  A  A   D  Y  A  Y  ·
2581     CTGGACTAAA  CTCCAAATTC  ACTTTCTCAA  TCCCGTACGT  ATCCGCCGCG  GATTACGCGT

.. T  A  S   D  T  A   E  T  I  N   V  Q  G   W  V  C   I  Y  Q  I  ·
2641     ACACAGCGTC  TGACACGGCA  GAAACAATCA  ACGTACAGGG  ATGGGTCTGC  ATCTACCAAA

.. T  H  G   K  A  E   N  D  T  L   V  V  S   V  S  A   G  K  D  F  ·
2701     TTACACACGG  AAGGCTGAA   AATGACACCT  TGGTCGTGTC  GGTTAGCGCC  GGCAAAGACT

⇒ VP1
         .. E  L  R   L  P  I   D  P  R  Q   T  T   A  T  G   E  S  A  D  ·
2761     TTGAGTTGCG  CCTCCCGATT  GACCCCCGCC  AGCAGACCAC  CGCTACCGGG  GAATCAGCAG

.. P  V  T   T  T  V   E  N  Y  G   E  T   Q  I  Q   R  R  H  H  ·
2821     ACCCGGTCAC  CACCACCGTG  GAGAACTACG  GCGGTGAGAC  ACAAATCCAG  AGACGTCACC

.. T  D  I   G  F  I   M  D  R  F   V  K  I   Q  S  L   S  P  T  H  ·
2881     ACACGGACAT  TGGTTTCATC  ATGGACAGAT  TTGTGAAGAT  CCAAAGCTTG  AGCCCAACAC

.. V  I  D   L  M  Q   A  H  Q  H   G  L  V   G  A  L   L  R  A  A  ·
2941     ATGTCATTGA  CCTCATGCAG  GCTCACCAAC  ACGGTCTGGT  GGGTGCCTTG  CTGCGTGCAG

.. T  Y  Y   F  S  D   L  E  I  V   V  R  H   E  G  N   L  T  W  V  ·
3001     CCACGTACTA  CTTTTCTGAC  CTGGAAATTG  TTGTACGGCA  CGAAGGCAAT  CTGACCTGGG

.. P  N  G   A  P  E   S  A  L  L   N  T  S   N  P  T   A  Y  N  K  ·
3061     TGCCCAACGG  CGCCCCTGAA  TCAGCCCTGT  TGAACACCAG  CAACCCCACT  GCCTACAACA

.. A  P  F   T  R  L   A  L  P  Y   T  A  P   H  R  V   L  A  T  V  ·
3121     AGGCACCATT  CACGAGACTC  GCTCTCCCCT  ACACTGCGCC  GCACCGTGTG  CTGGCAACAG

.. Y  N  G   T  S  K   Y  A  V  G   G  S  G   R  R  G   D  M  G  S  ·
3181     TGTACAACGG  GACGAGTAAG  TATGCTGTGG  GTGGTTCAGG  CAGAAGAGGC  GACATGGGT

.. L  A  A   R  V  V   K  Q  L  P   A  S  F   N  Y  G   A  I  K  A  ·
3241     CTCTCGCGGC  GCGAGTCGTG  AAACAGCTTC  CTGCTTCATT  TAACTACGGT  GCAATCAAGG

.. D  A  I   H  E  L   L  V  R  M   K  R  A   E  L  Y   C  P  R  P  ·
3301     CCGACGCCAT  CCACGAACTT  CTCGTGCGCA  TGAAACGGGC  CGAGCTCTAC  TGCCCCAGAC
```

Fig 23D
Sequence of the C6 7.5Kp FMDV gene cassette from the pC6 7.5Kp FMDV P1+3C donor plasmid, pHM-1310-4

```
            . . L   L   A     I   E   V     S   S   Q     D   R   H   K     Q   K   I     I   A   P   A  ·
      3361   CGCTGTTGGC      AATAGAGGTG      TCTTCGCAAG      ACAGGCACAA      GCAAAAGATC      ATTGCACCAG

⇒ A24 2A
            . . K   Q   L     L   N   F     D   L   L     K   L   A   G     D   V   E     S   N   P   G  ·
      3421   CAAAGCAGCT      TCTGAATTTT      GACCTGCTCA      AGTTGGCCGG      AGACGTTGAG      TCCAACCCCG

⇒ A24 2B
            . . P   F   F     F   A   D     V   R   S     N   F   S   K     L   V   D     T   I   N   Q  ·
      3481   GGCCATTCTT      CTTTGCTGAC      GTTAGGTCAA      ACTTTTCAAA      GTTGGTAGAC      ACAATCAACC

. . M   Q   E     D   M   S     T   K   H     G   P   D   F     N   R   L     V   S   A   F  ·
      3541   AGATGCAGGA      GGACATGTCC      ACAAAACACG      GGCCCGACTT      CAACCGGTTG      GTGTCCGCAT

. . E   E   L     A   T   G     V   K   A     I   R   T   G     L   D   E     A   K   P   W  ·
      3601   TTGAGGAATT      GGCCACTGGA      GTTAAAGCTA      TCAGGACCGG      TCTCGACGAG      GCCAAACCCT

. . Y   K   L     I   K   L     L   S   R     L   S   C   M     A   A   V     A   A   R   S  ·
      3661   GGTACAAGCT      TATCAAACTC      CTAAGCCGCC      TGTCGTGCAT      GGCCGCTGTG      GCAGCACGGT

A24/A12 junction   ⇒ A12 3B
            . . K   D   P     V   L   V     A   I   M     L   A   D   T     G   L   E     R   Q   R   P  ·
      3721   CCAAGGACCC      AGTCCTTGTG      GCCATCATGC      TGGCCGACAC      CGGT CTCGAG    CGTCAGAGAC . . L   K   V     R   A   K     L   P   Q     Q   E   G   P     Y   A   G     P   L   E   R  ·
      3781   CTCTGAAAGT      GAGAGCTAAG      CTCCCACAGC      AGGAAGGACC      TTACGCTGGC      CCGTTGGAGA . . Q   K   P     L   K   V     K   A   K     A   P   V   V     K   E   G     P   Y   E   G  ·
      3841   GACAGAAACC      GCTGAAAGTG      AAAGCAAAAG      CCCCGGTCGT      CAAGGAAGGA      CCTTACGAGG . . P   V   K     K   P   V     A   L   K     V   K   A   K     N   L   I     V   T   E   S  ·
      3901   GACCGGTGAA      GAAGCCTGTC      GCTTTGAAAG      TGAAAGCTAA      GAACTTGATA      GTCACTGAGA . . G   A   P     P   T   D     L   Q   K     M   V   M   G     N   T   K     P   V   E   L  ·
      3961   GTGGTGCCCC      ACCGACCGAC      TTGCAAAAGA      TGGTCATGGG      CAACACAAAG      CCTGTTGAGC . . I   L   D     G   K   T     V   A   I     C   C   A   T     G   V   F     G   T   A   Y  ·
      4021   TCATCCTTGA      CGGGAAGACA      GTAGCCATCT      GTTGTGCTAC      TGGAGTGTTT      GGCACTGCTT . . L   V   P     R   H   L     F   A   E     K   Y   D   K     I   M   L     D   G   R   A  ·
      4081   ACCTCGTGCC      TCGTCATCTT      TTCGCAGAGA      AGTATGACAA      GATCATGCTG      GATGGCAGAG . . M   T   D     S   D   Y     R   V   F     E   F   E   I     K   V   K     G   Q   D   M  ·
      4141   CCATGACAGA      CAGTGACTAC      AGAGTGTTTG      AGTTTGAGAT      TAAAGTAAAA      GGACAGGACA . . L   S   D     A   A   L     M   V   L     H   R   G   N     R   V   R     D   I   T   K  ·
      4201   TGCTCTCAGA      CGCTGCGCTC      ATGGTGCTCC      ACCGTGGGAA      CCGCGTGAGA      GATATCACGA . . H   F   R     D   T   A     R   M   K     K   G   T   P     V   V   G     V   V   N   N  ·
      4261   AACACTTTCG      TGATACAGCA      AGAATGAAGA      AAGGCACCCC      CGTCGTCGGT      GTGGTCAACA
```

Fig 23E
Sequence of the C6 7.5Kp FMDV gene cassette from the pC6 7.5Kp FMDV P1+3C donor plasmid, pHM-1310-4

```
           ..  A   D   V       G   R   L       I   F   S   G       E   A   L       T   Y   K       D   I   V   V  ·
     4321  ACGCCGACGT  TGGGAGACTG  ATTTTCTCTG  GTGAGGCCCT  CACCTACAAG  GATATTGTAG

..  C   M   D       G   D   T       M   P   G   L       F   A   Y       K   A   A       T   K   A   G  ·
     4381  TGTGCATGGA  CGGAGACACC  ATGCCTGGCC  TCTTTGCCTA  CAAAGCCGCC  ACCAAGGCAG

..  Y   C   G       G   A   V       L   A   K   D       G   A   D       T   F   I       V   G   T   H  ·
     4441  GCTACTGTGG  AGGAGCCGTT  CTCGCCAAGG  ACGGGGCCGA  CACTTTCATC  GTCGGCACTC

..  S   A   G       G   N   G       V   G   Y   C       S   C   V       S   R   S       M   L   L   R  ·
     4501  ACTCCGCAGG  AGGCAATGGA  GTTGGATACT  GCTCATGCGT  TTCCAGGTCC  ATGCTTCTCA

..  M   K   A       H   V   D       P   E   P   Q       H   E   *
     4561  GAATGAAGGC  ACACGTTGAC  CCTGAACCAC  AACACGAGTA  GTAATTTTTC  TGCAGCCCGG

4621  GTTTTTATAG  CTAATTAGTC  ATTTTTTCGT  AAGTAAGTAT  TTTTATTTAA  TACTTTTTAT

4681  TGTACTTATG  TTAAATATAA  CTGATGATAA  CAAAATCCAT  TATGTATTAT  TTATAACTGT

4741  AATTTCTTTA  GCGTAGTTAG  ATGTCCAATC  TCTCTCAAAT  ACATCGGCTA  TCTTTTTAGT

4801  GAGATTTTGA  TCTATGCAGT  TGAAACTTAT  GAACGCGTGA  TGATTAAAAT  GTGAACCGTC

4861  CAAATTTGCA  GTCATTATAT  GAGCGTATCT  ATTATCTACT  ATCATCATCT  TTGAGTTATT

4921  AATATCATCT  ACTTTAGAAT  TGATAGGAAA  TATGAATACC  TTTGTAGTAA  TATCTATACT

4981  ATCTACACCT  AACTCATTAA  GACTTTTGAT  AG
                                              C6L  ⇐
```

Fig 24A
Oligonucleotides used to generate the Pi promoter
Primers to PCR amplify a 1260 bp Pip 5'-FMDV fragment (EcoR I-NdeI)

```
                 Eco RI                    Pip                                                                   ⇒ VP4
                                                                                                                  M  G  A  G  Q  S  S  P
11356.CXL 5'  GAATTCACTGTAAAAATAGAAACTATAATCATATAATAGTGTAGGTTGGTAGTAGGGTACTCGTGATTAATTTTATTGTTAAACTTGATGGGAGCTGGGCAATCCAGCCCA
                   TGACATTTTTATCTTTGATATTAGTATATTATCACATCCAACCATCATCCCATGAGCACTAATTAAAATAACAATTTGAACTACCCTCGACCCGTTAGGTCGGGT

L  A  A  K  H  M  S            VP3
           5'  CTTGCCGCAAAACATATGTCCA
11358.CXL  3'  GAACGGCGTTTTGTATACAGGT
                           Nde I
```

Fig 24B
Oligonucleotides used to generate the Pi promoter
Primers to assemble the Pi promoter

```
11395.CXL    5' ACTGTAAAAATAGAAACTATAATCATA 3'

11396.CXL                       5' TAATAGTGTAGGTTGGTAGTAGGGTAC 3'

11397.CXL                                               5' TCGTGATTAATTTTATTGTTAAACTTG 3'

11399.CXL    3' TGACATTTTTATCTTTGATATTAGTATATTATCACATCCA  5'

11398.CXL                                          3' ACCATCATCCCATGAGCACTAATTAAAATAACAATTTGAAC 5'
```

Fig 24C
Oligonucleotides used to generate the Pi promoter
Primers to PCR amplify the Pi promoter

11400.CXL 5' ACTGTAAAAATAGAAACTATAAT

11401.CXL 3' ACTAATTAAAATAACAATTTGAAC 5'

Pip ⇒ *FMDV*

GAATTCACTGTAAAAATAGAAACTATAATCATATAATAGTGTAGGTTGGTAGTAGGGTACTCGTGATTAATTTTATTGTTAAACTTG*ATGGGAGCTGGGCAATCCAGCCCA*

TGACATTTTTATCTTTGATATTAGTATATTATCACATCCAACCATCATCCCATGAGCACTAATTAAAATAACAATTTGAAC*TACCCTCGACCCGTTAGGTCGGGT*

Figure 24D
Oligonucleotides used to generate the Pi promoter
Primers to amplify a 97bp Pip 5'-FMDV fragment

11402.CXL 5' GAATTCACTGTAAAAATAGAAACTAT

11403.CXL 3' TAAAATAACAATTTGAAC*TACCCTCGAC* 5'

Figure 24E
Oligonucleotides used to generate the Pi promoter
Primers to amplify a 648bp 3'-Pip 5'-FMDV fragment

11406.CXL 5' GTTAAACTTG*ATGGGAGCTGGGCAATCC* 3'

C L L V A M V P VP2
TGCCTCCTGGTGGCCATGGTACC
11407.CXL 3' ACGGAGGACCACCGGTACCATGG 5'
Kpn I

Fig 25A
Construction of pC6 Pip FMDV P1+3C, pHM-1284-25

Fig 25B
Construction of pC6 Pip FMDV P1+3C, pHM-1284-25

Fig 26A
Sequence of the C6 Pip FMDV gene cassette in pC6 Pip FMDV P1+3C, pHM-1284-25

```
   1  TTCATAAATA CAAGTTTGAT TAAACTTAAG TTGTTCTAAA GTTCTTTCCT CCGAAGGTAT
  61  AGAACAAAGT ATTTCTTCTA CATCCTTACT ATTTATTGCA GCTTTTAACA GCCTATCACG
 121  TATCCTATTT TTAGTATTGG TAGAACGTTT TAGTTCTAAA GTTAAAATAT TAGACATAAT
 181  TGGCATATTG CTTATTCCTT GCATAGTTGA GTCTGTAGAT CGTTTCAGTA TATCACTGAT
 241  TAATGTACTA CTGTTATGAT GAAATATAGA ATCGATATTG GCATTAACT GTTTTGTTAT
 301  ACTAAGTCTA GATTTAAAT CTTCTAGTAA TATGCTATTT AATATAAAAG CTTCCACGTT
 361  TTTGTATACA TTTCTTTCCA TATTAGTAGC TACTACTAAA TGATTATCTT CTTTCATATC
 421  TTGTAGATAA GATAGACTAT CTTTATCTTT ATTAGTAGAA AATACTTCTG GCCATACATC
 481  GTTAAATTTT TTTGTTGTTG TTAGATATAA TATTAAATAT CTAGAGGATC CTATTATTTG
 541  TGGTAAAATG TTTATAGAGT AAAATGATCT GGCTATTAAA CATAGGCCAG TTACCATAGA
 601  ATGCTGCTTC CCGTTACAGT GTTTTACCAT AACCATAGAT CTGCCTGTAT TGTTGATACA
 661  TATAACAGCT GTAAATCCTA AAAAATTCCT ATCATAATTA TTAATATTAG GTAATTCATT
 721  TCCATGTGAA AGATAGACTA ATTTTATATC CTTTACCTCC AAATAATTAT TTACATCTCT
 781  TAAACAATCT ATTTTAATAT CATTAACTGG TATTTTATAA TATCCAGAAA GGTTTGAAGG
 841  GGTTGATGGA ATAAGTCTAT TAACATCGTT AAGTAAATTA TTAATATCAT GAATCTTTAT
 901  TATATTATAC CCATAAGTTA AATTTATATT TACTTTCTCA TCATCTGACT TAGTTAGTTT
 961  GTAATAAGGT GTGTCTGAAA AAATTAAAAG GTAATTCGTT GAATGAAGCT GTATTTGCTG
1021  TATCATTTTT ATCTAATTTT GGAGATTTAG CAGTACTTAC TTCATTAGAA GAAGAATCTG
1081  CCAGTTCCTG TCTATTACTG ATATTTCGTT TCATTATTAT ATGATTTATA TTTTACTTTT
                    C6R ⇐                                     ⇒ Pip
1141  TCAATTATAT ATACTCATTT GACTAGTTAA TCAATAAAAA GAATTCACTG TAAAAATAGA
1201  AACTATAATC ATATAATAGT GTAGGTTGGT AGTAGGGTAC TCGTGATTAA TTTTATTGTT
                ⇒ VP4
            M   G   A   G   Q   S   S   P   A   T   G   S   Q   N   Q   S   G   N·
1261  AAACTTGATG GGAGCTGGGC AATCCAGCCC AGCAACCGGC TCGCAGAACC AGTCTGGCAA
      ·T   G   S   I   I   N   N   Y   Y   M   Q   Q   Y   Q   N   S   M   D   T   Q·
1321  CACTGGCAGC ATAATCAACA ACTACTACAT GCAACAGTAC CAGAACTCCA TGGACACACA
      ·L   G   D   N   A   I   S   G   G   S   N   E   G   S   T   D   T   T   S   T·
1381  GTTGGGAGAC AATGCCATCA GTGGAGGCTC AACGAGGGC TCCACGGACA CAACTTCAAC
```

Fig 26B
Sequence of the C6 Pip FMDV gene cassette in pC6 Pip FMDV P1+3C, pHM-1284-25

```
         .  H   T   T     N   T   Q     N   N   D     W   F   S     K   L   A     S   S   A   F   T  .
1441        ACACACAACC    AACACTCAAA    ACAATGACTG    GTTCTCGAAG    CTCGCCAGTT    CAGCTTTTAC

⇒ VP2
         .  G   L   F     G   A   L   L     A   D   K     K   T   E     E   T   T     L   E   D  .
1501        CGGTCTGTTC    GGTGCACTGC    TCGCCGACAA    GAAGACAGAG    GAAACGACAC    TTCTTGAGGA

.  R   I   L     T   T   R   N     G   H   T     T   S   T     T   Q   S     S   V   G   V  .
1561        CCGCATCCTC    ACCACCCGCA    ACGGGCACAC    CACCTCGACG    ACCCAATCGA    GTGTGGGTGT

.  T   H   G     Y   S   T   E     D   H     V   A   G     P   N   T     S   G   L   E  .
1621        CACACACGGG    TACTCCACAG    AGGAGGACCA    CGTTGCTGGG    CCCAACACAT    CGGGCCTGGA

.  T   R   V     V   Q   A   E     R   F   Y     K   K   Y     L   F   D     W   T   T   D  .
1681        GACGCGAGTG    GTGCAGGCAG    AGAGATTCTA    CAAAAAGTAC    TTGTTTGACT    GGACAACGGA

.  K   A   F     G   H   L   E     K   L   E     L   P   S     D   H   H     G   V   F   G  .
1741        CAAGGCATTT    GGACACCTGG    AAAAGCTGGA    GCTCCCGTCC    GACCACCACG    GTGTCTTTGG

.  H   L   V     D   S   Y   A     Y   M   R     N   G   W     D   V   E     V   S   A   V  .
1801        ACACTTGGTG    GACTCGTACG    CCTATATGAG    AAATGGCTGG    GATGTTGAGG    TGTCCGCTGT

.  G   N   Q     F   N   G   G     C   L   L     V   A   M     V   P   E     W   K   E   F  .
1861        TGGCAACCAG    TTCAACGGCG    GGTGCCTCCT    GGTGGCCATG    GTACCTGAAT    GGAAGGAATT

.  D   T   R     E   K   Y   Q     L   T   L     F   P   H     Q   F   I     S   P   R   T  .
1921        TGACACACGG    GAGAAATACC    AACTCACCCT    TTTCCCGCAC    CAGTTTATTA    GCCCCAGAAC

.  N   M   T     A   H   I   T     V   P   Y     L   G   V     N   R   Y     D   Q   Y   K  .
1981        TAACATGACT    GCCCACATCA    CGGTCCCCTA    CCTTGGTGTG    AACAGGTATG    ATCAGTACAA

.  K   H   K     P   W   T   L     V   V   M     V   V   S     P   L   T     V   N   N   T  .
2041        GAAGCATAAG    CCCTGGACAT    TGGTTGTCAT    GGTCGTGTCG    CCACTTACGG    TCAACAACAC

.  S   A   A     Q   I   K   V     Y   A   N     I   A   P     T   Y   V     H   V   A   G  .
2101        TAGTGCGGCA    CAAATCAAGG    TCTACGCCAA    CATAGCTCCG    ACCTATGTTC    ACGTGGCCGG

⇒ VP3
         .  E   L   P     S   K   E   G     I   F   P     V   A   C     A   D   G     Y   G   G   L  .
2161        TGAACTCCCC    TCGAAAGAGG    GGATTTTCCC    GGTTGCATGT    GCGGACGGTT    ACGGAGGATT

.  V   T   T     D   P   K   T     A   D   P     A   Y   G     K   V   Y   N     P   P   R  .
2221        GGTGACGACA    GACCCGAAGA    CAGCTGACCC    TGCTTATGGC    AAGGTGTACA    ACCCGCCTAG

.  T   N   Y     P   G   R   F     T   N   L     L   D   V     A   E   A     C   P   T   F  .
2281        GACTAACTAC    CCTGGGCGCT    TCACCAACCT    GTTGGACGTG    GCCGAAGCGT    GTCCCACTTT

.  L   C   F     D   D   G   K     P   Y   V     T   T   R     T   D   D     T   R   L   L  .
2341        CCTCTGCTTT    GACGACGGGA    AACCGTACGT    CACCACGCGG    ACGGATGACA    CCCGACTTTT

.  A   K   F     D   L   S   L     A   A   K     H   M   S     N   T   Y   L     S   G   I  .
2401        GGCCAAGTTT    GACCTTTCCC    TTGCCGCAAA    ACATATGTCC    AACACATACC    TGTCAGGGAT
```

Fig 26C
Sequence of the C6 Pip FMDV gene cassette in pC6 Pip FMDV P1+3C, pHM-1284-25

```
          . A   Q   Y   Y   T   Q   Y   S   G   T   I   N   L   H   F   M   F   T   G   S .
2461      TGCTCAGTAC TACACACAGT ACTCTGGCAC CATCAATTTG CATTTCATGT TTACAGGTTC

. T   D   S   K   A   R   Y   M   V   A   Y   I   P   P   G   V   E   T   P   P .
2521      CACTGATTCA AAGGCCCGAT ACATGGTGGC CTACATCCCA CCTGGGGTGG AGACACCACC

. D   T   P   E   R   A   A   H   C   I   H   A   E   W   D   T   G   L   N   S .
2581      GGACACACCT GAAAGGGCTG CCCACTGCAT TCACGCTGAA TGGACACTG GACTAAACTC

. K   F   T   F   S   I   P   Y   V   S   A   A   D   Y   A   Y   T   A   S   D .
2641      CAAATTCACT TTCTCAATCC CGTACGTATC CGCCGCGGAT TACGCGTACA CAGCGTCTGA

. T   A   E   T   I   N   V   Q   G   W   V   C   I   Y   Q   I   T   H   G   K .
2701      CACGGCAGAA ACAATCAACG TACAGGGATG GGTCTGCATC TACCAAATTA CACACGGGAA

. A   E   N   D   T   L   V   V   S   V   S   A   G   K   D   F   E   L   R   L .
2761      GGCTGAAAAT GACACCTTGG TCGTGTCGGT TAGCGCCGGC AAAGACTTTG AGTTGCGCCT
                                                 ⇒ VP1
          . P   I   D   P   R   Q   Q   T   T   A   T   G   E   S   A   D   P   V   T   T .
2821      CCCGATTGAC CCCCGCCAGC AGACCACCGC TACCGGGGAA TCAGCAGACC CGGTCACCAC

. T   V   E   N   Y   G   G   E   T   Q   I   Q   R   R   H   H   T   D   I   G .
2881      CACCGTGGAG AACTACGGCG GTGAGACACA AATCCAGAGA CGTCACCACA CGGACATTGG

. F   I   M   D   R   F   V   K   I   Q   S   L   S   P   T   H   V   I   D   L .
2941      TTTCATCATG GACAGATTTG TGAAGATCCA AAGCTTGAGC CCAACACATG TCATTGACCT

. M   Q   A   H   Q   H   G   L   V   G   A   L   L   R   A   A   T   Y   Y   F .
3001      CATGCAGGCT CACCAACACG GTCTGGTGGG TGCCTTGCTG CGTGCAGCCA CGTACTACTT

. S   D   L   E   I   V   V   R   H   E   G   N   L   T   W   V   P   N   G   A .
3061      TTCTGACCTG GAAATTGTTG TACGGCACGA AGGCAATCTG ACCTGGGTGC CCAACGGCGC

. P   E   S   A   L   L   N   T   S   N   P   T   A   Y   N   K   A   P   F   T .
3121      CCCTGAATCA GCCCTGTTGA ACACCAGCAA CCCCACTGCC TACAACAAGG CACCATTCAC

. R   L   A   L   P   Y   T   A   P   H   R   V   L   A   T   V   Y   N   G   T .
3181      GAGACTCGCT CTCCCCTACA CTGCGCCGCA CCGTGTGCTG GCAACAGTGT ACAACGGGAC

. S   K   Y   A   V   G   G   S   G   R   R   G   D   M   G   S   L   A   A   R .
3241      GAGTAAGTAT GCTGTGGGTG GTTCAGGCAG AAGAGGCGAC ATGGGGTCTC TCGCGGCGCG

. V   V   K   Q   L   P   A   S   F   N   Y   G   A   I   K   A   D   A   I   H .
3301      AGTCGTGAAA CAGCTTCCTG CTTCATTTAA CTACGGTGCA ATCAAGGCCG ACGCCATCCA

. E   L   L   V   R   M   K   R   A   E   L   Y   C   P   R   P   L   L   A   I .
3361      CGAACTTCTC GTGCGCATGA AACGGGCCGA GCTCTACTGC CCCAGACCGC TGTTGGCAAT
                                                                          ⇒ 2A
          . E   V   S   S   Q   D   R   H   K   Q   K   I   I   A   P   A   K   Q   L   L .
3421      AGAGGTGTCT TCGCAAGACA GGCACAAGCA AAAGATCATT GCACCAGCAA AGCAGCTTCT
```

Fig 26D
Sequence of the C6 Pip FMDV gene cassette in pC6 Pip FMDV P1+3C, pHM-1284-25

⇒ 2B

```
       .  N   F   D     L   L   K   L     A   G   D     V   E   S     N   P   G     P   F   F   F  .
3481      GAATTTTGAC    CTGCTCAAGT    TGGCCGGAGA    CGTTGAGTCC    AACCCCGGGC    CATTCTTCTT

.  A   D   V     R   S   N   F     S   K   L     V   D   T     I   N   Q     M   Q   E   D  .
3541      TGCTGACGTT    AGGTCAAACT    TTTCAAAGTT    GGTAGACACA    ATCAACCAGA    TGCAGGAGGA

.  M   S   T     K   H   G   P     D   F   N     R   L   V     S   A   F     E   E   L   A  .
3601      CATGTCCACA    AAACACGGGC    CCGACTTCAA    CCGGTTGGTG    TCCGCATTTG    AGGAATTGGC

.  T   G   V     K   A   I   R     T   G   L     D   E   A     K   P   W     Y   K   L   I  .
3661      CACTGGAGTT    AAAGCTATCA    GGACCGGTCT    CGACGAGGCC    AAACCCTGGT    ACAAGCTTAT

.  K   L   L     S   R   L   S     C   M   A     A   V   A     A   R   S     K   D   P   V  .
3721      CAAACTCCTA    AGCCGCCTGT    CGTGCATGGC    CGCTGTGGCA    GCACGGTCCA    AGGACCCAGT

A24/A12 junction ⇒ 3B
       .  L   V   A     I   M   L   A     D   T   G     L   E     R     Q   R   P     L   K   V   R  .
3781      CCTTGTGGCC    ATCATGCTGG    CCGACACCGG    TCTCGAGCGT    CAGAGACCTC    TGAAAGTGAG .  A   K   L     P   Q   Q   E     G   P   Y     A   G   P     L   E   R     Q   K   P   L  .
3841      AGCTAAGCTC    CCACAGCAGG    AAGGACCTTA    CGCTGGCCCG    TTGGAGAGAC    AGAAACCGCT .  K   V   K     A   K   A   P     V   V   K     E   G   P     Y   E   G     P   V   K   K  .
3901      GAAAGTGAAA    GCAAAAGCCC    CGGTCGTCAA    GGAAGGACCT    TACGAGGGAC    CGGTGAAGAA .  P   V   A     L   K   V   K     A   K   N     L   I   V     T   E   S     G   A   P   P  .
3961      GCCTGTCGCT    TTGAAAGTGA    AAGCTAAGAA    CTTGATAGTC    ACTGAGAGTG    GTGCCCCACC .  T   D   L     Q   K   M   V     M   G   N     T   K   P     V   E   L     I   L   D   G  .
4021      GACCGACTTG    CAAAAGATGG    TCATGGGCAA    CACAAAGCCT    GTTGAGCTCA    TCCTTGACGG .  K   T   V     A   I   C   C     A   T   G     V   F   G     T   A   Y     L   V   P   R  .
4081      GAAGACAGTA    GCCATCTGTT    GTGCTACTGG    AGTGTTTGGC    ACTGCTTACC    TCGTGCCTCG .  H   L   F     A   E   K   Y     D   K   I     M   L   D     G   R   A     M   T   D   S  .
4141      TCATCTTTTC    GCAGAGAAGT    ATGACAAGAT    CATGCTGGAT    GGCAGAGCCA    TGACAGACAG .  D   Y   R     V   F   E   F     E   I   K     V   K   G     Q   D   M     L   S   D   A  .
4201      TGACTACAGA    GTGTTTGAGT    TTGAGATTAA    AGTAAAAGGA    CAGGACATGC    TCTCAGACGC .  A   L   M     V   L   H   R     G   N   R     V   R   D     I   T   K     H   F   R   D  .
4261      TGCGCTCATG    GTGCTCCACC    GTGGGAACCG    CGTGAGAGAT    ATCACGAAAC    ACTTTCGTGA .  T   A   R     M   K   K   G     T   P   V     V   G   V     V   N   N     A   D   V   G  .
4321      TACAGCAAGA    ATGAAGAAAG    GCACCCCCGT    CGTCGGTGTG    GTCAACAACG    CCGACGTTGG .  R   L   I     F   S   G   E     A   L   T     Y   K   D     I   V   V     C   M   D   G  .
4381      GAGACTGATT    TTCTCTGGTG    AGGCCCTCAC    CTACAAGGAT    ATTGTAGTGT    GCATGGACGG .  D   T   M     P   G   L   F     A   Y   K     A   A   T     K   A   G     Y   C   G   G  .
4441      AGACACCATG    CCTGGCCTCT    TTGCCTACAA    AGCCGCCACC    AAGGCAGGCT    ACTGTGGAGG
```

Fig 26E
Sequence of the C6 Pip FMDV gene cassette in pC6 Pip FMDV P1+3C, pHM-1284-25

```
         . A   V   L     A   K   D     G   A   D   T     F   I   V     G   T   H     S   A   G   G .
4501     AGCCGTTCTC  GCCAAGGACG  GGGCCGACAC  TTTCATCGTC  GGCACTCACT  CCGCAGGAGG

. N   G   V     G   Y   C   S     C   V   S     R   S   M     L   L   R   M   K   A   H .
4561     CAATGGAGTT  GGATACTGCT  CATGCGTTTC  CAGGTCCATG  CTTCTCAGAA  TGAAGGCACA

. V   D   P     E   P   Q     H   E   *
4621     CGTTGACCCT  GAACCACAAC  ACGAGTAGTA  ATTTTTCTGC  AGCCCGGGTT  TTTATAGCTA

4681     ATTAGTCATT  TTTTCGTAAG  TAAGTATTTT  TATTTAATAC  TTTTTATTGT  ACTTATGTTA

4741     AATATAACTG  ATGATAACAA  AATCCATTAT  GTATTATTTA  TAACTGTAAT  TTCTTTAGCG

4801     TAGTTAGATG  TCCAATCTCT  CTCAAATACA  TCGGCTATCT  TTTTAGTGAG  ATTTGATCT

4861     ATGCAGTTGA  AACTTATGAA  CGCGTGATGA  TTAAAATGTG  AACCGTCCAA  ATTTGCAGTC

4921     ATTATATGAG  CGTATCTATT  ATCTACTATC  ATCATCTTTG  AGTTATTAAT  ATCATCTACT

4981     TTAGAATTGA  TAGGAAATAT  GAATACCTTT  GTAGTAATAT  CTATACTATC  TACACCTAAC

5041     TCATTAAGAC  TTTTGATAG
                    C6L  ⇐
```

Fig 27
Oligonucleotide primers to PCR amplify H6p* 5'-FMDV

```
                Hind III        H6p*
11506.HM     5' AAGCTTTTCTTTATTCTATACTTAAAAAG V  A  M  V  P  E  W  K
             5' GGTGGCCATGGTACCTGAATGGAAG   VP2
11279.SL     3' CCACCGGTACCATGGACTTACCTTC
                         Kpn I
```

Fig 28A
Construction of pF8 H6p* FMDV P1+3C, pHM-1354-1

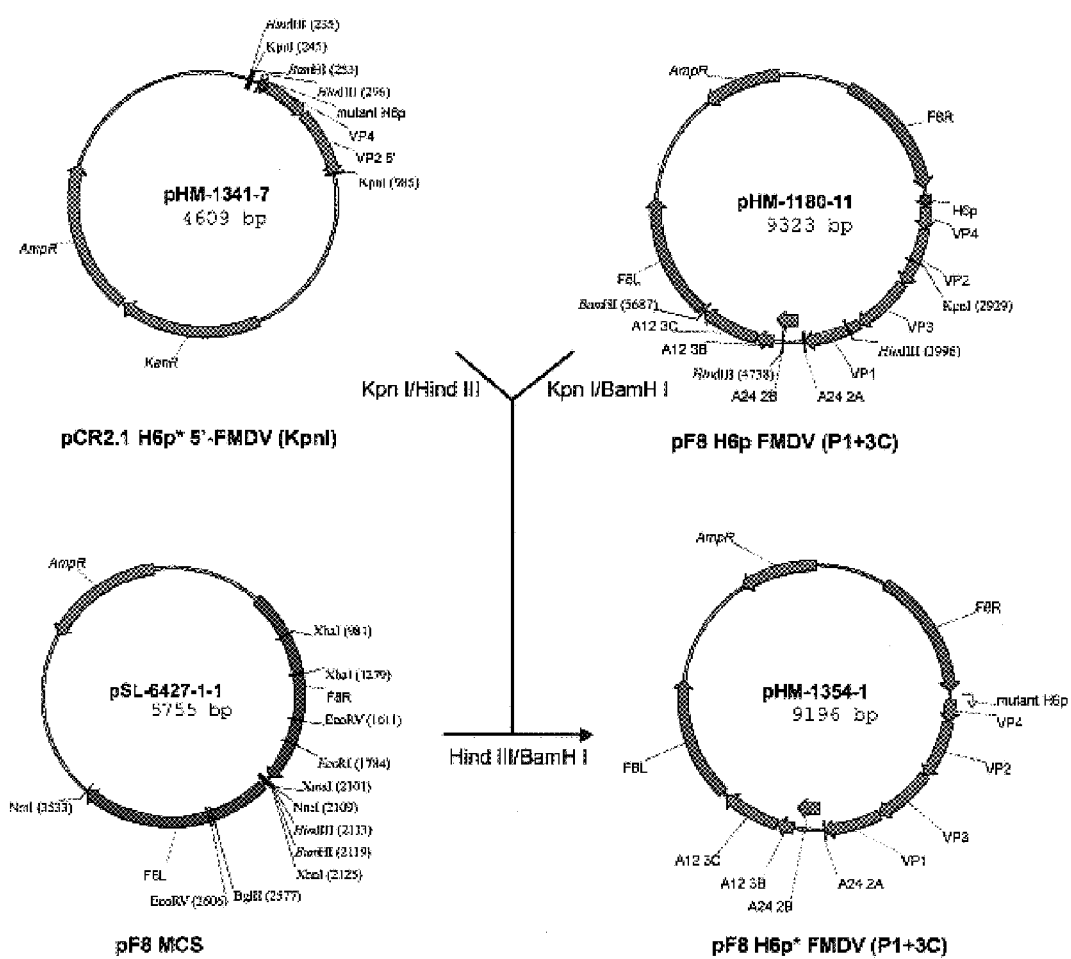

Fig 29A
Sequence of the F8 H6p* FMDV P1+3C gene cassette in pHM-1354-1, pF8 H6p* FMDV P1+3C

```
        ⇒ F8R
   1    GACCCTTTAC AAGAATAAAA GAAGAAACAA CTGTGAAATA GTTTATAAAT GTAATTCGTA
  61    TGCAGAAAAC GATAATATAT TTTGGTATGA GAAATCTAAA GGAGACATAG TTTGTATAGA
 121    CATGCGCTCT TCCGATGAGA TATTCGATGC TTTTCTAATG TATCATATAG CTACAAGATA
 181    TGCCTATCAT GATGATGATA TATATCTACA AATAGTGTTA TATTATTCTA ATAATCAAAA
 241    TGTTATATCT TATATTACGA AAAATAAATA CGTTAAGTAT ATAAGAAATA AAACTAGAGA
 301    CGATATTCAT AAAGTAAAAA TATTAGCTCT AGAAGACTTT ACAACGGAAG AAATATATTG
 361    TTGGATTAGT AATATATAAC AGCGTAGCTG CACGGTTTTG ATCATTTTCC AACAATATAA
 421    ACCAATGAAG GAGGACGACT CATCAAACAT AAATAACATT CACGGAAAAT ATTCAGTATC
 481    AGATTTATCA CAAGATGATT ATGTTATTGA ATGTATAGAC GGATCTTTTG ATTCGATCAA
 541    GTATAGAGAT ATAAAGGTTA TAATAATGAA GAATAACGGT TACGTTAATT GTAGTAAATT
 601    ATGTAAAATG CGGAATAAAT ACTTTTCTAG ATGGTTGCGT CTTTCTACTT CTAAAGCATT
 661    ATTAGACATT TACAATAATA AGTCAGTAGA TAATGCTATT GTTAAAGTCT ATGGTAAAGG
 721    TAAGAAACTT ATTATAACAG GATTTTATCT CAAACAAAAT ATGATACGTT ATGTTATTGA
 781    GTGGATAGGG GATGATTTTA CAAACGATAT ATACAAAATG ATTAATTTCT ATAATGCGTT
 841    ATTCGGTAAC GATGAATTAA AAATAGTATC CTGTGAAAAC ACTCTATGCC CGTTTATAGA
 901    ACTTGGTAGA TGCTATTATG GTAAAAAATG TAAGTATATA CACGGAGATC AATGTGATAT
 961    CTGTGGTCTA TATATACTAC ACCCTACCGA TATTAACCAA CGAGTTTCTC ACAAGAAAAC
1021    TTGTTTAGTA GATAGAGATT CTTTGATTGT GTTTAAAAGA AGTACCAGTA AAAAGTGTGG
1081    CATATGCATA GAAGAAATAA ACAAAAAACA TATTTCCGAA CAGTATTTTG GAATTCTCCC
1141    AAGTTGTAAA CATATTTTTT GCCTATCATG TATAAGACGT TGGGCAGATA CTACCAGAAA
1201    TACAGATACT GAAAATACGT GTCCTGAATG TAGAATAGTT TTTCCTTTCA TAATACCCAG
1261    TAGGTATTGG ATAGATAATA AATATGATAA AAAAATATTA TATAATAGAT ATAAGAAAAT
1321    GATTTTTACA AAAATACCTA TAAGAACAAT AAAAATATAA TTACATTTAC GGAAAATAGC
1381    TGGTTTTAGT TTACCAACTT AGAGTAATTA TCATATTGAA TCTATATTGC TAATTAGCTA
        ⇒ H6p*
1441    ATAAAAACCC GGGTCGCGAA AGCTTTTCTT TATTCTATAC TTAAAAAGTG CAAATAAATA
```

Fig 29B
Sequence of the F8 H6p* FMDV P1+3C gene cassette in pHM-1354-1, pF8 H6p* FMDV P1+3C

```
              ⇒ A24 VP4
             M  G  A   G  Q  S    S  P  A  T    G  S  Q  N    Q  S
1501  CAAAGGTTCT TGATGGGAGC TGGGCAATCC AGCCCAGCAA CCGGCTCGCA GAACCAGTCT

G  N  T  G   S  I  I    N  N  Y    Y  M  Q  Q    Y  Q  N   S  M  D
1561  GGCAACACTG GCAGCATAAT CAACAACTAC TACATGCAAC AGTACCAGAA CTCCATGGAC

T  Q  L  G   D  N  A    I  S  G    G  S  N  E    G  S  T   D  T  T
1621  ACACAGTTGG GAGACAATGC CATCAGTGGA GGCTCCAACG AGGGCTCCAC GGACACAACT

S  T  H  T   T  N  T    Q  N  N    D  W  F  S    K  L  A   S  S  A
1681  TCAACACACA CAACCAACAC TCAAAACAAT GACTGGTTCT CGAAGCTCGC CAGTTCAGCT
                                        ⇒ A24 VP2
       F  T  G  L   F  G  A    L  L  A    D  K  K  T    E  E  T   T  L  L
1741  TTTACCGGTC TGTTCGGTGC ACTGCTCGCC GACAAGAAGA CAGAGGAAAC GACACTTCTT

E  D  R  I   L  T  T    R  N  G    H  T  T  S    T  T  Q   S  S  V
1801  GAGGACCGCA TCCTCACCAC CCGCAACGGG CACACCACCT CGACGACCCA ATCGAGTGTG

G  V  T  H   G  Y  S    T  E  E    D  H  V  A    G  P  N   T  S  G
1861  GGTGTCACAC ACGGGTACTC CACAGAGGAG GACCACGTTG CTGGGCCCAA CACATCGGGC

L  E  T  R   V  V  Q    A  E  R    F  Y  K  K    Y  L  F   D  W  T
1921  CTGGAGACGC GAGTGGTGCA GGCAGAGAGA TTCTACAAAA AGTACTTGTT TGACTGGACA

T  D  K  A   F  G  H    L  E  K    L  E  L  P    S  D  H   G  V
1981  ACGGACAAGG CATTTGGACA CCTGGAAAAG CTGGAGCTCC CGTCCGACCA CCACGGTGTC

F  G  H  L   V  D  S    Y  A  Y    M  R  N  G    W  D  V   E  V  S
2041  TTTGGACACT TGGTGGACTC GTACGCCTAT ATGAGAAATG GCTGGGATGT TGAGGTGTCC

A  V  G  N   Q  F  N    G  G  C    L  L  V  A    M  V  P   E  W  K
2101  GCTGTTGGCA ACCAGTTCAA CGGCGGGTGC CTCCTGGTGG CCATGGTACC TGAATGGAAG

E  F  D  T   R  E  K    Y  Q  L    T  L  F  P    H  Q  F   I  S  P
2161  GAATTTGACA CACGGGAGAA ATACCAACTC ACCCTTTTCC CGCACCAGTT TATTAGCCCC

R  T  N  M   T  A  H    I  T  V    P  Y  L  G    V  N  R   Y  D  Q
2221  AGAACTAACA TGACTGCCCA CATCACGGTC CCCTACCTTG GTGTGAACAG GTATGATCAG

Y  K  K  H   K  P  W    T  L  V    V  M  V  V    S  P  L   T  V  N
2281  TACAAGAAGC ATAAGCCCTG GACATTGGTT GTCATGGTCG TGTCGCCACT TACGGTCAAC

N  T  S  A   Q  I      K  V  Y    A  N  I  A    P  T  Y   V  H  V
2341  AACACTAGTG CGGCACAAAT CAAGGTCTAC GCCAACATAG CTCCGACCTA TGTTCACGTG
                                        ⇒ A24 VP3
       A  G  E  L   P  S  K    E  G  I    F  P  V  A    C  A  D   G  Y  G
2401  GCCGGTGAAC TCCCCTCGAA AGAGGGGATT TTCCCGGTTG CATGTGCGGA CGGTTACGGA
```

Fig 29C
Sequence of the F8 H6p* FMDV P1+3C gene cassette in pHM-1354-1, pF8 H6p* FMDV P1+3C

```
       G  L  V  T     T  D  P     K  T  A     D  P  A  Y     G  K  V     Y  N  P
2461   GGATTGGTGA CGACAGACCC GAAGACAGCT GACCCTGCTT ATGGCAAGGT GTACAACCCG

P  R  T  N     Y  P  G     R  F  T     N  L  L  D     V  A  E     A  C  P
2521   CCTAGGACTA ACTACCCTGG GCGCTTCACC AACCTGTTGG ACGTGGCCGA AGCGTGTCCC
       T  F  L  C     F  D  D     G  K  P     Y  V  T  T     R  T  D     D  T  R
2581   ACTTTCCTCT GCTTTGACGA CGGGAAACCG TACGTCACCA CGCGGACGGA TGACACCCGA

L  L  A  K     F  D  L     S  L  A     A  K  H  M     S  N  T     Y  L  S
2641   CTTTTGGCCA AGTTTGACCT TTCCCTTGCC GCAAAACATA TGTCCAACAC ATACCTGTCA

G  I  A  Q     Y  Y  T     Q  Y  S     G  T  I  N     L  H  F     M  F  T
2701   GGGATTGCTC AGTACTACAC ACAGTACTCT GGCACCATCA ATTTGCATTT CATGTTTACA

G  S  T  D     S  K  A     R  Y  M     V  A  Y  I     P  P  G     V  E  T
2761   GGTTCCACTG ATTCAAAGGC CCGATACATG GTGGCCTACA TCCCACCTGG GGTGGAGACA

P  P  D  T     P  E  R     A  A  H     C  I  H  A     E  W  D     T  G  L
2821   CCACCGGACA CACCTGAAAG GGCTGCCCAC TGCATTCACG CTGAATGGGA CACTGGACTA

N  S  K  F     T  F  S     I  P  Y     V  S  A  A     D  Y  A     Y  T  A
2881   AACTCCAAAT TCACTTTCTC AATCCCGTAC GTATCCGCCG CGGATTACGC GTACACAGCG

S  D  T  A     E  T  I     N  V  Q     G  W  V  C     I  Y  Q     I  T  H
2941   TCTGACACGG CAGAAACAAT CAACGTACAG GGATGGGTCT GCATCTACCA AATTACACAC

G  K  A  E     N  D  T     L  V  V     S  V  S  A     G  K  D     F  E  L
3001   GGGAAGGCTG AAAATGACAC CTTGGTCGTG TCGGTTAGCG CCGGCAAAGA CTTTGAGTTG

⇒ A24 VP1
       R  L  P  I     D  P  R     Q  Q  T     T  A  T  G     E  S  A     D  P  V
3061   CGCCTCCCGA TTGACCCCCG CCAGCAGACC ACCGCTACCG GGAATCAGC AGACCCGGTC

T  T  T  V     E  N  Y     G  G  E     T  Q  I  Q     R  R  H     H  T  D
3121   ACCACCACCG TGGAGAACTA CGGCGGTGAG ACACAAATCC AGAGACGTCA CCACACGGAC

I  G  F  I     M  D  R     F  V  K     I  Q  S  L     S  P  T     H  V  I
3181   ATTGGTTTCA TCATGGACAG ATTTGTGAAG ATCCAAAGCT TGAGCCCAAC ACATGTCATT

D  L  M  Q     A  H  Q     H  G  L     V  G  A  L     L  R  A     A  T  Y
3241   GACCTCATGC AGGCTCACCA ACACGGTCTG GTGGGTGCCT TGCTGCGTGC AGCCACGTAC

Y  F  S  D     L  E  I     V  V  R     H  E  G  N     L  T  W     V  P  N
3301   TACTTTTCTG ACCTGGAAAT TGTTGTACGG CACGAAGGCA ATCTGACCTG GGTGCCCAAC

G  A  P  E     S  A  L     L  N  T     S  N  P  T     A  Y  N     K  A  P
3361   GGCGCCCCTG AATCAGCCCT GTTGAACACC AGCAACCCCA CTGCCTACAA CAAGGCACCA

F  T  R  L     A  L  P     Y  T  A     P  H  R  V     L  A  T     V  Y  N
3421   TTCACGAGAC TCGCTCTCCC CTACACTGCG CCGCACCGTG TGCTGGCAAC AGTGTACAAC
```

Fig 29D
Sequence of the F8 H6p* FMDV P1+3C gene cassette in pHM-1354-1, pF8 H6p* FMDV P1+3C

```
           G  T  S  K   Y  A  V    G  G  S    G  R  R    G  D  M    S  L  A
3481    GGGACGAGTA AGTATGCTGT GGGTGGTTCA GGCAGAAGAG GCGACATGGG GTCTCTCGCG

A  R  V  V   K  Q  L    P  A  S    F  N  Y    A  I  K    A  D  A
3541    GCGCGAGTCG TGAAACAGCT TCCTGCTTCA TTTAACTACG GTGCAATCAA GGCCGACGCC

I  H  E  L   L  V  R    M  K  R    A  E  L  Y    C  P  R    P  L  L
3601    ATCCACGAAC TTCTCGTGCG CATGAAACGG GCCGAGCTCT ACTGCCCCAG ACCGCTGTTG

A  I  E  V   S  S  Q    D  R  H    K  Q  K  I    A  P    A  K  Q
3661    GCAATAGAGG TGTCTTCGCA AGACAGGCAC AAGCAAAAGA TCATTGCACC AGCAAAGCAG
        ⇒ A24 2A                                                  A24 2B ⇒
           L  L  N   F  D  L  L    K  L  A    G  D  V  E    S  N  P    G  P  F
3721    CTTCTGAATT TTGACCTGCT CAAGTTGGCC GGAGACGTTG AGTCCAACCC CGGGCCATTC

F  F  A  D   V  R  S    N  F  S    K  L  V  D    T  I  N    Q  M  Q
3781    TTCTTTGCTG ACGTTAGGTC AAACTTTTCA AAGTTGGTAG ACACAATCAA CCAGATGCAG

E  D  M  S   T  K  H    G  P  D    F  N  R  L    V  S  A    F  E  E
3841    GAGGACATGT CCACAAAACA CGGGCCCGAC TTCAACCGGT TGGTGTCCGC ATTTGAGGAA

L  A  T  G   V  K  A    I  R  T    G  L  D  E    A  K  P    W  Y  K
3901    TTGGCCACTG GAGTTAAAGC TATCAGGACC GGTCTCGACG AGGCCAAACC CTGGTACAAG

L  I  K  L   L  S  R    L  S  C    M  A  A  V    A  A  R    S  K  D
3961    CTTATCAAAC TCCTAAGCCG CCTGTCGTGC ATGGCCGCTG TGGCAGCACG GTCCAAGGAC
                                                           A24/A12 junction ⇒ A12 3B
           P  V  L  V   A  I  M    L  A  D    T  G  L  E    R  Q  R    P  L  K
4021    CCAGTCCTTG TGGCCATCAT GCTGGCCGAC ACCGGTCTCG AGCGTCAGAG ACCTCTGAAA V  R  A  K   L  P  Q    Q  E  G    P  Y  A  G    P  L  E    R  Q  K
4081    GTGAGAGCTA AGCTCCCACA GCAGGAAGGA CCTTACGCTG GCCCGTTGGA GAGACAGAAA P  L  K  V   K  A  K    A  P  V    V  K  E  G    P  Y  E    G  P  V
4141    CCGCTGAAAG TGAAAGCAAA AGCCCCGGTC GTCAAGGAAG GACCTTACGA GGGACCGGTG ⇒ A12 3C
           K  K  P  V   A  L  K    V  K  A    K  N  L  I    V  T  E    S  G  A
4201    AAGAAGCCTG TCGCTTTGAA AGTGAAAGCT AAGAACTTGA TAGTCACTGA GAGTGGTGCC P  P  T  D   L  Q  K    M  V  M    G  N  T  K    P  V  E    L  I  L
4261    CCACCGACCG ACTTGCAAAA GATGGTCATG GGCAACACAA AGCCTGTTGA GCTCATCCTT D  G  K  T   V  A  I    C  C  A    T  G  V  F    G  T  A    Y  L  V
4321    GACGGGAAGA CAGTAGCCAT CTGTTGTGCT ACTGGAGTGT TTGGCACTGC TTACCTCGTG P  R  H  L   F  A  E    K  Y  D    K  I  M  L    D  G  R    A  M  T
4381    CCTCGTCATC TTTTCGCAGA GAAGTATGAC AAGATCATGC TGGATGGCAG AGCCATGACA D  S  D  Y   R  V  F    E  F  E    I  K  V  K    G  Q  D    M  L  S
4441    GACAGTGACT ACAGAGTGTT TGAGTTTGAG ATTAAAGTAA AAGGACAGGA CATGCTCTCA
```

Fig 29E
Sequence of the F8 H6p* FMDV P1+3C gene cassette in pHM-1354-1, pF8 H6p* FMDV P1+3C

```
           D  A  A  L     M  V  L     H  R  G     N  R  V     R  D  I  T     K  H  F
4501     GACGCTGCGC TCATGGTGCT CCACCGTGGG AACCGCGTGA GAGATATCAC GAAACACTTT

R  D  T  A     R  M  K     K  G  T     P  V  V     G  V  V        N  A  D
4561     CGTGATACAG CAAGAATGAA GAAAGGCACC CCCGTCGTCG GTGTGGTCAA CAACGCCGAC

V  G  R  L     I  F  S     G  E  A     L  T  Y     K  D  I        V  C  M
4621     GTTGGGAGAC TGATTTTCTC TGGTGAGGCC CTCACCTACA AGGATATTGT AGTGTGCATG

D  G  D        T  M  P     G  L  F  A     Y  K  A     A  T  K     A  G  Y  C
4681     GACGGAGACA CCATGCCTGG CCTCTTTGCC TACAAAGCCG CCACCAAGGC AGGCTACTGT

G  G  A        L  A  K     D  G  A     D  T  F     I  V  G        T  H  S  A
4741     GGAGGAGCCG TTCTCGCCAA GGACGGGGCC GACACTTTCA TCGTCGGCAC TCACTCCGCA
           G  G  N        G  V  G     Y  C  S     C  V  S  R     S  M  L     L  R  M  K
4801     GGAGGCAATG GAGTTGGATA CTGCTCATGC GTTTCCAGGT CCATGCTTCT CAGAATGAAG

A  H  V     D  P  E  P     Q  H  E
4861     GCACACGTTG ACCCTGAACC ACAACACGAG TAGTAATTTT TCTAGAGGAT CCCTCGAGTT

⇒ F8L
4921     TTTATTGACT AGTTAATCAT AAGATAAATA ATATACAGCA TTGTAACCAT CGTCATCCGT

4981     TATACGGGGA ATAATATTAC CATACAGTAT TATTAAATTT CTTACGAAG  AATATAGATC

5041     GGTATTTATC GTTAGTTTAT TTACATTTA  TTAATTAAAC ATGTCTACTA TTACCTGTTA

5101     TGGAAATGAC AAATTTAGTT ATATAATTTA TGATAAAATT AAGATAATAA TAATGAAATC

5161     AAATAATTAT GTAAATGCTA CTAGATTATG TGAATTACGA GGAAGAAAGT TTACGAACTG

5221     GAAAAAATTA AGTGAATCTA AAATATTAGT CGATAATGTA AAAAAAATAA ATGATAAAAC

5281     TAACCAGTTA AAAACGGATA TGATTATATA CGTTAAGGAT ATTGATCATA AAGGAAGAGA

5341     TACTTGCGGT TACTATGTAC ACCAAGATCT GGTATCTTCT ATATCAAATT GGATATCTCC

5401     GTTATTCGCC GTTAAGGTAA ATAAAATTAT TAACTATTAT ATATGTAATG AATATGATAT

5461     ACGACTTAGC GAAATGGAAT CTGATATGAC AGAAGTAATA GATGTAGTTG ATAAATTAGT

5521     AGGAGGATAC AATGATGAAA TAGCAGAAAT AATATATTTG TTTAATAAAT TTATAGAAAA

5581     ATATATTGCT AACATATCGT TATCAACTGA ATTATCTAGT ATATTAAATA ATTTTATAAA

5641     TTTTAATAAA AAATACAATA ACGACATAAA AGATATTAAA TCTTTAATTC TTGATCTGAA

5701     AAACACATCT ATAAAACTAG ATAAAAAGTT ATTCGATAAA GATAATAATG AATCGAACGA

5761     TGAAAAATTG GAAACAGAAG TTGATAAGCT AATTTTTTC  ATCTAAATAG TATTATTTTA

5821     TTGAAGTACG AAGTTTTACG TTAGATAAAT AATAAAGGTC GATTTTTATT TTGTTAAATA
```

Fig 29F
Sequence of the F8 H6p* FMDV P1+3C gene cassette in pHM-1354-1, pF8 H6p* FMDV P1+3C

```
5881   TCAAATATGT CATTATCTGA TAAAGATACA AAAACACACG GTGATTATCA ACCATCTAAC

5941   GAACAGATAT TACAAAAAAT ACGTCGGACT ATGGAAAACG AAGCTGATAG CCTCAATAGA

6001   AGAAGCATTA AAGAAATTGT TGTAGATGTT ATGAAGAATT GGGATCATCC TCTCAACGAA

6061   GAAATAGATA AAGTTCTAAA CTGGAAAAAT GATACATTAA ACGATTTAGA TCATCTAAAT

6121   ACAGATGATA ATATTAAGGA AATCATACAA TGTCTGATTA GAGAATTTGC GTTTAAAAAG

6181   ATCAATTCTA TTATGTATAG TTATGCTATG GTAAAACTCA ATTCAGATAA CGAAACATTG

6241   AAAGATAAAA TTAAGGATTA TTTTATAGAA ACTATTCTTA AGACAAACG TGGTTATAAA

6301   CAAAAGCCAT TACCC
```

Fig 30
Immunoblot analysis of ALVAC recombinants expressing FMDV P1+3C genes 1 2 3 4 5 6 7 8 9 10 11 12 13 14

VP0 →
VP1, VP3 →

- 81.2 kDa
- 60.7 kDa
- 47.4 kDa
- 36.1 kDa
- 25.3 kDa
- 19.0 kDa

Lane 1: ALVAC pellet
Lane 3: vCP2181 pellet
Lane 4: vCP2181 pellet
Lane 5: vCP2186 pellet
Lane 7: Invitrogen Benchmark markers
Lane 8: BioRad Kaleidoscope markers
Lane 9: ALVAC supernatant
Lane 11: vCP2181 supernatant
Lane 12: vCP2181 supernatant
Lane 13: vCP2186 supernatant

AVIPOX RECOMBINANTS EXPRESSING FOOT AND MOUTH DISEASE VIRUS GENES

CROSS-REFERENCE TO RELATED APPLICATIONS

This application claims priority to provisional U.S. application Ser. No. 60/563,786 filed on Jun. 25, 2004.

This application makes reference to U.S. application Ser. No. 10/327,481, filed on Dec. 20, 2002, which is a continuation of International application No. PCT/FR01/02042, filed on Jun. 27, 2001, published on Jan. 3, 2002 as WO 02/00251, and claiming priority to French application No. 00/08437, filed on Jun. 29, 2000.

All of the foregoing applications, as well as all documents cited in the foregoing applications ("application documents") and all documents cited or referenced in the application documents are incorporated herein by reference. Also, all documents cited in this application ("herein-cited documents") and all documents cited or referenced in herein-cited documents are incorporated herein by reference. In addition, any manufacturer's instructions or catalogues for any products cited or mentioned in each of the application documents or herein-cited documents are incorporated by reference. Documents incorporated by reference into this text or any teachings therein can be used in the practice of the invention. Documents incorporated by reference into this text are not admitted to be prior art.

FIELD OF THE INVENTION

The present invention relates to vectors, such as viruses, e.g., modified viruses such as poxviruses, and to methods of making and using the same. In particular, the invention relates to recombinant avipox vectors and viruses that express antigens of foot and mouth disease virus (FMDV), and to methods of making and using the same. The invention further relates to methods of eliciting an immune response to FMDV in a subject.

BACKGROUND OF THE INVENTION

Foot-and-mouth disease (FMD) is one of the most virulent and contagious diseases affecting farm animals. This disease is endemic in numerous countries in the world, especially in Africa, Asia and South America. In addition, epidemic outbreaks can occur periodically. The presence of this disease in a country may have very severe economic consequences resulting from loss of productivity, loss of weight and milk production in infected herds, and from trade embargoes imposed on these countries. The measures taken against this disease consist of strict application of import restrictions, hygiene controls and quarantine, slaughtering sick animals and vaccination programs using inactivated vaccines, either as a preventive measure at the national or regional level, or periodically when an epidemic outbreak occurs.

FMD is characterized by its short incubation period, its highly contagious nature, the formation of ulcers in the mouth and on the feet and sometimes, the death of young animals. FMD affects a number of animal species, in particular cattle, pigs, sheep and goats. The agent responsible for this disease is a ribonucleic acid (RNA) virus belonging to the *Aphthovirus* genus of the Picornaviridae family (Cooper et al., Intervirology, 1978, 10, 165-180). At present, at least seven types of foot-and-mouth disease virus (FMDV) are known: the European types (A, O and C), the African types (SAT1, SAT2 and SAT3) and an Asiatic type (Asia 1). Numerous sub-types have also been distinguished (Kleid et al. Science (1981), 214, 1125-1129).

FMDV is a naked icosahedral virus of about 25 nm in diameter, containing a single-stranded RNA molecule consisting of about 8500 nucleotides, with a positive polarity. This RNA molecule comprises a single open reading frame (ORF), encoding a single polyprotein containing, inter alia, the capsid precursor also known as protein P1 or P88. The protein P1 is myristylated at its amino-terminal end. During the maturation process, the protein P1 is cleaved by the protease 3C into three proteins known as VP0, VP1 and VP3 (or 1AB, 1D and 1C respectively; Belsham G. J., Progress in Biophysics and Molecular Biology, 1993, 60, 241-261). In the virion, the protein VP0 is then cleaved into two proteins, VP4 and VP2 (or 1A and 1B respectively). The mechanism for the conversion of the proteins VP0 into VP1 and VP3, and for the formation of mature virions is not known. The proteins VP1, VP2 and VP3 have a molecular weight of about 26,000 Da, while the protein VP4 is smaller at about 8,000 Da.

The simple combination of the capsid proteins forms the protomer or 5S molecule, which is the elementary constituent of the FMDV capsid. This protomer is then complexed into a pentamer to form the 12S molecule. The virion results from the encapsidation of a genomic RNA molecule by assembly of twelve 12S pentamers, thus constituting the 146S particles. The viral capsid may also be formed without the presence of an RNA molecule inside it (hereinafter "empty capsid"). The empty capsid is also designated as particle 70S. The formation of empty capsids may occur naturally during viral replication or may be produced artificially by chemical treatment.

Many hypotheses, research routes, and proposals have been developed in an attempt to design effective vaccines against FMD. Currently, the only vaccines on the market comprise inactivated virus. Concerns about safety of the FMDV vaccine exist, as outbreaks of FMD in Europe have been associated with shortcomings in vaccine manufacture (King, A.M. Q. et al, (1981) Nature 293: 479-480). The inactivated vaccines do not confer long-term immunity, thus requiring booster injections given every year, or more often in the event of epidemic outbreaks. In addition, there are risks linked to incomplete inactivation and/or to the escape of virus during the production of inactivated vaccines (King, A.M.Q., ibid). A goal in the art has been to construct conformationally correct immunogens lacking the infective FMDV genome to make effective and safe vaccines.

Vaccinia virus has been used successfully to immunize against smallpox, culminating in the worldwide eradication of smallpox in 1980. Thus, a new role for poxviruses became important, that of a genetically engineered vector for the expression of foreign genes (Panicali and Paoletti, 1982; Paoletti et al., 1984). Genes encoding heterologous antigens have been expressed in vaccinia, often resulting in protective immunity against challenge by the corresponding pathogen (reviewed in Tartaglia et al., 1990). A highly attenuated strain of vaccines, designated MVA, has also been used as a vector for poxvirus-based vaccines. Use of MVA is described in U.S. Pat. No. 5,185,146.

Additional vaccine vector systems involve the use of avipox viruses, which are naturally host-restricted poxviruses. Both fowlpoxvirus (FPV; Taylor et al. 1988a, b) and canarypoxvirus (CPV; Taylor et al., 1991 & 1992) have been engineered to express foreign gene products. Fowlpox virus (FPV) is the prototypic virus of the Avipox genus of the Poxvirus family. The virus causes an economically important disease of poultry that has been well controlled since the 1920's by the use of live attenuated vaccines. Replication of the avipox viruses is limited to avian species (Matthews, 1982) and there are no reports in the literature of avipox virus causing a productive infection in any non-avian species including man. This host restriction provides an inherent safety barrier against transmission of the virus to other species and makes the use of avipox virus based vaccine vectors in veterinary and human applications an attractive proposition.

Other attenuated poxvirus vectors have been prepared by genetic modifications of wild type strains of virus. The NYVAC vector, derived by deletion of specific virulence and host-range genes from the Copenhagen strain of vaccinia (Tartaglia et al., 1992) has proven useful as a recombinant vector in eliciting a protective immune response against an expressed foreign antigen. Another engineered poxvirus vector is ALVAC, derived from canarypox virus (see U.S. Pat. No. 5,756,103). ALVAC does not productively replicate in non-avian hosts, a characteristic thought to improve its safety profile (Taylor et al., 1991 & 1992). ALVAC was deposited under the terms of the Budapest Treaty with the American Type Culture Collection under accession number VR-2547. Yet another engineered poxvirus vector is TROVAC, derived from fowlpox virus (see U.S. Pat. No. 5,766,599).

Recombinant poxviruses can be constructed in two steps known in the art and analogous to the methods for creating synthetic recombinants of poxviruses such as the vaccinia virus and avipox virus described in U.S. Pat. Nos. 4,769,330; 4,722,848; 4,603,112; 5,110,587; 5,174,993; 5,494,807; and 5,505,941, the disclosures of which are incorporated herein by reference. It can thus be appreciated that provision of a FMDV recombinant poxvirus, and of compositions and products therefrom, particularly ALVAC or TROVAC-based FMDV recombinants and compositions and products therefrom, especially such recombinants containing the P1 genes and/or C3 protease gene of FMDV, and compositions and products therefrom, would be a highly desirable advance over the current state of technology.

SUMMARY OF THE INVENTION

Accordingly, one aspect of the present invention provides a recombinant avipox vector comprising at least one nucleic acid molecule encoding one or more foot-and-mouth disease virus (FMDV) antigen(s). In advantageous embodiments, the avipox is ALVAC or TROVAC.

Advantageously, the FMDV antigen(s) can be VP1, VP2, VP3, VP4, 2A, 2B or 3C. Advantageously, the nucleic acid molecule encoding one or more foot-and-mouth disease virus (FMDV) antigen(s) is a cDNA encoding FMDV P1 region and a cDNA encoding FMDV 3C protease of FMDV.

In one embodiment, the FMDV antigens are operably linked to a promoter sequence, which can be the H6 vaccinia promoter, I3L vaccinia promoter, 42K vaccinia promoter, 7.5K vaccinia promoter, or Pi vaccinia promoter. In another embodiment, the promoter is the H6 vaccinia promoter, which is mutated such that the expression levels of the FMDV antigens are decreased compared with expression levels of the FMDV antigens under a wild type (i.e. unmutated) H6 vaccinia promoter.

In another embodiment, the avipox vector of the present invention comprises a C6 insertion locus, wherein flanking sequences of the C6 insertion locus promote homologous recombination of the FMDV antigens with the C6 insertion locus. Advantageously, the flanking sequences comprise the C6L and C6R open reading frames of canarypox.

In a further embodiment, the avipox vector of the present invention comprises a F8 insertion locus, wherein the flanking sequences of the F8 insertion locus promote homologous recombination of the FMDV antigens with the F8 insertion locus. Advantageously, the flanking sequences comprise the F8L and F8R open reading frames of fowlpox.

A second aspect of the present invention provides a recombinant avipox virus, comprising at least one nucleic acid molecule encoding one or more FMDV antigens. The present invention also provides recombinant avipox viruses vCP2186, vCP2181, vCP2176, and vFP2215.

A further aspect of the invention relates to a method of eliciting an immune response to FMDV in a subject, comprising administering the avipox vector or avipox virus of the present invention to the subject.

In yet another aspect of the present invention, a method of producing a recombinant avipox vector comprising at least one nucleic acid molecule encoding one or more FMDV antigen(s), comprising the steps of: a) linearizing a donor plasmid with a restriction endonuclease, wherein the donor plasmid comprises restriction endonuclease cleavage sites or a multiple cloning site; and b) ligating at least one nucleic acid molecule comprising (i) a nucleic acid sequence encoding one or more FMDV antigen(s), (ii) a viral promoter sequence, and (iii) insertion sequences flanking (i) and (ii) that have complementary restriction endonuclease cleavage sites to the donor plasmid at FMDV antigens, thereby producing the recombinant avipox vector.

The method can further comprise the steps of c) introducing the vector into a cell permissive for replication of the vector; and d) isolating the vector from the cell. Advantageously, the cell permissive for replication of the vector is a chicken embryonic fibroblast.

In another embodiment, the vector further comprises a reporter gene, which is selected from the group consisting of the neomycin resistance gene, the ampicillin resistance gene, lacZ (β-galactosidase), luciferase, and green fluorescent protein (GFP).

These and other objects of the invention will be described in further detail in connection with the detailed description of the invention.

BRIEF DESCRIPTION OF THE DRAWINGS

The following Detailed Description, given by way of example, but not intended to limit the invention to specific embodiments described, may be understood in conjunction with the accompanying drawings, incorporated herein by reference. Various preferred features and embodiments of the present invention will now be described by way of non-limiting examples and with reference to the accompanying drawings in which:

FIG. 1 shows the genome of foot and mouth disease virus (FMDV) and the genes inserted into the avipox recombinants.

FIG. 2 shows the oligonucleotide primers used to PCR-amplify the H6p FMDV gene cassette (SEQ ID NO:1-3), and the amino acids encoded by the nucleotides (SEQ ID NO:4 and 5).

FIGS. 3A and 3B show the construction of a pC5 H6p FMDV P1+3C donor plasmid for generating ALVAC recombinants, with inserts at the C5 loci.

FIGS. 4A-4E show the nucleotide (SEQ ID NO:6) and amino acid sequences (SEQ ID NO:7) of the C5 H6p FMDV gene cassette of the pC5 H6p FMDV P1+3C donor plasmid.

FIGS. 5A and 5B show the construction of a pF8 H6p FMDV P1+3C donor plasmid for generating fowlpox recombinants, with the insert at the unique F8 locus.

FIGS. 6A-6F show the nucleotide (SEQ ID NO:8) and amino acid sequences (SEQ ID NO:9) of the F8 H6p FMDV gene cassette of the pF8 H6p FMDV P1+3C donor plasmid.

FIG. 7 shows the oligonucleotide primers used to PCR amplify the 3'-end of the FMDV gene cassette (SEQ ID NO:10-12), and the amino acids encoded by the nucleotides (SEQ ID NO:13 and 14).

FIG. 8 shows the construction of a promoter-less pC6 FMDV P1+3C insertion plasmid for introduction of different promoters.

FIGS. 9A and 9B show the construction of a pC6 H6p FMDV P1+3C donor plasmid for generating ALVAC recombinants, with the insert at the unique C6 locus.

FIGS. 10A-10E show the nucleotide (SEQ ID NO:15) and amino acid sequences (SEQ ID NO: 16) of the C6 H6p FMDV gene cassette of the pC6 H6p FMDV P1+3C donor plasmid.

FIG. 11 shows the nucleotide sequences of the wild-type early/late H6 promoter (H6p) (SEQ ID NO:17) and the mutant early H6 promoter (H6p*) (SEQ ID NO:18).

FIGS. 12A and 12B show the oligonucleotide primers used to amplify an H6p* 5'-FMDV fragment (SEQ ID NO: 19-23) and the amino acids encoded by the nucleotides (SEQ ID NO:24 and 25)

FIGS. 13A and 13B show the construction of a pC6 H6p* FMDV P1+3C donor plasmid for generating ALVAC recombinants, with the insert at the unique C6 locus.

FIGS. 14A-14E show the nucleotide (SEQ ID NO:26) and amino acid sequences (SEQ ID NO:27) of the C6 H6p* FMDV gene cassette of the pC6 H6p* FMDV P1+3C donor plasmid.

FIGS. 15A and 15B show the oligonucleotide primers used to amplify the I3Lp 5'-FMDV fragment (SEQ ID NOS:28-33), and the amino acids encoded by the nucleotides (SEQ ID NO:34 and 35).

FIGS. 16A and 16B show the construction of a pC6 I3Lp FMDV P1+3C donor plasmid for generating ALVAC recombinants, with the insert at the unique C6 locus.

FIGS. 17A-17E show the nucleotide (SEQ ID NO:36) and amino acid sequences (SEQ ID NO:37) of the C6 I3Lp FMDV gene cassettes of the pC6 I3Lp FMDV P1+3C donor plasmid.

FIGS. 18A and 18B show the oligonucleotide primers used to amplify the 42 Kp 5'-FMDV fragment (SEQ ID NO:38-43) and the amino acids encoded by the nucleotides (SEQ ID NO:44 and 45)

FIGS. 19A and 19B show the construction of a pC6 42 Kp FMDV P1+3C donor plasmid for generating ALVAC recombinants, with the insert at the unique C6 locus.

FIGS. 20A-20E show the nucleotide (SEQ ID NO:46) and amino acid sequences (SEQ ID NO:47) of the C6 42 Kp FMDV gene cassette of the pC6 42 Kp FMDV P1+3C donor plasmid.

FIGS. 21A-21C show the oligonucleotide primers used to amplify and repair the 7.5 Kp 5'-FMDV fragment (SEQ ID NO:48-54), and the amino acids encoded by the nucleotides (SEQ ID NO:55-57).

FIGS. 22A and 22B show the construction of a pC6 7.5K FMDV P1+3C donor plasmid for generating ALVAC recombinants, with the insert at the unique C6 locus.

FIGS. 23A-23E shows the nucleotide (SEQ ID NO:58) and amino acid sequences (SEQ ID NO:59) of the C6 7.5 Kp FMDV gene cassette of the pC6 7.5 Kp FMDV P1+3C donor plasmid.

FIGS. 24A-24E show the oligonucleotide primers used to amplify and repair the Pip 5'-FMDV fragment (SEQ ID NO:60-77), and the amino acids encoded by the nucleotides (SEQ ID NO:78-80).

FIGS. 25A and 25B show the construction of a pC6 Pip FMDV P1+3C donor plasmid for generating ALVAC recombinants, with the insert at the unique C6 locus.

FIGS. 26A-26E show the nucleotide (SEQ ID NO:81) and amino acid sequences (SEQ ID NO:82) of the C6 Pip FMDV gene cassette of the pC6 Pip FMDV P1+3C donor plasmid.

FIG. 27 describes the oligonucleotide primers used to PCR amplify an H6p* 5'-FMDV fragment for insertion into a pF8 donor plasmid (SEQ ID NO:83-86).

FIGS. 28A and 28B illustrate the construction of a pF8 H6p* FMDV P1+3C donor plasmid for generating fowlpox recombinants.

FIGS. 29A-29F depict the nucleotide (SEQ ID NO:87) and amino acid (SEQ ID NO:88) sequences of the F8 H6p* FMDV P1+3C gene cassette of the pF8 H6p* FMDV P1+3C donor plasmid.

FIG. 30 shows the expression analysis of ALVAC recombinants containing the FMDV P1+3C gene cassette under the 13L or 42K promoters.

DETAILED DESCRIPTION OF THE INVENTION

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As used herein, the term "operably linked" means that the components described are in a relationship permitting them to function in their intended manner.

An "antigen" is a substance that is recognized by the immune system and induces an immune response. A similar term used in this context is "immunogen".

It is therefore an object of this invention to provide compositions and methods for treatment and prophylaxis of infection with FMDV. It is also an object to provide a means to treat or prevent foot and mouth disease.

In one aspect, the present invention relates to a modified recombinant avipox vector expressing at least one nucleic acid sequences encoding for one or more FMDV antigens. The viral vector according to the present invention is advantageously an avipox virus, such as fowlpox virus and canarypox virus and more particularly, ALVAC or TROVAC. The modified recombinant vector comprises a heterologous nucleic acid sequence, which encodes an antigenic protein, e.g., derived from FMDV ORFs that are encoded by the P1 (comprising VP1, VP2, VP3, VP4, and 2A), 2B, and/or 3C regions.

In another aspect, the present invention relates to a modified recombinant avipox virus that includes, in a non-essential region of the virus genome, at least one heterologous nucleic acid sequence that encodes one or more antigens from FMDV, such as gene products of the P1 gene (comprising VP1, VP2, VP3, VP4, 2A), 2B, and/or 3C.

In a still further aspect, the present invention relates to methods of eliciting an immune response to FMDV in a subject, comprising administering the recombinant avipox vector of the present invention. The present invention also relates to methods of eliciting an immune response to FMDV in a subject, comprising administering the recombinant avipox virus of the present invention. Advantageously, the avipox virus is selected from the group consisting of vCP2186, vCP2181, vCP2176, and vFP2215.

The virus used according to the present invention is advantageously a poxvirus, particularly an avipox virus, such as fowlpox virus or canarypox virus. TROVAC refers to an attenuated fowlpox that was a plaque-cloned isolate derived from the FP-1 vaccine strain of fowlpoxvirus that is licensed for vaccination of 1-day-old chicks. ALVAC is an attenuated canarypox virus-based vector that was a plaque-cloned derivative of the licensed canarypox vaccine, Kanapox (Tartaglia et al., 1992). ALVAC-based recombinant viruses expressing extrinsic immunogens have also been demonstrated efficacious as vaccine vectors (Tartaglia et al., 1993 a,b). This avipox vector is restricted to avian species for productive replication. On human cell cultures, canarypox virus replication is aborted early in the viral replication cycle prior to viral DNA synthesis. Nevertheless, when engineered to express extrinsic immunogens, authentic expression and processing is observed in vitro in mammalian cells and inoculation into numerous mammalian species induces antibody and cellular immune responses to the extrinsic immunogen and provides protection against challenge with the cognate pathogen (Taylor et al., 1992; Taylor et al., 1991).

ALVAC and TROVAC have also been recognized as unique among avipoxviruses in that the National Institutes of Health ("NIH"; U.S. Public Health Service), Recombinant DNA Advisory Committee, which issues guidelines for the physical containment of genetic material such as viruses and vectors, i.e., guidelines for safety procedures for the use of such viruses and vectors, which are based upon the pathogenicity of the particular virus or vector, granted a reduction in physical containment level: from BSL2 to BSL1. No other avipoxvirus has a BSL1 physical containment level. Even the Copenhagen strain of vaccinia virus—the common smallpox vaccine—has a higher physical containment level; namely, BSL2. Accordingly, the art has recognized that ALVAC and TROVAC have a lower pathogenicity than other avipox viruses.

Advantageously, the avipox virus vector is an ALVAC or a canarypox virus (Rentschler vaccine strain), which was attenuated through 200 or more serial passages on chick embryo fibroblasts, after which a master seed therefrom was subjected to four successive plaque purifications under agar, from which a clone was amplified through five additional passages. The avipox virus vector can also be a fowlpox virus, or an attenuated fowlpox virus such as TROVAC.

The invention further relates to the product of expression of the inventive recombinant avipox virus and uses therefor, such as to form antigenic, immunological or vaccine compositions for treatment, prevention, diagnosis or testing; and, to DNA from the recombinant avipox virus which are useful in constructing DNA probes and PCR primers.

In one aspect, the present invention relates to recombinant avipox viruses containing at least one nucleic acid sequence expressing one or more antigens from FMDV, advantageously in a non-essential region of the avipox virus genome. The avipox virus can be a fowlpox virus, especially an attenuated fowlpox virus such as TROVAC, or a canarypox virus, especially an attenuated canarypox virus, such as ALVAC.

According to the present invention, the recombinant avipox virus and avipox viral vectors express at least one nucleic acid sequence encoding one or more FMDV antigens. In particular, any or all genes or open reading frames (ORFs) encoding FMDV antigens can be isolated, characterized and inserted into ALVAC recombinants. The resulting recombinant avipox virus is used to infect an animal. Expression in the animal of FMDV antigens results in an immune response in the animal to FMDV. Thus, the recombinant avipox virus of the present invention may be used in an immunological composition or vaccine to provide a means to induce an immune response, which may, but need not be, protective. The molecular biology techniques used are described by Sambrook et al. (1989).

The invention also contemplates FMDV antigens that can be delivered as a naked DNA plasmid or vector, or DNA vaccine or immunological or immunogenic compositions comprising nucleic acid molecules encoding and expressing in vivo an FMDV antigen(s).

The FMDV antigen of interest can be obtained from FMDV or can be obtained from in vitro and/or in vivo recombinant expression of FMDV gene(s) or portions thereof. The FMDV antigen of interest can also be provided using synthetic FMDV sequences. The FMDV antigen of interest can be, but are not limited to: $L_b$, $L_{ab}$, P1-2A (comprising VP1, VP2, VP3, VP4, and 2A); P2 (comprising 2B and 2C), and P3 (comprising 3A, 3B, VPg, 3C, and 3D), or portions thereof. In an advantageous embodiment, the FMDV antigens are P1 and 3C. In a particularly preferred embodiment, the FMDV antigens are P1-2A or P1-2A, 2B. Reference is made herein to U.S. patent application Ser. No. 10/327,481, relating to isolation of FMDV genome sequences, the contents of which are incorporated by reference.

Non-essential regions have been defined in the art (Johnson et al., (1993) Virology 196: 381-401) for vaccinia virus. These sites, also referred to herein as "insertion loci", are described in U.S. Pat. Nos. 6,340,462, and 5,756,103 for ALVAC, the contents of which are incorporated herein by reference, and include, but are not limited to, thymidine kinase (TK), hemagglutinin (HA), M2L, C6, and other loci. In one embodiment, where canarypox is used, the insertion locus is C6. In another embodiment, where fowlpox is used, the insertion locus is F8.

Insertion of nucleic acid sequences encoding FMDV antigens can be facilitated by homologous recombination, wherein the FMDV sequence of interest is flanked by sequences corresponding to avipox viral open reading frames immediately adjacent to the insertion locus (hereinafter referred to as "flanking sequences" or "insertion sequences"). Homologous recombination is facilitated by recognition of homologous flanking sequences, which promotes integration of the FMDV sequences into the insertion locus of interest. By way of example, insertion of FMDV sequences into the C6 locus requires the presence of the C6L and C6R ORFs on either side of the nucleic acid sequence encoding the FMDV antigen of interest in the viral vector. Thus, advantageously the insertion loci is C6 and the flanking sequences comprise C6L and C6R. Where the F8 insertion locus is used, the flanking sequences comprise F8L and F8R.

The recombinant viral vectors of the invention expressing FMDV antigens can be replicated or produced in cells or cell lines, or in vivo in a host or subject. One alternative embodiment consists of replicating the vector in cells permissive for replication of the vector.

It must be noted that avipox viruses can only productively replicate in or be passaged through avian species or avian cell lines such as, for example, chicken embryonic fibroblasts or QT35. The recombinant avipox viruses harvested from avian host cells, when inoculated into a non-avian vertebrate, such as a mammal, in a manner analogous to the inoculation of mammals by vaccinia virus, without productive replication of the avipox virus. Despite the failure of the avipox virus to productively replicate in such an inoculated non-avian vertebrate, sufficient expression of the virus occurs so that the inoculated animal responds immunologically to the antigenic determinants of the recombinant avipox virus and also to the antigenic determinants encoded in exogenous genes therein. Thus, in an advantageous embodiment, when avipox viruses or viral vectors are used, chicken embryonic fibroblasts or QT35 are preferred as the cells permissive for viral vector replication.

The recombinant viral vectors and recombinant viruses can contain promoters that are operably linked to the FMDV antigens of the present invention. The promoter is advantageously of poxviral origin and advantageously early or early-late promoters, which may be, in particular, the promoter P11K of the vaccinia virus, 13L poxviral promoter, 42K poxviral promoter, H6 poxviral promoter, Pi poxviral promoter, P28K of the vaccinia virus, P160K ATI of the cowpox virus. In particular, the sequence driving the early transcription of an early-late promoter can be used instead of the full-length promoter (Moss, B. (1990) Ann. Rev. Biochem. 59: 661-688; Mars, M. et al, (1987) J. Mol. Biol. 198: 619-631; Davison, A. et al (1989) J. Mol. Biol. 210: 749-769; Vassef, A. (1987) Nucl. Acid. Res. 15: 1427-1443). The promoter is advantageously a weak promoter. The terms "strong promoter" and "weak promoter" are known in the art and are defined by the relative frequency of transcription initiation (times per minute) at the promoter.

The invention also provides for poxviral promoters that are mutated. The present inventors have found that expression of certain FMDV antigens is not possible from strong poxviral promoters. Without being bound by theory, it is believed that high levels of expression of potentially toxic FMDV antigens can preclude formation of stable poxviral recombinants. Therefore, the present invention also comprehends the use of a mutated poxviral promoter, such as, for example, a mutated H6 promoter, such that the expression levels of the FMDV antigens are decreased compared with expression levels of the FMDV antigens under a wild type promoter (Davison, A. et al (1989) J. Mol. Biol. 210: 749-769). The mutated H6 promoter of the instant invention can be considered a weak promoter.

The mutated H6 promoter taught herein contains a point mutation. The invention can also employ promoters other than H6, which contain point mutations that reduce their frequency of transcription initiation compared with the wild type promoter. In addition, other types of mutated promoters are suitable for use in the instant invention. For example, U.S. application Ser. No. 10/679,520, incorporated herein by reference, describes a truncated form of the H6 promoter (see also Davison, A. et al (1989) J. Mol. Biol. 210: 749-769; Taylor J. et al., Vaccine, 1988, 6, 504-508; Guo P. et al. J. Virol., 1989, 63, 4189-4198; Perkus M. et al., J. Virol., 1989, 63, 3829-3836).

The present invention also relates to a method of producing a recombinant avipox vector comprising FMDV antigens, comprising the steps of linearizing a donor plasmid with a restriction endonuclease, wherein the donor plasmid comprises restriction endonuclease cleavage sites or a multiple cloning site, and ligating at least one nucleic acid sequence comprising (i) a nucleic acid sequence encoding one or more FMDV antigen(s), (ii) a viral promoter sequence, and (iii) insertion sequences flanking (i) and (ii) that have complementary restriction endonuclease cleavage sites to the donor plasmid at FMDV antigens, thereby producing the recombinant avipox vector. Advantageously, the method further comprises the steps of introducing the vector into a cell permissive for replication of the vector, and isolating the vector from the cell.

By definition, a donor plasmid expression vector (or donor plasmid) includes a DNA transcription unit comprising a polynucleotide sequence containing the cDNA to be expressed and the elements necessary for its expression in vivo. The donor plasmid can also include a poxviral early termination signal at the 3' terminus of the foreign gene (Moss, B. (1990) Ann. Rev. Biochem. 59: 661-688). The circular, super-coiled or uncoiled plasmid form is preferred. The linear form also comes under the scope of this invention.

Methods for making and/or using vectors (or recombinants) for expression and uses of expression products and products therefrom (such as antibodies) can be by or analogous to the methods disclosed in herein cited documents and documents referenced or cited in herein cited documents. See, for example, Sambrook et al. *Molecular Cloning* (1999). The invention also includes the use of the avipox vectors expressing FMDV antigens in the research setting. The recombinant avipox vectors and recombinant avipox viruses can be used to transfect or infect cells or cell lines of interest to study, for example, cellular responses to FMDV antigens, or signal transduction pathways mediated by FMDV antigens.

In the research setting, it is often advantageous to design recombinant vectors or viruses that comprise reporter genes that can be easily detected by laboratory assays and techniques. Reporter genes are well known in the art and can comprise resistance genes to antibiotics such as, but not limited to, ampicillin, neomycin, zeocin, kanamycin, bleomycin, hygromycin, chloramphenicol, among others. Reporter genes can also comprise green fluorescent protein, the lacZ gene (which encodes β-galactosidase), luciferase, and β-glucuronidase.

The invention also relates to a method of eliciting an immune response against foot-and-mouth disease in a subject comprising administering the recombinant avipox vectors or recombinant avipox viruses according to the present invention to the subject. The subject can be any animal which can become infected with FMDV, in particular, bovine, ovine, porcine or caprine species. Methods of administration and doses are defined herein.

The recombinant avipox vectors and viruses expressing FMDV antigens or an expression product thereof, immunological, antigenic or vaccine compositions or therapeutic compositions, can be administered via a parenteral route (intradermal, intramuscular or subcutaneous). Such an administration enables a systemic immune response, or humoral or cell-mediated responses.

As used herein, the terms "immunogenic composition" and "immunological composition" and "immunogenic or immunological composition" cover any composition that elicits an immune response against the targeted FMDV antigen; for instance, after administration of injection into the animal, elicits an immune response against the targeted FMDV antigen. The terms "vaccinal composition" and "vaccine" and "vaccine composition" covers any composition that induces a protective immune response against the FMDV antigen or which efficaciously protects against the antigen after administration or injection into the animal. The invention also comprehends recombinant avipox viral vectors administered as a plasmid DNA vector or vaccine.

More generally, the inventive recombinant avipox viral vectors and recombinant avipox viruses expressing FMDV antigens, antigenic, immunogenic, immunological or vaccine avipox virus-FMDV compositions or therapeutic compositions, can be prepared in accordance with standard techniques well known to those skilled in the pharmaceutical or veterinary arts. Such compositions can be administered in dosages and by techniques well known to those skilled in the medical or veterinary arts taking into consideration such factors as the age, sex, weight, species and condition of the particular patient, and the route of administration.

The compositions can be administered alone, or can be co-administered or sequentially administered with compositions, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages can be determined taking into consideration such factors as the age, sex, weight, species and condition of the particular subject, and the route of administration. In this regard, reference is made to U.S. Pat. No. 5,843,456, incorporated herein by reference, and directed to rabies compositions and combination compositions and uses thereof.

Examples of compositions of the invention include liquid preparations for orifice, or mucosal, e.g., oral, nasal, anal, vaginal, peroral, intragastric, etc., administration such as suspensions, solutions, sprays, syrups or elixirs; and, preparations for parenteral, subcutaneous, intradermal, intramuscular or intravenous administration (e.g., injectable administration) such as sterile suspensions or emulsions. In such compositions, the recombinant avipox virus or recombinant avipox viral vectors may be in admixture with a suitable carrier, diluent, or excipient such as sterile water, physiological saline, glucose or the like. The compositions can also be lyophilized. The compositions can contain auxiliary substances, such as wetting or emulsifying agents, pH buffering agents, adjuvants, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions in forms for various administration routes are envisioned by the invention. And again, the effective dosage and route of administration are determined by known factors, such as age, sex, weight, condition and nature of the animal, as well as $LD_{50}$ and other screening procedures which are known and do not require undue experimentation. Dosages of each active agent can be as in herein cited documents (or documents referenced or cited in herein cited documents) and/or can range from one or a few to a few hundred or thousand micrograms, e.g., 1 µg to 1 mg, for an immunogenic, immunological or vaccine composition; and, $10^4$ to $10^{10}$ $TCID_{50}$ advantageously $10^6$ to $10^8$ $TCID_{50}$ for an immunogenic, immunological or vaccine composition.

Recombinants or vectors can be administered in a suitable amount to obtain in vivo expression corresponding to the dosages described herein and/or in herein cited documents. For instance, suitable ranges for viral suspensions can be determined empirically. The viral vector or recombinant in the invention can be administered to an animal or infected or transfected into cells in an amount of about at least $10^3$ pfu; more advantageously about $10^4$ pfu to about $10^{10}$ pfu, e.g., about $10^5$ pfu to about $10^9$ pfu, for instance about $10^6$ pfu to about $10^8$ pfu, with doses generally ranging from about $10^6$ to about $10^{10}$, advantageously about $10^8$ pfu/dose, and advantageously about $10^7$ pfu per dose of 2 ml. And, if more than one gene product is expressed by more than one recombinant, each recombinant can be administered in these amounts; or, each recombinant can be administered such that there is, in combination, a sum of recombinants comprising these amounts.

In vector or plasmid compositions employed in the invention, dosages can be as described in documents cited herein or as described herein or as in documents referenced or cited in herein cited documents. Advantageously, the dosage should be a sufficient amount of plasmid to elicit a response analogous to compositions wherein the antigen(s) of FMDV are directly present; or to have expression analogous to dosages in such compositions; or to have expression analogous to expression obtained in vivo by recombinant compositions. For instance, where DNA vaccines are administered, suitable quantities of each plasmid DNA in plasmid compositions can be 1 μg to 2 mg, advantageously 50 μg to 1 mg. Documents cited herein (or documents cited or referenced in herein cited documents) regarding DNA plasmid vectors may be consulted by the skilled artisan to ascertain other suitable dosages for DNA plasmid vector compositions of the invention, without undue experimentation.

However, the dosage of the composition(s), concentration of components therein and timing of administering the composition(s), which elicit a suitable immunological response, can be determined by methods such as by antibody titrations of sera, e.g., by ELISA and/or seroneutralization assay analysis. Such determinations do not require undue experimentation from the knowledge of the skilled artisan, this disclosure and the documents cited herein. And, the time for sequential administrations can be likewise ascertained with methods ascertainable from this disclosure, and the knowledge in the art, without undue experimentation.

The immunogenic or immunological compositions contemplated by the invention can also contain an adjuvant. Particularly suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one ore more non-methylated CpG units (Klinman D. M. et al., Proc. Natl. Acad. Sci., USA, 1996, 93, 2879-2883; WO98/16247), (3) an oil in water emulsion, such as the SPT emulsion described on p 147 of "Vaccine Design, The Subunit and Adjuvant Approach" published by M. Powell, M. Newman, Plenum Press 1995, and the emulsion MF59 described on p 183 of the same work, (4) cationic lipids containing a quaternary ammonium salt, (5) cytokines, (6) aluminum hydroxide or aluminum phosphate or (7) other adjuvants discussed in any document cited and incorporated by reference into the instant application, or (8) any combinations or mixtures thereof. The DNA vaccines or immunogenic or immunological compositions encompassed by the invention can be formulated with a liposome, in the presence or absence of an adjuvant as described above.

Other suitable adjuvants include fMLP (N-formyl-methionyl-leucyl-phenylalanine; U.S. Pat. No. 6,017,537) and/or acrylic acid or methacrylic acid polymer and/or a copolymer of maleic anhydride and of alkenyl derivative. The acrylic acid or methacrylic acid polymers can be cross-linked, e.g., with polyalkenyl ethers of sugars or of polyalcohols. These compounds are known under the term "carbomer" (*Pharmeuropa*, Vol. 8, No. 2, June 1996). A person skilled in the art may also refer to U.S. Pat. No. 2,909,462 (incorporated by reference), which discusses such acrylic polymers cross-linked with a polyhydroxylated compound containing at least 3 hydroxyl groups: in one embodiment, a polyhydroxylated compound contains not more than 8 hydroxyl groups; in another embodiment, the hydrogen atoms of at least 3 hydroxyls are replaced with unsaturated aliphatic radicals containing at least 2 carbon atoms; in other embodiments, radicals contain from about 2 to about 4 carbon atoms, e.g., vinyls, allyls and other ethylenically unsaturated groups. The unsaturated radicals can themselves contain other substituents, such as methyl. The products sold under the name Carbopol® (Noveon Inc., Ohio, USA) are particularly suitable for use as an adjuvant. They are cross-linked with an allyl sucrose or with allylpentaerythritol, as to which, mention is made of the products Carbopol® 974P, 934P, and 971P.

As to the copolymers of maleic anhydride and of alkenyl derivative, mention is made of the EMA® products (Monsanto), which are copolymers of maleic anhydride and of ethylene, which may be linear or cross-linked, for example cross-linked with divinyl ether. Also, reference may be made to J. Fields et al., Nature 186:778-780, 1960 (incorporated by reference).

With regard to structure, the acrylic or methacrylic acid polymers and EMA are advantageously formed by basic units having the following formula:

$$----\underset{COOH}{\underset{|}{C}}-(CH_2)_{x}-\underset{COOH}{\underset{|}{C}}-(CH_2)_{y}----$$
$$\phantom{----}\overset{R_1}{\phantom{C}}\phantom{-(CH_2)_{x}-}\overset{R_2}{\phantom{C}}$$

in which:

$R_1$ and $R_2$, which can be the same or different, represent H or $CH_3$ x=0 or 1, advantageously x=1 y=1 or 2, with x+y=2.

For EMA, x=0 and y=2 and for carbomers x=y=1.

These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final vaccine composition can range between 0.01 and 1.5% w/v, advantageously 0.05 to 1% w/v and advantageously 0.1 to 0.4% w/v.

The cationic lipids containing a quaternary ammonium salt which are advantageously but not exclusively suitable for plasmids, are advantageously those having the following formula:

$$R_1-O-CH_2-CH-CH_2-\overset{\overset{CH_3}{|}}{\underset{\underset{CH_3}{|}}{N^+}}-R_2-X$$
$$\phantom{R_1-O-CH_2-}\underset{OR_1}{|}$$

in which $R_1$ is a saturated or unsaturated straight-chain aliphatic radical having 12 to 18 carbon atoms, $R_2$ is another aliphatic radical containing 2 or 3 carbon atoms and X is an amine or hydroxyl group.

Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr J. P., 1994, Bioconjugate Chemistry, 5, 382-389), to form DMRIE-DOPE.

Advantageously, the plasmid mixture with the adjuvant is formed extemporaneously or contemporaneously with administration of the preparation or shortly before administration of the preparation; for instance, shortly before or prior to administration, the plasmid-adjuvant mixture is formed, advantageously so as to give enough time prior to administration for the mixture to form a complex, e.g. between about 10 and about 60 minutes prior to administration, such as approximately 30 minutes prior to administration.

When DOPE is present, the DMRIE:DOPE molar ratio is advantageously about 95: about 5 to about 5: about 95, more advantageously about 1: about 1, e.g., 1:1.

The DMRIE or DMRIE-DOPE adjuvant:plasmid weight ratio can be between about 50: about 1 and about 1: about 10, such as about 10: about 1 and about 1: about 5, and advantageously about 1: about 1 and about 1: about 2, e.g., 1:1 and 1:2.

A recombinant vaccine or immunogenic or immunological composition can also be formulated in the form of an oil-in-water emulsion. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri(caprylate/caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant can be a mixture of emulsifier(s), micelle-forming agent, and oil such as that which is available under the name Provax® (IDEC Pharmaceuticals, San Diego, Calif.).

The term "prime-boost" refers to the successive administrations of two different types of vaccine or immunogenic or immunological compositions having at least one antigen in common. The priming administration (priming) is the administration of a first vaccine or immunogenic or immunological composition type and may comprise one, two or more administrations. The boost administration is the administration of a second vaccine or immunogenic or immunological composition type and may comprise one, two or more administrations, and, for instance, may comprise or consist essentially of annual administrations.

Thus, the invention encompasses prime-boost immunization or vaccination method of an animal against at least one FMDV antigen comprising administering to the animal a priming DNA vaccine or immunological or immunogenic composition comprising nucleic acid molecule(s) encoding and expressing in vivo an antigen(s) from FMDV, and thereafter administering a boosting composition that comprises the FMDV antigen expressed by the DNA vaccine or immunogenic or immunological composition, or a recombinant or modified vector, e.g., virus, such as an avipox virus (such as ALVAC, canarypox, TROVAC, or fowlpox virus) that contains and expresses in an animal host cell a nucleotide sequence encoding the antigen of FMDV expressed by the DNA vaccine or immunogenic or immunological composition. The boosting vaccine or immunogenic or immunological composition can be the same as or different than the priming vaccine or immunogenic or immunological composition.

For instance, the boosting vaccine or immunogenic or immunological composition can be advantageously the FMDV antigen expressed by the DNA vaccine (or immunogenic or immunological composition) and/or a recombinant or modified avipox vector, e.g., virus, vaccine or immunogenic or immunological composition. A recombinant or modified vector is advantageously an in vivo expression vector, such as a modified or recombinant bacteria, yeast, virus, e.g. avipox virus, comprising nucleic acid molecule(s) encoding and expressing in vivo the antigen(s) from FMDV expressed by the DNA vaccine or immunogenic or immunological composition. The boost is advantageously performed with an inactivated vaccine or immunogenic or immunological composition, or with a vaccine or immunogenic or immunological composition comprising a recombinant live viral vector, such as a recombinant avipox virus, that comprises nucleic acid molecule(s) encoding and expressing in vivo the antigen(s) from the FMDV antigen expressed by the DNA vaccine or immunogenic or immunological composition. Thus, it is advantageous that the boost either comprises the antigen expressed by the DNA vaccine or immunogenic or immunological composition or expresses in vivo the same FMDV antigen expressed by the DNA vaccine or immunogenic or immunological composition. Advantageously, the boost comprises the recombinant avipox virus expressing FMDV antigens described herein.

Alternatively, the prime-boost immunization or vaccination method can comprise administering to the animal a priming vaccine comprising the recombinant avipox viruses of the present invention, and boosting thereafter with the DNA vaccine.

The DNA plasmid, or recombinant avipox vector expressing one or more nucleic acid sequences encoding at least one FMDV antigen, e.g., vector according to this disclosure, can be preserved and/or conserved and stored either in liquid form, at about 5° C., or in lyophilised or freeze-dried form, in the presence of a stabilizer. Freeze-drying can be according to well-known standard freeze-drying procedures. The pharmaceutically acceptable stabilizers may be SPGA (sucrose phosphate glutamate albumin; Bovarnik et al., *J. Bacteriology* 59:509, 1950), carbohydrates (e.g., sorbitol, mannitol, lactose, sucrose, glucose, dextran, trehalose), sodium glutamate (Tsvetkov T et al., *Cryobiology* 20(3): 318-23, 1983; Israeli E et al., *Cryobiology* 30(5): 519-23, 1993), proteins such as peptone, albumin or casein, protein containing agents such as skimmed milk (Mills C K et al., *Cryobiology* 25(2): 148-52, 1988; Wolff E et al., *Cryobiology* 27(5):569-75, 1990), and buffers (e.g., phosphate buffer, alkaline metal phosphate buffer). An adjuvant and/or a vehicle or excipient may be used to make soluble the freeze-dried preparations.

The invention will now be further described by way of the following non-limiting Examples, given by way of illustration.

EXAMPLES

Example 1

Construction of a pC5 H6p FMDV P1+3C Donor Plasmid for Introduction of FMDV Genes into the C5 Loci of ALVAC Plasmid pAd5-A24 was used as the donor plasmid to generate the adenovirus Ad5A24 recombinant. It is a ~39 kb plasmid containing the strain A24 P1 genes and the strain A12 3C protease. Several deletions of the FMDV genome were made for safety reasons and are indicated in FIG. 1.

Plasmid pAd5-A24 was digested with EcoRI and XbaI and the ~3.4 kb fragment containing the FMDV genes was inserted in pUC8:2 (pUC8 with BglII and XbaI sites added to the multiple cloning site). The resulting 6 kb pUC FMDV plasmid (designated pHM-1119-1) was used as the source of the FMDV genes in all future constructs.

The H6 promoter (H6p) is an early/late promoter derived from the vaccinia H6 gene (Perkus, M. E. et al, (1989) J. Virol. 63: 3829-3836), which is designated as the H5 gene in the Copenhagen vaccinia strain. The H6p is a strong promoter that has been used extensively in avipox recombinants for foreign gene expression.

Plasmid pHM-1119-1 was used as the template for PCR amplification with primers 11277. SL and 11282. SL. These primers introduced the 3'end of the vaccinia H6 promoter, as well as translation and transcription stop signals, and XbaI or BamHI restriction sites for cloning. The primer sequences are shown in FIG. 2. The 3.4 kb PCR product was cloned into pCR2.1 to generate plasmid pHM-1151-4, pCR2.1 H6p FMDV.

Figure 3A:
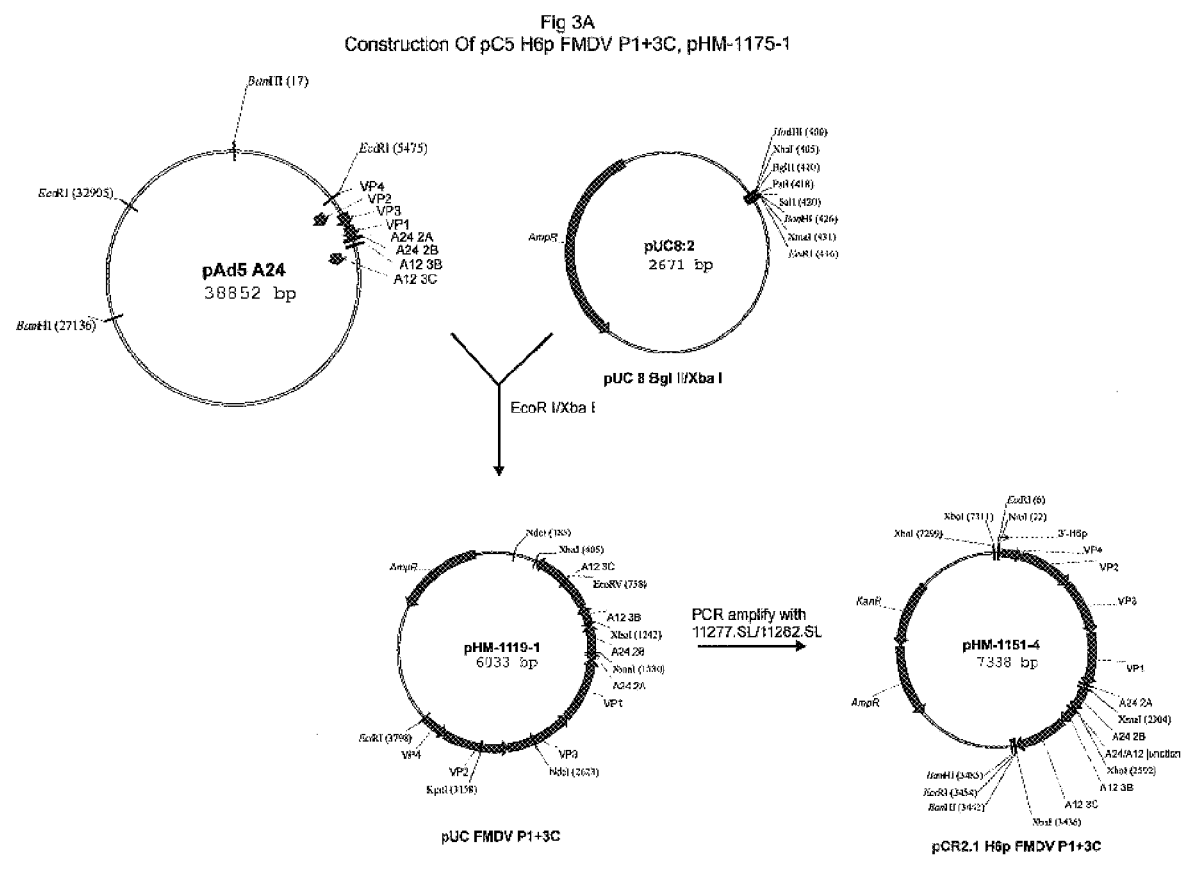
Figure 3B:
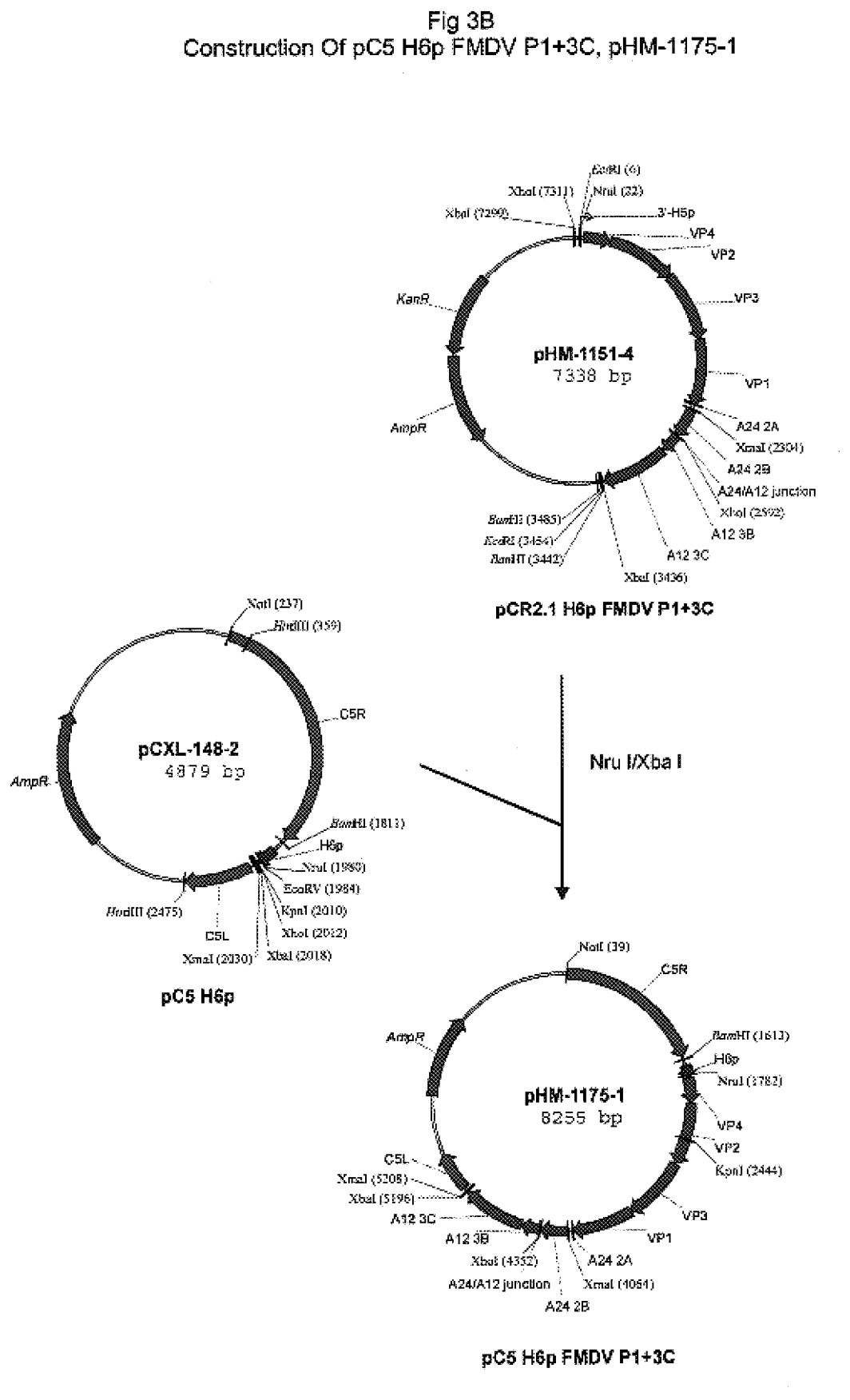

Plasmid pCXL-148-2 is an ALVAC insertion plasmid for the CS loci, which contains the vaccinia virus H6 promoter. The 3.4 kb NruI-XbaI fragment from pHM-1151-4 was inserted into pCXL-148-2, to generate pC5 H6p FMDV P1+3C (pHM-1175-1). The construction of pHM-1175-1 is illustrated in FIGS. 3A and 3B and the sequence of the C5 H6p FMDV gene cassette is shown in FIGS. 4A-4E.

Despite multiple attempts, no ALVAC recombinants were generated from pC5 H6p FMDV P1+3C, pHM-1175-1.

Example 2

Figure 5A:
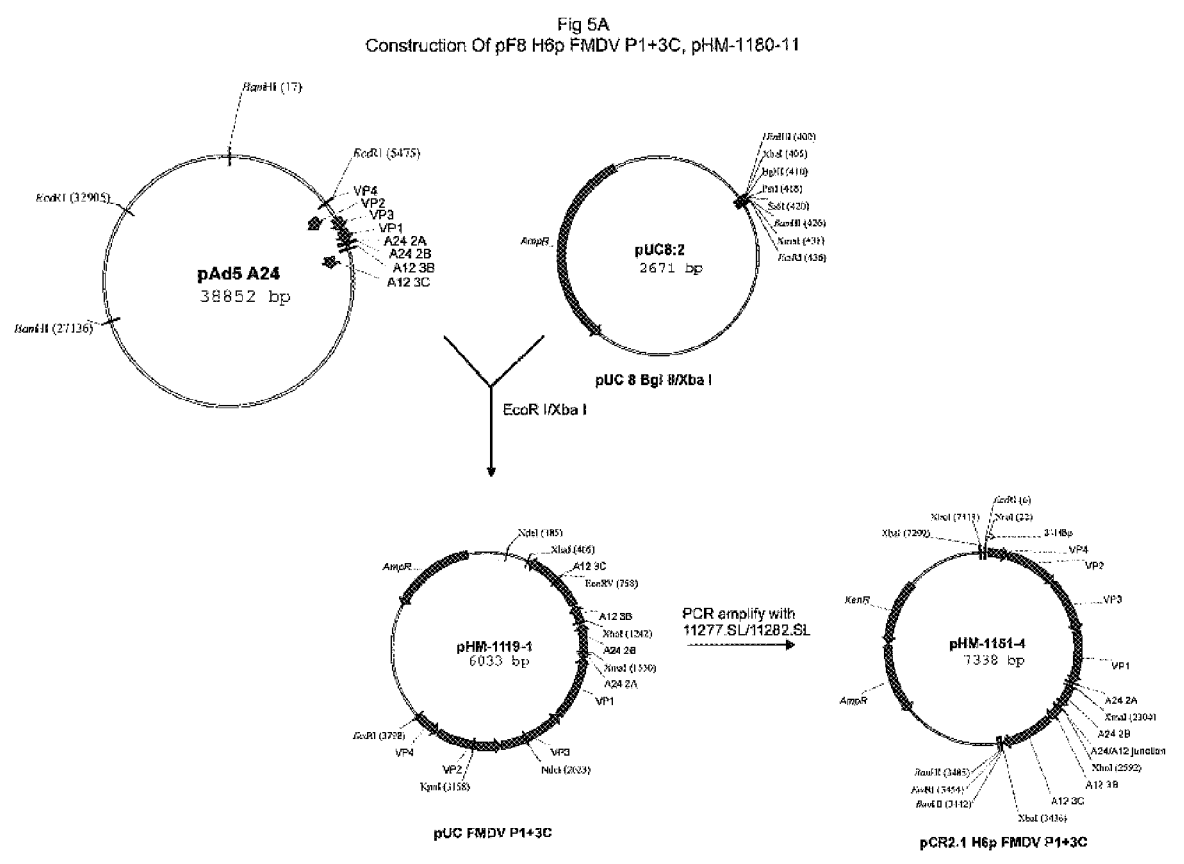
Figure 5B:
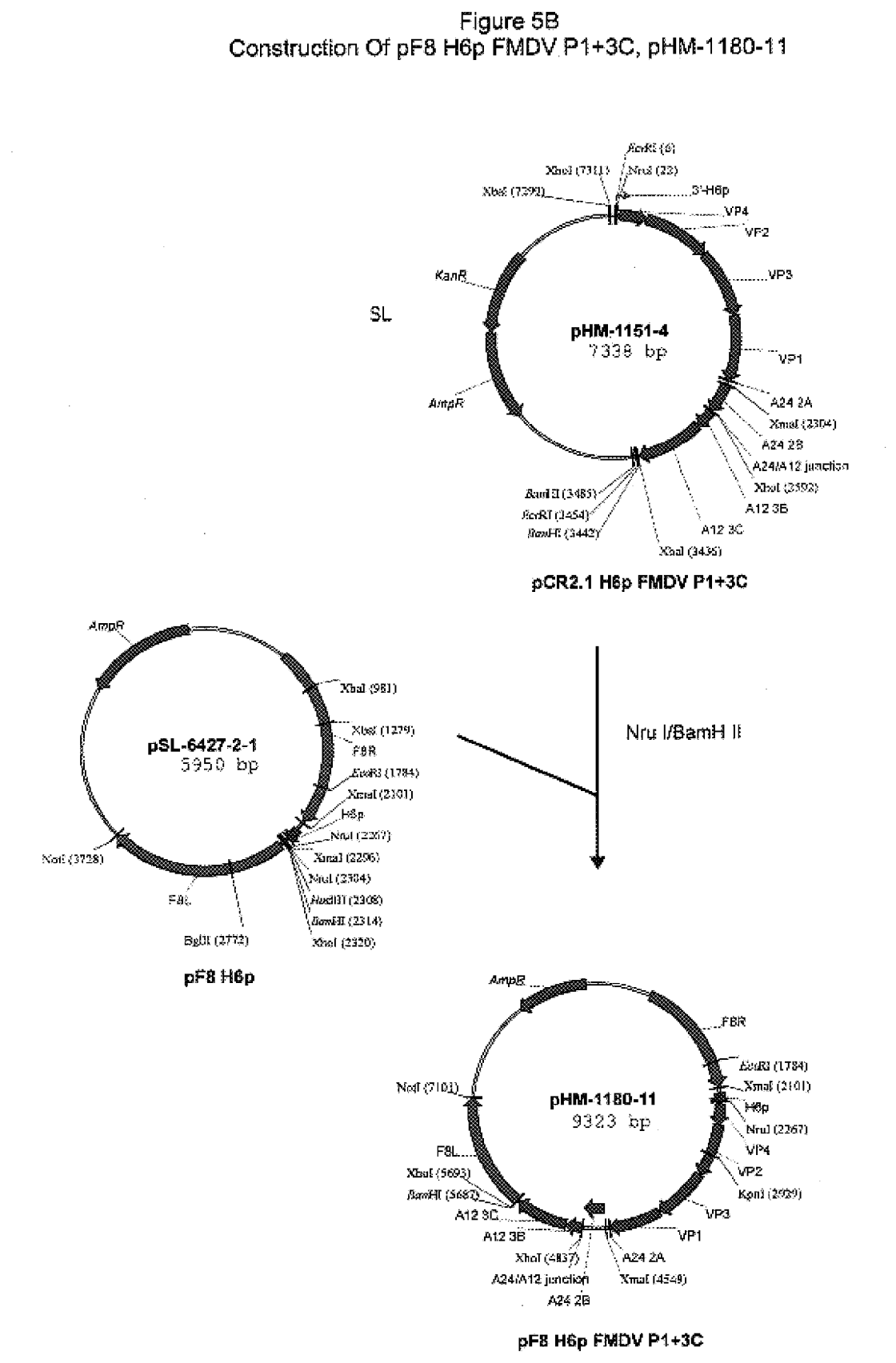

Construction of a pF8 H6p FMDV P1+3C Donor Plasmid for Introduction of FMDV Genes into the F8 Locus of Fowlpox Plasmid pSL-6427-2-1 (pF8 H6p) is a fowlpox insertion plasmid, which contains the vaccinia virus H6 promoter. The 3.4 kb NruI-BamHI fragment from pHM-1151-4 (pCR2.1 H6p FMDV; see Example 1) was inserted into pSL-6427-2-1, generating vector pHM-1180-11 (pF8 H6p FMDV P1+3C). The construction of pHM-1180-11 is illustrated in FIGS. 5A and 5B and the sequence of the F8 H6p FMDV gene cassette is shown in FIGS. 6A-6F.

Despite multiple attempts, no fowlpox recombinants could be generated from pF8 H6p FMDV P1+3C, pHM-1180-1.

Example 3

Construction of a Promoter-Less pC6 FMDV P1+3C Insertion Plasmid

The failure to generate avipox recombinants expressing FMDV genes could be due to to the use of the strong vaccinia virus H6 promoter in the pC5 H6p FMDV P1+3C and pF8 H6p FMDV P1+3C plasmids described in Examples 1 and 2. In addition, the ALVAC donor plasmid results in the insertion of gene cassettes at the two C5 loci. For ALVAC, different viral promoters and the unique C6 insertion locus was used.

Plasmid pHM-1119-1 (pUC FMDV, see Example 1) was used as the template for PCR amplification of a 3'-fragment of FMDV, with primers 11280. SL and 11352.CXL. The ~900 bp PCR fragment contains the 3'-end of FMDV from the XhoI site and introduces translational and transcriptional stops and a PstI cloning site. The primers are illustrated in FIG. 7. The PCR fragment was cloned into pCR2.1, generating plasmid pHM-1240-2, pCR2.1 3'-FMDV.

Figure 8:
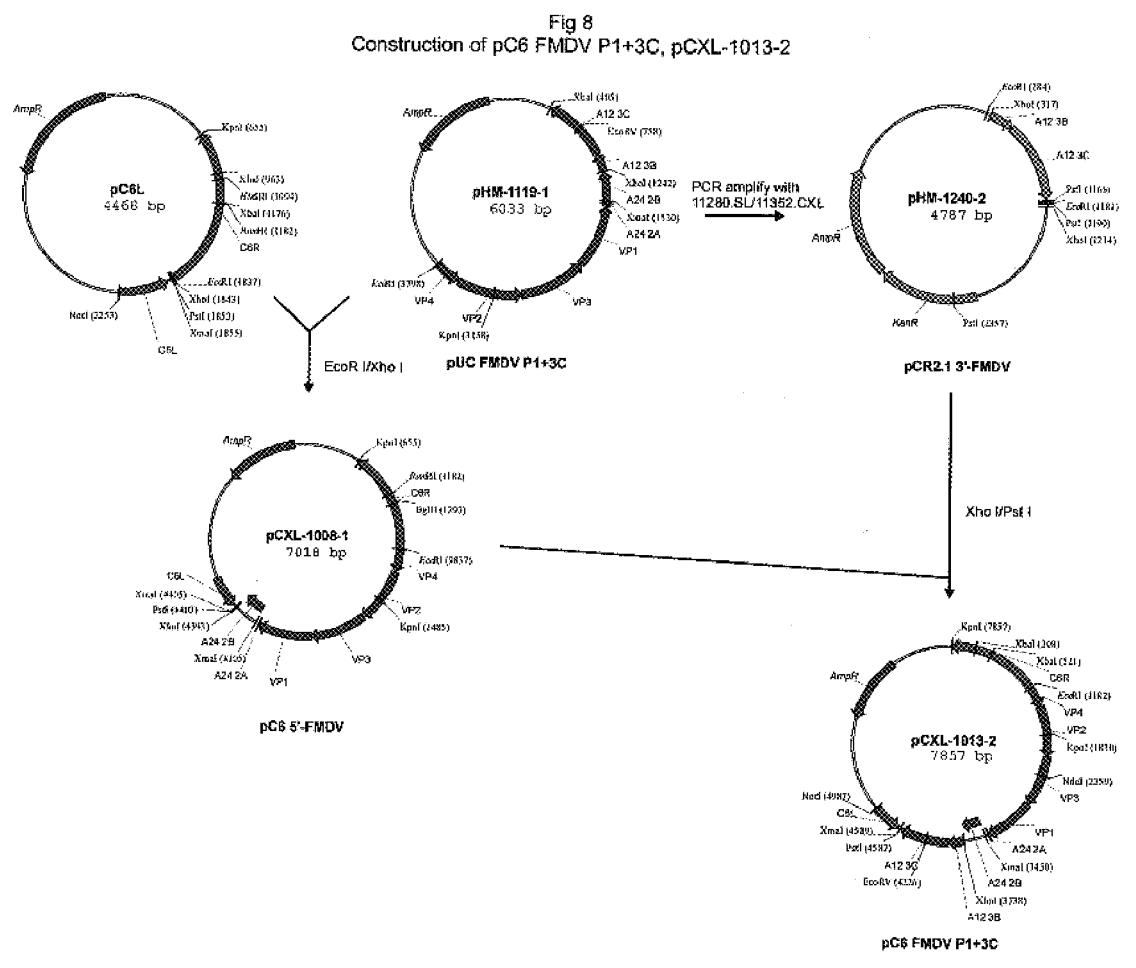

Plasmid pC6L is an ALVAC insertion plasmid for the unique ALVAC C6 site. The ~2.6 kb EcoRI-XhoI 5'-FMDV fragment from pHM-1119-1 was inserted into pC6L, generating plasmid pCXL-1008-1, pC6 5'-FMDV. The ~900 bp XhoI-PstI fragment from pHM-1240-2 was inserted into pCXL-1008-1, generating pCXL-1013-2, pC6 FMDV. The construction of pC6 FMDV is illustrated in FIG. 8.

17

Example 4

Construction of a pC6 H6p FMDV P1+3C Donor Plasmid for Insertion of the FMDV Gene Cassette at the Unique C6 Locus of ALVAC

Figure 9B:
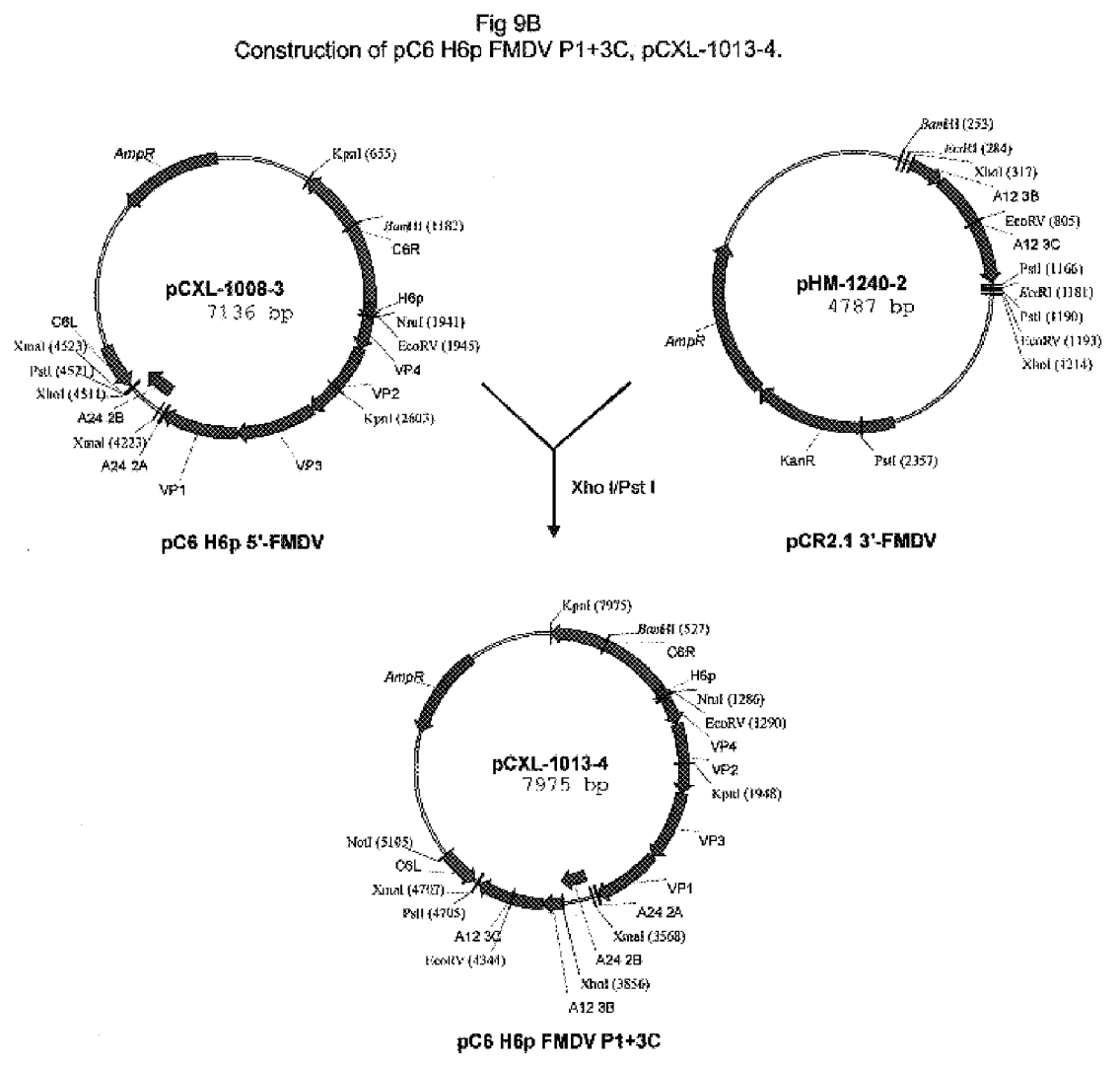

Plasmid pSL-6407-7 is a pC6 H6p insertion plasmid for the ALVAC C6 locus, which contains the vaccinia virus H6 promoter. The H6 promoter is in the opposite orientation to the C6 arms. The ~2.6 kb NruI-XhoI 5'-FMDV fragment from pHM-1151-4 (pCR2.1 FMDV, see Example 1) was inserted into pSL-6407-7, generating pC6 H6p 5'-FMDV, pCXL-1008-3. The ~900 bp XhoI-PstI 3'-FMDV fragment from pHM-1240-2 (pCR2.1 3'-FMDV, see Example 3) was inserted into pCXL-1008-3, generating pC6 H6p FMDV P1+3C, pCXL-1013-4. The construction of pC6 H6p FMDV P1+3C is illustrated in FIGS. 9A and 9B and the sequence of the C6 H6p FMDV gene cassette is shown in FIGS. 10A-10E.

Despite multiple attempts, ALVAC recombinants could not be generated using the pC6 H6p FMDV P1+3C donor plasmid, suggesting that insertion at a single site with a strong promoter was not feasible.

Example 5

**Construction of a pC6 H6p* FMDV P1+3C Donor Plasmid for Insertion of the FMDV Gene Cassette at the Unique C6 Locus of ALVAC**

Based upon studies with the vaccinia virus 7.5K early promoter (Davison, A. J. and Moss, B. (1989) J. Mol. Biol. 210: 749-769), a point mutation was introduced into the vaccinia virus H6 early promoter region, generating a mutant H6 promoter, H6p*. The wild-type early/late H6p and mutant early H6p* sequences are shown in FIG. 11.

Plasmid pHM-1119-1 (pUC FMDV, see Example 1) was used as the template to PCR amplify the H6p* 5'-FMDV fragment, with primers 11353.CXL and 11358.CXL. The ~1.2 kb fragment contained the H6p* and the 5'-FMDV genes up to a unique NdeI site. The fragment was cloned into pCR2.1, generating plasmid pHM-1249-1-3. This clone was missing a nucleotide in VP4, so site-directed mutagenesis was performed with primers 11410.HM and 11411.HM to repair the PCR error. Clone pHM-1260-2, pCR2.1 H6p* 5'-FMDV, was confirmed by sequence analysis. FIG. 12A describes the PCR amplification primers and FIG. 12B describes the mutagenesis primers.

Figure 13A:
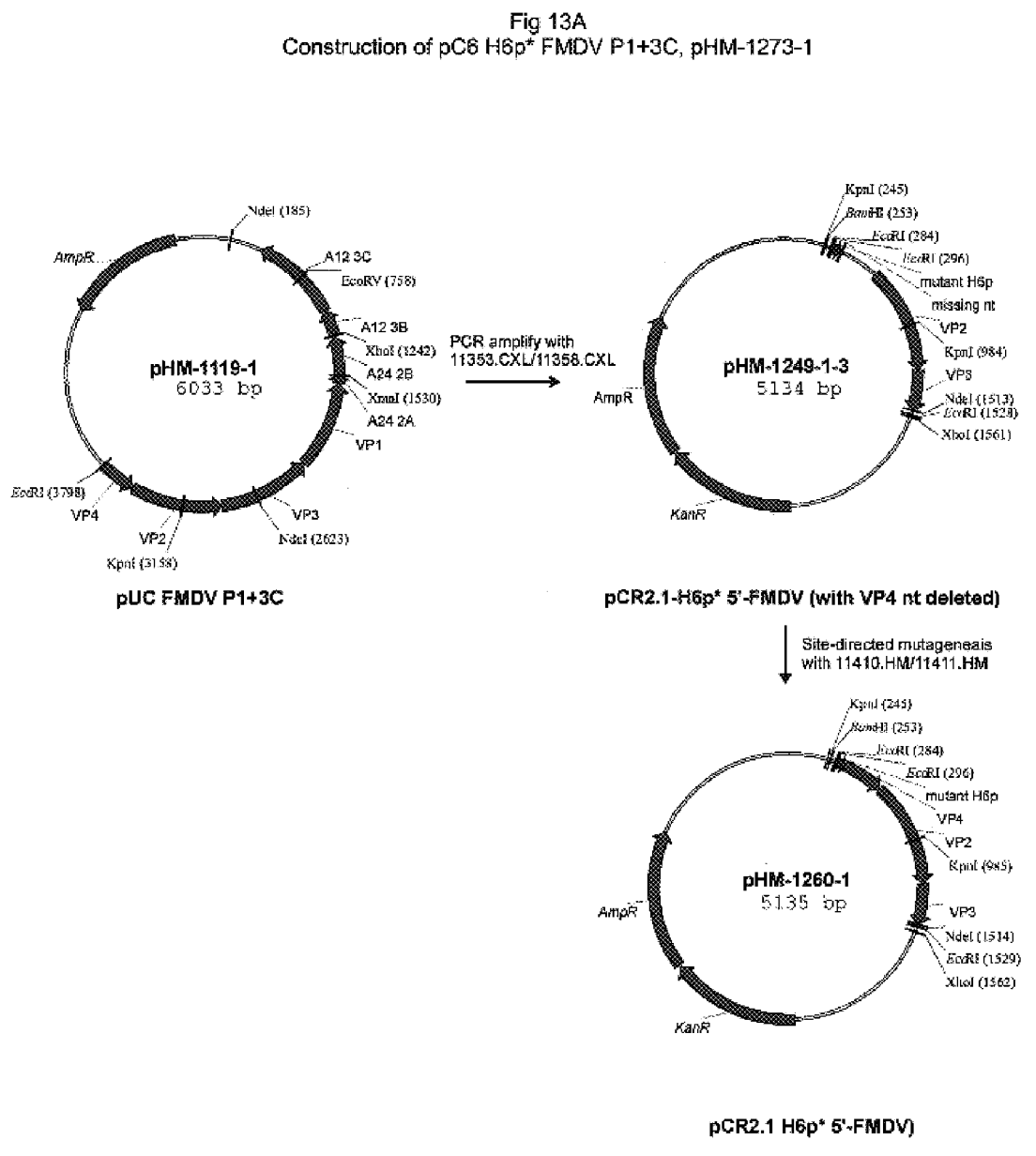
Figure 13B:
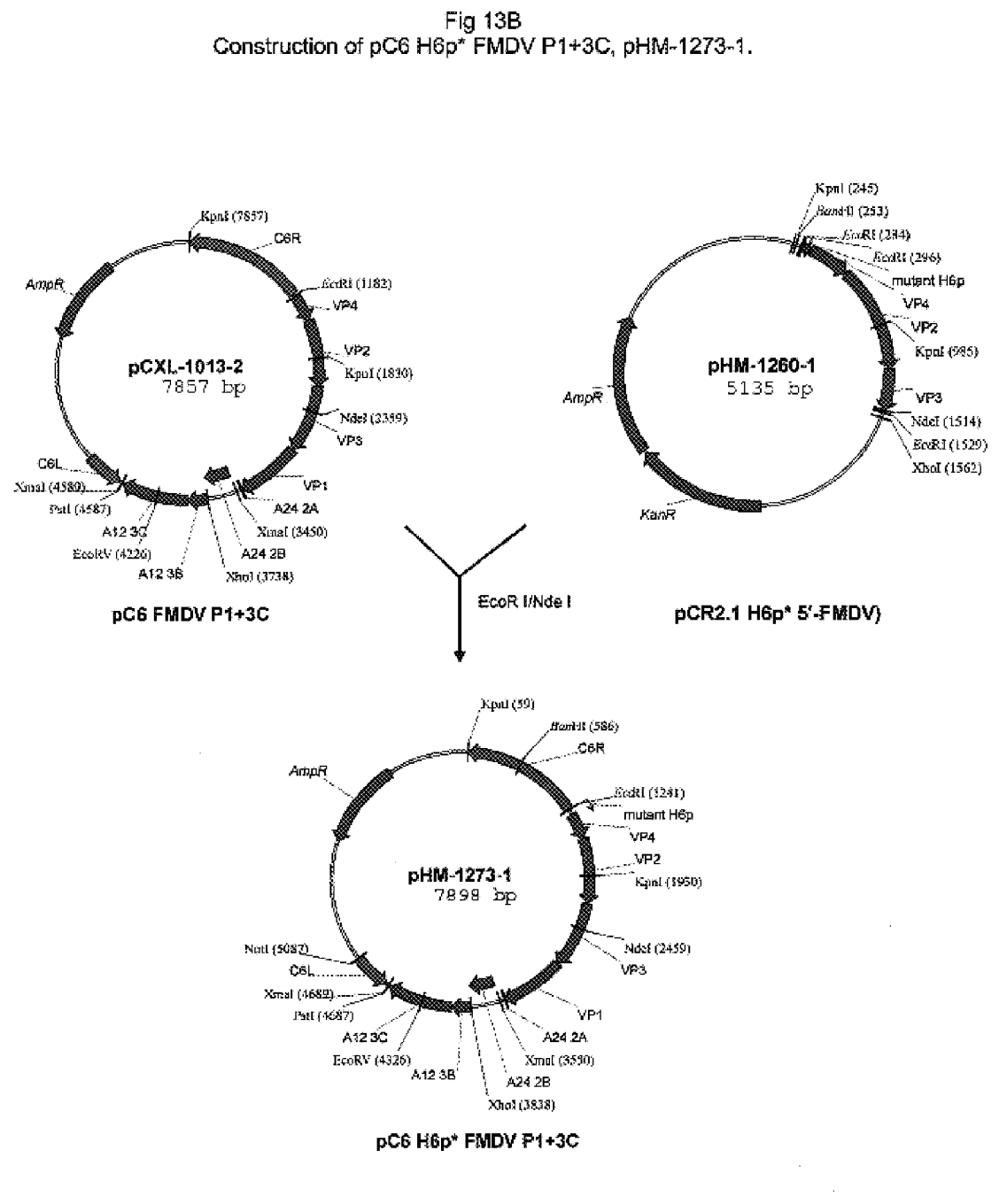

The ~1.2 kb EcoR I-Nde I H6p* 5'-FMDV fragment from pHM-1260-2 was inserted into pCXL-1013-2 (pC6 FMDV P1+3C, see Example 3), generating plasmid pHM-1273-1, pC6 H6p* FMDV P1+3C. The construction of pC6 H6p* FMDV P1+3C is illustrated in FIGS. 13A and 13B and the sequence of the C6 H6p* FMDV gene cassette is shown in FIGS. 14A-14E.

To generate an ALVAC recombinant, primary chicken embryonic fibroblasts (CEF) were transfected with SapI-linearized pHM-1273-1 donor plasmid, in the presence of FuGENE-6® reagent (Roche). The transfected cells were subsequently infected with ALVAC as rescue virus at an MOI of 10 and after 24 hours, the transfected-infected cells were harvested, sonicated, and used for recombinant virus screening. Recombinant plaques were screened based on the plaque lift hybridization method using a 1.7 kb FMDV-specific probe labeled with horseradish peroxidase (HRP) according to the manufacturer's protocol (Amersham). ALVAC recombinants were generated and designated as vCP2176.

18

Example 6

Construction of a pC6 I3Lp FMDV P1+3C Donor Plasmid for Introduction of the FMDV Genes into the Unique C6 Locus of ALVAC

The early/intermediate I3L promoter (I3Lp) from vaccinia virus (Schmitt, J. F. and Stunnenberg, H. G. (1988) J. Virol. 62: 1889-1897) has been used previously in avipox recombinants.

Plasmid pCXL-1-4 is pC5 H6p EHV-1 gB (-TM)/42 Kp EHV-1gD (-TM)/I3Lp EHV-1 gC (-TM), a donor plasmid used to introduce the EHV-1 gB, gC, and gD genes into ALVAC (described in U.S. Pat. No. 5,756,103). Each gene utilizes a different viral promoter, so pCXL-1-4 was used as the template to PCR amplify the 13 L promoter. Primers 11407.CXL and 11423.CXL were used to amplify a 75 bp fragment containing the I3L promoter and the 5'-end of the FMDV genes. The PCR primers are described in FIG. 15A.

A 648 bp PCR fragment, which contains a 20 bp overlap with the 75 bp I3Lp fragment, was amplified using primers 11425.CXL and 11407.CXL, with pHM-11119-1 (pUC FMDV, see Example 1) as template. This fragment contained the 5'-FMDV genes up to the unique KpnI site. The PCR primers are described in FIG. 15B.

The two PCR fragments were mixed at a 1:1 molar ratio and PCR amplified using primers 11423.CXL and 11407.CXL. The resultant 703 bp fragment was cloned into pCR2.1, generating pCXL-1068-1 (pCR2.1 I3Lp 5'-FMDV).

The ~700 bp EcoRI-KpnI I3Lp 5'-FMDV fragment from pCXL-1068-1 was inserted into pHM1119-1, generating pCXL-1072-2 (pUC I3Lp FMDV P1+3C).

Figure 16A:
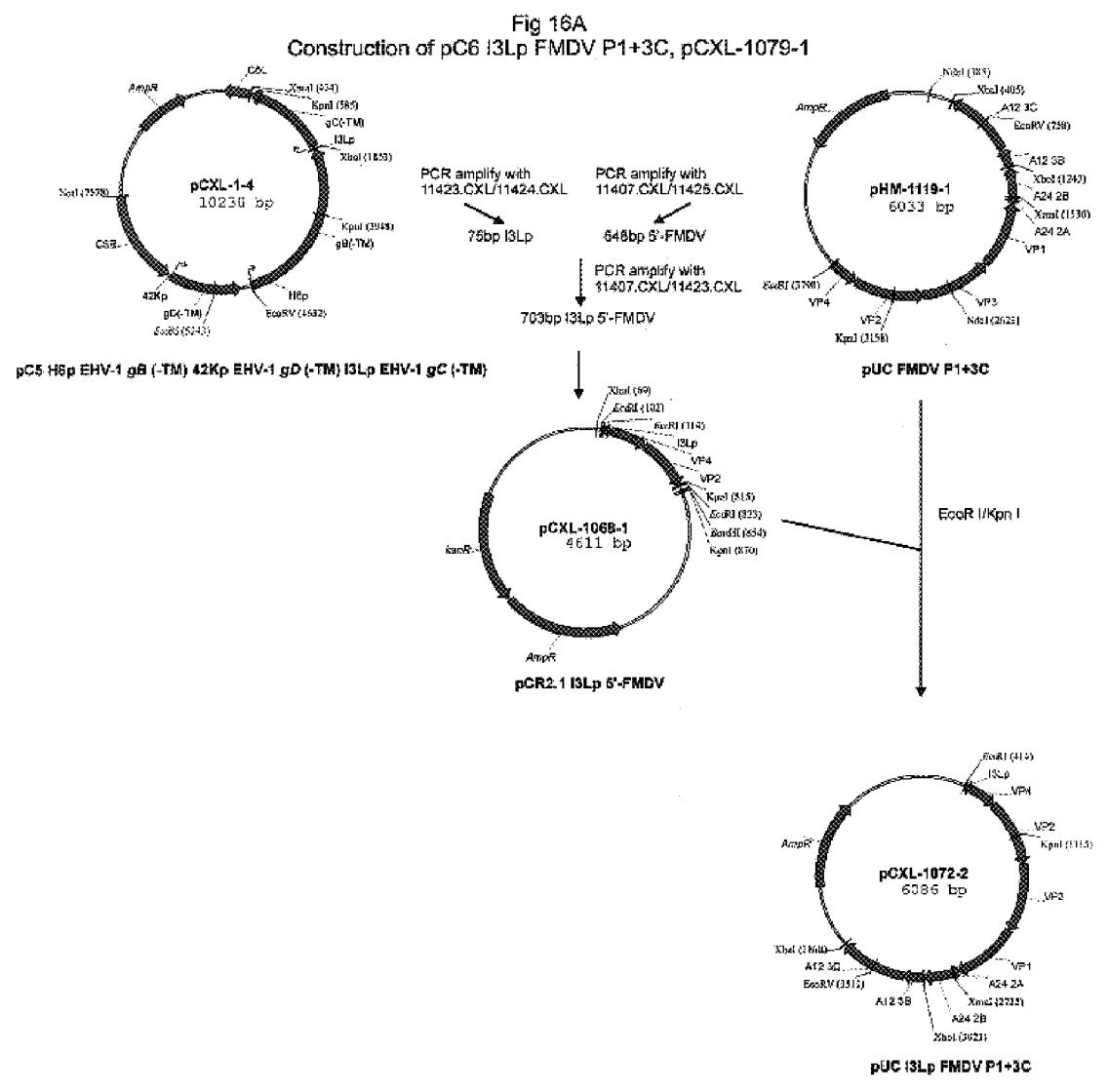
Figure 16B:
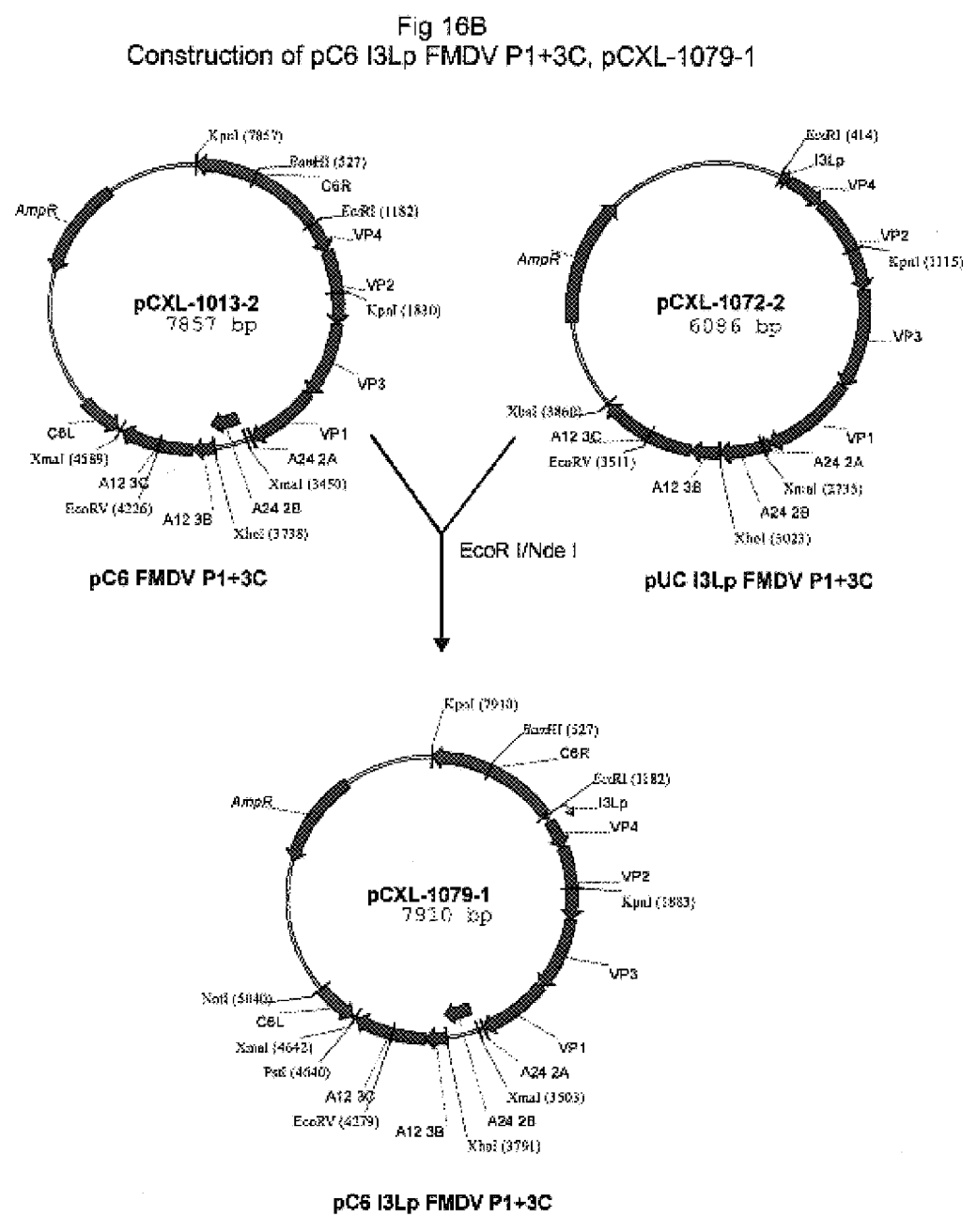

The ~1.2 kb EcoRI-NdeI I3 Lp 5'-FMDV fragment from pCXL-1072-2 was inserted into pCXL-1013-2 (pC6 FMDV P1+3C). The construction of pC6 I3Lp FMDV P1+3C is illustrated in FIGS. 16A and 16B and the sequence of the C6 I3Lp FMDV gene cassette is shown in FIGS. 17A-17E.

To generate an ALVAC recombinant, primary CEFs were transfected with 20 μg of SapI-linearized donor plasmid pCXL-1079-1 using FuGENE-6® reagent (Roche). The transfected cells were subsequently infected with ALVAC as rescue virus at an MOI of 10 and after 24 hours, the transfected-infected cells were harvested, sonicated, and used for recombinant virus screening. Recombinant plaques were screened based on the plaque lift hybridization method using a 1.7 kb FMDV-specific probe labeled with horseradish peroxidase (HRP) according to the manufacturer's protocol (Amersham). After four sequential rounds of plaque purification, the recombinants designated as vCP2181.4.1.1.1 and vCP2181.5.1.1.1 were generated and confirmed by hybridization as 100% positive for the FMDV insert and 100% negative for the C6 ORF.

Single plaques were selected from the 4$^{th}$ round of plaque purification and expanded to obtain P1 (1×T25 flask per sister), P2 (1×T75 flask per sister) and P3 (4× roller bottlles per sister) amplified stocks of the vCP2181 recombinants. The infected cells from the roller bottles were harvested and concentrated to produce virus stock. The viral concentrate was re-confirmed by hybridization of plaque lifts with the FMDV- and C6-specific probes. Viral DNA was prepared and the correct insertion of the FMDV gene cassette at the ALVAC C6 locus was confirmed by Southern blot and sequence analyses.

Immunoblot and immunoplaque assays were performed using specific antibodies as described in Example 7 (see FIG. 30).

Example 7

Construction of a pC6 42kDp FMDV P1+3C Donor Plasmid for the Introduction of the FMDV Genes into the Unique C6 Locus of ALVAC A 42K promoter (42 Kp) derived from the AMV091 gene (vaccinia virus A23R homolog) of the insect poxvirus *Amsacta moorei* (Bawden, A. L. et al, (2000) Virology 274: 120-139) has been used previously in avipox recombinants (U.S. Pat. No. 5,756,103).

Plasmid pCXL-1-4 is pC5 H6p EHV-1 gB (-TM)/42 Kp EHV-1 gD (-TM)/I3Lp EHV-1 gC (-TM), a donor plasmid used to introduce the EHV-1 gB, gC, and gD genes into ALVAC (see Example 6). Each gene uses a different viral promoter, so pCXL-1 -4 was used as the template to PCR amplify the 42K promoter. Primers 11426.CXL and 11427.CXL were used to amplify a 48 bp fragment containing the 42K promoter and the 5'-end of the FMDV genes. The PCR primers are described in FIG. 18A.

A 647 bp PCR fragment, which contains a 20-bp overlap with the 48 bp 42 Kp fragment, was amplified using primers 11428.CXL and 11407.CXL, with pHM-1119-1 (pUC FMDV, see Example 1) as a template. This fragment contains the 5'-FMDV genes up to the unique KpnI site. The PCR primers are described in FIG. 18B.

The two PCR fragments were mixed at a 1:1 molar ratio and PCR amplified using primers 11426.CXL and 11407.CXL. The resultant 676 bp fragment was cloned into pCR2.1, generating pCXL-1080-2-2 (pCR2.1 42 Kp 5'-FMDV).

The 676 bp EcoRI-KpnI 42 Kp 5'-FMDV fragment from pCXL-1080-2-2 was inserted into pHM-1119-1, generating pCXL-1089-1 (pUC 42 Kp FMDV P1+3C).

Figure 19A:
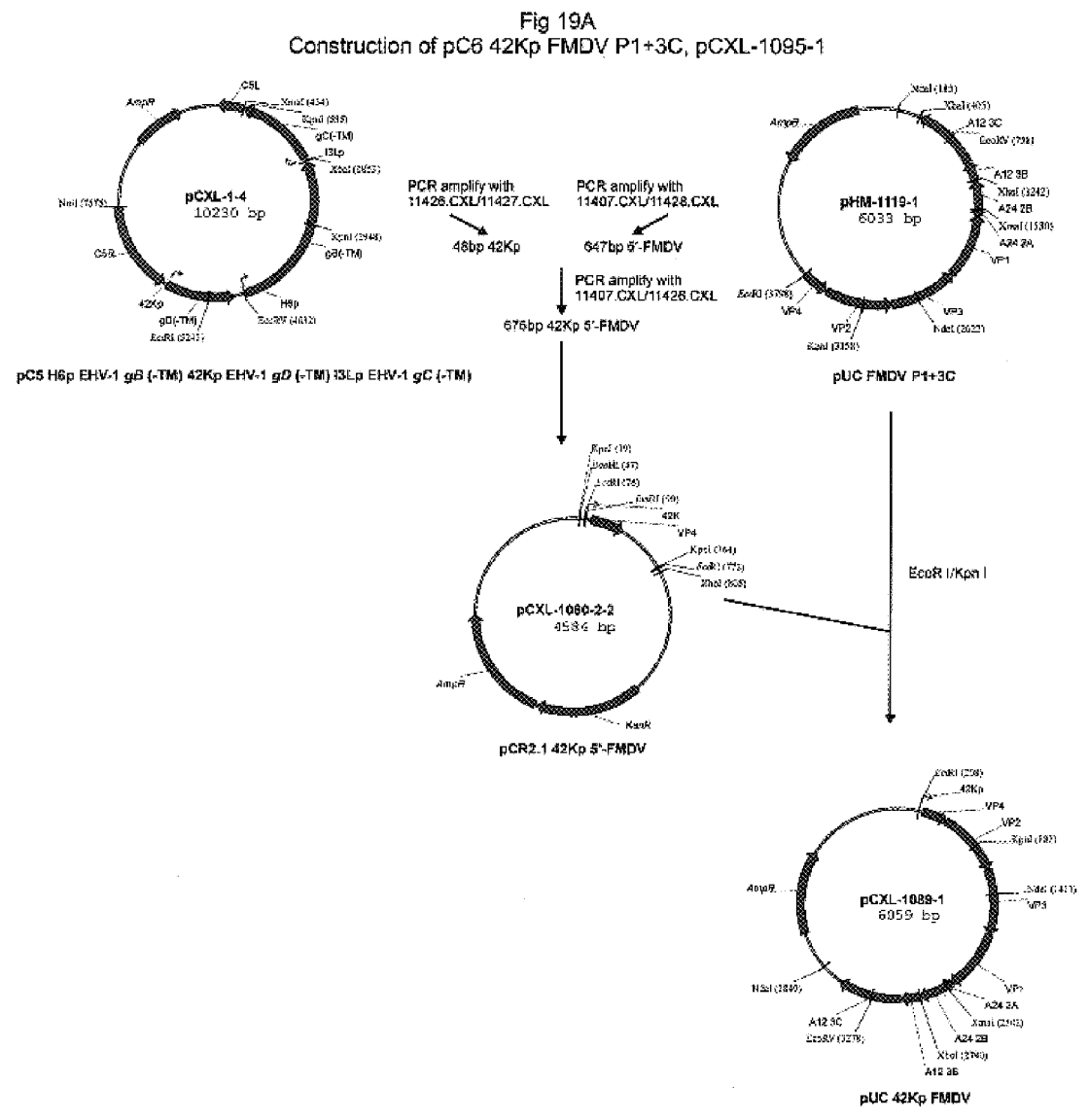

The ~1.2 kb EcoRI-NdeI 42 Kp 5'-FMDV fragment from pCXL-1089-1 was inserted into pCXL-1013-2 (pC6 FMDV P1+3C, see Example 3), generating pCXL-1095-1 (pC6 42 Kp FMDV P1+3C). The construction of pC6 42 Kp FMDV P1+3C is illustrated in FIGS. 19A and 19B and the sequence of the C6 42 Kp FMDV gene cassette is shown in FIGS. 20A-20E.

To generate an ALVAC recombinant, primary CEFs were transfected with 20 μg of SapI-linearized donor plasmid pCXL-1095-1, using FuGENE-6® reagent (Roche). The transfected cells were subsequently infected with ALVAC as rescue virus at an MOI of 10 and after 29 hours, the transfected-infected cells were harvested, sonicated, and used for recombinant virus screening. Recombinant plaques were screened based on the plaque lift hybridization method using the 1.7 kb FMDV-specific probe labeled with horseradish peroxidase (HRP) according to the manufacturer's protocol (Amersham). After four sequential rounds of plaque purification, the recombinant designated as vCP2186.6.2.1.1 was generated and confirmed by hybridization as 100% positive for the FMDV insert and 100% negative for the C6 ORF.

Single plaques were selected from the 4$^{th}$ round of plaque purification, and expanded to obtain P1 (1×T25 flask), P2 (1× T75 flask) and P3 (8× roller bottles) amplified stocks. The infected cells from the roller bottles were harvested and concentrated to produce virus stock. The virl concentrate was characterized by performing hybridization of plaque lifts with the FMDV- and C6-specific probes to confirm 100% genetic purity. Viral DNA was extracted and Southern blotting and sequence analyses confirmed the correct insertion of the FMDV gene cassette.

For expression analysis, CEFs were infected at an MOI of 10 with vCP2181 (ALVAC C6 I3Lp FMDV P1+3C; see Example 6) or vCP2186 (ALVAC C6 42 Kp FMDV P1+3C) and grown at 37° C., in the presence of 5% $CO_2$, for 24 hours. The supernatant was harvested and clarified and the cell monolayer was resuspended in PBS, and then pelleted. The pellets were resuspended in water, and then SDS PAGE sample buffer was added to the supernatants. The protein samples were separated on a 10% SDS PAGE gel, then electrotransferred to a nylon membrane. The membrane was blocked, and then probed with rabbit anti-FMDV VP1, VP2, and VP3 antisera. Secondary antibody and colorimetric analysis revealed that both recombinants expressed specific proteins of sizes consistent with VP0, VP1 and VP3 in both the pellets and supernatants. These data are illustrated in FIG. 30.

Example 8

Construction of a pC6 7.5 Kp FMDV P1+3C Donor Plasmid for the Introduction of the FMDV Genes into the Unique C6 Locus of ALVAC The early 7.5K promoter (7.5 Kp) of vaccinia virus (Davison, A. J. and Moss, B. (1989) J. Mol. Biol. 210: 749-769) has been used previously in avipox recombinants.

Plasmid pHM-1119-1 (pUC FMDV, see Example 1) was used as the template for PCr amplification of the 7.5K promoter and FMDV genes, up to the unique NdeI site. Primers 11357.CXL and 11358.CXL were used to amplify a 1214 bp 7.5 Kp 5'-FMDV fragment, which was cloned into pCR2.1, generating pHM-1249-5-3. The PCR amplification primers are describe in FIG. 21A.

Sequence analysis revealed that three base pair deletions in pHM-1249-5-3. Oligonucleotide primers 11429.HM and 11430.HM were designed to re-introduce the missing uclet-otides by site-directed mutagenesis. The mutagenesis primers are described I FIG. 21B. The resultant clones contained 2 of the 3 re-introduced nucleotides, so clone pHM-1267-4 was subjected to a further round of site-directed mutagenesis with primers 11445.HM and 11446.HM. The mutagenesis primers are described in FIG. 21C. Clone pHM-1299-2 (pCR2.1 7.5 Kp 5'-FMDV) was confirmed to be correct by sequence analysis.

Figure 22A:
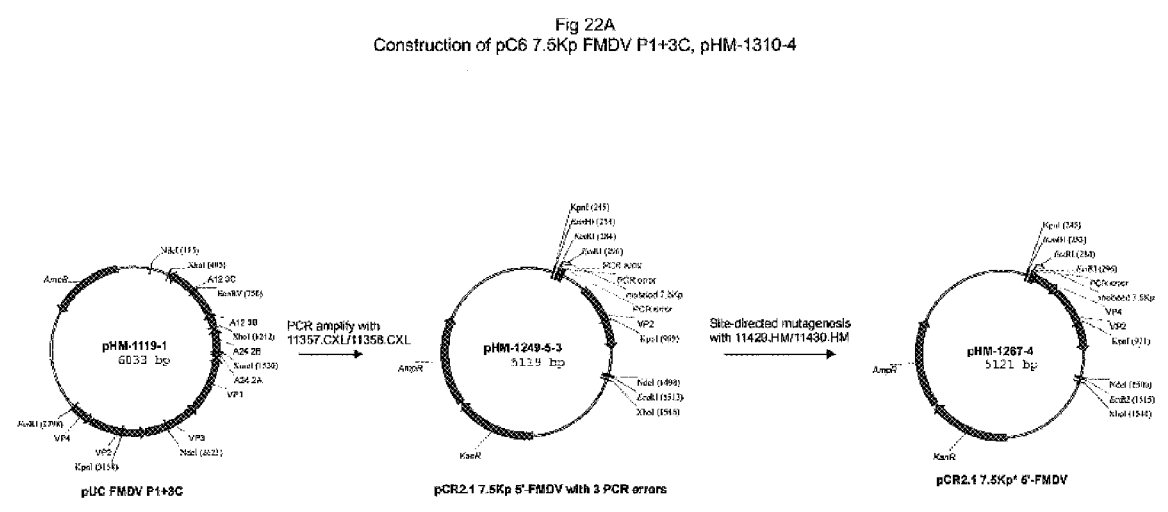
Figure 22B:
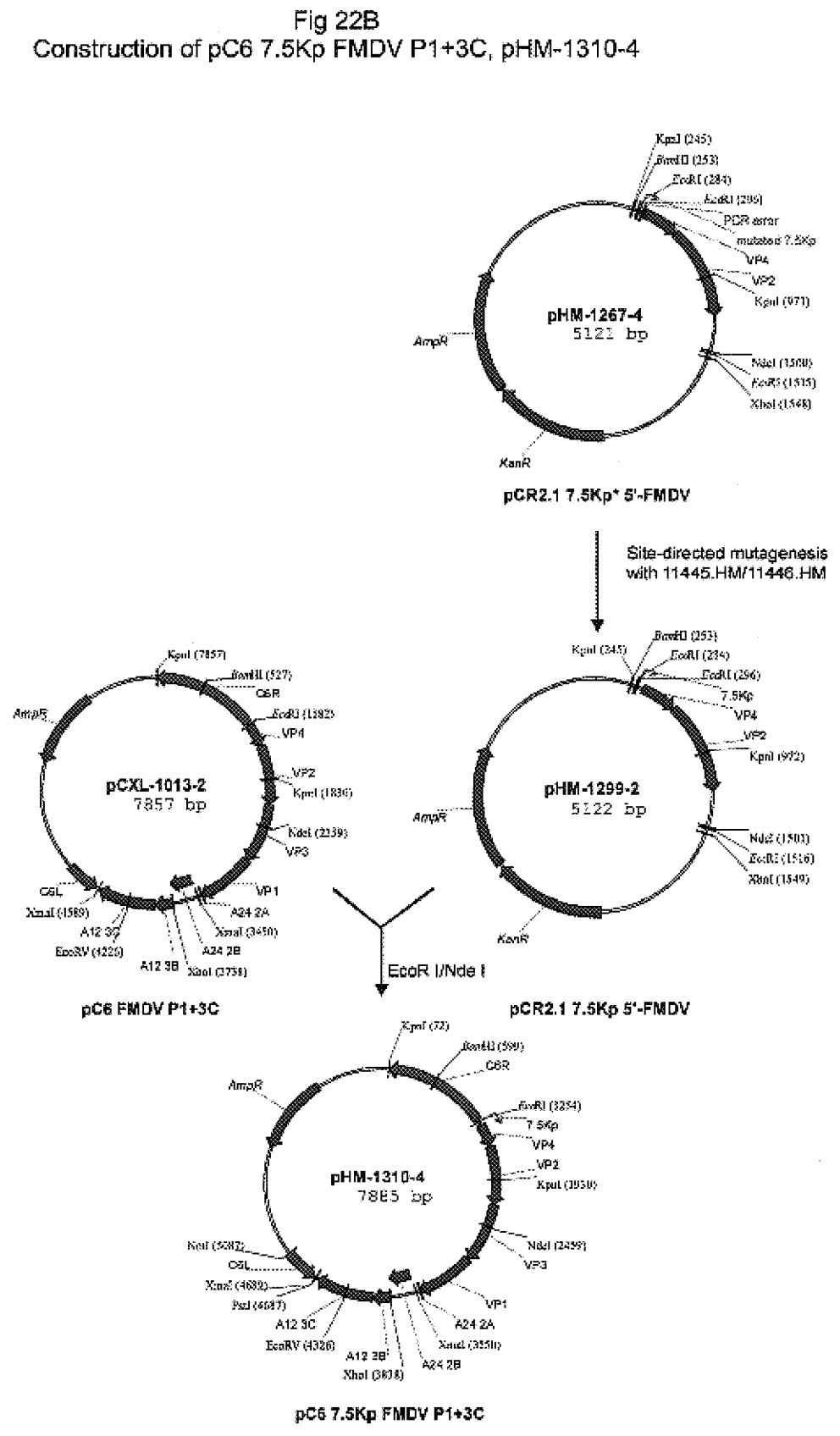

The ~1.2 kb EcoRI-NdeI fragment from pHM-1299-2 was inserted into pCXL- 1013-2 (pC6 FMDV, see Example 3), generating plasmid pHM-1310-4 (pC6 7.5 Kp FMDV P1+3C). The construction of pHM-1310-4 is illustrated in FIGS. 22A and 22B and the sequence of the C6 7.5 Kp FMDV gene cassette is shown in FIGS. 23A-23E.

ALVAC recombinant vCP2189 was obtained after two rounds of screening, but could not be purified/amplified and was lost, suggesting that it was unstable and/or toxic.

Example 9

Construction of a pC6 Pip FMDV P1+3C Donor Plasmid for the Insertion of the FMDV Genes into the Unique C6 Locus of ALVAC The early Pi promoter (Pip) from vaccinia virus (Wachsman, M. et al, (1987) J. Infect. Dis. 155: 1188-1197) has been used previously in avipox recombinants. It is 81 nucleotides in length and is thought to be a relatively weak promoter.

Plasmid pHM-1119-1 (pUC FMDV, see Example 1) was used as a template to PCR-amplify the Pip 5'-FMDV fragment, with primers 11356.CXL and 11358.CXL (FIG. 24A). The amplified fragment was cloned into pCR2.1 and several clones were screened by sequence analysis. The clone with the fewest PCR errors (pHM-1249-4-4, pCR2.1 Pip* 5'-FMDV) was missing 28 nucleotides randomly throughout the Pi promoter region, including the EcoRI cloning site.

Oligonucleotides 11395.CXL and 11399.CXL (FIG. 24B) were used to assemble the correct Pi promoter. The Pip was PCR amplified with primers 11400.CXL and 11401.CXL (FIG. 24C) and cloned into pCR2.1 to generate pHM-1263-1 (pCR2.1 Pip). Plasmid pHM-1263-1 was used as a template to PCR-amplify a 97 bp Pip 5'-FMDV fragment, using primers 11402.CXL and 1140.CXL (FIG. 24D). This fragment contains the EcoRI cloning site, the full-length Pip and 10 bp of FMDV.

Using pHM-1249-4-4 as template, a 648 bp fragment was PCR-amplified using primers 11406.CXL and 11407.CXL (FIG. 24E). This fragment contains 10 bp of the 3' end of Pip and the 5'-FMDV genes up to a unique KpnI site.

Equimolar amounts of the 97 bp Pip 5'-FMDV and 648 bp 3'-Pip 5'-FMDV PCR fragments were mixed and amplified using primers 11402.CXL and 11407.CXL. The resulting 745 bp Pip 5'-FMDV (EcoRI-KpnI) fragment was cloned into pCR2.1 to generate pHM-1268-1 (pCR2.1 Pip 5'-FMDV, EcoRI-KpnI). The EcoRI-KpnI fragment from pHM-1268-1 was inserted into pHM-11119-1, generating pHM-1277-6 (pUC Pip FMDV).

Figure 25A:
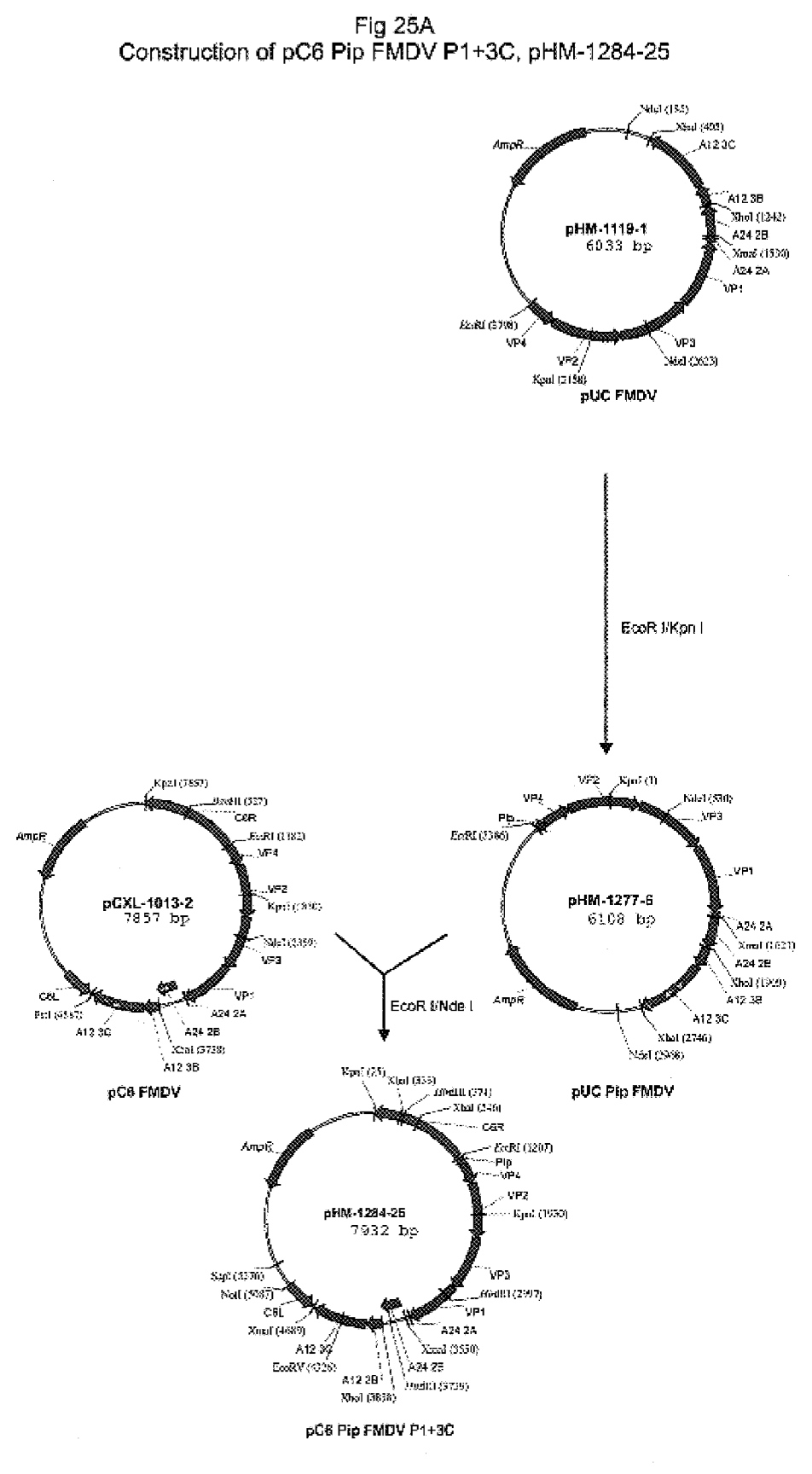
Figure 25B:
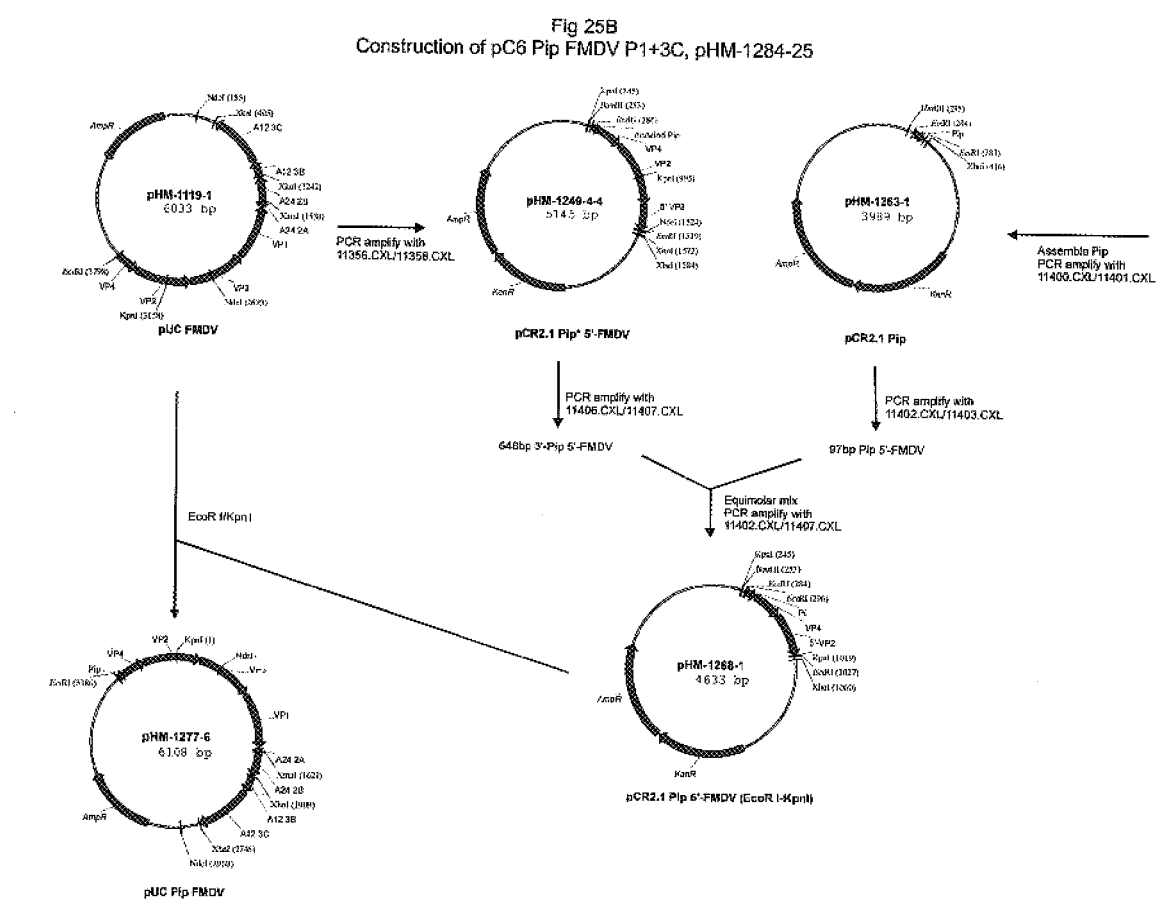

The 1252 bp EcoRI-NdeI Pip 5'-FMDV fragment from pHM-1277-6 was inserted into plasmid pCXL-1013-2 (pC6 FMDV P1+3C, see Example 3), generating plasmid pHM-1284-25 (pC6 Pip FMDV P1+3C). The construction of pC6 Pip FMDV P1+3C is illustrated in FIG. 25 and the sequence of the C6 Pip FMDV gene cassette is shown in FIGS. 26A-26E.

ALVAC recombinant vCP2184 was obtained after two rounds of purification, but was lost at the third round of screening/amplification, suggesting that it was toxic and/or unstable.

Example 10

Construction of a pF8 H6p* FMDV P1+3C Donor Plasmid for Insertion of the FMDV Gene Cassette at the Unique F8 Locus of Fowlpox Plasmid pHM-1260-2 (pCR2.1 H6p* 5'-FMDV (Nde); see Example 5) was used as the template to PCR amplify an H6p* 5'-FMDV fragment, with primers 11506.HM and 11279. SL. Primer 11506.HM was designed to introduce a Hind III site in front of H6p* and primer 11279. SL was designed to amplify the FMDV genes up to the unique KpnI site in the VP2 gene. The ~700 bp fragment was cloned into pCR2.1, generating pHM-1341-7 (pCR2.1 H6p* 5'-FMDV KpnI), which was confirmed as correct by sequence analysis. FIG. 27 describes the PCR primers.

Figure 28A:
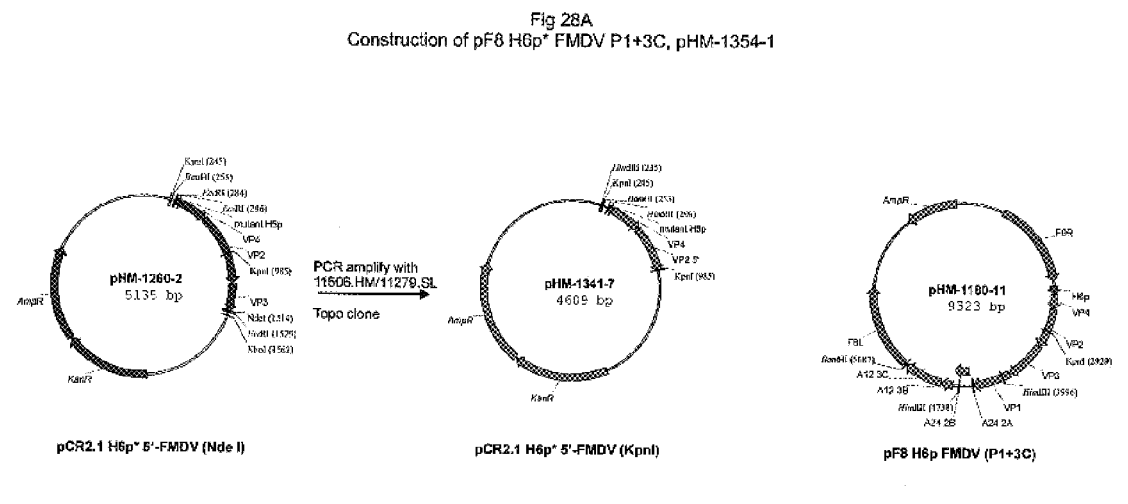

Plasmid pHM-1180-11 is pF8 H6p FMDV P1+3C, containing the wild-type H6 promoter (see Example 2 and FIGS. 5A and 5B). Plasmid pSL-6427-1-1 (pF8 MCS) is a promoter-less plasmid used for insertion into the fowlpox F8 site. The 0.7 kb HindIII-KpnI H6p* 5'-FMDV fragment from pHM-1341-7 and the 2.7 kb KpnI-BamH I 3'-FMDV fragment from pHM- 1180-11 were ligated into plasmid pSL-6427-1-1 that had been digested with HindIII and BamHI, generating pHM-1354-1 (pF8 H6p* FMDV P1+3C). The construction of pHM-1354-1 is illustrated in FIGS. 28A and 28B and the sequence of the F8 H6p* FMDV P1+3C gene cassette is shown in FIGS. 29A-29F.

To generate a fowlpox recombinant, primary CEFs were transfected with NotI-linearized pHM-1354-1, in the presence of Fugene-6® reagent (Roche). The transfected cells were subsequently infected with fowlpox as rescue virus at MOI of 10 and after 51 hours, the transfected-infected cells were harvested, sonicated and used for recombinant virus screening. Recombinant plaques were screened based on the plaque lift hybridization method using a 1.7 kb FMDV-specific probe labelled with horseradish peroxidase (HRP) according to the manufacturer's protocol (Amersham Cat# RPN3001). After five sequential rounds of plaque purification, a fowlpox recombinant designated as vFP2215.1.3.1.1.1 was generated and confirmed by hybridization as 100% positive for the FMDV insert and 100% negative for the F8 ORF.

Single plaques were selected from the $5^{th}$ round of plaque purification, and expanded to obtain P1 (1× T25 flask), P2 (2× T75 flask) and P3 (10× roller bottles) stocks to amplify vFP2215. The infected cells from the roller bottles was harvested and concentrated to produce virus stock. The viral concentrate was re-confirmed by hybridization of plaque lifts with the FMDV- and F8-specific probes. Viral DNA was prepared and the correct insertion of the FMDV gene cassette at the fowlpox F8 locus was confirmed by Southern blot and sequence analyses.

Example 11

Preparation and Purification of Plasmids

For the preparation of the plasmids intended for the vaccination of animals, any technique may be used which makes it possible to obtain a suspension of purified plasmids predominantly in a supercoiled form. These techniques are well known to persons skilled in the art. There may be mentioned in particular the alkaline lysis technique followed by two successive ultracentrifugations on a caesium chloride gradient in the presence of ethidium bromide as described in J. Sambrook et al. (Molecular Cloning: A Laboratory Manual, 2nd edition, Cold Spring Harbor Laboratory, Cold Spring Harbor, New York, 1989). Reference may also be made to Patent Applications PCT WO 95/21250 and PCT WO 96/02658, which describe methods for producing, on an industrial scale, plasmids which can be used for vaccination. For the purposes of the manufacture of vaccines (see Example 11), the purified plasmids are resuspended so as to obtain solutions at a high concentration (>2 mg/ml), which are compatible with storage. To do this, the plasmids are resuspended either in ultrapure water or in TE buffer (10 mM Tris-HCl; 1 mM EDTA, pH 8.0).

Example 12

Manufacture of the Associated Vaccine

The various plasmids necessary for the manufacture of an associated vaccine are mixed starting with their concentrated solutions (Example 10). The mixtures are prepared such that the final concentration of each plasmid corresponds to the effective dose of each plasmid. The solutions, which can be used to adjust the final concentration of the vaccine may be either a 0.9M NaCl solution, or PBS buffer.

Specific formulations such as liposomes or cationic lipids may also be used for the manufacture of the vaccines.

Example 13

Vaccination of Animals

The animals are vaccinated with doses of 100 pg, 250 μg or 500 μg per plasmid. The injections are performed with a needle by the intramuscular route either at the level of the gluteus muscle, or at the level of the neck muscles. The vaccinal doses are administered in volumes of between 1 and 5 ml.

Having thus described in detail preferred embodiments of the present invention, it is to be understood that the invention defined by the appended claims is not to be limited to particular details set forth in the above description as many apparent variations thereof are possible without departing from the spirit or scope of the present invention.

We claim:

1. A recombinant avipox vector selected from canarypox or fowlpox, comprising at least one nucleic acid molecule encoding one or more foot-and-mouth disease virus (FMDV) antigen(s), wherein the nucleic acid molecule is inserted into a single insertion site and wherein:
   (a) the nucleic acid molecule is operably linked to an early or early late promoter sequence; or
   (b) the nucleic acid molecule is operably linked to a relatively weak promoter;
   wherein if the avipox vector is canarypox, the promoter is in the opposite orientation to the flanking sequences and wherein expression levels of the FMDV antigen(s) are decreased compared with expression levels of the FMDV antigen(s) under a relatively strong promoter.

2. The avipox vector of claim 1, wherein the antigen is selected from the group consisting of FMDV VP1, VP2, VP3, VP4, 2A, 2B, and 3C.

3. The avipox vector of claim 1, wherein the nucleic acid molecule encoding one or more foot-and-mouth disease virus (FMDV) antigen(s) is a cDNA encoding FMDV P1 region and a cDNA encoding FMDV 3C protease.

4. The avipox vector of claim 1, wherein the promoter sequence is selected from the group consisting of H6 vaccinia promoter, 13L vaccinia promoter, 42K poxviral promoter, 7.5K vaccinia promoter and Pi vaccinia promoter.

5. The avipox vector of claim 1, wherein the promoter is the H6 vaccinia promoter, which is mutated such that expression levels of the FMDV antigen(s) are decreased compared with expression levels of the FMDV antigen(s) under a wild type H6 vaccinia promoter.

6. The avipox vector of claim 1, wherein the vector comprises a C6 insertion locus, and wherein flanking sequences of the C6 insertion locus promote homologous recombination of the FMDV antigens with the C6 insertion locus.

7. The avipox vector of claim 6, wherein the flanking sequences comprise C6L and C6R open reading frames of avipox.

8. The avipox vector of claim 1, wherein the vector comprises a F8 insertion locus, and wherein flanking sequences of the F8 insertion locus promote homologous recombination of the FMDV antigens with the F8 insertion locus.

9. The avipox vector of claim 8, wherein the flanking sequences comprise F8L and F8R open reading frames of avipox.

10. A recombinant avipox virus selected from ALVAC or fowlpox, comprising at least one nucleic acid molecule encoding one or more foot-and-mouth disease virus (FMDV) antigen(s)), wherein the nucleic acid molecule is inserted into a single insertion site and wherein:
   (a) the nucleic acid molecule is operably linked to an early or early late promoter sequence; or (b) the nucleic acid molecule is operably linked to a relatively weak promoter;

wherein if the avipox vector is ALVAC, the promoter is in the opposite orientation to the flanking sequences and wherein expression levels of the FMDV antigen(s) are decreased compared with expression levels of the FMDV antigen(s) under a relatively strong promoter.

11. The avipox virus of claim 10, wherein the antigen is selected from the group consisting of FMDV VP1, VP2, VP3, VP4, 2A, 2B, and 3C.

12. The avipox virus of claim 10, wherein the nucleic acid molecule encoding one or more foot-and-mouth disease virus (FMDV) antigen(s) is a cDNA encoding FMDV P1 region and a cDNA encoding FMDV 3C protease.

13. The avipox virus of claim 10, wherein the promoter sequence is selected from the group consisting of H6 vaccinia promoter, 13L vaccinia promoter, 42K poxviral promoter, 7.5K vaccinia promoter and Pi vaccinia promoter.

14. The avipox virus of claim 10, wherein the promoter is the H6 vaccinia promoter, which is mutated such that expression levels of the FMDV antigen(s) are decreased compared with expression levels of the FMDV antigen(s) under a wild type H6 vaccinia promoter.

15. The avipox virus of claim 10, wherein the vector comprises a C6 insertion locus, and wherein flanking sequences of the C6 insertion locus promote homologous recombination of the FMDV antigens with the C6 insertion locus.

16. The avipox vector of claim 15, wherein the flanking sequences comprise C6L and C6R open reading frames of avipox.

17. The avipox virus of claim 10, wherein the vector comprises a F8 insertion locus, and wherein flanking sequences of the F8 insertion locus promote homologous recombination of the FMDV antigens with the F8 insertion locus.

18. The avipox vector of claim 17, wherein the flanking sequences comprise F8L and F8R open reading frames of avipox.

19. A recombinant avipox virus, wherein the avipox virus is selected from the group consisting of vCP2186, vCP2181, vCP2176, and vFP2215.

20. A method of eliciting an immune response to FMDV in a subject, comprising administering the vector of claim 1 to the subject.

21. A method of eliciting an immune response to FMDV in a subject, comprising administering the virus of claim 10 to the subject.

22. A method of eliciting an immune response to FMDV in a subject, comprising administering the virus of claim 19 to the subject.

* * * * *

SEQUENCE LISTING

```
<160> NUMBER OF SEQ ID NOS: 88

<210> SEQ ID NO 1
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tatcgcgata tccgttaagt ttgtatcgta atgggagctg ggcaatccag ccca           54

<210> SEQ ID NO 2
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gttgaccctg aaccacaaca cgagtagtaa tttttctaga ggatcc                   46

<210> SEQ ID NO 3
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggatcctcta gaaaaattac tactcgtgtt gtggttcagg gtcaac                   46

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Met Gly Ala Gly Gln Ser Ser Pro
 1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 5

Val Asp Pro Glu Pro Gln His Glu
  1               5

<210> SEQ ID NO 6
<211> LENGTH: 5594
<212> TYPE: DNA
<213> ORGANISM: Foot-and-mouth disease virus
<220> FEATURE:
<221> NAME/KEY: CDS
<222> LOCATION: (1758)..(5135)

<400> SEQUENCE: 6
tgaatgttaa atgttatact ttggatgaag ctataaatat gcattggaaa ataatccat      60 ttaaagaaag gattcaaata ctacaaaacc taagcgataa tatgttaact aagcttattc    120
ttaacgacgc tttaaatata cacaaataaa cataattttt gtataaccta acaaataact    180
aaaacataaa aataataaaa ggaaatgtaa tatcgtaatt attttactca ggaatggggt    240
taaatattta tatcacgtgt atatctatac tgttatcgta tactctttac aattactatt    300
acgaatatgc aagagataat aagattacgt atttaagaga atcttgtcat gataattggg    360
tacgacatag tgataaatgc tatttcgcat cgttacataa agtcagttgg aaagatggat    420
ttgacagatg taacttaata ggtgcaaaaa tgttaaataa cagcattcta tcggaagata    480
ggataccagt tatattatac aaaaatcact ggttggataa aacagattct gcaatattcg    540
taaaagatga agattactgc gaatttgtaa actatgacaa taaaaagcca tttatctcaa    600
cgacatcgtg taattcttcc atgttttatg tatgtgtttc agatattatg agattactat    660 aaacttttg tatacttata ttccgtaaac tatattaatc atgaagaaaa tgaaaaagta    720
tagaagctgt tcacgagcgg ttgttgaaaa caacaaaatt atacattcaa gatggcttac    780
atatacgtct gtgaggctat catggataat gacaatgcat ctctaaatag gttttttggac    840 aatggattcg accctaacac ggaatatggt actctacaat ctcctcttga atggctgta     900 atgttcaaga ataccgaggc tataaaaatc ttgatgaggt atggagctaa acctgtagtt    960
actgaatgca caacttcttg tctgcatgat gcggtgttga gagacgacta caaaatagtg   1020
aaagatctgt tgaagaataa ctatgtaaac aatgttcttt acagcggagg ctttactcct   1080
ttgtgtttgg cagcttacct taacaaagtt aatttggtta aacttctatt ggctcattcg   1140
gcggatgtag atatttcaaa cacggatcgg ttaactcctc tacatatagc cgtatcaaat   1200
aaaaatttaa caatggttaa acttctattg aacaaaggtg ctgatactga cttgctggat   1260
aacatgggac gtactccttt aatgatcgct gtacaatctg gaaatattga aatatgtagc   1320
acactactta aaaaaataa aatgtccaga actgggaaaa attgatcttg ccagctgtaa    1380
ttcatggtag aaaagaagtg ctcaggctac ttttcaacaa aggagcagat gtaaactaca   1440
tctttgaaag aaatggaaaa tcatatactg tttttggaatt gattaaagaa agttactctg   1500
agacacaaaa gaggtagctg aagtggtact ctcaaaggta cgtgactaat agctataaa    1560 aaggatccgg gttaattaat tagtcatcag gcagggcgag aacgagacta tctgctcgtt   1620
aattaattag agcttcttta ttctatactt aaaaagtgaa ataaataca aaggttcttg    1680 agggttgtgt taaattgaaa gcgagaaata atcataaatt atttcattat cgcgatatcc   1740
gttaagtttg tatcgta atg gga gct ggg caa tcc agc cca gca acc ggc       1790
                  Met Gly Ala Gly Gln Ser Ser Pro Ala Thr Gly
                    1               5                  10 tcg cag aac cag tct ggc aac act ggc agc ata atc aac aac tac tac     1838
```

```
Ser Gln Asn Gln Ser Gly Asn Thr Gly Ser Ile Ile Asn Asn Tyr Tyr
            15                  20                  25 atg caa cag tac cag aac tcc atg gac aca cag ttg gga gac aat gcc    1886
Met Gln Gln Tyr Gln Asn Ser Met Asp Thr Gln Leu Gly Asp Asn Ala
         30                  35                  40 atc agt gga ggc tcc aac gag ggc tcc acg gac aca act tca aca cac    1934
Ile Ser Gly Gly Ser Asn Glu Gly Ser Thr Asp Thr Thr Ser Thr His
     45                  50                  55 aca acc aac act caa aac aat gac tgg ttc tcg aag ctc gcc agt tca    1982
Thr Thr Asn Thr Gln Asn Asn Asp Trp Phe Ser Lys Leu Ala Ser Ser
 60                  65                  70                  75 gct ttt acc ggt ctg ttc ggt gca ctc gcc gac aag aag aca gag        2030
Ala Phe Thr Gly Leu Phe Gly Ala Leu Leu Ala Asp Lys Lys Thr Glu
                 80                  85                  90 gaa acg aca ctt ctt gag gac cgc atc ctc acc acc cgc aac ggg cac    2078
Glu Thr Thr Leu Leu Glu Asp Arg Ile Leu Thr Thr Arg Asn Gly His
             95                 100                 105 acc acc tcg acg acc caa tcg agt gtg ggt gtc aca cac ggg tac tcc    2126
Thr Thr Ser Thr Thr Gln Ser Ser Val Gly Val Thr His Gly Tyr Ser
        110                 115                 120 aca gag gag gac cac gtt gct ggg ccc aac aca tcg ggc ctg gag acg    2174
Thr Glu Glu Asp His Val Ala Gly Pro Asn Thr Ser Gly Leu Glu Thr
    125                 130                 135 cga gtg gtg cag gca gag aga ttc tac aaa aag tac ttg ttt gac tgg    2222
Arg Val Val Gln Ala Glu Arg Phe Tyr Lys Lys Tyr Leu Phe Asp Trp
140                 145                 150                 155 aca acg gac aag gca ttt gga cac ctg gaa aag ctg gag ctc ccg tcc    2270
Thr Thr Asp Lys Ala Phe Gly His Leu Glu Lys Leu Glu Leu Pro Ser
                160                 165                 170 gac cac cac ggt gtc ttt gga cac ttg gtg gac tcg tac gcc tat atg    2318
Asp His His Gly Val Phe Gly His Leu Val Asp Ser Tyr Ala Tyr Met
            175                 180                 185 aga aat ggc tgg gat gtt gag gtg tcc gct gtt ggc aac cag ttc aac    2366
Arg Asn Gly Trp Asp Val Glu Val Ser Ala Val Gly Asn Gln Phe Asn
        190                 195                 200 ggc ggg tgc ctc ctg gtg gcc atg gta cct gaa tgg aag gaa ttt gac    2414
Gly Gly Cys Leu Leu Val Ala Met Val Pro Glu Trp Lys Glu Phe Asp
    205                 210                 215 aca cgg gag aaa tac caa ctc acc ctt ttc ccg cac cag ttt att agc    2462
Thr Arg Glu Lys Tyr Gln Leu Thr Leu Phe Pro His Gln Phe Ile Ser
220                 225                 230                 235 ccc aga act aac atg act gcc cac atc acg gtc ccc tac ctt ggt gtg    2510
Pro Arg Thr Asn Met Thr Ala His Ile Thr Val Pro Tyr Leu Gly Val
                240                 245                 250 aac agg tat gat cag tac aag aag cat aag ccc tgg aca ttg gtt gtc    2558
Asn Arg Tyr Asp Gln Tyr Lys Lys His Lys Pro Trp Thr Leu Val Val
            255                 260                 265 atg gtc gtg tcg cca ctt acg gtc aac aac act agt gcg gca caa atc    2606
Met Val Val Ser Pro Leu Thr Val Asn Asn Thr Ser Ala Ala Gln Ile
        270                 275                 280 aag gtc tac gcc aac ata gct ccg acc tat gtt cac gtg gcc ggt gaa    2654
Lys Val Tyr Ala Asn Ile Ala Pro Thr Tyr Val His Val Ala Gly Glu
    285                 290                 295 ctc ccc tcg aaa gag ggg att ttc ccg gtt gca tgt gcg gac ggt tac    2702
Leu Pro Ser Lys Glu Gly Ile Phe Pro Val Ala Cys Ala Asp Gly Tyr
300                 305                 310                 315 gga gga ttg gtg acg aca gac ccg aag aca gct gac cct gct tat ggc    2750
Gly Gly Leu Val Thr Thr Asp Pro Lys Thr Ala Asp Pro Ala Tyr Gly
                320                 325                 330
```

```
aag gtg tac aac ccg cct agg act aac tac cct ggg cgc ttc acc aac          2798
Lys Val Tyr Asn Pro Pro Arg Thr Asn Tyr Pro Gly Arg Phe Thr Asn
            335                 340                 345 ctg ttg gac gtg gcc gaa gcg tgt ccc act ttc ctc tgc ttt gac gac          2846
Leu Leu Asp Val Ala Glu Ala Cys Pro Thr Phe Leu Cys Phe Asp Asp
350                 355                 360 ggg aaa ccg tac gtc acc acg cgg acg gat gac acc cga ctt ttg gcc          2894
Gly Lys Pro Tyr Val Thr Thr Arg Thr Asp Asp Thr Arg Leu Leu Ala
    365                 370                 375 aag ttt gac ctt tcc ctt gcc gca aaa cat atg tcc aac aca tac ctg          2942
Lys Phe Asp Leu Ser Leu Ala Ala Lys His Met Ser Asn Thr Tyr Leu
380                 385                 390                 395 tca ggg att gct cag tac tac aca cag tac tct ggc acc atc aat ttg          2990
Ser Gly Ile Ala Gln Tyr Tyr Thr Gln Tyr Ser Gly Thr Ile Asn Leu
                400                 405                 410 cat ttc atg ttt aca ggt tcc act gat tca aag gcc cga tac atg gtg          3038
His Phe Met Phe Thr Gly Ser Thr Asp Ser Lys Ala Arg Tyr Met Val
            415                 420                 425 gcc tac atc cca cct ggg gtg gag aca cca ccg gac aca cct gaa agg          3086
Ala Tyr Ile Pro Pro Gly Val Glu Thr Pro Pro Asp Thr Pro Glu Arg
        430                 435                 440 gct gcc cac tgc att cac gct gaa tgg gac act gga cta aac tcc aaa          3134
Ala Ala His Cys Ile His Ala Glu Trp Asp Thr Gly Leu Asn Ser Lys
    445                 450                 455 ttc act ttc tca atc ccg tac gta tcc gcc gcg gat tac gcg tac aca          3182
Phe Thr Phe Ser Ile Pro Tyr Val Ser Ala Ala Asp Tyr Ala Tyr Thr
460                 465                 470                 475 gcg tct gac acg gca gaa aca atc aac gta cag gga tgg gtc tgc atc          3230
Ala Ser Asp Thr Ala Glu Thr Ile Asn Val Gln Gly Trp Val Cys Ile
                480                 485                 490 tac caa att aca cac ggg aag gct gaa aat gac acc ttg gtc gtg tcg          3278
Tyr Gln Ile Thr His Gly Lys Ala Glu Asn Asp Thr Leu Val Val Ser
            495                 500                 505 gtt agc gcc ggc aaa gac ttt gag ttg cgc ctc ccg att gac ccc cgc          3326
Val Ser Ala Gly Lys Asp Phe Glu Leu Arg Leu Pro Ile Asp Pro Arg
        510                 515                 520 cag cag acc acc gct acc ggg gaa tca gca gac ccg gtc acc acc acc          3374
Gln Gln Thr Thr Ala Thr Gly Glu Ser Ala Asp Pro Val Thr Thr Thr
    525                 530                 535 gtg gag aac tac ggc ggt gag aca caa atc cag aga cgt cac cac acg          3422
Val Glu Asn Tyr Gly Gly Glu Thr Gln Ile Gln Arg Arg His His Thr
540                 545                 550                 555 gac att ggt ttc atc atg gac aga ttt gtg aag atc caa agc ttg agc          3470
Asp Ile Gly Phe Ile Met Asp Arg Phe Val Lys Ile Gln Ser Leu Ser
                560                 565                 570 cca aca cat gtc att gac ctc atg cag gct cac caa cac ggt ctg gtg          3518
Pro Thr His Val Ile Asp Leu Met Gln Ala His Gln His Gly Leu Val
            575                 580                 585 ggt gcc ttg ctg cgt gca gcc acg tac tac ttt tct gac ctg gaa att          3566
Gly Ala Leu Leu Arg Ala Ala Thr Tyr Tyr Phe Ser Asp Leu Glu Ile
        590                 595                 600 gtt gta cgg cac gaa ggc aat ctg acc tgg gtg ccc aac ggc gcc cct          3614
Val Val Arg His Glu Gly Asn Leu Thr Trp Val Pro Asn Gly Ala Pro
    605                 610                 615 gaa tca gcc ctg ttg aac acc agc aac ccc act gcc tac aac aag gca          3662
Glu Ser Ala Leu Leu Asn Thr Ser Asn Pro Thr Ala Tyr Asn Lys Ala
620                 625                 630                 635 cca ttc acg aga ctc gct ctc ccc tac act gcg ccg cac cgt gtg ctg          3710
Pro Phe Thr Arg Leu Ala Leu Pro Tyr Thr Ala Pro His Arg Val Leu
                640                 645                 650
```

-continued

| | | |
|---|---|---|
| gca aca gtg tac aac ggg acg agt aag tat gct gtg ggt ggt tca ggc<br>Ala Thr Val Tyr Asn Gly Thr Ser Lys Tyr Ala Val Gly Gly Ser Gly<br>655                                  660                              665 | 3758 |
| aga aga ggc gac atg ggg tct ctc gcg gcg cga gtc gtg aaa cag ctt<br>Arg Arg Gly Asp Met Gly Ser Leu Ala Ala Arg Val Val Lys Gln Leu<br>                670                              675                          680 | 3806 |
| cct gct tca ttt aac tac ggt gca atc aag gcc gac gcc atc cac gaa<br>Pro Ala Ser Phe Asn Tyr Gly Ala Ile Lys Ala Asp Ala Ile His Glu<br>685                                  690                              695 | 3854 |
| ctt ctc gtg cgc atg aaa cgg gcc gag ctc tac tgc ccc aga ccg ctg<br>Leu Leu Val Arg Met Lys Arg Ala Glu Leu Tyr Cys Pro Arg Pro Leu<br>700                                  705                              710                          715 | 3902 |
| ttg gca ata gag gtg tct tcg caa gac agg cac aag caa aag atc att<br>Leu Ala Ile Glu Val Ser Ser Gln Asp Arg His Lys Gln Lys Ile Ile<br>                720                              725                          730 | 3950 |
| gca cca gca aag cag ctt ctg aat ttt gac ctg ctc aag ttg gcc gga<br>Ala Pro Ala Lys Gln Leu Leu Asn Phe Asp Leu Leu Lys Leu Ala Gly<br>                        735                              740                              745 | 3998 |
| gac gtt gag tcc aac ccc ggg cca ttc ttc ttt gct gac gtt agg tca<br>Asp Val Glu Ser Asn Pro Gly Pro Phe Phe Phe Ala Asp Val Arg Ser<br>             750                              755                          760 | 4046 |
| aac ttt tca aag ttg gta gac aca atc aac cag atg cag gag gac atg<br>Asn Phe Ser Lys Leu Val Asp Thr Ile Asn Gln Met Gln Glu Asp Met<br>765                                  770                              775 | 4094 |
| tcc aca aaa cac ggg ccc gac ttc aac cgg ttg gtg tcc gca ttt gag<br>Ser Thr Lys His Gly Pro Asp Phe Asn Arg Leu Val Ser Ala Phe Glu<br>780                                  785                          790                          795 | 4142 |
| gaa ttg gcc act gga gtt aaa gct atc agg acc ggt ctc gac gag gcc<br>Glu Leu Ala Thr Gly Val Lys Ala Ile Arg Thr Gly Leu Asp Glu Ala<br>                800                              805                          810 | 4190 |
| aaa ccc tgg tac aag ctt atc aaa ctc cta agc cgc ctg tcg tgc atg<br>Lys Pro Trp Tyr Lys Leu Ile Lys Leu Leu Ser Arg Leu Ser Cys Met<br>                        815                              820                              825 | 4238 |
| gcc gct gtg gca gca cgg tcc aag gac cca gtc ctt gtg gcc atc atg<br>Ala Ala Val Ala Ala Arg Ser Lys Asp Pro Val Leu Val Ala Ile Met<br>830                                  835                              840 | 4286 |
| ctg gcc gac acc ggt ctc gag cgt cag aga cct ctg aaa gtg aga gct<br>Leu Ala Asp Thr Gly Leu Glu Arg Gln Arg Pro Leu Lys Val Arg Ala<br>845                                  850                              855 | 4334 |
| aag ctc cca cag cag gaa gga cct tac gct ggc ccg ttg gag aga cag<br>Lys Leu Pro Gln Gln Glu Gly Pro Tyr Ala Gly Pro Leu Glu Arg Gln<br>860                                  865                          870                          875 | 4382 |
| aaa ccg ctg aaa gtg aaa gca aaa gcc ccg gtc gtc aag gaa gga cct<br>Lys Pro Leu Lys Val Lys Ala Lys Ala Pro Val Val Lys Glu Gly Pro<br>                        880                              885                          890 | 4430 |
| tac gag gga ccg gtg aag aag cct gtc gct ttg aaa gtg aaa gct aag<br>Tyr Glu Gly Pro Val Lys Lys Pro Val Ala Leu Lys Val Lys Ala Lys<br>                    895                              900                          905 | 4478 |
| aac ttg ata gtc act gag agt ggt gcc cca ccg acc gac ttg caa aag<br>Asn Leu Ile Val Thr Glu Ser Gly Ala Pro Pro Thr Asp Leu Gln Lys<br>                910                              915                          920 | 4526 |
| atg gtc atg ggc aac aca aag cct gtt gag ctc atc ctt gac ggg aag<br>Met Val Met Gly Asn Thr Lys Pro Val Glu Leu Ile Leu Asp Gly Lys<br>925                                  930                              935 | 4574 |
| aca gta gcc atc tgt tgt gct act gga gtg ttt ggc act gct tac ctc<br>Thr Val Ala Ile Cys Cys Ala Thr Gly Val Phe Gly Thr Ala Tyr Leu<br>940                                  945                          950                          955 | 4622 |
| gtg cct cgt cat ctt ttc gca gag aag tat gac aag atc atg ctg gat<br>Val Pro Arg His Leu Phe Ala Glu Lys Tyr Asp Lys Ile Met Leu Asp | 4670 |

-continued

```
                960                 965                 970
ggc aga gcc atg aca gac agt gac tac aga gtg ttt gag ttt gag att      4718
Gly Arg Ala Met Thr Asp Ser Asp Tyr Arg Val Phe Glu Phe Glu Ile
            975                 980                 985 aaa gta aaa gga cag gac atg ctc tca gac gct gcg ctc atg gtg ctc      4766
Lys Val Lys Gly Gln Asp Met Leu Ser Asp Ala Ala Leu Met Val Leu
        990                 995                 1000 cac cgt ggg aac cgc gtg aga gat atc acg aaa cac ttt cgt gat aca      4814
His Arg Gly Asn Arg Val Arg Asp Ile Thr Lys His Phe Arg Asp Thr
    1005                1010                1015 gca aga atg aag aaa ggc acc ccc gtc gtc ggt gtg gtc aac aac gcc      4862
Ala Arg Met Lys Lys Gly Thr Pro Val Val Gly Val Val Asn Asn Ala
1020                1025                1030                1035 gac gtt ggg aga ctg att ttc tct ggt gag gcc ctc acc tac aag gat      4910
Asp Val Gly Arg Leu Ile Phe Ser Gly Glu Ala Leu Thr Tyr Lys Asp
            1040                1045                1050 att gta gtg tgc atg gac gga gac acc atg cct ggc ctc ttt gcc tac      4958
Ile Val Val Cys Met Asp Gly Asp Thr Met Pro Gly Leu Phe Ala Tyr
        1055                1060                1065 aaa gcc gcc acc aag gca ggc tac tgt gga gga gcc gtt ctc gcc aag      5006
Lys Ala Ala Thr Lys Ala Gly Tyr Cys Gly Gly Ala Val Leu Ala Lys
    1070                1075                1080 gac ggg gcc gac act ttc atc gtc ggc act cac tcc gca gga ggc aat      5054
Asp Gly Ala Asp Thr Phe Ile Val Gly Thr His Ser Ala Gly Gly Asn
1085                1090                1095 gga gtt gga tac tgc tca tgc gtt tcc agg tcc atg ctt ctc aga atg      5102
Gly Val Gly Tyr Cys Ser Cys Val Ser Arg Ser Met Leu Leu Arg Met
1100                1105                1110                1115 aag gca cac gtt gac cct gaa cca caa cac gag tagtaatttt tctagaatcg    5155
Lys Ala His Val Asp Pro Glu Pro Gln His Glu
            1120                1125 atcccgggtt tttatgacta gttaatcacg gccgcttata aagatctaaa atgcataatt    5215
tctaaataat gaaaaaagt acatcatgag caacgcgtta gtatatttta caatggagat     5275
taacgctcta taccgttcta tgtttattga ttcagatgat gttttagaaa agaaagttat    5335
tgaatatgaa aactttaatg aagatgaaga tgacgacgat gattattgtt gtaaatctgt    5395
tttagatgaa gaagatgacg cgctaaagta ctactatggtt acaaagtata agtctatact   5455
actaatggcg acttgtgcaa gaaggtatag tatagtgaaa atgttgttag attatgatta    5515
tgaaaaacca aataaatcag atccatatct aaaggtatct cctttgcaca taatttcatc    5575
tattcctagt ttagaatac                                                 5594
```

<210> SEQ ID NO 7
<211> LENGTH: 1126
<212> TYPE: PRT
<213> ORGANISM: Foot-and-mouth disease virus

<400> SEQUENCE: 7

```
Met Gly Ala Gly Gln Ser Ser Pro Ala Thr Gly Ser Gln Asn Gln Ser
  1               5                  10                  15

Gly Asn Thr Gly Ser Ile Ile Asn Asn Tyr Tyr Met Gln Gln Tyr Gln
                20                  25                  30

Asn Ser Met Asp Thr Gln Leu Gly Asp Asn Ala Ile Ser Gly Gly Ser
            35                  40                  45

Asn Glu Gly Ser Thr Asp Thr Thr Ser Thr His Thr Thr Asn Thr Gln
        50                  55                  60

Asn Asn Asp Trp Phe Ser Lys Leu Ala Ser Ser Ala Phe Thr Gly Leu
```

```
            65                  70                  75                  80
Phe Gly Ala Leu Leu Ala Asp Lys Lys Thr Glu Thr Thr Leu Leu
                85                  90                  95
Glu Asp Arg Ile Leu Thr Thr Arg Asn Gly His Thr Thr Ser Thr Thr
            100                 105                 110
Gln Ser Ser Val Gly Val Thr His Gly Tyr Ser Thr Glu Glu Asp His
            115                 120                 125
Val Ala Gly Pro Asn Thr Ser Gly Leu Glu Thr Arg Val Val Gln Ala
            130                 135                 140
Glu Arg Phe Tyr Lys Lys Tyr Leu Phe Asp Trp Thr Thr Asp Lys Ala
145                 150                 155                 160
Phe Gly His Leu Glu Lys Leu Glu Leu Pro Ser Asp His His Gly Val
                165                 170                 175
Phe Gly His Leu Val Asp Ser Tyr Ala Tyr Met Arg Asn Gly Trp Asp
                180                 185                 190
Val Glu Val Ser Ala Val Gly Asn Gln Phe Asn Gly Gly Cys Leu Leu
                195                 200                 205
Val Ala Met Val Pro Glu Trp Lys Glu Phe Asp Thr Arg Glu Lys Tyr
            210                 215                 220
Gln Leu Thr Leu Phe Pro His Gln Phe Ile Ser Pro Arg Thr Asn Met
225                 230                 235                 240
Thr Ala His Ile Thr Val Pro Tyr Leu Gly Val Asn Arg Tyr Asp Gln
                245                 250                 255
Tyr Lys Lys His Lys Pro Trp Thr Leu Val Val Met Val Val Ser Pro
                260                 265                 270
Leu Thr Val Asn Asn Thr Ser Ala Ala Gln Ile Lys Val Tyr Ala Asn
            275                 280                 285
Ile Ala Pro Thr Tyr Val His Val Ala Gly Glu Leu Pro Ser Lys Glu
            290                 295                 300
Gly Ile Phe Pro Val Ala Cys Ala Asp Gly Tyr Gly Gly Leu Val Thr
305                 310                 315                 320
Thr Asp Pro Lys Thr Ala Asp Pro Ala Tyr Gly Lys Val Tyr Asn Pro
                325                 330                 335
Pro Arg Thr Asn Tyr Pro Gly Arg Phe Thr Asn Leu Leu Asp Val Ala
            340                 345                 350
Glu Ala Cys Pro Thr Phe Leu Cys Phe Asp Asp Gly Lys Pro Tyr Val
            355                 360                 365
Thr Thr Arg Thr Asp Asp Thr Arg Leu Leu Ala Lys Phe Asp Leu Ser
            370                 375                 380
Leu Ala Ala Lys His Met Ser Asn Thr Tyr Leu Ser Gly Ile Ala Gln
385                 390                 395                 400
Tyr Tyr Thr Gln Tyr Ser Gly Thr Ile Asn Leu His Phe Met Phe Thr
                405                 410                 415
Gly Ser Thr Asp Ser Lys Ala Arg Tyr Met Val Ala Tyr Ile Pro Pro
            420                 425                 430
Gly Val Glu Thr Pro Pro Asp Thr Pro Glu Arg Ala Ala His Cys Ile
            435                 440                 445
His Ala Glu Trp Asp Thr Gly Leu Asn Ser Lys Phe Thr Phe Ser Ile
            450                 455                 460
Pro Tyr Val Ser Ala Ala Asp Tyr Ala Tyr Thr Ala Ser Asp Thr Ala
465                 470                 475                 480
Glu Thr Ile Asn Val Gln Gly Trp Val Cys Ile Tyr Gln Ile Thr His
                485                 490                 495
```

-continued

```
Gly Lys Ala Glu Asn Asp Thr Leu Val Val Ser Val Ser Ala Gly Lys
            500                 505                 510

Asp Phe Glu Leu Arg Leu Pro Ile Asp Pro Arg Gln Gln Thr Thr Ala
            515                 520                 525

Thr Gly Glu Ser Ala Asp Pro Val Thr Thr Val Glu Asn Tyr Gly
            530                 535                 540

Gly Glu Thr Gln Ile Gln Arg Arg His His Thr Asp Ile Gly Phe Ile
545                 550                 555                 560

Met Asp Arg Phe Val Lys Ile Gln Ser Leu Ser Pro Thr His Val Ile
                565                 570                 575

Asp Leu Met Gln Ala His Gln His Gly Leu Val Gly Ala Leu Leu Arg
            580                 585                 590

Ala Ala Thr Tyr Tyr Phe Ser Asp Leu Glu Ile Val Val Arg His Glu
            595                 600                 605

Gly Asn Leu Thr Trp Val Pro Asn Gly Ala Pro Glu Ser Ala Leu Leu
            610                 615                 620

Asn Thr Ser Asn Pro Thr Ala Tyr Asn Lys Ala Pro Phe Thr Arg Leu
625                 630                 635                 640

Ala Leu Pro Tyr Thr Ala Pro His Arg Val Leu Ala Thr Val Tyr Asn
                645                 650                 655

Gly Thr Ser Lys Tyr Ala Val Gly Gly Ser Gly Arg Arg Gly Asp Met
                660                 665                 670

Gly Ser Leu Ala Ala Arg Val Val Lys Gln Leu Pro Ala Ser Phe Asn
            675                 680                 685

Tyr Gly Ala Ile Lys Ala Asp Ala Ile His Glu Leu Leu Val Arg Met
690                 695                 700

Lys Arg Ala Glu Leu Tyr Cys Pro Arg Pro Leu Leu Ala Ile Glu Val
705                 710                 715                 720

Ser Ser Gln Asp Arg His Lys Gln Lys Ile Ile Ala Pro Ala Lys Gln
                725                 730                 735

Leu Leu Asn Phe Asp Leu Leu Lys Leu Ala Gly Asp Val Glu Ser Asn
            740                 745                 750

Pro Gly Pro Phe Phe Phe Ala Asp Val Arg Ser Asn Phe Ser Lys Leu
            755                 760                 765

Val Asp Thr Ile Asn Gln Met Gln Glu Asp Met Ser Thr Lys His Gly
            770                 775                 780

Pro Asp Phe Asn Arg Leu Val Ser Ala Phe Glu Glu Leu Ala Thr Gly
785                 790                 795                 800

Val Lys Ala Ile Arg Thr Gly Leu Asp Glu Ala Lys Pro Trp Tyr Lys
                805                 810                 815

Leu Ile Lys Leu Leu Ser Arg Leu Ser Cys Met Ala Ala Val Ala Ala
            820                 825                 830

Arg Ser Lys Asp Pro Val Leu Val Ala Ile Met Leu Ala Asp Thr Gly
            835                 840                 845

Leu Glu Arg Gln Arg Pro Leu Lys Val Arg Ala Lys Leu Pro Gln Gln
            850                 855                 860

Glu Gly Pro Tyr Ala Gly Pro Leu Glu Arg Gln Lys Pro Leu Lys Val
865                 870                 875                 880

Lys Ala Lys Ala Pro Val Val Lys Glu Gly Pro Tyr Glu Gly Pro Val
                885                 890                 895

Lys Lys Pro Val Ala Leu Lys Val Lys Ala Lys Asn Leu Ile Val Thr
            900                 905                 910
```

-continued

```
Glu Ser Gly Ala Pro Pro Thr Asp Leu Gln Lys Met Val Met Gly Asn
        915                 920                 925

Thr Lys Pro Val Glu Leu Ile Leu Asp Gly Lys Thr Val Ala Ile Cys
    930                 935                 940

Cys Ala Thr Gly Val Phe Gly Thr Ala Tyr Leu Val Pro Arg His Leu
945                 950                 955                 960

Phe Ala Glu Lys Tyr Asp Lys Ile Met Leu Asp Gly Arg Ala Met Thr
                965                 970                 975

Asp Ser Asp Tyr Arg Val Phe Glu Phe Glu Ile Lys Val Lys Gly Gln
            980                 985                 990

Asp Met Leu Ser Asp Ala Ala Leu Met Val Leu His Arg Gly Asn Arg
        995                 1000                1005

Val Arg Asp Ile Thr Lys His Phe Arg Asp Thr Ala Arg Met Lys Lys
    1010                1015                1020

Gly Thr Pro Val Val Gly Val Val Asn Asn Ala Asp Val Gly Arg Leu
1025                1030                1035                1040

Ile Phe Ser Gly Glu Ala Leu Thr Tyr Lys Asp Ile Val Val Cys Met
                1045                1050                1055

Asp Gly Asp Thr Met Pro Gly Leu Phe Ala Tyr Lys Ala Ala Thr Lys
            1060                1065                1070

Ala Gly Tyr Cys Gly Gly Ala Val Leu Ala Lys Asp Gly Ala Asp Thr
        1075                1080                1085

Phe Ile Val Gly Thr His Ser Ala Gly Gly Asn Gly Val Gly Tyr Cys
    1090                1095                1100

Ser Cys Val Ser Arg Ser Met Leu Leu Arg Met Lys Ala His Val Asp
1105                1110                1115                1120

Pro Glu Pro Gln His Glu
                1125

<210> SEQ ID NO 8
<211> LENGTH: 6442
<212> TYPE: DNA
<213> ORGANISM: Foot-and-mouth disease virus
<220> FEATURE:
<221> NAME/KEY: CDS
<222> LOCATION: (1640)..(5017)

<400> SEQUENCE: 8 gacccttac aagaataaaa gaagaaacaa ctgtgaaata gtttataaat gtaattcgta      60
tgcagaaaac gataatatat tttggtatga gaaatctaaa ggagacatag tttgtataga     120
catgcgctct tccgatgaga tattcgatgc ttttctaatg tatcatatag ctacaagata     180
tgcctatcat gatgatgata tatatctaca aatagtgtta tattattcta ataatcaaaa     240
tgttatatct tatattacga aaaataaata cgttaagtat ataagaaata aaactagaga     300
cgatattcat aaagtaaaaa tattagctct agaagacttt acaacggaag aaatatattg     360
ttggattagt aatatataac agcgtagctg cacggttttg atcattttcc aacaatataa     420
accaatgaag gaggacgact catcaaacat aaataacatt cacggaaaat attcagtatc     480
agatttatca caagatgatt atgttattga atgtatagac ggatcttttg attcgatcaa     540
gtatagagat ataaaggtta taataatgaa gaataacggt tacgttaatt gtagtaaatt     600
atgtaaaatg cggaataaat acttttctag atggttgcgt ctttctactt ctaaagcatt     660
attagacatt tacaataata agtcagtaga taatgctatt gttaaagtct atggtaaagg     720
taagaaactt attataacag gattttatct caaacaaaat atgatacgtt atgttattga     780
```

-continued

```
gtggataggg gatgatttta caaacgatat atacaaaatg attaatttct ataatgcgtt      840
attcggtaac gatgaattaa aaatagtatc ctgtgaaaac actctatgcc cgtttataga      900
acttggtaga tgctattatg gtaaaaaatg taagtatata cacggagatc aatgtgatat      960
ctgtggtcta tatatactac accctaccga tattaaccaa cgagtttctc acaagaaaac     1020
ttgtttagta gatagagatt ctttgattgt gtttaaaaga agtaccagta aaaagtgtgg     1080
catatgcata gaagaaataa acaaaaaaca tatttccgaa cagtattttg gaattctccc     1140
aagttgtaaa catatttttt gcctatcatg tataagacgt tgggcagata ctaccagaaa     1200
tacagatact gaaaatacgt gtcctgaatg tagaatagtt tttcctttca taatacccag     1260
taggtattgg atagataata aatatgataa aaaatatta tataatagat ataagaaaat      1320 gattttaca aaaataccta taagaacaat aaaaaatataa ttcatttac ggaaaatagc      1380 tggttttagt ttaccaactt agagtaatta tcatattgaa tctatattgc taattagcta    1440 ataaaaccc gggttaatta attagtcatc aggcagggcg agaacgagac tatctgctcg     1500
ttaattaatt agagcttctt tattctatac ttaaaaagtg aaaataaata caaaggttct    1560
tgagggttgt gttaaattga aagcgagaaa taatcataaa ttatttcatt atcgcgatat   1620
ccgttaagtt tgtatcgta atg gga gct ggg caa tcc agc cca gca acc ggc     1672
                       Met Gly Ala Gly Gln Ser Ser Pro Ala Thr Gly
                        1               5                  10 tcg cag aac cag tct ggc aac act ggc agc ata atc aac aac tac tac     1720
Ser Gln Asn Gln Ser Gly Asn Thr Gly Ser Ile Ile Asn Asn Tyr Tyr
         15                  20                  25 atg caa cag tac cag aac tcc atg gac aca cag ttg gga gac aat gcc     1768
Met Gln Gln Tyr Gln Asn Ser Met Asp Thr Gln Leu Gly Asp Asn Ala
     30                  35                  40 atc agt gga ggc tcc aac gag ggc tcc acg gac aca act tca aca cac     1816
Ile Ser Gly Gly Ser Asn Glu Gly Ser Thr Asp Thr Thr Ser Thr His
 45                  50                  55 aca acc aac act caa aac aat gac tgg ttc tcg aag ctc gcc agt tca     1864
Thr Thr Asn Thr Gln Asn Asn Asp Trp Phe Ser Lys Leu Ala Ser Ser
 60                  65                  70                  75 gct ttt acc ggt ctg ttc ggt gca ctc ctc gcc gac aag aag aca gag     1912
Ala Phe Thr Gly Leu Phe Gly Ala Leu Leu Ala Asp Lys Lys Thr Glu
             80                  85                  90 gaa acg aca ctt ctt gag gac cgc atc ctc acc acc cgc aac ggg cac     1960
Glu Thr Thr Leu Leu Glu Asp Arg Ile Leu Thr Thr Arg Asn Gly His
         95                 100                 105 acc acc tcg acg acc caa tcg agt gtg ggt gtc aca cac ggg tac tcc     2008
Thr Thr Ser Thr Thr Gln Ser Ser Val Gly Val Thr His Gly Tyr Ser
    110                 115                 120 aca gag gag gac cac gtt gct ggg ccc aac aca tcg ggc ctg gag acg     2056
Thr Glu Glu Asp His Val Ala Gly Pro Asn Thr Ser Gly Leu Glu Thr
125                 130                 135 cga gtg gtg cag gca gag aga ttc tac aaa aag tac ttg ttt gac tgg     2104
Arg Val Val Gln Ala Glu Arg Phe Tyr Lys Lys Tyr Leu Phe Asp Trp
140                 145                 150                 155 aca acg gac aag gca ttt gga cac ctg gaa aag ctg gag ctc ccg tcc     2152
Thr Thr Asp Lys Ala Phe Gly His Leu Glu Lys Leu Glu Leu Pro Ser
             160                 165                 170 gac cac cac ggt gtc ttt gga cac ttg gtg gac tcg tac gcc tat atg     2200
Asp His His Gly Val Phe Gly His Leu Val Asp Ser Tyr Ala Tyr Met
        175                 180                 185 aga aat ggc tgg gat gtt gag gtg tcc gct gtt ggc aac cag ttc aac     2248
Arg Asn Gly Trp Asp Val Glu Val Ser Ala Val Gly Asn Gln Phe Asn
    190                 195                 200
```

```
ggc ggg tgc ctc ctg gtg gcc atg gta cct gaa tgg aag gaa ttt gac      2296
Gly Gly Cys Leu Leu Val Ala Met Val Pro Glu Trp Lys Glu Phe Asp
205                 210                 215 aca cgg gag aaa tac caa ctc acc ctt ttc ccg cac cag ttt att agc      2344
Thr Arg Glu Lys Tyr Gln Leu Thr Leu Phe Pro His Gln Phe Ile Ser
220                 225                 230                 235 ccc aga act aac atg act gcc cac atc acg gtc ccc tac ctt ggt gtg     2392
Pro Arg Thr Asn Met Thr Ala His Ile Thr Val Pro Tyr Leu Gly Val
                240                 245                 250 aac agg tat gat cag tac aag aag cat aag ccc tgg aca ttg gtt gtc     2440
Asn Arg Tyr Asp Gln Tyr Lys Lys His Lys Pro Trp Thr Leu Val Val
            255                 260                 265 atg gtc gtg tcg cca ctt acg gtc aac aac act agt gcg gca caa atc     2488
Met Val Val Ser Pro Leu Thr Val Asn Asn Thr Ser Ala Ala Gln Ile
        270                 275                 280 aag gtc tac gcc aac ata gct ccg acc tat gtt cac gtg gcc ggt gaa     2536
Lys Val Tyr Ala Asn Ile Ala Pro Thr Tyr Val His Val Ala Gly Glu
285                 290                 295 ctc ccc tcg aaa gag ggg att ttc ccg gtt gca tgt gcg gac ggt tac     2584
Leu Pro Ser Lys Glu Gly Ile Phe Pro Val Ala Cys Ala Asp Gly Tyr
300                 305                 310                 315 gga gga ttg gtg acg aca gac ccg aag aca gct gac cct gct tat ggc     2632
Gly Gly Leu Val Thr Thr Asp Pro Lys Thr Ala Asp Pro Ala Tyr Gly
                320                 325                 330 aag gta tac aac ccg cct agg act aac tac cct ggg cgc ttc acc aac     2680
Lys Val Tyr Asn Pro Pro Arg Thr Asn Tyr Pro Gly Arg Phe Thr Asn
            335                 340                 345 ctg ttg gac gtg gcc gaa gcg tgt ccc act ttc ctc tgc ttt gac gac     2728
Leu Leu Asp Val Ala Glu Ala Cys Pro Thr Phe Leu Cys Phe Asp Asp
        350                 355                 360 ggg aaa ccg tac gtc acc acg cgg acg gat gac acc cga ctt ttg gcc     2776
Gly Lys Pro Tyr Val Thr Thr Arg Thr Asp Asp Thr Arg Leu Leu Ala
365                 370                 375 aag ttt gac ctt tcc ctt gcc gca aaa cat atg tcc aac aca tac ctg     2824
Lys Phe Asp Leu Ser Leu Ala Ala Lys His Met Ser Asn Thr Tyr Leu
380                 385                 390                 395 tca ggg att gct cag tac tac aca cag tac tct ggc acc atc aat ttg     2872
Ser Gly Ile Ala Gln Tyr Tyr Thr Gln Tyr Ser Gly Thr Ile Asn Leu
                400                 405                 410 cat ttc atg ttt aca ggt tcc act gat tca aag gcc cga tac atg gtg     2920
His Phe Met Phe Thr Gly Ser Thr Asp Ser Lys Ala Arg Tyr Met Val
            415                 420                 425 gcc tac atc cca cct ggg gtg gag aca cca ccg gac aca cct gaa agg     2968
Ala Tyr Ile Pro Pro Gly Val Glu Thr Pro Pro Asp Thr Pro Glu Arg
        430                 435                 440 gct gcc cac tgc att cac gct gaa tgg gac act gga cta aac tcc aaa     3016
Ala Ala His Cys Ile His Ala Glu Trp Asp Thr Gly Leu Asn Ser Lys
445                 450                 455 ttc act ttc tca atc ccg tac gta tcc gcc gcg gat tac gcg tac aca     3064
Phe Thr Phe Ser Ile Pro Tyr Val Ser Ala Ala Asp Tyr Ala Tyr Thr
460                 465                 470                 475 gcg tct gac acg gca gaa aca atc aac gta cag gga tgg gtc tgc atc     3112
Ala Ser Asp Thr Ala Glu Thr Ile Asn Val Gln Gly Trp Val Cys Ile
                480                 485                 490 tac caa att aca cac ggg aag gct gaa aat gac acc ttg gtc gtg tcg     3160
Tyr Gln Ile Thr His Gly Lys Ala Glu Asn Asp Thr Leu Val Val Ser
            495                 500                 505 gtt agc gcc ggc aaa gac ttt gag ttg cgc ctc ccg att gac ccc cgc     3208
Val Ser Ala Gly Lys Asp Phe Glu Leu Arg Leu Pro Ile Asp Pro Arg
```

-continued

|  |  |  |  | 510 |  |  |  |  | 515 |  |  |  |  | 520 |  |  |
|---|---|---|---|---|---|---|---|---|---|---|---|---|---|---|---|---|
| cag | cag | acc | acc | gct | acc | ggg | gaa | tca | gca | gac | ccg | gtc | acc | acc | acc | 3256 |
| Gln | Gln<br>525 | Thr | Thr | Ala | Thr | Gly<br>530 | Glu | Ser | Ala | Asp | Pro<br>535 | Val | Thr | Thr | Thr |  |
| gtg | gag | aac | tac | ggc | ggt | gag | aca | caa | atc | cag | aga | cgt | cac | cac | acg | 3304 |
| Val<br>540 | Glu | Asn | Tyr | Gly | Gly<br>545 | Glu | Thr | Gln | Ile | Gln<br>550 | Arg | Arg | His | His | Thr<br>555 |  |
| gac | att | ggt | ttc | atc | atg | gac | aga | ttt | gtg | aag | atc | caa | agc | ttg | agc | 3352 |
| Asp | Ile | Gly | Phe | Ile<br>560 | Met | Asp | Arg | Phe | Val<br>565 | Lys | Ile | Gln | Ser | Leu<br>570 | Ser |  |
| cca | aca | cat | gtc | att | gac | ctc | atg | cag | gct | cac | caa | cac | ggt | ctg | gtg | 3400 |
| Pro | Thr | His<br>575 | Val | Ile | Asp | Leu | Met<br>580 | Gln | Ala | His | Gln | His<br>585 | Gly | Leu | Val |  |
| ggt | gcc | ttg | ctg | cgt | gca | gcc | acg | tac | tac | ttt | tct | gac | ctg | gaa | att | 3448 |
| Gly | Ala | Leu | Leu<br>590 | Arg | Ala | Ala | Thr | Tyr<br>595 | Tyr | Phe | Ser | Asp | Leu<br>600 | Glu | Ile |  |
| gtt | gta | cgg | cac | gaa | ggc | aat | ctg | acc | tgg | gtg | ccc | aac | ggc | gcc | cct | 3496 |
| Val | Val | Arg<br>605 | His | Glu | Gly | Asn | Leu<br>610 | Thr | Trp | Val | Pro | Asn<br>615 | Gly | Ala | Pro |  |
| gaa | tca | gcc | ctg | ttg | aac | acc | agc | aac | ccc | act | gcc | tac | aac | aag | gca | 3544 |
| Glu<br>620 | Ser | Ala | Leu | Leu | Asn<br>625 | Thr | Ser | Asn | Pro | Thr<br>630 | Ala | Tyr | Asn | Lys | Ala<br>635 |  |
| cca | ttc | acg | aga | ctc | gct | ctc | ccc | tac | act | gcg | ccg | cac | cgt | gtg | ctg | 3592 |
| Pro | Phe | Thr | Arg | Leu<br>640 | Ala | Leu | Pro | Tyr | Thr<br>645 | Ala | Pro | His | Arg | Val<br>650 | Leu |  |
| gca | aca | gtg | tac | aac | ggg | acg | agt | aag | tat | gct | gtg | ggt | ggt | tca | ggc | 3640 |
| Ala | Thr | Val | Tyr | Asn<br>655 | Gly | Thr | Ser | Lys | Tyr<br>660 | Ala | Val | Gly | Gly | Ser<br>665 | Gly |  |
| aga | aga | ggc | gac | atg | ggg | tct | ctc | gcg | gcg | cga | gtc | gtg | aaa | cag | ctt | 3688 |
| Arg | Arg | Gly | Asp | Met<br>670 | Gly | Ser | Leu | Ala | Ala<br>675 | Arg | Val | Val | Lys | Gln<br>680 | Leu |  |
| cct | gct | tca | ttt | aac | tac | ggt | gca | atc | aag | gcc | gac | gcc | atc | cac | gaa | 3736 |
| Pro | Ala | Ser | Phe | Asn<br>685 | Tyr | Gly | Ala | Ile | Lys<br>690 | Ala | Asp | Ala | Ile | His<br>695 | Glu |  |
| ctt | ctc | gtg | cgc | atg | aaa | cgg | gcc | gag | ctc | tac | tgc | ccc | aga | ccg | ctg | 3784 |
| Leu<br>700 | Leu | Val | Arg | Met | Lys<br>705 | Arg | Ala | Glu | Leu | Tyr<br>710 | Cys | Pro | Arg | Pro | Leu<br>715 |  |
| ttg | gca | ata | gag | gtg | tct | tcg | caa | gac | agg | cac | aag | caa | aag | atc | att | 3832 |
| Leu | Ala | Ile | Glu | Val<br>720 | Ser | Ser | Gln | Asp | Arg<br>725 | His | Lys | Gln | Lys | Ile<br>730 | Ile |  |
| gca | cca | gca | aag | cag | ctt | ctg | aat | ttt | gac | ctg | ctc | aag | ttg | gcc | gga | 3880 |
| Ala | Pro | Ala | Lys | Gln<br>735 | Leu | Leu | Asn | Phe | Asp<br>740 | Leu | Leu | Lys | Leu | Ala<br>745 | Gly |  |
| gac | gtt | gag | tcc | aac | ccc | ggg | cca | ttc | ttc | ttt | gct | gac | gtt | agg | tca | 3928 |
| Asp | Val | Glu | Ser | Asn<br>750 | Pro | Gly | Pro | Phe | Phe<br>755 | Phe | Ala | Asp | Val | Arg<br>760 | Ser |  |
| aac | ttt | tca | aag | ttg | gta | gac | aca | atc | aac | cag | atg | cag | gag | gac | atg | 3976 |
| Asn | Phe | Ser | Lys<br>765 | Leu | Val | Asp | Thr | Ile<br>770 | Asn | Gln | Met | Gln | Glu<br>775 | Asp | Met |  |
| tcc | aca | aaa | cac | ggg | ccc | gac | ttc | aac | cgg | ttg | gtg | tcc | gca | ttt | gag | 4024 |
| Ser | Thr | Lys | His<br>780 | Gly | Pro | Asp | Phe | Asn<br>785 | Arg | Leu | Val | Ser | Ala<br>790 | Phe | Glu<br>795 |  |
| gaa | ttg | gcc | act | gga | gtt | aaa | gct | atc | agg | acc | ggt | ctc | gac | gag | gcc | 4072 |
| Glu | Leu | Ala | Thr | Gly<br>800 | Val | Lys | Ala | Ile | Arg<br>805 | Thr | Gly | Leu | Asp | Glu<br>810 | Ala |  |
| aaa | ccc | tgg | tac | aag | ctt | atc | aaa | ctc | cta | agc | cgc | ctg | tcg | tgc | atg | 4120 |
| Lys | Pro | Trp | Tyr | Lys<br>815 | Leu | Ile | Lys | Leu | Leu<br>820 | Ser | Arg | Leu | Ser | Cys<br>825 | Met |  |
| gcc | gct | gtg | gca | gca | cgg | tcc | aag | gac | cca | gtc | ctt | gtg | gcc | atc | atg | 4168 |

```
Ala Ala Val Ala Ala Arg Ser Lys Asp Pro Val Leu Val Ala Ile Met
        830                 835                 840 ctg gcc gac acc ggt ctc gag cgt cag aga cct ctg aaa gtg aga gct     4216
Leu Ala Asp Thr Gly Leu Glu Arg Gln Arg Pro Leu Lys Val Arg Ala
845                 850                 855 aag ctc cca cag cag gaa gga cct tac gct ggc ccg ttg gag aga cag     4264
Lys Leu Pro Gln Gln Glu Gly Pro Tyr Ala Gly Pro Leu Glu Arg Gln
860                 865                 870                 875 aaa ccg ctg aaa gtg aaa gca aaa gcc ccg gtc gtc aag gaa gga cct     4312
Lys Pro Leu Lys Val Lys Ala Lys Ala Pro Val Val Lys Glu Gly Pro
            880                 885                 890 tac gag gga ccg gtg aag aag cct gtc gct ttg aaa gtg aaa gct aag     4360
Tyr Glu Gly Pro Val Lys Lys Pro Val Ala Leu Lys Val Lys Ala Lys
                895                 900                 905 aac ttg ata gtc act gag agt ggt gcc cca ccg acc gac ttg caa aag     4408
Asn Leu Ile Val Thr Glu Ser Gly Ala Pro Pro Thr Asp Leu Gln Lys
            910                 915                 920 atg gtc atg ggc aac aca aag cct gtt gag ctc atc ctt gac ggg aag     4456
Met Val Met Gly Asn Thr Lys Pro Val Glu Leu Ile Leu Asp Gly Lys
925                 930                 935 aca gta gcc atc tgt tgt gct act gga gtg ttt ggc act gct tac ctc     4504
Thr Val Ala Ile Cys Cys Ala Thr Gly Val Phe Gly Thr Ala Tyr Leu
940                 945                 950                 955 gtg cct cgt cat ctt ttc gca gag aag tat gac aag atc atg ctg gat     4552
Val Pro Arg His Leu Phe Ala Glu Lys Tyr Asp Lys Ile Met Leu Asp
                960                 965                 970 ggc aga gcc atg aca gac agt gac tac aga gtg ttt gag ttt gag att     4600
Gly Arg Ala Met Thr Asp Ser Asp Tyr Arg Val Phe Glu Phe Glu Ile
                    975                 980                 985 aaa gta aaa gga cag gac atg ctc tca gac gct gcg ctc atg gtg ctc     4648
Lys Val Lys Gly Gln Asp Met Leu Ser Asp Ala Ala Leu Met Val Leu
                990                 995                 1000 cac cgt ggg aac cgc gtg aga gat atc acg aaa cac ttt cgt gat aca     4696
His Arg Gly Asn Arg Val Arg Asp Ile Thr Lys His Phe Arg Asp Thr
        1005                1010                1015 gca aga atg aag aaa ggc acc ccc gtc gtc ggt gtg gtc aac aac gcc     4744
Ala Arg Met Lys Lys Gly Thr Pro Val Val Gly Val Val Asn Asn Ala
1020                1025                1030                1035 gac gtt ggg aga ctg att ttc tct ggt gag gcc ctc acc tac aag gat     4792
Asp Val Gly Arg Leu Ile Phe Ser Gly Glu Ala Leu Thr Tyr Lys Asp
                1040                1045                1050 att gta gtg tgc atg gac gga gac acc atg cct ggc ctc ttt gcc tac     4840
Ile Val Val Cys Met Asp Gly Asp Thr Met Pro Gly Leu Phe Ala Tyr
            1055                1060                1065 aaa gcc gcc acc aag gca ggc tac tgt gga gga gcc gtt ctc gcc aag     4888
Lys Ala Ala Thr Lys Ala Gly Tyr Cys Gly Gly Ala Val Leu Ala Lys
        1070                1075                1080 gac ggg gcc gac act ttc atc gtc ggc act cac tcc gca gga ggc aat     4936
Asp Gly Ala Asp Thr Phe Ile Val Gly Thr His Ser Ala Gly Gly Asn
1085                1090                1095 gga gtt gga tac tgc tca tgc gtt tcc agg tcc atg ctt ctc aga atg     4984
Gly Val Gly Tyr Cys Ser Cys Val Ser Arg Ser Met Leu Leu Arg Met
1100                1105                1110                1115 aag gca cac gtt gac cct gaa cca caa cac gag tagtaatttt tctagaggat   5037
Lys Ala His Val Asp Pro Glu Pro Gln His Glu
                1120                1125 ccctcgagtt tttattgact agttaatcat aagataaata atatacagca ttgtaaccat    5097
cgtcatccgt tatacgggga ataatattac catacagtat tattaatttt tcttacgaag    5157
```

```
aatatagatc ggtatttatc gttagtttat tttacattta ttaattaaac atgtctacta     5217
ttacctgtta tggaaatgac aaatttagtt atataattta tgataaaatt aagataataa     5277
taatgaaatc aaataattat gtaaatgcta ctagattatg tgaattacga ggaagaaagt     5337
ttacgaactg gaaaaaatta agtgaatcta aatatattagt cgataatgta aaaaaaataa    5397
atgataaaac taaccagtta aaaacggata tgattatata cgttaaggat attgatcata    5457
aaggaagaga tacttgcggt tactatgtac accaagatct ggtatcttct atatcaaatt    5517
ggatatctcc gttattcgcc gttaaggtaa ataaaattat taactattat atatgtaatg    5577
aatatgatat acgacttagc gaaatggaat ctgatatgac agaagtaata gatgtagttg    5637
ataaattagt aggaggatac aatgatgaaa tagcagaaat aatatatttg tttaataaat    5697
ttatagaaaa atatattgct aacatatcgt tatcaactga attatctagt atattaaata    5757
attttataaa ttttaataaa aaatacaata acgacataaa agatattaaa tctttaattc    5817
ttgatctgaa aaacacatct ataaaactag ataaaaagtt attcgataaa gataataatg    5877
aatcgaacga tgaaaaattg gaaacagaag ttgataagct aatttttttc atctaaatag    5937
tattatttta ttgaagtacg aagttttacg ttagataaat aataaaggtc gattttattt    5997
ttgttaaata tcaaatatgt cattatctga taaagataca aaaacacacg gtgattatca    6057
accatctaac gaacagatat tacaaaaaat acgtcggact atggaaaacg aagctgatag    6117
cctcaataga agaagcatta aagaaattgt tgtagatgtt atgaagaatt gggatcatcc    6177
tctcaacgaa gaaatagata aagttctaaa ctggaaaaat gatacattaa acgatttaga    6237
tcatctaaat acagatgata atattaagga aatcatacaa tgtctgatta gagaatttgc    6297
gtttaaaaag atcaattcta ttatgtatag ttatgctatg gtaaaactca attcagataa    6357
cgaaacattg aaagataaaa ttaaggatta ttttatagaa actattctta aagacaaacg    6417
tggttataaa caaaagccat taccc                                            6442
```

<210> SEQ ID NO 9
<211> LENGTH: 1126
<212> TYPE: PRT
<213> ORGANISM: Foot-and-mouth disease virus

<400> SEQUENCE: 9

```
Met Gly Ala Gly Gln Ser Ser Pro Ala Thr Gly Ser Gln Asn Gln Ser
 1               5                  10                  15

Gly Asn Thr Gly Ser Ile Ile Asn Asn Tyr Tyr Met Gln Gln Tyr Gln
             20                  25                  30

Asn Ser Met Asp Thr Gln Leu Gly Asp Asn Ala Ile Ser Gly Gly Ser
         35                  40                  45

Asn Glu Gly Ser Thr Asp Thr Thr Ser Thr His Thr Thr Asn Thr Gln
     50                  55                  60

Asn Asn Asp Trp Phe Ser Lys Leu Ala Ser Ala Phe Thr Gly Leu
 65                  70                  75                  80

Phe Gly Ala Leu Leu Ala Asp Lys Lys Thr Glu Glu Thr Thr Leu Leu
                 85                  90                  95

Glu Asp Arg Ile Leu Thr Thr Arg Asn Gly His Thr Thr Ser Thr Thr
            100                 105                 110

Gln Ser Ser Val Gly Val Thr His Gly Tyr Ser Thr Glu Glu Asp His
        115                 120                 125

Val Ala Gly Pro Asn Thr Ser Gly Leu Glu Thr Arg Val Val Gln Ala
    130                 135                 140
```

```
Glu Arg Phe Tyr Lys Lys Tyr Leu Phe Asp Trp Thr Thr Asp Lys Ala
145                 150                 155                 160

Phe Gly His Leu Glu Lys Leu Glu Leu Pro Ser Asp His His Gly Val
                165                 170                 175

Phe Gly His Leu Val Asp Ser Tyr Ala Tyr Met Arg Asn Gly Trp Asp
            180                 185                 190

Val Glu Val Ser Ala Val Gly Asn Gln Phe Asn Gly Gly Cys Leu Leu
                195                 200                 205

Val Ala Met Val Pro Glu Trp Lys Glu Phe Asp Thr Arg Glu Lys Tyr
        210                 215                 220

Gln Leu Thr Leu Phe Pro His Gln Phe Ile Ser Pro Arg Thr Asn Met
225                 230                 235                 240

Thr Ala His Ile Thr Val Pro Tyr Leu Gly Val Asn Arg Tyr Asp Gln
                245                 250                 255

Tyr Lys Lys His Lys Pro Trp Thr Leu Val Val Met Val Val Ser Pro
                260                 265                 270

Leu Thr Val Asn Asn Thr Ser Ala Ala Gln Ile Lys Val Tyr Ala Asn
        275                 280                 285

Ile Ala Pro Thr Tyr Val His Val Ala Gly Leu Pro Ser Lys Glu
290                 295                 300

Gly Ile Phe Pro Val Ala Cys Ala Asp Gly Tyr Gly Gly Leu Val Thr
305                 310                 315                 320

Thr Asp Pro Lys Thr Ala Asp Pro Ala Tyr Gly Lys Val Tyr Asn Pro
                325                 330                 335

Pro Arg Thr Asn Tyr Pro Gly Arg Phe Thr Asn Leu Leu Asp Val Ala
                340                 345                 350

Glu Ala Cys Pro Thr Phe Leu Cys Phe Asp Gly Lys Pro Tyr Val
                355                 360                 365

Thr Thr Arg Thr Asp Asp Thr Arg Leu Leu Ala Lys Phe Asp Leu Ser
        370                 375                 380

Leu Ala Ala Lys His Met Ser Asn Thr Tyr Leu Ser Gly Ile Ala Gln
385                 390                 395                 400

Tyr Tyr Thr Gln Tyr Ser Gly Thr Ile Asn Leu His Phe Met Phe Thr
                405                 410                 415

Gly Ser Thr Asp Ser Lys Ala Arg Tyr Met Val Ala Tyr Ile Pro Pro
            420                 425                 430

Gly Val Glu Thr Pro Pro Asp Thr Pro Glu Arg Ala Ala His Cys Ile
        435                 440                 445

His Ala Glu Trp Asp Thr Gly Leu Asn Ser Lys Phe Thr Phe Ser Ile
    450                 455                 460

Pro Tyr Val Ser Ala Ala Asp Tyr Ala Tyr Thr Ala Ser Asp Thr Ala
465                 470                 475                 480

Glu Thr Ile Asn Val Gln Gly Trp Val Cys Ile Tyr Gln Ile Thr His
                485                 490                 495

Gly Lys Ala Glu Asn Asp Thr Leu Val Val Ser Val Ser Ala Gly Lys
            500                 505                 510

Asp Phe Glu Leu Arg Leu Pro Ile Asp Pro Arg Gln Gln Thr Thr Ala
        515                 520                 525

Thr Gly Glu Ser Ala Asp Pro Val Thr Thr Val Glu Asn Tyr Gly
        530                 535                 540

Gly Glu Thr Gln Ile Gln Arg Arg His His Thr Asp Ile Gly Phe Ile
545                 550                 555                 560

Met Asp Arg Phe Val Lys Ile Gln Ser Leu Ser Pro Thr His Val Ile
```

-continued

```
                565                 570                 575
Asp Leu Met Gln Ala His Gln His Gly Leu Val Gly Ala Leu Leu Arg
            580                 585                 590
Ala Ala Thr Tyr Tyr Phe Ser Asp Leu Glu Ile Val Val Arg His Glu
            595                 600                 605
Gly Asn Leu Thr Trp Val Pro Asn Gly Ala Pro Glu Ser Ala Leu Leu
            610                 615                 620
Asn Thr Ser Asn Pro Thr Ala Tyr Asn Lys Ala Pro Phe Thr Arg Leu
625                 630                 635                 640
Ala Leu Pro Tyr Thr Ala Pro His Arg Val Leu Ala Thr Val Tyr Asn
            645                 650                 655
Gly Thr Ser Lys Tyr Ala Val Gly Gly Ser Gly Arg Arg Gly Asp Met
            660                 665                 670
Gly Ser Leu Ala Ala Arg Val Val Lys Gln Leu Pro Ala Ser Phe Asn
            675                 680                 685
Tyr Gly Ala Ile Lys Ala Asp Ala Ile His Glu Leu Leu Val Arg Met
            690                 695                 700
Lys Arg Ala Glu Leu Tyr Cys Pro Arg Pro Leu Leu Ala Ile Glu Val
705                 710                 715                 720
Ser Ser Gln Asp Arg His Lys Gln Lys Ile Ile Ala Pro Ala Lys Gln
            725                 730                 735
Leu Leu Asn Phe Asp Leu Leu Lys Leu Ala Gly Asp Val Glu Ser Asn
            740                 745                 750
Pro Gly Pro Phe Phe Ala Asp Val Arg Ser Asn Phe Ser Lys Leu
            755                 760                 765
Val Asp Thr Ile Asn Gln Met Gln Glu Asp Met Ser Thr Lys His Gly
            770                 775                 780
Pro Asp Phe Asn Arg Leu Val Ser Ala Phe Glu Glu Leu Ala Thr Gly
785                 790                 795                 800
Val Lys Ala Ile Arg Thr Gly Leu Asp Glu Ala Lys Pro Trp Tyr Lys
            805                 810                 815
Leu Ile Lys Leu Leu Ser Arg Leu Ser Cys Met Ala Ala Val Ala Ala
            820                 825                 830
Arg Ser Lys Asp Pro Val Leu Val Ala Ile Met Leu Ala Asp Thr Gly
            835                 840                 845
Leu Glu Arg Gln Arg Pro Leu Lys Val Arg Ala Lys Leu Pro Gln Gln
            850                 855                 860
Glu Gly Pro Tyr Ala Gly Pro Leu Glu Arg Gln Lys Pro Leu Lys Val
865                 870                 875                 880
Lys Ala Lys Ala Pro Val Val Lys Glu Gly Pro Tyr Glu Gly Pro Val
            885                 890                 895
Lys Lys Pro Val Ala Leu Lys Val Lys Ala Lys Asn Leu Ile Val Thr
            900                 905                 910
Glu Ser Gly Ala Pro Pro Thr Asp Leu Gln Lys Met Val Met Gly Asn
            915                 920                 925
Thr Lys Pro Val Glu Leu Ile Leu Asp Gly Lys Thr Val Ala Ile Cys
930                 935                 940
Cys Ala Thr Gly Val Phe Gly Thr Ala Tyr Leu Val Pro Arg His Leu
945                 950                 955                 960
Phe Ala Glu Lys Tyr Asp Lys Ile Met Leu Asp Gly Arg Ala Met Thr
            965                 970                 975
Asp Ser Asp Tyr Arg Val Phe Glu Phe Glu Ile Lys Val Lys Gly Gln
            980                 985                 990
```

```
Asp Met Leu Ser Asp Ala Ala Leu Met Val Leu His Arg Gly Asn Arg
        995                 1000                1005

Val Arg Asp Ile Thr Lys His Phe Arg Asp Thr Ala Arg Met Lys Lys
    1010                1015                1020

Gly Thr Pro Val Val Gly Val Val Asn Asn Ala Asp Val Gly Arg Leu
1025                1030                1035                1040

Ile Phe Ser Gly Glu Ala Leu Thr Tyr Lys Asp Ile Val Cys Met
                1045                1050                1055

Asp Gly Asp Thr Met Pro Gly Leu Phe Ala Tyr Lys Ala Ala Thr Lys
            1060                1065                1070

Ala Gly Tyr Cys Gly Gly Ala Val Leu Ala Lys Asp Gly Ala Asp Thr
        1075                1080                1085

Phe Ile Val Gly Thr His Ser Ala Gly Gly Asn Gly Val Gly Tyr Cys
        1090                1095                1100

Ser Cys Val Ser Arg Ser Met Leu Leu Arg Met Lys Ala His Val Asp
1105                1110                1115                1120

Pro Glu Pro Gln His Glu
                1125

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cgacaccggt ctcgagcgtc agag                                          24

<210> SEQ ID NO 11
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gttgaccctg aaccacaaca cgagtagtaa tttttctgca g                       41

<210> SEQ ID NO 12
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctgcagaaaa attactactc gtgttgtggt tcagggtcaa c                       41

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Thr Gly Leu Glu Arg Gln Arg
```

-continued

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Asp Pro Glu Pro Gln His Glu
  1               5

<210> SEQ ID NO 15
<211> LENGTH: 5102
<212> TYPE: DNA
<213> ORGANISM: Foot-and-mouth disease virus
<220> FEATURE:
<221> NAME/KEY: CDS
<222> LOCATION: (1311)..(4688)

<400> SEQUENCE: 15

```
ttcataaata caagtttgat taaacttaag ttgttctaaa gttctttcct ccgaaggtat      60
agaacaaagt atttcttcta catccttact atttattgca gcttttaaca gcctatcacg     120
tatcctattt ttagtattgg tagaacgttt tagttctaaa gttaaaatat tagacataat     180
tggcatattg cttattcctt gcatagttga gtctgtagat cgtttcagta tatcactgat     240
taatgtacta ctgttatgat gaaatataga atcgatattg gcatttaact gttttgttat     300
actaagtcta gatttaaat cttctagtaa tatgctattt aatataaaag cttccacgtt      360
tttgtataca tttcttttcca tattagtagc tactactaaa tgattatctt ctttcatatc    420
ttgtagataa gatagactat ctttatcttt attagtagaa aatacttctg gccatacatc     480
gttaaatttt tttgttgttg ttagatataa tattaaaatat ctagaggatc ctattatttg    540
tggtaaaatg tttatagagt aaaatgatct ggctattaaa cataggccag ttaccataga    600
atgctgcttc ccgttacagt gttttaccat aaccatagat ctgcctgtat tgttgataca    660
tataacagct gtaaatccta aaaaattcct atcataatta ttaatattag gtaattcatt    720
tccatgtgaa agatagacta attttatatc ctttacctcc aaataattat ttacatctct    780
taaacaatct attttaatat cattaactgg tattttataa tatccagaaa ggtttgaagg     840
ggttgatgga ataagtctat taacatcgtt aagtaaatta ttaatatcat gaatctttat    900
tatattatac ccataagtta aatttatatt tactttctca tcatctgact tagttagttt    960
gtaataaggt gtgtctgaaa aaattaaaag gtaattcgtt gaatgaagct gtatttgctg   1020
tatcattttt atctaatttt ggagatttag cagtacttac ttcattagaa gaagaatctg    1080
ccagttcctg tctattactg atatttcgtt tcattattat atgatttata ttttactttt   1140
tcaattatat atactcattt gactagttaa tcaataaaaa gaattgttct ttattctata   1200
cttaaaaagt gaaataaat acaaaggttc ttgagggttg tgttaaattg aaagcgagaa    1260
ataatcataa attatttcat tatcgcgata tccgttaagt ttgtatcgta atg gga     1316
                                                     Met Gly
                                                       1 gct ggg caa tcc agc cca gca acc ggc tcg cag aac cag tct ggc aac    1364
Ala Gly Gln Ser Ser Pro Ala Thr Gly Ser Gln Asn Gln Ser Gly Asn
        5                   10                  15 act ggc agc ata atc aac aac tac tac atg caa cag tac cag aac tcc    1412
Thr Gly Ser Ile Ile Asn Asn Tyr Tyr Met Gln Gln Tyr Gln Asn Ser
```

```
                       20                  25                  30
atg gac aca cag ttg gga gac aat gcc atc agt gga ggc tcc aac gag         1460
Met Asp Thr Gln Leu Gly Asp Asn Ala Ile Ser Gly Gly Ser Asn Glu
 35                  40                  45                  50 ggc tcc acg gac aca act tca aca cac aca acc aac act caa aac aat         1508
Gly Ser Thr Asp Thr Thr Ser Thr His Thr Asn Thr Gln Asn Asn
                 55                  60                  65 gac tgg ttc tcg aag ctc gcc agt tca gct ttt acc ggt ctg ttc ggt         1556
Asp Trp Phe Ser Lys Leu Ala Ser Ser Ala Phe Thr Gly Leu Phe Gly
         70                  75                  80 gca ctg ctc gcc gac aag aag aca gag gaa acg aca ctt ctt gag gac         1604
Ala Leu Leu Ala Asp Lys Lys Thr Glu Glu Thr Thr Leu Leu Glu Asp
     85                  90                  95 cgc atc ctc acc acc cgc aac ggg cac acc acc tcg acg acc caa tcg         1652
Arg Ile Leu Thr Thr Arg Asn Gly His Thr Thr Ser Thr Thr Gln Ser
 100                 105                 110 agt gtg ggt gtc aca cac ggg tac tcc aca gag gag gac cac gtt gct         1700
Ser Val Gly Val Thr His Gly Tyr Ser Thr Glu Glu Asp His Val Ala
115                 120                 125                 130 ggg ccc aac aca tcg ggc ctg gag acg cga gtg gtg cag gca gag aga         1748
Gly Pro Asn Thr Ser Gly Leu Glu Thr Arg Val Val Gln Ala Glu Arg
                135                 140                 145 ttc tac aaa aag tac ttg ttt gac tgg aca acg gac aag gca ttt gga         1796
Phe Tyr Lys Lys Tyr Leu Phe Asp Trp Thr Thr Asp Lys Ala Phe Gly
        150                 155                 160 cac ctg gaa aag ctg gag ctc ccg tcc gac cac cac ggt gtc ttt gga         1844
His Leu Glu Lys Leu Glu Leu Pro Ser Asp His His Gly Val Phe Gly
    165                 170                 175 cac ttg gtg gac tcg tac gcc tat atg aga aat ggc tgg gat gtt gag         1892
His Leu Val Asp Ser Tyr Ala Tyr Met Arg Asn Gly Trp Asp Val Glu
180                 185                 190 gtg tcc gct gtt ggc aac cag ttc aac ggc ggg tgc ctc ctg gtg gcc         1940
Val Ser Ala Val Gly Asn Gln Phe Asn Gly Gly Cys Leu Leu Val Ala
195                 200                 205                 210 atg gta cct gaa tgg aag gaa ttt gac aca cgg gag aaa tac caa ctc         1988
Met Val Pro Glu Trp Lys Glu Phe Asp Thr Arg Glu Lys Tyr Gln Leu
                215                 220                 225 acc ctt ttc ccg cac cag ttt att agc ccc aga act aac atg act gcc         2036
Thr Leu Phe Pro His Gln Phe Ile Ser Pro Arg Thr Asn Met Thr Ala
        230                 235                 240 cac atc acg gtc ccc tac ctt ggt gtg aac agg tat gat cag tac aag         2084
His Ile Thr Val Pro Tyr Leu Gly Val Asn Arg Tyr Asp Gln Tyr Lys
    245                 250                 255 aag cat aag ccc tgg aca ttg gtt gtc atg gtc gtg tcg cca ctt acg         2132
Lys His Lys Pro Trp Thr Leu Val Val Met Val Val Ser Pro Leu Thr
260                 265                 270 gtc aac aac act agt gcg gca caa atc aag gtc tac gcc aac ata gct         2180
Val Asn Asn Thr Ser Ala Ala Gln Ile Lys Val Tyr Ala Asn Ile Ala
275                 280                 285                 290 ccg acc tat gtt cac gtg gcc ggt gaa ctc ccc tcg aaa gag ggg att         2228
Pro Thr Tyr Val His Val Ala Gly Glu Leu Pro Ser Lys Glu Gly Ile
                295                 300                 305 ttc ccg gtt gca tgt gcg gac ggt tac gga gga ttg gtg acg aca gac         2276
Phe Pro Val Ala Cys Ala Asp Gly Tyr Gly Gly Leu Val Thr Thr Asp
        310                 315                 320 ccg aag aca gct gac cct gct tat ggc aag gtg tac aac ccg cct agg         2324
Pro Lys Thr Ala Asp Pro Ala Tyr Gly Lys Val Tyr Asn Pro Pro Arg
    325                 330                 335 act aac tac cct ggg cgc ttc acc aac ctg ttg gac gtg gcc gaa gcg         2372
```

```
        Thr Asn Tyr Pro Gly Arg Phe Thr Asn Leu Leu Asp Val Ala Glu Ala
            340                 345                 350 tgt ccc act ttc ctc tgc ttt gac gac ggg aaa ccg tac gtc acc acg          2420
Cys Pro Thr Phe Leu Cys Phe Asp Asp Gly Lys Pro Tyr Val Thr Thr
355                 360                 365                 370 cgg acg gat gac acc cga ctt ttg gcc aag ttt gac ctt tcc ctt gcc          2468
Arg Thr Asp Asp Thr Arg Leu Leu Ala Lys Phe Asp Leu Ser Leu Ala
                375                 380                 385 gca aaa cat atg tcc aac aca tac ctg tca ggg att gct cag tac tac          2516
Ala Lys His Met Ser Asn Thr Tyr Leu Ser Gly Ile Ala Gln Tyr Tyr
        390                 395                 400 aca cag tac tct ggc acc atc aat ttg cat ttc atg ttt aca ggt tcc          2564
Thr Gln Tyr Ser Gly Thr Ile Asn Leu His Phe Met Phe Thr Gly Ser
            405                 410                 415 act gat tca aag gcc cga tac atg gtg gcc tac atc cca cct ggg gtg          2612
Thr Asp Ser Lys Ala Arg Tyr Met Val Ala Tyr Ile Pro Pro Gly Val
420                 425                 430 gag aca cca ccg gac aca cct gaa agg gct gcc cac tgc att cac gct          2660
Glu Thr Pro Pro Asp Thr Pro Glu Arg Ala Ala His Cys Ile His Ala
435                 440                 445                 450 gaa tgg gac act gga cta aac tcc aaa ttc act ttc tca atc ccg tac          2708
Glu Trp Asp Thr Gly Leu Asn Ser Lys Phe Thr Phe Ser Ile Pro Tyr
                455                 460                 465 gta tcc gcc gcg gat tac gcg tac aca gcg tct gac acg gca gaa aca          2756
Val Ser Ala Ala Asp Tyr Ala Tyr Thr Ala Ser Asp Thr Ala Glu Thr
        470                 475                 480 atc aac gta cag gga tgg gtc tgc atc tac caa att aca cac ggg aag          2804
Ile Asn Val Gln Gly Trp Val Cys Ile Tyr Gln Ile Thr His Gly Lys
            485                 490                 495 gct gaa aat gac acc ttg gtc gtg tcg gtt agc gcc ggc aaa gac ttt          2852
Ala Glu Asn Asp Thr Leu Val Val Ser Val Ser Ala Gly Lys Asp Phe
500                 505                 510 gag ttg cgc ctc ccg att gac ccc cgc cag cag acc acc gct acc ggg          2900
Glu Leu Arg Leu Pro Ile Asp Pro Arg Gln Gln Thr Thr Ala Thr Gly
515                 520                 525                 530 gaa tca gca gac ccg gtc acc acc acc gtg gag aac tac ggc ggt gag          2948
Glu Ser Ala Asp Pro Val Thr Thr Thr Val Glu Asn Tyr Gly Gly Glu
                535                 540                 545 aca caa atc cag aga cgt cac cac acg gac att ggt ttc atc atg gac          2996
Thr Gln Ile Gln Arg Arg His His Thr Asp Ile Gly Phe Ile Met Asp
        550                 555                 560 aga ttt gtg aag atc caa agc ttg agc cca aca cat gtc att gac ctc          3044
Arg Phe Val Lys Ile Gln Ser Leu Ser Pro Thr His Val Ile Asp Leu
            565                 570                 575 atg cag gct cac caa cac ggt ctg gtg ggt gcc ttg ctg cgt gca gcc          3092
Met Gln Ala His Gln His Gly Leu Val Gly Ala Leu Leu Arg Ala Ala
580                 585                 590 acg tac tac ttt tct gac ctg gaa att gtt gta cgg cac gaa ggc aat          3140
Thr Tyr Tyr Phe Ser Asp Leu Glu Ile Val Val Arg His Glu Gly Asn
595                 600                 605                 610 ctg acc tgg gtg ccc aac ggc gcc cct gaa tca gcc ctg ttg aac acc          3188
Leu Thr Trp Val Pro Asn Gly Ala Pro Glu Ser Ala Leu Leu Asn Thr
                615                 620                 625 agc aac ccc act gcc tac aac aag gca cca ttc acg aga ctc gct ctc          3236
Ser Asn Pro Thr Ala Tyr Asn Lys Ala Pro Phe Thr Arg Leu Ala Leu
        630                 635                 640 ccc tac act gcg ccg cac cgt gtg ctg gca aca gtg tac aac ggg acg          3284
Pro Tyr Thr Ala Pro His Arg Val Leu Ala Thr Val Tyr Asn Gly Thr
            645                 650                 655
```

```
agt aag tat gct gtg ggt ggt tca ggc aga aga ggc gac atg ggg tct      3332
Ser Lys Tyr Ala Val Gly Gly Ser Gly Arg Arg Gly Asp Met Gly Ser
    660             665             670 ctc gcg gcg cga gtc gtg aaa cag ctt cct gct tca ttt aac tac ggt      3380
Leu Ala Ala Arg Val Val Lys Gln Leu Pro Ala Ser Phe Asn Tyr Gly
675             680             685             690 gca atc aag gcc gac gcc atc cac gaa ctt ctc gtg cgc atg aaa cgg      3428
Ala Ile Lys Ala Asp Ala Ile His Glu Leu Leu Val Arg Met Lys Arg
                695             700             705 gcc gag ctc tac tgc ccc aga ccg ctg ttg gca ata gag gtg tct tcg      3476
Ala Glu Leu Tyr Cys Pro Arg Pro Leu Leu Ala Ile Glu Val Ser Ser
            710             715             720 caa gac agg cac aag caa aag atc att gca cca gca aag cag ctt ctg      3524
Gln Asp Arg His Lys Gln Lys Ile Ile Ala Pro Ala Lys Gln Leu Leu
        725             730             735 aat ttt gac ctg ctc aag ttg gcc gga gac gtt gag tcc aac ccc ggg      3572
Asn Phe Asp Leu Leu Lys Leu Ala Gly Asp Val Glu Ser Asn Pro Gly
740             745             750 cca ttc ttc ttt gct gac gtt agg tca aac ttt tca aag ttg gta gac      3620
Pro Phe Phe Phe Ala Asp Val Arg Ser Asn Phe Ser Lys Leu Val Asp
755             760             765             770 aca atc aac cag atg cag gag gac atg tcc aca aaa cac ggg ccc gac      3668
Thr Ile Asn Gln Met Gln Glu Asp Met Ser Thr Lys His Gly Pro Asp
                775             780             785 ttc aac cgg ttg gtg tcc gca ttt gag gaa ttg gcc act gga gtt aaa      3716
Phe Asn Arg Leu Val Ser Ala Phe Glu Glu Leu Ala Thr Gly Val Lys
            790             795             800 gct atc agg acc ggt ctc gac gag gcc aaa ccc tgg tac aag ctt atc      3764
Ala Ile Arg Thr Gly Leu Asp Glu Ala Lys Pro Trp Tyr Lys Leu Ile
        805             810             815 aaa ctc cta agc cgc ctg tcg tgc atg gcc gct gtg gca gca cgg tcc      3812
Lys Leu Leu Ser Arg Leu Ser Cys Met Ala Ala Val Ala Ala Arg Ser
820             825             830 aag gac cca gtc ctt gtg gcc atc atg ctg gcc gac acc ggt ctc gag      3860
Lys Asp Pro Val Leu Val Ala Ile Met Leu Ala Asp Thr Gly Leu Glu
835             840             845             850 cgt cag aga cct ctg aaa gtg aga gct aag ctc cca cag cag gaa gga      3908
Arg Gln Arg Pro Leu Lys Val Arg Ala Lys Leu Pro Gln Gln Glu Gly
                855             860             865 cct tac gct ggc ccg ttg gag aga cag aaa ccg ctg aaa gtg aaa gca      3956
Pro Tyr Ala Gly Pro Leu Glu Arg Gln Lys Pro Leu Lys Val Lys Ala
            870             875             880 aaa gcc ccg gtc gtc aag gaa gga cct tac gag gga ccg gtg aag aag      4004
Lys Ala Pro Val Val Lys Glu Gly Pro Tyr Glu Gly Pro Val Lys Lys
        885             890             895 cct gtc gct ttg aaa gtg aaa gct aag aac ttg ata gtc act gag agt      4052
Pro Val Ala Leu Lys Val Lys Ala Lys Asn Leu Ile Val Thr Glu Ser
900             905             910 ggt gcc cca ccg acc gac ttg caa aag atg gtc atg ggc aac aca aag      4100
Gly Ala Pro Pro Thr Asp Leu Gln Lys Met Val Met Gly Asn Thr Lys
                915             920             925             930 cct gtt gag ctc atc ctt gac ggg aag aca gta gcc atc tgt tgt gct      4148
Pro Val Glu Leu Ile Leu Asp Gly Lys Thr Val Ala Ile Cys Cys Ala
            935             940             945 act gga gtg ttt ggc act gct tac ctc gtg cct cgt cat ctt ttc gca      4196
Thr Gly Val Phe Gly Thr Ala Tyr Leu Val Pro Arg His Leu Phe Ala
        950             955             960 gag aag tat gac aag atc atg ctg gat ggc aga gcc atg aca gac agt      4244
Glu Lys Tyr Asp Lys Ile Met Leu Asp Gly Arg Ala Met Thr Asp Ser
965             970             975
```

-continued

| | |
|---|---|
| gac tac aga gtg ttt gag ttt gag att aaa gta aaa gga cag gac atg<br>Asp Tyr Arg Val Phe Glu Phe Glu Ile Lys Val Lys Gly Gln Asp Met<br>980                   985                     990 | 4292 |
| ctc tca gac gct gcg ctc atg gtg ctc cac cgt ggg aac cgc gtg aga<br>Leu Ser Asp Ala Ala Leu Met Val Leu His Arg Gly Asn Arg Val Arg<br>995                   1000                 1005                1010 | 4340 |
| gat atc acg aaa cac ttt cgt gat aca gca aga atg aag aaa ggc acc<br>Asp Ile Thr Lys His Phe Arg Asp Thr Ala Arg Met Lys Lys Gly Thr<br>                1015                1020                1025 | 4388 |
| ccc gtc gtc ggt gtg gtc aac aac gcc gac gtt ggg aga ctg att ttc<br>Pro Val Val Gly Val Val Asn Asn Ala Asp Val Gly Arg Leu Ile Phe<br>1030                1035                1040 | 4436 |
| tct ggt gag gcc ctc acc tac aag gat att gta gtg tgc atg gac gga<br>Ser Gly Glu Ala Leu Thr Tyr Lys Asp Ile Val Val Cys Met Asp Gly<br>1045                1050                1055 | 4484 |
| gac acc atg cct ggc ctc ttt gcc tac aaa gcc gcc acc aag gca ggc<br>Asp Thr Met Pro Gly Leu Phe Ala Tyr Lys Ala Ala Thr Lys Ala Gly<br>1060                1065                1070 | 4532 |
| tac tgt gga gga gcc gtt ctc gcc aag gac ggg gcc gac act ttc atc<br>Tyr Cys Gly Gly Ala Val Leu Ala Lys Asp Gly Ala Asp Thr Phe Ile<br>1075                1080                1085                1090 | 4580 |
| gtc ggc act cac tcc gca gga ggc aat gga gtt gga tac tgc tca tgc<br>Val Gly Thr His Ser Ala Gly Gly Asn Gly Val Gly Tyr Cys Ser Cys<br>                1095                1100                1105 | 4628 |
| gtt tcc agg tcc atg ctt ctc aga atg aag gca cac gtt gac cct gaa<br>Val Ser Arg Ser Met Leu Leu Arg Met Lys Ala His Val Asp Pro Glu<br>1110                1115                1120 | 4676 |
| cca caa cac gag tagtaatttt tctgcagccc gggttttat agctaattag<br>Pro Gln His Glu<br>        1125 | 4728 |
| tcatttttc gtaagtaagt attttattt aatactttt attgtactta tgttaaatat | 4788 |
| aactgatgat aacaaaatcc attatgtatt atttataact gtaatttctt tagcgtagtt | 4848 |
| agatgtccaa tctctctcaa atacatcggc tatctttta gtgagatttt gatctatgca | 4908 |
| gttgaaactt atgaacgcgt gatgattaaa atgtgaaccg tccaaatttg cagtcattat | 4968 |
| atgagcgtat ctattatcta ctatcatcat ctttgagtta ttaatatcat ctactttaga | 5028 |
| attgatagga aatatgaata cctttgtagt aatatctata ctatctacac ctaactcatt | 5088 |
| aagacttttg atag | 5102 |

<210> SEQ ID NO 16
<211> LENGTH: 1126
<212> TYPE: PRT
<213> ORGANISM: Foot-and-mouth disease virus

<400> SEQUENCE: 16

Met Gly Ala Gly Gln Ser Ser Pro Ala Thr Gly Ser Gln Asn Gln Ser
1                 5                    10                 15

Gly Asn Thr Gly Ser Ile Ile Asn Asn Tyr Tyr Met Gln Gln Tyr Gln
                20                   25                  30

Asn Ser Met Asp Thr Gln Leu Gly Asp Asn Ala Ile Ser Gly Gly Ser
        35                   40                   45

Asn Glu Gly Ser Thr Asp Thr Thr Ser Thr His Thr Asn Thr Gln
     50                 55                 60

Asn Asn Asp Trp Phe Ser Lys Leu Ala Ser Ser Ala Phe Thr Gly Leu
65                70                   75                  80

Phe Gly Ala Leu Leu Ala Asp Lys Lys Thr Glu Glu Thr Thr Leu Leu

-continued

```
                    85                  90                  95
Glu Asp Arg Ile Leu Thr Thr Arg Asn Gly His Thr Thr Ser Thr Thr
                100                 105                 110
Gln Ser Ser Val Gly Val Thr His Gly Tyr Ser Thr Glu Glu Asp His
            115                 120                 125
Val Ala Gly Pro Asn Thr Ser Gly Leu Glu Thr Arg Val Val Gln Ala
        130                 135                 140
Glu Arg Phe Tyr Lys Lys Tyr Leu Phe Asp Trp Thr Thr Asp Lys Ala
145                 150                 155                 160
Phe Gly His Leu Glu Lys Leu Glu Leu Pro Ser Asp His His Gly Val
                165                 170                 175
Phe Gly His Leu Val Asp Ser Tyr Ala Tyr Met Arg Asn Gly Trp Asp
            180                 185                 190
Val Glu Val Ser Ala Val Gly Asn Gln Phe Asn Gly Gly Cys Leu Leu
        195                 200                 205
Val Ala Met Val Pro Glu Trp Lys Glu Phe Asp Thr Arg Glu Lys Tyr
        210                 215                 220
Gln Leu Thr Leu Phe Pro His Gln Phe Ile Ser Pro Arg Thr Asn Met
225                 230                 235                 240
Thr Ala His Ile Thr Val Pro Tyr Leu Gly Val Asn Arg Tyr Asp Gln
                245                 250                 255
Tyr Lys Lys His Lys Pro Trp Thr Leu Val Val Met Val Val Ser Pro
                260                 265                 270
Leu Thr Val Asn Asn Thr Ser Ala Ala Gln Ile Lys Val Tyr Ala Asn
            275                 280                 285
Ile Ala Pro Thr Tyr Val His Val Ala Gly Glu Leu Pro Ser Lys Glu
        290                 295                 300
Gly Ile Phe Pro Val Ala Cys Ala Asp Gly Tyr Gly Gly Leu Val Thr
305                 310                 315                 320
Thr Asp Pro Lys Thr Ala Asp Pro Ala Tyr Gly Lys Val Tyr Asn Pro
                325                 330                 335
Pro Arg Thr Asn Tyr Pro Gly Arg Phe Thr Asn Leu Leu Asp Val Ala
            340                 345                 350
Glu Ala Cys Pro Thr Phe Leu Cys Phe Asp Asp Gly Lys Pro Tyr Val
        355                 360                 365
Thr Thr Arg Thr Asp Asp Thr Arg Leu Leu Ala Lys Phe Asp Leu Ser
    370                 375                 380
Leu Ala Ala Lys His Met Ser Asn Thr Tyr Leu Ser Gly Ile Ala Gln
385                 390                 395                 400
Tyr Tyr Thr Gln Tyr Ser Gly Thr Ile Asn Leu His Phe Met Phe Thr
                405                 410                 415
Gly Ser Thr Asp Ser Lys Ala Arg Tyr Met Val Ala Tyr Ile Pro Pro
            420                 425                 430
Gly Val Glu Thr Pro Pro Asp Thr Pro Glu Arg Ala Ala His Cys Ile
        435                 440                 445
His Ala Glu Trp Asp Thr Gly Leu Asn Ser Lys Phe Thr Phe Ser Ile
    450                 455                 460
Pro Tyr Val Ser Ala Ala Asp Tyr Ala Tyr Thr Ala Ser Asp Thr Ala
465                 470                 475                 480
Glu Thr Ile Asn Val Gln Gly Trp Val Cys Ile Tyr Gln Ile Thr His
                485                 490                 495
Gly Lys Ala Glu Asn Asp Thr Leu Val Val Ser Val Ser Ala Gly Lys
            500                 505                 510
```

```
Asp Phe Glu Leu Arg Leu Pro Ile Asp Pro Arg Gln Gln Thr Thr Ala
            515                 520                 525

Thr Gly Glu Ser Ala Asp Pro Val Thr Thr Val Glu Asn Tyr Gly
    530                 535                 540

Gly Glu Thr Gln Ile Gln Arg Arg His His Thr Asp Ile Gly Phe Ile
545                 550                 555                 560

Met Asp Arg Phe Val Lys Ile Gln Ser Leu Ser Pro Thr His Val Ile
            565                 570                 575

Asp Leu Met Gln Ala His Gln His Gly Leu Val Gly Ala Leu Leu Arg
                580                 585                 590

Ala Ala Thr Tyr Tyr Phe Ser Asp Leu Glu Ile Val Val Arg His Glu
        595                 600                 605

Gly Asn Leu Thr Trp Val Pro Asn Gly Ala Pro Glu Ser Ala Leu Leu
    610                 615                 620

Asn Thr Ser Asn Pro Thr Ala Tyr Asn Lys Ala Pro Phe Thr Arg Leu
625                 630                 635                 640

Ala Leu Pro Tyr Thr Ala Pro His Arg Val Leu Ala Thr Val Tyr Asn
            645                 650                 655

Gly Thr Ser Lys Tyr Ala Val Gly Gly Ser Gly Arg Arg Gly Asp Met
                660                 665                 670

Gly Ser Leu Ala Ala Arg Val Val Lys Gln Leu Pro Ala Ser Phe Asn
        675                 680                 685

Tyr Gly Ala Ile Lys Ala Asp Ala Ile His Glu Leu Leu Val Arg Met
    690                 695                 700

Lys Arg Ala Glu Leu Tyr Cys Pro Arg Pro Leu Leu Ala Ile Glu Val
705                 710                 715                 720

Ser Ser Gln Asp Arg His Lys Gln Lys Ile Ile Ala Pro Ala Lys Gln
            725                 730                 735

Leu Leu Asn Phe Asp Leu Leu Lys Leu Ala Gly Asp Val Glu Ser Asn
                740                 745                 750

Pro Gly Pro Phe Phe Phe Ala Asp Val Arg Ser Asn Phe Ser Lys Leu
        755                 760                 765

Val Asp Thr Ile Asn Gln Met Gln Glu Asp Met Ser Thr Lys His Gly
    770                 775                 780

Pro Asp Phe Asn Arg Leu Val Ser Ala Phe Glu Glu Leu Ala Thr Gly
785                 790                 795                 800

Val Lys Ala Ile Arg Thr Gly Leu Asp Glu Ala Lys Pro Trp Tyr Lys
            805                 810                 815

Leu Ile Lys Leu Leu Ser Arg Leu Ser Cys Met Ala Ala Val Ala Ala
                820                 825                 830

Arg Ser Lys Asp Pro Val Leu Val Ala Ile Met Leu Ala Asp Thr Gly
        835                 840                 845

Leu Glu Arg Gln Arg Pro Leu Lys Val Arg Ala Lys Leu Pro Gln Gln
    850                 855                 860

Glu Gly Pro Tyr Ala Gly Pro Leu Glu Arg Gln Lys Pro Leu Lys Val
865                 870                 875                 880

Lys Ala Lys Ala Pro Val Val Lys Glu Gly Pro Tyr Glu Gly Pro Val
            885                 890                 895

Lys Lys Pro Val Ala Leu Lys Val Lys Ala Lys Asn Leu Ile Val Thr
                900                 905                 910

Glu Ser Gly Ala Pro Pro Thr Asp Leu Gln Lys Met Val Met Gly Asn
        915                 920                 925
```

-continued

```
        Thr Lys Pro Val Glu Leu Ile Leu Asp Gly Lys Thr Val Ala Ile Cys
            930                 935                 940

Cys Ala Thr Gly Val Phe Gly Thr Ala Tyr Leu Val Pro Arg His Leu
        945                 950                 955                 960

Phe Ala Glu Lys Tyr Asp Lys Ile Met Leu Asp Gly Arg Ala Met Thr
                        965                 970                 975

Asp Ser Asp Tyr Arg Val Phe Glu Phe Glu Ile Lys Val Lys Gly Gln
                    980                 985                 990

Asp Met Leu Ser Asp Ala Ala Leu Met Val Leu His Arg Gly Asn Arg
                995                 1000                1005

Val Arg Asp Ile Thr Lys His Phe Arg Asp Thr Ala Arg Met Lys Lys
            1010                1015                1020

Gly Thr Pro Val Val Gly Val Val Asn Asn Ala Asp Val Gly Arg Leu
        1025                1030                1035                1040

Ile Phe Ser Gly Glu Ala Leu Thr Tyr Lys Asp Ile Val Val Cys Met
                        1045                1050                1055

Asp Gly Asp Thr Met Pro Gly Leu Phe Ala Tyr Lys Ala Ala Thr Lys
                    1060                1065                1070

Ala Gly Tyr Cys Gly Gly Ala Val Leu Ala Lys Asp Gly Ala Asp Thr
                1075                1080                1085

Phe Ile Val Gly Thr His Ser Ala Gly Gly Asn Gly Val Gly Tyr Cys
            1090                1095                1100

Ser Cys Val Ser Arg Ser Met Leu Leu Arg Met Lys Ala His Val Asp
        1105                1110                1115                1120

Pro Glu Pro Gln His Glu
                        1125

<210> SEQ ID NO 17
<211> LENGTH: 124
<212> TYPE: DNA
<213> ORGANISM: Vaccinia virus

<400> SEQUENCE: 17
ttctttattc tatacttaaa aagtgaaaat aaatacaaag gttcttgagg gttgtgttaa      60
attgaaagcg agaaataatc ataaattatt tcattatcgc gatatccgtt aagtttgtat     120
cgta                                                                  124

<210> SEQ ID NO 18
<211> LENGTH: 47
<212> TYPE: DNA
<213> ORGANISM: Vaccinia virus

<400> SEQUENCE: 18
ttctttattc tatacttaaa aagtgcaaat aaatacaaag gttcttg                    47

<210> SEQ ID NO 19
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gaattcttct ttattctata cttaaaaagt gcaaataaat acaaaggttc ttgatgggag      60

<210> SEQ ID NO 20
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cttgccgcaa aacatatgtc ca                                              22

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tggacatatg ttttgcggca ag                                              22

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cttgatggga gctgggcaat ccagc                                           25

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gctggattgc ccagctccca tcaag                                           25

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Leu Ala Ala Lys His Met Ser
  1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Met Gly Ala Gly Gln Ser Ser
  1               5

<210> SEQ ID NO 26
```

```
<211> LENGTH: 5025
<212> TYPE: DNA
<213> ORGANISM: Foot-and-mouth disease virus
<220> FEATURE:
<221> NAME/KEY: CDS
<222> LOCATION: (1234)..(4611)

<400> SEQUENCE: 26
ttcataaata caagtttgat taaacttaag ttgttctaaa gttctttcct ccgaaggtat      60
agaacaaagt atttcttcta catccttact atttattgca gcttttaaca gcctatcacg     120
tatcctattt ttagtattgg tagaacgttt tagttctaaa gttaaaatat tagacataat     180
tggcatattg cttattcctt gcatagttga gtctgtagat cgtttcagta tatcactgat     240
taatgtacta ctgttatgat gaaatataga atcgatattg gcatttaact gttttgttat     300
actaagtcta gattttaaat cttctagtaa tatgctattt aatataaaag cttccacgtt     360
tttgtataca tttctttcca tattagtagc tactactaaa tgattatctt ctttcatatc     420
ttgtagataa gatagactat ctttatcttt attagtagaa aatacttctg gccatacatc     480
gttaaatttt tttgttgttg ttagatataa tattaaatat ctagaggatc ctattatttg     540
tggtaaaatg tttatagagt aaaatgatct ggctattaaa cataggccag ttaccataga     600
atgctgcttc ccgttacagt gttttaccat aaccatagat ctgcctgtat tgttgataca     660
tataacagct gtaaatccta aaaaattcct atcataatta ttaatattag gtaattcatt     720
tccatgtgaa agatagacta atttttatatc ctttacctcc aaataattat ttacatctct     780
taaacaatct attttaatat cattaactgg tattttaaa tatccagaaa ggtttgaagg     840
ggttgatgga ataagtctat taacatcgtt aagtaaatta ttaatatcat gaatctttat     900
tatattatac ccataagtta aatttatatt tactttctca tcatctgact tagttagttt     960
gtaataaggt gtgtctgaaa aaattaaaag gtaattcgtt gaatgaagct gtatttgctg    1020
tatcattttt atctaatttt ggagatttag cagtacttac ttcattagaa gaagaatctg    1080
ccagttcctg tctattactg atatttcgtt tcattattat atgatttata ttttactttt    1140
tcaattatat atactcattt gactagttaa tcaataaaaa gaattcttct ttattctata    1200 cttaaaagt gcaaataaat acaaggttc ttg atg gga gct ggg caa tcc agc       1254
                                    Met Gly Ala Gly Gln Ser Ser
                                     1               5 cca gca acc ggc tcg cag aac cag tct ggc aac act ggc agc ata atc      1302
Pro Ala Thr Gly Ser Gln Asn Gln Ser Gly Asn Thr Gly Ser Ile Ile
         10                  15                  20 aac aac tac tac atg caa cag tac cag aac tcc atg gac aca cag ttg      1350
Asn Asn Tyr Tyr Met Gln Gln Tyr Gln Asn Ser Met Asp Thr Gln Leu
 25                  30                  35 gga gac aat gcc atc agt gga ggc tcc aac gag ggc tcc acg gac aca      1398
Gly Asp Asn Ala Ile Ser Gly Gly Ser Asn Glu Gly Ser Thr Asp Thr
     40                  45                  50                  55 act tca aca cac aca acc aac act caa aac aat gac tgg ttc tcg aag      1446
Thr Ser Thr His Thr Thr Asn Thr Gln Asn Asn Asp Trp Phe Ser Lys
                 60                  65                  70 ctc gcc agt tca gct ttt acc ggt ctg ttc ggt gca ctg ctc gcc gac      1494
Leu Ala Ser Ser Ala Phe Thr Gly Leu Phe Gly Ala Leu Leu Ala Asp
             75                  80                  85 aag aag aca gag gaa acg aca ctt ctt gag gac cgc atc ctc acc acc      1542
Lys Lys Thr Glu Glu Thr Thr Leu Leu Glu Asp Arg Ile Leu Thr Thr
         90                  95                 100 cgc aac ggg cac acc acc tcg acg acc caa tcg agt gtg ggt gtc aca      1590
Arg Asn Gly His Thr Thr Ser Thr Thr Gln Ser Ser Val Gly Val Thr
```

-continued

```
         105                 110                 115
cac ggg tac tcc aca gag gag gac cac gtt gct ggg ccc aac aca tcg    1638
His Gly Tyr Ser Thr Glu Glu Asp His Val Ala Gly Pro Asn Thr Ser
120                 125                 130                 135 ggc ctg gag acg cga gtg gtg cag gca gag aga ttc tac aaa aag tac    1686
Gly Leu Glu Thr Arg Val Val Gln Ala Glu Arg Phe Tyr Lys Lys Tyr
                140                 145                 150 ttg ttt gac tgg aca acg gac aag gca ttt gga cac ctg gaa aag ctg    1734
Leu Phe Asp Trp Thr Thr Asp Lys Ala Phe Gly His Leu Glu Lys Leu
            155                 160                 165 gag ctc ccg tcc gac cac cac ggt gtc ttt gga cac ttg gtg gac tcg    1782
Glu Leu Pro Ser Asp His His Gly Val Phe Gly His Leu Val Asp Ser
        170                 175                 180 tac gcc tat atg aga aat ggc tgg gat gtt gag gtg tcc gct gtt ggc    1830
Tyr Ala Tyr Met Arg Asn Gly Trp Asp Val Glu Val Ser Ala Val Gly
    185                 190                 195 aac cag ttc aac ggc ggg tgc ctc ctg gtg gcc atg gta cct gaa tgg    1878
Asn Gln Phe Asn Gly Gly Cys Leu Leu Val Ala Met Val Pro Glu Trp
200                 205                 210                 215 aag gaa ttt gac aca cgg gag aaa tac caa ctc acc ctt ttc ccg cac    1926
Lys Glu Phe Asp Thr Arg Glu Lys Tyr Gln Leu Thr Leu Phe Pro His
                220                 225                 230 cag ttt att agc ccc aga act aac atg act gcc cac atc acg gtc ccc    1974
Gln Phe Ile Ser Pro Arg Thr Asn Met Thr Ala His Ile Thr Val Pro
            235                 240                 245 tac ctt ggt gtg aac agg tat gat cag tac aag aag cat aag ccc tgg    2022
Tyr Leu Gly Val Asn Arg Tyr Asp Gln Tyr Lys Lys His Lys Pro Trp
        250                 255                 260 aca ttg gtt gtc atg gtc gtg tcg cca ctt acg gtc aac aac act agt    2070
Thr Leu Val Val Met Val Val Ser Pro Leu Thr Val Asn Asn Thr Ser
    265                 270                 275 gcg gca caa atc aag gtc tac gcc aac ata gct ccg acc tat gtt cac    2118
Ala Ala Gln Ile Lys Val Tyr Ala Asn Ile Ala Pro Thr Tyr Val His
280                 285                 290                 295 gtg gcc ggt gaa ctc ccc tcg aaa gag ggg att ttc ccg gtt gca tgt    2166
Val Ala Gly Glu Leu Pro Ser Lys Glu Gly Ile Phe Pro Val Ala Cys
                300                 305                 310 gcg gac ggt tac gga gga ttg gtg acg aca gac ccg aag aca gct gac    2214
Ala Asp Gly Tyr Gly Gly Leu Val Thr Thr Asp Pro Lys Thr Ala Asp
            315                 320                 325 cct gct tat ggc aag gtg tac aac ccg cct agg act aac tac cct ggg    2262
Pro Ala Tyr Gly Lys Val Tyr Asn Pro Pro Arg Thr Asn Tyr Pro Gly
        330                 335                 340 cgc ttc acc aac ctg ttg gac gtg gcc gaa gcg tgt ccc act ttc ctc    2310
Arg Phe Thr Asn Leu Leu Asp Val Ala Glu Ala Cys Pro Thr Phe Leu
    345                 350                 355 tgc ttt gac gac ggg aaa ccg tac gtc acc acg cgg acg gat gac acc    2358
Cys Phe Asp Asp Gly Lys Pro Tyr Val Thr Thr Arg Thr Asp Asp Thr
360                 365                 370                 375 cga ctt ttg gcc aag ttt gac ctt tcc ctt gcc gca aaa cat atg tcc    2406
Arg Leu Leu Ala Lys Phe Asp Leu Ser Leu Ala Ala Lys His Met Ser
                380                 385                 390 aac aca tac ctg tca ggg att gct cag tac tac aca cag tac tct ggc    2454
Asn Thr Tyr Leu Ser Gly Ile Ala Gln Tyr Tyr Thr Gln Tyr Ser Gly
            395                 400                 405 acc atc aat ttg cat ttc atg ttt aca ggt tcc act gat tca aag gcc    2502
Thr Ile Asn Leu His Phe Met Phe Thr Gly Ser Thr Asp Ser Lys Ala
        410                 415                 420 cga tac atg gtg gcc tac atc cca cct ggg gtg gag aca cca ccg gac    2550
```

-continued

```
Arg Tyr Met Val Ala Tyr Ile Pro Pro Gly Val Glu Thr Pro Pro Asp
    425                 430                 435 aca cct gaa agg gct gcc cac tgc att cac gct gaa tgg gac act gga    2598
Thr Pro Glu Arg Ala Ala His Cys Ile His Ala Glu Trp Asp Thr Gly
440                 445                 450                 455 cta aac tcc aaa ttc act ttc tca atc ccg tac gta tcc gcc gcg gat    2646
Leu Asn Ser Lys Phe Thr Phe Ser Ile Pro Tyr Val Ser Ala Ala Asp
                460                 465                 470 tac gcg tac aca gcg tct gac acg gca gaa aca atc aac gta cag gga    2694
Tyr Ala Tyr Thr Ala Ser Asp Thr Ala Glu Thr Ile Asn Val Gln Gly
            475                 480                 485 tgg gtc tgc atc tac caa att aca cac ggg aag gct gaa aat gac acc    2742
Trp Val Cys Ile Tyr Gln Ile Thr His Gly Lys Ala Glu Asn Asp Thr
        490                 495                 500 ttg gtc gtg tcg gtt agc gcc ggc aaa gac ttt gag ttg cgc ctc ccg    2790
Leu Val Val Ser Val Ser Ala Gly Lys Asp Phe Glu Leu Arg Leu Pro
    505                 510                 515 att gac ccc cgc cag cag acc acc gct acc ggg gaa tca gca gac ccg    2838
Ile Asp Pro Arg Gln Gln Thr Thr Ala Thr Gly Glu Ser Ala Asp Pro
520                 525                 530                 535 gtc acc acc acc gtg gag aac tac ggc ggt gag aca caa atc cag aga    2886
Val Thr Thr Thr Val Glu Asn Tyr Gly Gly Glu Thr Gln Ile Gln Arg
                540                 545                 550 cgt cac cac acg gac att ggt ttc atc atg gac aga ttt gtg aag atc    2934
Arg His His Thr Asp Ile Gly Phe Ile Met Asp Arg Phe Val Lys Ile
            555                 560                 565 caa agc ttg agc cca aca cat gtc att gac ctc atg cag gct cac caa    2982
Gln Ser Leu Ser Pro Thr His Val Ile Asp Leu Met Gln Ala His Gln
        570                 575                 580 cac ggt ctg gtg ggt gcc ttg ctg cgt gca gcc acg tac tac ttt tct    3030
His Gly Leu Val Gly Ala Leu Leu Arg Ala Ala Thr Tyr Tyr Phe Ser
    585                 590                 595 gac ctg gaa att gtt gta cgg cac gaa ggc aat ctg acc tgg gtg ccc    3078
Asp Leu Glu Ile Val Val Arg His Glu Gly Asn Leu Thr Trp Val Pro
600                 605                 610                 615 aac ggc gcc cct gaa tca gcc ctg ttg aac acc agc aac ccc act gcc    3126
Asn Gly Ala Pro Glu Ser Ala Leu Leu Asn Thr Ser Asn Pro Thr Ala
                620                 625                 630 tac aac aag gca cca ttc acg aga ctc gct ctc ccc tac act gcg ccg    3174
Tyr Asn Lys Ala Pro Phe Thr Arg Leu Ala Leu Pro Tyr Thr Ala Pro
            635                 640                 645 cac cgt gtg ctg gca aca gtg tac aac ggg acg agt aag tat gct gtg    3222
His Arg Val Leu Ala Thr Val Tyr Asn Gly Thr Ser Lys Tyr Ala Val
        650                 655                 660 ggt ggt tca ggc aga aga ggc gac atg ggg tct ctc gcg gcg cga gtc    3270
Gly Gly Ser Gly Arg Arg Gly Asp Met Gly Ser Leu Ala Ala Arg Val
    665                 670                 675 gtg aaa cag ctt cct gct tca ttt aac tac ggt gca atc aag gcc gac    3318
Val Lys Gln Leu Pro Ala Ser Phe Asn Tyr Gly Ala Ile Lys Ala Asp
680                 685                 690                 695 gcc atc cac gaa ctt ctc gtg cgc atg aaa cgg gcc gag ctc tac tgc    3366
Ala Ile His Glu Leu Leu Val Arg Met Lys Arg Ala Glu Leu Tyr Cys
                700                 705                 710 ccc aga ccg ctg ttg gca ata gag gtg tct tcg caa gac agg cac aag    3414
Pro Arg Pro Leu Leu Ala Ile Glu Val Ser Ser Gln Asp Arg His Lys
            715                 720                 725 caa aag atc att gca cca gca aag cag ctt ctg aat ttt gac ctg ctc    3462
Gln Lys Ile Ile Ala Pro Ala Lys Gln Leu Leu Asn Phe Asp Leu Leu
        730                 735                 740
```

-continued

| | | |
|---|---|---|
| aag ttg gcc gga gac gtt gag tcc aac ccc ggg cca ttc ttc ttt gct<br>Lys Leu Ala Gly Asp Val Glu Ser Asn Pro Gly Pro Phe Phe Phe Ala<br>745 750 755 | 3510 | |
| gac gtt agg tca aac ttt tca aag ttg gta gac aca atc aac cag atg<br>Asp Val Arg Ser Asn Phe Ser Lys Leu Val Asp Thr Ile Asn Gln Met<br>760 765 770 775 | 3558 | |
| cag gag gac atg tcc aca aaa cac ggg ccc gac ttc aac cgg ttg gtg<br>Gln Glu Asp Met Ser Thr Lys His Gly Pro Asp Phe Asn Arg Leu Val<br>780 785 790 | 3606 | |
| tcc gca ttt gag gaa ttg gcc act gga gtt aaa gct atc agg acc ggt<br>Ser Ala Phe Glu Glu Leu Ala Thr Gly Val Lys Ala Ile Arg Thr Gly<br>795 800 805 | 3654 | |
| ctc gac gag gcc aaa ccc tgg tac aag ctt atc aaa ctc cta agc cgc<br>Leu Asp Glu Ala Lys Pro Trp Tyr Lys Leu Ile Lys Leu Leu Ser Arg<br>810 815 820 | 3702 | |
| ctg tcg tgc atg gcc gct gtg gca gca cgg tcc aag gac cca gtc ctt<br>Leu Ser Cys Met Ala Ala Val Ala Ala Arg Ser Lys Asp Pro Val Leu<br>825 830 835 | 3750 | |
| gtg gcc atc atg ctg gcc gac acc ggt ctc gag cgt cag aga cct ctg<br>Val Ala Ile Met Leu Ala Asp Thr Gly Leu Glu Arg Gln Arg Pro Leu<br>840 845 850 855 | 3798 | |
| aaa gtg aga gct aag ctc cca cag cag gaa gga cct tac gct ggc ccg<br>Lys Val Arg Ala Lys Leu Pro Gln Gln Glu Gly Pro Tyr Ala Gly Pro<br>860 865 870 | 3846 | |
| ttg gag aga cag aaa ccg ctg aaa gtg aaa gca aaa gcc ccg gtc gtc<br>Leu Glu Arg Gln Lys Pro Leu Lys Val Lys Ala Lys Ala Pro Val Val<br>875 880 885 | 3894 | |
| aag gaa gga cct tac gag gga ccg gtg aag aag cct gtc gct ttg aaa<br>Lys Glu Gly Pro Tyr Glu Gly Pro Val Lys Lys Pro Val Ala Leu Lys<br>890 895 900 | 3942 | |
| gtg aaa gct aag aac ttg ata gtc act gag agt ggt gcc cca ccg acc<br>Val Lys Ala Lys Asn Leu Ile Val Thr Glu Ser Gly Ala Pro Pro Thr<br>905 910 915 | 3990 | |
| gac ttg caa aag atg gtc atg ggc aac aca aag cct gtt gag ctc atc<br>Asp Leu Gln Lys Met Val Met Gly Asn Thr Lys Pro Val Glu Leu Ile<br>920 925 930 935 | 4038 | |
| ctt gac ggg aag aca gta gcc atc tgt tgt gct act gga gtg ttt ggc<br>Leu Asp Gly Lys Thr Val Ala Ile Cys Cys Ala Thr Gly Val Phe Gly<br>940 945 950 | 4086 | |
| act gct tac ctc gtg cct cgt cat ctt ttc gca gag aag tat gac aag<br>Thr Ala Tyr Leu Val Pro Arg His Leu Phe Ala Glu Lys Tyr Asp Lys<br>955 960 965 | 4134 | |
| atc atg ctg gat ggc aga gcc atg aca gac agt gac tac aga gtg ttt<br>Ile Met Leu Asp Gly Arg Ala Met Thr Asp Ser Asp Tyr Arg Val Phe<br>970 975 980 | 4182 | |
| gag ttt gag att aaa gta aaa gga cag gac atg ctc tca gac gct gcg<br>Glu Phe Glu Ile Lys Val Lys Gly Gln Asp Met Leu Ser Asp Ala Ala<br>985 990 995 | 4230 | |
| ctc atg gtg ctc cac cgt ggg aac cgc gtg aga gat atc acg aaa cac<br>Leu Met Val Leu His Arg Gly Asn Arg Val Arg Asp Ile Thr Lys His<br>1000 1005 1010 1015 | 4278 | |
| ttt cgt gat aca gca aga atg aag aaa ggc acc ccc gtc gtc ggt gtg<br>Phe Arg Asp Thr Ala Arg Met Lys Lys Gly Thr Pro Val Val Gly Val<br>1020 1025 1030 | 4326 | |
| gtc aac aac gcc gac gtt ggg aga ctg att ttc tct ggt gag gcc ctc<br>Val Asn Asn Ala Asp Val Gly Arg Leu Ile Phe Ser Gly Glu Ala Leu<br>1035 1040 1045 | 4374 | |
| acc tac aag gat att gta gtg tgc atg gac gga gac acc atg cct ggc<br>Thr Tyr Lys Asp Ile Val Val Cys Met Asp Gly Asp Thr Met Pro Gly<br>1050 1055 1060 | 4422 | |

-continued

```
ctc ttt gcc tac aaa gcc gcc acc aag gca ggc tac tgt gga gga gcc       4470
Leu Phe Ala Tyr Lys Ala Ala Thr Lys Ala Gly Tyr Cys Gly Gly Ala
    1065                1070                1075 gtt ctc gcc aag gac ggg gcc gac act ttc atc gtc ggc act cac tcc       4518
Val Leu Ala Lys Asp Gly Ala Asp Thr Phe Ile Val Gly Thr His Ser
1080                1085                1090                1095 gca gga ggc aat gga gtt gga tac tgc tca tgc gtt tcc agg tcc atg       4566
Ala Gly Gly Asn Gly Val Gly Tyr Cys Ser Cys Val Ser Arg Ser Met
                1100                1105                1110 ctt ctc aga atg aag gca cac gtt gac cct gaa cca caa cac gag           4611
Leu Leu Arg Met Lys Ala His Val Asp Pro Glu Pro Gln His Glu
            1115                1120                1125 tagtaatttt tctgcagccc gggttttat  agctaattag tcattttttc gtaagtaagt     4671 attttattt  aatactttt  attgtactta tgttaaatat aactgatgat aacaaaatcc     4731
attatgtatt atttataact gtaatttctt tagcgtagtt agatgtccaa tctctctcaa     4791
atacatcggc tatctttta  gtgagatttt gatctatgca gttgaaactt atgaacgcgt     4851
gatgattaaa atgtgaaccg tccaaatttg cagtcattat atgagcgtat ctattatcta     4911
ctatcatcat ctttgagtta ttaatatcat ctactttaga attgatagga aatatgaata     4971
cctttgtagt aatatctata ctatctacac ctaactcatt aagacttttg atag           5025
```

<210> SEQ ID NO 27
<211> LENGTH: 1126
<212> TYPE: PRT
<213> ORGANISM: Foot-and-mouth disease virus

<400> SEQUENCE: 27

```
Met Gly Ala Gly Gln Ser Ser Pro Ala Thr Gly Ser Gln Asn Gln Ser
1               5                   10                  15

Gly Asn Thr Gly Ser Ile Ile Asn Asn Tyr Tyr Met Gln Gln Tyr Gln
            20                  25                  30

Asn Ser Met Asp Thr Gln Leu Gly Asp Asn Ala Ile Ser Gly Gly Ser
        35                  40                  45

Asn Glu Gly Ser Thr Asp Thr Ser Thr His Thr Thr Asn Thr Gln
    50                  55                  60

Asn Asn Asp Trp Phe Ser Lys Leu Ala Ser Ser Ala Phe Thr Gly Leu
65                  70                  75                  80

Phe Gly Ala Leu Leu Ala Asp Lys Lys Thr Glu Glu Thr Thr Leu Leu
                85                  90                  95

Glu Asp Arg Ile Leu Thr Thr Arg Asn Gly His Thr Thr Ser Thr Thr
            100                 105                 110

Gln Ser Ser Val Gly Val Thr His Gly Tyr Ser Thr Glu Glu Asp His
        115                 120                 125

Val Ala Gly Pro Asn Thr Ser Gly Leu Glu Thr Arg Val Val Gln Ala
    130                 135                 140

Glu Arg Phe Tyr Lys Lys Tyr Leu Phe Asp Trp Thr Thr Asp Lys Ala
145                 150                 155                 160

Phe Gly His Leu Glu Lys Leu Glu Leu Pro Ser Asp His His Gly Val
                165                 170                 175

Phe Gly His Leu Val Asp Ser Tyr Ala Tyr Met Arg Asn Gly Trp Asp
            180                 185                 190

Val Glu Val Ser Ala Val Gly Asn Gln Phe Asn Gly Gly Cys Leu Leu
        195                 200                 205

Val Ala Met Val Pro Glu Trp Lys Glu Phe Asp Thr Arg Glu Lys Tyr
```

```
            210                 215                 220
Gln Leu Thr Leu Phe Pro His Gln Phe Ile Ser Pro Arg Thr Asn Met
225                 230                 235                 240

Thr Ala His Ile Thr Val Pro Tyr Leu Gly Val Asn Arg Tyr Asp Gln
                245                 250                 255

Tyr Lys Lys His Lys Pro Trp Thr Leu Val Val Met Val Val Ser Pro
            260                 265                 270

Leu Thr Val Asn Asn Thr Ser Ala Ala Gln Ile Lys Val Tyr Ala Asn
                275                 280                 285

Ile Ala Pro Thr Tyr Val His Val Ala Gly Glu Leu Pro Ser Lys Glu
            290                 295                 300

Gly Ile Phe Pro Val Ala Cys Ala Asp Gly Tyr Gly Gly Leu Val Thr
305                 310                 315                 320

Thr Asp Pro Lys Thr Ala Asp Pro Ala Tyr Gly Lys Val Tyr Asn Pro
                325                 330                 335

Pro Arg Thr Asn Tyr Pro Gly Arg Phe Thr Asn Leu Leu Asp Val Ala
            340                 345                 350

Glu Ala Cys Pro Thr Phe Leu Cys Phe Asp Asp Gly Lys Pro Tyr Val
            355                 360                 365

Thr Thr Arg Thr Asp Asp Thr Arg Leu Leu Ala Lys Phe Asp Leu Ser
        370                 375                 380

Leu Ala Ala Lys His Met Ser Asn Thr Tyr Leu Ser Gly Ile Ala Gln
385                 390                 395                 400

Tyr Tyr Thr Gln Tyr Ser Gly Thr Ile Asn Leu His Phe Met Phe Thr
                405                 410                 415

Gly Ser Thr Asp Ser Lys Ala Arg Tyr Met Val Ala Tyr Ile Pro Pro
                420                 425                 430

Gly Val Glu Thr Pro Pro Asp Thr Pro Glu Arg Ala Ala His Cys Ile
            435                 440                 445

His Ala Glu Trp Asp Thr Gly Leu Asn Ser Lys Phe Thr Phe Ser Ile
        450                 455                 460

Pro Tyr Val Ser Ala Ala Asp Tyr Ala Tyr Thr Ala Ser Asp Thr Ala
465                 470                 475                 480

Glu Thr Ile Asn Val Gln Gly Trp Val Cys Ile Tyr Gln Ile Thr His
                485                 490                 495

Gly Lys Ala Glu Asn Asp Thr Leu Val Val Ser Val Ser Ala Gly Lys
            500                 505                 510

Asp Phe Glu Leu Arg Leu Pro Ile Asp Pro Arg Gln Gln Thr Thr Ala
            515                 520                 525

Thr Gly Glu Ser Ala Asp Pro Val Thr Thr Thr Val Glu Asn Tyr Gly
        530                 535                 540

Gly Glu Thr Gln Ile Gln Arg Arg His His Thr Asp Ile Gly Phe Ile
545                 550                 555                 560

Met Asp Arg Phe Val Lys Ile Gln Ser Leu Ser Pro Thr His Val Ile
                565                 570                 575

Asp Leu Met Gln Ala His Gln His Gly Leu Val Gly Ala Leu Leu Arg
                580                 585                 590

Ala Ala Thr Tyr Tyr Phe Ser Asp Leu Glu Ile Val Val Arg His Glu
            595                 600                 605

Gly Asn Leu Thr Trp Val Pro Asn Gly Ala Pro Glu Ser Ala Leu Leu
        610                 615                 620

Asn Thr Ser Asn Pro Thr Ala Tyr Asn Lys Ala Pro Phe Thr Arg Leu
625                 630                 635                 640
```

```
Ala Leu Pro Tyr Thr Ala Pro His Arg Val Leu Ala Thr Val Tyr Asn
                645                 650                 655

Gly Thr Ser Lys Tyr Ala Val Gly Gly Ser Gly Arg Arg Gly Asp Met
            660                 665                 670

Gly Ser Leu Ala Ala Arg Val Lys Gln Leu Pro Ala Ser Phe Asn
        675                 680                 685

Tyr Gly Ala Ile Lys Ala Asp Ala Ile His Glu Leu Leu Val Arg Met
    690                 695                 700

Lys Arg Ala Glu Leu Tyr Cys Pro Arg Pro Leu Leu Ala Ile Glu Val
705                 710                 715                 720

Ser Ser Gln Asp Arg His Lys Gln Lys Ile Ile Ala Pro Ala Lys Gln
                725                 730                 735

Leu Leu Asn Phe Asp Leu Leu Lys Leu Ala Gly Asp Val Glu Ser Asn
            740                 745                 750

Pro Gly Pro Phe Phe Phe Ala Asp Val Arg Ser Asn Phe Ser Lys Leu
        755                 760                 765

Val Asp Thr Ile Asn Gln Met Gln Glu Asp Met Ser Thr Lys His Gly
    770                 775                 780

Pro Asp Phe Asn Arg Leu Val Ser Ala Phe Glu Glu Leu Ala Thr Gly
785                 790                 795                 800

Val Lys Ala Ile Arg Thr Gly Leu Asp Glu Ala Lys Pro Trp Tyr Lys
                805                 810                 815

Leu Ile Lys Leu Leu Ser Arg Leu Ser Cys Met Ala Ala Val Ala Ala
            820                 825                 830

Arg Ser Lys Asp Pro Val Leu Val Ala Ile Met Leu Ala Asp Thr Gly
        835                 840                 845

Leu Glu Arg Gln Arg Pro Leu Lys Val Arg Ala Lys Leu Pro Gln Gln
    850                 855                 860

Glu Gly Pro Tyr Ala Gly Pro Leu Glu Arg Gln Lys Pro Leu Lys Val
865                 870                 875                 880

Lys Ala Lys Ala Pro Val Val Lys Glu Gly Pro Tyr Glu Gly Pro Val
                885                 890                 895

Lys Lys Pro Val Ala Leu Lys Val Lys Ala Lys Asn Leu Ile Val Thr
            900                 905                 910

Glu Ser Gly Ala Pro Pro Thr Asp Leu Gln Lys Met Val Met Gly Asn
        915                 920                 925

Thr Lys Pro Val Glu Leu Ile Leu Asp Gly Lys Thr Val Ala Ile Cys
    930                 935                 940

Cys Ala Thr Gly Val Phe Gly Thr Ala Tyr Leu Val Pro Arg His Leu
945                 950                 955                 960

Phe Ala Glu Lys Tyr Asp Lys Ile Met Leu Asp Gly Arg Ala Met Thr
                965                 970                 975

Asp Ser Asp Tyr Arg Val Phe Glu Phe Glu Ile Lys Val Lys Gly Gln
            980                 985                 990

Asp Met Leu Ser Asp Ala Ala Leu Met Val Leu His Arg Gly Asn Arg
        995                 1000                1005

Val Arg Asp Ile Thr Lys His Phe Arg Asp Thr Ala Arg Met Lys Lys
    1010                1015                1020

Gly Thr Pro Val Val Gly Val Val Asn Asn Ala Asp Val Gly Arg Leu
1025                1030                1035                1040

Ile Phe Ser Gly Glu Ala Leu Thr Tyr Lys Asp Ile Val Val Cys Met
                1045                1050                1055
```

-continued

```
Asp Gly Asp Thr Met Pro Gly Leu Phe Ala Tyr Lys Ala Ala Thr Lys
            1060                1065                1070

Ala Gly Tyr Cys Gly Gly Ala Val Leu Ala Lys Asp Gly Ala Asp Thr
        1075                1080                1085

Phe Ile Val Gly Thr His Ser Ala Gly Gly Asn Gly Val Gly Tyr Cys
    1090                1095                1100

Ser Cys Val Ser Arg Ser Met Leu Leu Arg Met Lys Ala His Val Asp
1105                1110                1115                1120

Pro Glu Pro Gln His Glu
            1125

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gaattctgag ataaagtgaa aatatat                                          27

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
acaattattt aggtttaatc atgggagctg                                       30

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cagctcccat gattaaacct aaataattgt                                       30

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aggtttaatc atgggagctg ggcaatcca                                        29

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tgcctcctgg tggccatggt acc                                              23
```

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
ggtaccatgg ccaccaggag gca                                          23

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Met Gly Ala Gly Gln Ser
 1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Cys Leu Leu Val Ala Met Val Pro
 1               5

<210> SEQ ID NO 36
<211> LENGTH: 5037
<212> TYPE: DNA
<213> ORGANISM: Foot-and-mouth disease virus
<220> FEATURE:
<221> NAME/KEY: CDS
<222> LOCATION: (1246)..(4623)

<400> SEQUENCE: 36
ttcataaata caagtttgat taaacttaag ttgttctaaa gttctttcct ccgaaggtat     60
agaacaaagt atttcttcta catccttact atttattgca gcttttaaca gcctatcacg    120
tatcctattt ttagtattgg tagaacgttt tagttctaaa gttaaaatat tagacataat    180
tggcatattg cttattcctt gcatagttga gtctgtagat cgtttcagta tatcactgat    240
taatgtacta ctgttatgat gaaatataga atcgatattg gcatttaact gttttgttat    300
actaagtcta gattttaaat cttctagtaa tatgctattt aatataaaag cttccacgtt    360
tttgtataca tttctttcca tattagtagc tactactaaa tgattatctt ctttcatatc    420
ttgtagataa gatagactat ctttatcttt attagtagaa atacttctg gccatacatc     480 gttaaatttt tttgttgttg ttagatataa tattaaatat ctagaggatc ctattatttg    540
tggtaaaatg tttatagagt aaaatgatct ggctattaaa cataggccag ttaccataga    600
atgctgcttc ccgttacagt gttttaccat aaccatagat ctgcctgtat tgttgataca    660
tataacagct gtaaatccta aaaaattcct atcataatta ttaatattag gtaattcatt    720
tccatgtgaa agatagacta attttatatc ctttacctcc aaataattat ttacatctct    780

```
taaacaatct attttaatat cattaactgg tattttataa tatccagaaa ggtttgaagg      840
ggttgatgga ataagtctat taacatcgtt aagtaaatta ttaatatcat gaatctttat      900
tatattatac ccataagtta aatttatatt tactttctca tcatctgact tagttagttt      960
gtaataaggt gtgtctgaaa aaattaaaag gtaattcgtt gaatgaagct gtatttgctg     1020
tatcattttt atctaatttt ggagatttag cagtacttac ttcattagaa gaagaatctg     1080
ccagttcctg tctattactg atatttcgtt tcattattat atgatttata ttttactttt     1140
tcaattatat atactcattt gactagttaa tcaataaaaa gaattctgag ataaagtgaa     1200
aatatatatc attatattac aaagtacaat tatttaggtt taatc atg gga gct ggg     1257
                                               Met Gly Ala Gly
                                                1
```

| | | | | | | | | | | | | | | | | |
|---|---|---|---|---|---|---|---|---|---|---|---|---|---|---|---|---|
| caa tcc agc cca gca acc ggc tcg cag aac cag tct ggc aac act ggc | | | | | | | | | | | | | | | | 1305 |
| Gln Ser Ser Pro Ala Thr Gly Ser Gln Asn Gln Ser Gly Asn Thr Gly | | | | | | | | | | | | | | | | |
| 5 | | | | | 10 | | | | | 15 | | | | | 20 | |

```
agc ata atc aac aac tac tac atg caa cag tac cag aac tcc atg gac      1353
Ser Ile Ile Asn Asn Tyr Tyr Met Gln Gln Tyr Gln Asn Ser Met Asp
            25                  30                  35 aca cag ttg gga gac aat gcc atc agt gga ggc tcc aac gag ggc tcc      1401
Thr Gln Leu Gly Asp Asn Ala Ile Ser Gly Gly Ser Asn Glu Gly Ser
        40                  45                  50 acg gac aca act tca aca cac aca acc aac act caa aac aat gac tgg      1449
Thr Asp Thr Thr Ser Thr His Thr Thr Asn Thr Gln Asn Asn Asp Trp
    55                  60                  65 ttc tcg aag ctc gcc agt tca gct ttt acc ggt ctg ttc ggt gca ctg      1497
Phe Ser Lys Leu Ala Ser Ser Ala Phe Thr Gly Leu Phe Gly Ala Leu
70                  75                  80 ctc gcc gac aag aag aca gag gaa acg aca ctt ctt gag gac cgc atc      1545
Leu Ala Asp Lys Lys Thr Glu Glu Thr Thr Leu Leu Glu Asp Arg Ile
85                  90                  95                 100 ctc acc acc cgc aac ggg cac acc acc tcg acg acc caa tcg agt gtg      1593
Leu Thr Thr Arg Asn Gly His Thr Thr Ser Thr Thr Gln Ser Ser Val
            105                 110                 115 ggt gtc aca cac ggg tac tcc aca gag gag gac cac gtt gct ggg ccc      1641
Gly Val Thr His Gly Tyr Ser Thr Glu Glu Asp His Val Ala Gly Pro
        120                 125                 130 aac aca tcg ggc ctg gag acg cga gtg gtg cag gca gag aga ttc tac      1689
Asn Thr Ser Gly Leu Glu Thr Arg Val Val Gln Ala Glu Arg Phe Tyr
    135                 140                 145 aaa aag tac ttg ttt gac tgg aca acg gac aag gca ttt gga cac ctg      1737
Lys Lys Tyr Leu Phe Asp Trp Thr Thr Asp Lys Ala Phe Gly His Leu
150                 155                 160 gaa aag ctg gag ctc ccg tcc gac cac cac ggt gtc ttt gga cac ttg      1785
Glu Lys Leu Glu Leu Pro Ser Asp His His Gly Val Phe Gly His Leu
165                 170                 175                 180 gtg gac tcg tac gcc tat atg aga aat ggc tgg gat gtt gag gtg tcc      1833
Val Asp Ser Tyr Ala Tyr Met Arg Asn Gly Trp Asp Val Glu Val Ser
            185                 190                 195 gct gtt ggc aac cag ttc aac ggc ggg tgc ctc ctg gtg gcc atg gta      1881
Ala Val Gly Asn Gln Phe Asn Gly Gly Cys Leu Leu Val Ala Met Val
        200                 205                 210 cct gaa tgg aag gaa ttt gac aca cgg gag aaa tac caa ctc acc ctt      1929
Pro Glu Trp Lys Glu Phe Asp Thr Arg Glu Lys Tyr Gln Leu Thr Leu
215                 220                 225 ttc ccg cac cag ttt att agc ccc aga act aac atg act gcc cac atc      1977
Phe Pro His Gln Phe Ile Ser Pro Arg Thr Asn Met Thr Ala His Ile
230                 235                 240 acg gtc ccc tac ctt ggt gtg aac agg tat gat cag tac aag aag cat      2025
```

```
                                           -continued

Thr Val Pro Tyr Leu Gly Val Asn Arg Tyr Asp Gln Tyr Lys Lys His
245                 250                 255                 260 aag ccc tgg aca ttg gtt gtc atg gtc gtg tcg cca ctt acg gtc aac       2073
Lys Pro Trp Thr Leu Val Val Met Val Val Ser Pro Leu Thr Val Asn
                265                 270                 275 aac act agt gcg gca caa atc aag gtc tac gcc aac ata gct ccg acc       2121
Asn Thr Ser Ala Ala Gln Ile Lys Val Tyr Ala Asn Ile Ala Pro Thr
            280                 285                 290 tat gtt cac gtg gcc ggt gaa ctc ccc tcg aaa gag ggg att ttc ccg       2169
Tyr Val His Val Ala Gly Glu Leu Pro Ser Lys Glu Gly Ile Phe Pro
        295                 300                 305 gtt gca tgt gcg gac ggt tac gga gga ttg gtg acg aca gac ccg aag       2217
Val Ala Cys Ala Asp Gly Tyr Gly Gly Leu Val Thr Thr Asp Pro Lys
    310                 315                 320 aca gct gac cct gct tat ggc aag gtg tac aac ccg cct agg act aac       2265
Thr Ala Asp Pro Ala Tyr Gly Lys Val Tyr Asn Pro Pro Arg Thr Asn
325                 330                 335                 340 tac cct ggg cgc ttc acc aac ctg ttg gac gtg gcc gaa gcg tgt ccc       2313
Tyr Pro Gly Arg Phe Thr Asn Leu Leu Asp Val Ala Glu Ala Cys Pro
                345                 350                 355 act ttc ctc tgc ttt gac gac ggg aaa ccg tac gtc acc acg cgg acg       2361
Thr Phe Leu Cys Phe Asp Asp Gly Lys Pro Tyr Val Thr Thr Arg Thr
            360                 365                 370 gat gac acc cga ctt ttg gcc aag ttt gac ctt tcc ctt gcc gca aaa       2409
Asp Asp Thr Arg Leu Leu Ala Lys Phe Asp Leu Ser Leu Ala Ala Lys
        375                 380                 385 cat atg tcc aac aca tac ctg tca ggg att gct cag tac tac aca cag       2457
His Met Ser Asn Thr Tyr Leu Ser Gly Ile Ala Gln Tyr Tyr Thr Gln
    390                 395                 400 tac tct ggc acc atc aat ttg cat ttc atg ttt aca ggt tcc act gat       2505
Tyr Ser Gly Thr Ile Asn Leu His Phe Met Phe Thr Gly Ser Thr Asp
405                 410                 415                 420 tca aag gcc cga tac atg gtg gcc tac atc cca cct ggg gtg gag aca       2553
Ser Lys Ala Arg Tyr Met Val Ala Tyr Ile Pro Pro Gly Val Glu Thr
                425                 430                 435 cca ccg gac aca cct gaa agg gct gcc cac tgc att cac gct gaa tgg       2601
Pro Pro Asp Thr Pro Glu Arg Ala Ala His Cys Ile His Ala Glu Trp
            440                 445                 450 gac act gga cta aac tcc aaa ttc act ttc tca atc ccg tac gta tcc       2649
Asp Thr Gly Leu Asn Ser Lys Phe Thr Phe Ser Ile Pro Tyr Val Ser
        455                 460                 465 gcc gcg gat tac gcg tac aca gcg tct gac acg gca gaa aca atc aac       2697
Ala Ala Asp Tyr Ala Tyr Thr Ala Ser Asp Thr Ala Glu Thr Ile Asn
    470                 475                 480 gta cag gga tgg gtc tgc atc tac caa att aca cac ggg aag gct gaa       2745
Val Gln Gly Trp Val Cys Ile Tyr Gln Ile Thr His Gly Lys Ala Glu
485                 490                 495                 500 aat gac acc ttg gtc gtg tcg gtt agc gcc ggc aaa gac ttt gag ttg       2793
Asn Asp Thr Leu Val Val Ser Val Ser Ala Gly Lys Asp Phe Glu Leu
                505                 510                 515 cgc ctc ccg att gac ccc cgc cag cag acc acc gct acc ggg gaa tca       2841
Arg Leu Pro Ile Asp Pro Arg Gln Gln Thr Thr Ala Thr Gly Glu Ser
            520                 525                 530 gca gac ccg gtc acc acc acc gtg gag aac tac ggc ggt gag aca caa       2889
Ala Asp Pro Val Thr Thr Thr Val Glu Asn Tyr Gly Gly Glu Thr Gln
        535                 540                 545 atc cag aga cgt cac cac acg gac att ggt ttc atc atg gac aga ttt       2937
Ile Gln Arg Arg His His Thr Asp Ile Gly Phe Ile Met Asp Arg Phe
    550                 555                 560
```

```
gtg aag atc caa agc ttg agc cca aca cat gtc att gac ctc atg cag     2985
Val Lys Ile Gln Ser Leu Ser Pro Thr His Val Ile Asp Leu Met Gln
565                 570                 575                 580 gct cac caa cac ggt ctg gtg ggt gcc ttg ctg cgt gca gcc acg tac     3033
Ala His Gln His Gly Leu Val Gly Ala Leu Leu Arg Ala Ala Thr Tyr
                585                 590                 595 tac ttt tct gac ctg gaa att gtt gta cgg cac gaa ggc aat ctg acc     3081
Tyr Phe Ser Asp Leu Glu Ile Val Val Arg His Glu Gly Asn Leu Thr
            600                 605                 610 tgg gtg ccc aac ggc gcc cct gaa tca gcc ctg ttg aac acc agc aac     3129
Trp Val Pro Asn Gly Ala Pro Glu Ser Ala Leu Leu Asn Thr Ser Asn
        615                 620                 625 ccc act gcc tac aac aag gca cca ttc acg aga ctc gct ctc ccc tac     3177
Pro Thr Ala Tyr Asn Lys Ala Pro Phe Thr Arg Leu Ala Leu Pro Tyr
630                 635                 640 act gcg ccg cac cgt gtg ctg gca aca gtg tac aac ggg acg agt aag     3225
Thr Ala Pro His Arg Val Leu Ala Thr Val Tyr Asn Gly Thr Ser Lys
645                 650                 655                 660 tat gct gtg ggt ggt tca ggc aga aga ggc gac atg ggg tct ctc gcg     3273
Tyr Ala Val Gly Gly Ser Gly Arg Arg Gly Asp Met Gly Ser Leu Ala
                665                 670                 675 gcg cga gtc gtg aaa cag ctt cct gct tca ttt aac tac ggt gca atc     3321
Ala Arg Val Val Lys Gln Leu Pro Ala Ser Phe Asn Tyr Gly Ala Ile
            680                 685                 690 aag gcc gac gcc atc cac gaa ctt ctc gtg cgc atg aaa cgg gcc gag     3369
Lys Ala Asp Ala Ile His Glu Leu Leu Val Arg Met Lys Arg Ala Glu
        695                 700                 705 ctc tac tgc ccc aga ccg ctg ttg gca ata gag gtg tct tcg caa gac     3417
Leu Tyr Cys Pro Arg Pro Leu Leu Ala Ile Glu Val Ser Ser Gln Asp
710                 715                 720 agg cac aag caa aag atc att gca cca gca aag cag ctt ctg aat ttt     3465
Arg His Lys Gln Lys Ile Ile Ala Pro Ala Lys Gln Leu Leu Asn Phe
725                 730                 735                 740 gac ctg ctc aag ttg gcc gga gac gtt gag tcc aac ccc ggg cca ttc     3513
Asp Leu Leu Lys Leu Ala Gly Asp Val Glu Ser Asn Pro Gly Pro Phe
                745                 750                 755 ttc ttt gct gac gtt agg tca aac ttt tca aag ttg gta gac aca atc     3561
Phe Phe Ala Asp Val Arg Ser Asn Phe Ser Lys Leu Val Asp Thr Ile
            760                 765                 770 aac cag atg cag gag gac atg tcc aca aaa cac ggg ccc gac ttc aac     3609
Asn Gln Met Gln Glu Asp Met Ser Thr Lys His Gly Pro Asp Phe Asn
        775                 780                 785 cgg ttg gtg tcc gca ttt gag gaa ttg gcc act gga gtt aaa gct atc     3657
Arg Leu Val Ser Ala Phe Glu Glu Leu Ala Thr Gly Val Lys Ala Ile
790                 795                 800 agg acc ggt ctc gac gag gcc aaa ccc tgg tac aag ctt atc aaa ctc     3705
Arg Thr Gly Leu Asp Glu Ala Lys Pro Trp Tyr Lys Leu Ile Lys Leu
805                 810                 815                 820 cta agc cgc ctg tcg tgc atg gcc gct gtg gca gca cgg tcc aag gac     3753
Leu Ser Arg Leu Ser Cys Met Ala Ala Val Ala Ala Arg Ser Lys Asp
                825                 830                 835 cca gtc ctt gtg gcc atc atg ctg gcc gac acc ggt ctc gag cgt cag     3801
Pro Val Leu Val Ala Ile Met Leu Ala Asp Thr Gly Leu Glu Arg Gln
            840                 845                 850 aga cct ctg aaa gtg aga gct aag ctc cca cag cag gaa gga cct tac     3849
Arg Pro Leu Lys Val Arg Ala Lys Leu Pro Gln Gln Glu Gly Pro Tyr
        855                 860                 865 gct ggc ccg ttg gag aga cag aaa ccg ctg aaa gtg aaa gca aaa gcc     3897
Ala Gly Pro Leu Glu Arg Gln Lys Pro Leu Lys Val Lys Ala Lys Ala
870                 875                 880
```

```
ccg gtc gtc aag gaa gga cct tac gag gga ccg gtg aag aag cct gtc    3945
Pro Val Val Lys Glu Gly Pro Tyr Glu Gly Pro Val Lys Lys Pro Val
885             890                 895                 900 gct ttg aaa gtg aaa gct aag aac ttg ata gtc act gag agt ggt gcc    3993
Ala Leu Lys Val Lys Ala Lys Asn Leu Ile Val Thr Glu Ser Gly Ala
                905                 910                 915 cca ccg acc gac ttg caa aag atg gtc atg ggc aac aca aag cct gtt    4041
Pro Pro Thr Asp Leu Gln Lys Met Val Met Gly Asn Thr Lys Pro Val
            920                 925                 930 gag ctc atc ctt gac ggg aag aca gta gcc atc tgt tgt gct act gga    4089
Glu Leu Ile Leu Asp Gly Lys Thr Val Ala Ile Cys Cys Ala Thr Gly
        935                 940                 945 gtg ttt ggc act gct tac ctc gtg cct cgt cat ctt ttc gca gag aag    4137
Val Phe Gly Thr Ala Tyr Leu Val Pro Arg His Leu Phe Ala Glu Lys
    950                 955                 960 tat gac aag atc atg ctg gat ggc aga gcc atg aca gac agt gac tac    4185
Tyr Asp Lys Ile Met Leu Asp Gly Arg Ala Met Thr Asp Ser Asp Tyr
965             970                 975                 980 aga gtg ttt gag ttt gag att aaa gta aaa gga cag gac atg ctc tca    4233
Arg Val Phe Glu Phe Glu Ile Lys Val Lys Gly Gln Asp Met Leu Ser
                985                 990                 995 gac gct gcg ctc atg gtg ctc cac cgt ggg aac cgc gtg aga gat atc    4281
Asp Ala Ala Leu Met Val Leu His Arg Gly Asn Arg Val Arg Asp Ile
            1000                1005                1010 acg aaa cac ttt cgt gat aca gca aga atg aag aaa ggc acc ccc gtc    4329
Thr Lys His Phe Arg Asp Thr Ala Arg Met Lys Lys Gly Thr Pro Val
        1015                1020                1025 gtc ggt gtg gtc aac aac gcc gac gtt ggg aga ctg att ttc tct ggt    4377
Val Gly Val Val Asn Asn Ala Asp Val Gly Arg Leu Ile Phe Ser Gly
    1030                1035                1040 gag gcc ctc acc tac aag gat att gta gtg tgc atg gac gga gac acc    4425
Glu Ala Leu Thr Tyr Lys Asp Ile Val Val Cys Met Asp Gly Asp Thr
1045                1050                1055                1060 atg cct ggc ctc ttt gcc tac aaa gcc gcc acc aag gca ggc tac tgt    4473
Met Pro Gly Leu Phe Ala Tyr Lys Ala Ala Thr Lys Ala Gly Tyr Cys
                1065                1070                1075 gga gga gcc gtt ctc gcc aag gac ggg gcc gac act ttc atc gtc ggc    4521
Gly Gly Ala Val Leu Ala Lys Asp Gly Ala Asp Thr Phe Ile Val Gly
            1080                1085                1090 act cac tcc gca gga ggc aat gga gtt gga tac tgc tca tgc gtt tcc    4569
Thr His Ser Ala Gly Gly Asn Gly Val Gly Tyr Cys Ser Cys Val Ser
        1095                1100                1105 agg tcc atg ctt ctc aga atg aag gca cac gtt gac cct gaa cca caa    4617
Arg Ser Met Leu Leu Arg Met Lys Ala His Val Asp Pro Glu Pro Gln
    1110                1115                1120 cac gag tagtaatttt tctgcagccc gggttttat agctaattag tcatttttc       4673
His Glu
1125 gtaagtaagt attttttattt aatactttttt attgtactta tgttaaatat aactgatgat  4733 aacaaaatcc attatgtatt atttataact gtaatttctt tagcgtagtt agatgtccaa   4793 tctctctcaa atacatcggc tatcttttta gtgagatttt gatctatgca gttgaaactt   4853 atgaacgcgt gatgattaaa atgtgaaccg tccaaatttg cagtcattat atgagcgtat   4913 ctattatcta ctatcatcat ctttgagtta ttaatatcat ctactttaga attgatagga   4973 aatatgaata cctttgtagt aatatctata ctatctacac ctaactcatt aagactttt g  5033 atag                                                               5037
```

<210> SEQ ID NO 37
<211> LENGTH: 1126
<212> TYPE: PRT
<213> ORGANISM: Foot-and-mouth disease virus

<400> SEQUENCE: 37

| | | | | | | | | | | | | | | |
|---|---|---|---|---|---|---|---|---|---|---|---|---|---|---|
| Met | Gly | Ala | Gly | Gln | Ser | Ser | Pro | Ala | Thr | Gly | Ser | Gln | Asn | Gln | Ser |
| 1 | | | | 5 | | | | | 10 | | | | | 15 | |
| Gly | Asn | Thr | Gly | Ser | Ile | Ile | Asn | Asn | Tyr | Tyr | Met | Gln | Gln | Tyr | Gln |
| | | | 20 | | | | | 25 | | | | | 30 | | |
| Asn | Ser | Met | Asp | Thr | Gln | Leu | Gly | Asp | Asn | Ala | Ile | Ser | Gly | Gly | Ser |
| | | 35 | | | | | 40 | | | | | 45 | | | |
| Asn | Glu | Gly | Ser | Thr | Asp | Thr | Thr | Ser | Thr | His | Thr | Thr | Asn | Thr | Gln |
| | 50 | | | | | 55 | | | | | 60 | | | | |
| Asn | Asn | Asp | Trp | Phe | Ser | Lys | Leu | Ala | Ser | Ser | Ala | Phe | Thr | Gly | Leu |
| 65 | | | | | 70 | | | | | 75 | | | | | 80 |
| Phe | Gly | Ala | Leu | Leu | Ala | Asp | Lys | Lys | Thr | Glu | Glu | Thr | Thr | Leu | Leu |
| | | | | 85 | | | | | 90 | | | | | 95 | |
| Glu | Asp | Arg | Ile | Leu | Thr | Thr | Arg | Asn | Gly | His | Thr | Thr | Ser | Thr | Thr |
| | | | 100 | | | | | 105 | | | | | 110 | | |
| Gln | Ser | Ser | Val | Gly | Val | Thr | His | Gly | Tyr | Ser | Thr | Glu | Glu | Asp | His |
| | | 115 | | | | | 120 | | | | | 125 | | | |
| Val | Ala | Gly | Pro | Asn | Thr | Ser | Gly | Leu | Glu | Thr | Arg | Val | Val | Gln | Ala |
| | 130 | | | | | 135 | | | | | 140 | | | | |
| Glu | Arg | Phe | Tyr | Lys | Lys | Tyr | Leu | Phe | Asp | Trp | Thr | Thr | Asp | Lys | Ala |
| 145 | | | | | 150 | | | | | 155 | | | | | 160 |
| Phe | Gly | His | Leu | Glu | Lys | Leu | Glu | Leu | Pro | Ser | Asp | His | His | Gly | Val |
| | | | | 165 | | | | | 170 | | | | | 175 | |
| Phe | Gly | His | Leu | Val | Asp | Ser | Tyr | Ala | Tyr | Met | Arg | Asn | Gly | Trp | Asp |
| | | | 180 | | | | | 185 | | | | | 190 | | |
| Val | Glu | Val | Ser | Ala | Val | Gly | Asn | Gln | Phe | Asn | Gly | Gly | Cys | Leu | Leu |
| | | 195 | | | | | 200 | | | | | 205 | | | |
| Val | Ala | Met | Val | Pro | Glu | Trp | Lys | Glu | Phe | Asp | Thr | Arg | Glu | Lys | Tyr |
| | 210 | | | | | 215 | | | | | 220 | | | | |
| Gln | Leu | Thr | Leu | Phe | Pro | His | Gln | Phe | Ile | Ser | Pro | Arg | Thr | Asn | Met |
| 225 | | | | | 230 | | | | | 235 | | | | | 240 |
| Thr | Ala | His | Ile | Thr | Val | Pro | Tyr | Leu | Gly | Val | Asn | Arg | Tyr | Asp | Gln |
| | | | | 245 | | | | | 250 | | | | | 255 | |
| Tyr | Lys | Lys | His | Lys | Pro | Trp | Thr | Leu | Val | Val | Met | Val | Val | Ser | Pro |
| | | | 260 | | | | | 265 | | | | | 270 | | |
| Leu | Thr | Val | Asn | Asn | Thr | Ser | Ala | Ala | Gln | Ile | Lys | Val | Tyr | Ala | Asn |
| | | 275 | | | | | 280 | | | | | 285 | | | |
| Ile | Ala | Pro | Thr | Tyr | Val | His | Val | Ala | Gly | Glu | Leu | Pro | Ser | Lys | Glu |
| | 290 | | | | | 295 | | | | | 300 | | | | |
| Gly | Ile | Phe | Pro | Val | Ala | Cys | Ala | Asp | Gly | Tyr | Gly | Gly | Leu | Val | Thr |
| 305 | | | | | 310 | | | | | 315 | | | | | 320 |
| Thr | Asp | Pro | Lys | Thr | Ala | Asp | Pro | Ala | Tyr | Gly | Lys | Val | Tyr | Asn | Pro |
| | | | | 325 | | | | | 330 | | | | | 335 | |
| Pro | Arg | Thr | Asn | Tyr | Pro | Gly | Arg | Phe | Thr | Asn | Leu | Leu | Asp | Val | Ala |
| | | | 340 | | | | | 345 | | | | | 350 | | |
| Glu | Ala | Cys | Pro | Thr | Phe | Leu | Cys | Phe | Asp | Asp | Gly | Lys | Pro | Tyr | Val |
| | | 355 | | | | | 360 | | | | | 365 | | | |
| Thr | Thr | Arg | Thr | Asp | Asp | Thr | Arg | Leu | Leu | Ala | Lys | Phe | Asp | Leu | Ser |
| | 370 | | | | | 375 | | | | | 380 | | | | |

```
Leu Ala Ala Lys His Met Ser Asn Thr Tyr Leu Ser Gly Ile Ala Gln
385                 390                 395                 400

Tyr Tyr Thr Gln Tyr Ser Gly Thr Ile Asn Leu His Phe Met Phe Thr
                405                 410                 415

Gly Ser Thr Asp Ser Lys Ala Arg Tyr Met Val Ala Tyr Ile Pro Pro
                420                 425                 430

Gly Val Glu Thr Pro Pro Asp Thr Pro Glu Arg Ala Ala His Cys Ile
            435                 440                 445

His Ala Glu Trp Asp Thr Gly Leu Asn Ser Lys Phe Thr Phe Ser Ile
        450                 455                 460

Pro Tyr Val Ser Ala Ala Asp Tyr Ala Tyr Thr Ala Ser Asp Thr Ala
465                 470                 475                 480

Glu Thr Ile Asn Val Gln Gly Trp Val Cys Ile Tyr Gln Ile Thr His
                485                 490                 495

Gly Lys Ala Glu Asn Asp Thr Leu Val Val Ser Val Ser Ala Gly Lys
                500                 505                 510

Asp Phe Glu Leu Arg Leu Pro Ile Asp Pro Arg Gln Gln Thr Thr Ala
            515                 520                 525

Thr Gly Glu Ser Ala Asp Pro Val Thr Thr Thr Val Glu Asn Tyr Gly
530                 535                 540

Gly Glu Thr Gln Ile Gln Arg Arg His His Thr Asp Ile Gly Phe Ile
545                 550                 555                 560

Met Asp Arg Phe Val Lys Ile Gln Ser Leu Ser Pro Thr His Val Ile
                565                 570                 575

Asp Leu Met Gln Ala His Gln His Gly Leu Val Gly Ala Leu Leu Arg
            580                 585                 590

Ala Ala Thr Tyr Tyr Phe Ser Asp Leu Glu Ile Val Val Arg His Glu
            595                 600                 605

Gly Asn Leu Thr Trp Val Pro Asn Gly Ala Pro Glu Ser Ala Leu Leu
610                 615                 620

Asn Thr Ser Asn Pro Thr Ala Tyr Asn Lys Ala Pro Phe Thr Arg Leu
625                 630                 635                 640

Ala Leu Pro Tyr Thr Ala Pro His Arg Val Leu Ala Thr Val Tyr Asn
                645                 650                 655

Gly Thr Ser Lys Tyr Ala Val Gly Gly Ser Gly Arg Arg Gly Asp Met
                660                 665                 670

Gly Ser Leu Ala Ala Arg Val Val Lys Gln Leu Pro Ala Ser Phe Asn
            675                 680                 685

Tyr Gly Ala Ile Lys Ala Asp Ala Ile His Glu Leu Leu Val Arg Met
        690                 695                 700

Lys Arg Ala Glu Leu Tyr Cys Pro Arg Pro Leu Leu Ala Ile Glu Val
705                 710                 715                 720

Ser Ser Gln Asp Arg His Lys Gln Lys Ile Ile Ala Pro Ala Lys Gln
                725                 730                 735

Leu Leu Asn Phe Asp Leu Leu Lys Leu Ala Gly Asp Val Glu Ser Asn
                740                 745                 750

Pro Gly Pro Phe Phe Phe Ala Asp Val Arg Ser Asn Phe Ser Lys Leu
            755                 760                 765

Val Asp Thr Ile Asn Gln Met Gln Glu Asp Met Ser Thr Lys His Gly
770                 775                 780

Pro Asp Phe Asn Arg Leu Val Ser Ala Phe Glu Glu Leu Ala Thr Gly
785                 790                 795                 800
```

```
Val Lys Ala Ile Arg Thr Gly Leu Asp Glu Ala Lys Pro Trp Tyr Lys
                805                 810                 815

Leu Ile Lys Leu Leu Ser Arg Leu Ser Cys Met Ala Ala Val Ala Ala
            820                 825                 830

Arg Ser Lys Asp Pro Val Leu Val Ala Ile Met Leu Ala Asp Thr Gly
        835                 840                 845

Leu Glu Arg Gln Arg Pro Leu Lys Val Arg Ala Lys Leu Pro Gln Gln
850                 855                 860

Glu Gly Pro Tyr Ala Gly Pro Leu Glu Arg Gln Lys Pro Leu Lys Val
865                 870                 875                 880

Lys Ala Lys Ala Pro Val Val Lys Glu Gly Pro Tyr Glu Gly Pro Val
                885                 890                 895

Lys Lys Pro Val Ala Leu Lys Val Lys Ala Lys Asn Leu Ile Val Thr
            900                 905                 910

Glu Ser Gly Ala Pro Pro Thr Asp Leu Gln Lys Met Val Met Gly Asn
        915                 920                 925

Thr Lys Pro Val Glu Leu Ile Leu Asp Gly Lys Thr Val Ala Ile Cys
    930                 935                 940

Cys Ala Thr Gly Val Phe Gly Thr Ala Tyr Leu Val Pro Arg His Leu
945                 950                 955                 960

Phe Ala Glu Lys Tyr Asp Lys Ile Met Leu Asp Gly Arg Ala Met Thr
                965                 970                 975

Asp Ser Asp Tyr Arg Val Phe Glu Phe Glu Ile Lys Val Lys Gly Gln
            980                 985                 990

Asp Met Leu Ser Asp Ala Ala Leu Met Val Leu His Arg Gly Asn Arg
        995                 1000                1005

Val Arg Asp Ile Thr Lys His Phe Arg Asp Thr Ala Arg Met Lys Lys
    1010                1015                1020

Gly Thr Pro Val Val Gly Val Val Asn Asn Ala Asp Val Gly Arg Leu
1025                1030                1035                1040

Ile Phe Ser Gly Glu Ala Leu Thr Tyr Lys Asp Ile Val Val Cys Met
                1045                1050                1055

Asp Gly Asp Thr Met Pro Gly Leu Phe Ala Tyr Lys Ala Ala Thr Lys
            1060                1065                1070

Ala Gly Tyr Cys Gly Gly Ala Val Leu Ala Lys Asp Gly Ala Asp Thr
        1075                1080                1085

Phe Ile Val Gly Thr His Ser Ala Gly Gly Asn Gly Val Gly Tyr Cys
    1090                1095                1100

Ser Cys Val Ser Arg Ser Met Leu Leu Arg Met Lys Ala His Val Asp
1105                1110                1115                1120

Pro Glu Pro Gln His Glu
            1125

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gaattctcaa aattgaaaat atat                                          24

<210> SEQ ID NO 39
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
atatataatt acaatataaa atgggagctg                                        30

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cagctcccat tttatattgt aattatatat                                        30

<210> SEQ ID NO 41
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
caatataaaa tgggagctgg gcaatcca                                          28

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tgcctcctgg tggccatggt acc                                               23

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ggtaccatgg ccaccaggag gca                                               23

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Met Gly Ala Gly Gln Ser
 1               5

<210> SEQ ID NO 45
<211> LENGTH: 8
```

<212> TYPE: PRT
<213> ORGANISM: Artificial Sequence
<220> FEATURE:
<223> OTHER INFORMATION: Description of Artificial Sequence: Synthetic peptide

<400> SEQUENCE: 45

Cys Leu Leu Val Ala Met Val Pro
 1               5

<210> SEQ ID NO 46
<211> LENGTH: 5010
<212> TYPE: DNA
<213> ORGANISM: Foot-and-mouth disease virus
<220> FEATURE:
<221> NAME/KEY: CDS
<222> LOCATION: (1219)..(4596)

<400> SEQUENCE: 46

```
ttcataaata caagtttgat taaacttaag ttgttctaaa gttctttcct ccgaaggtat     60
agaacaaagt atttcttcta catccttact atttattgca gcttttaaca gcctatcacg    120
tatcctattt ttagtattgg tagaacgttt tagttctaaa gttaaaatat tagacataat    180
tggcatattg cttattcctt gcatagttga gtctgtagat cgtttcagta tatcactgat    240
taatgtacta ctgttatgat gaaatataga atcgatattg gcatttaact gttttgttat    300
actaagtcta gattttaaat cttctagtaa tatgctattt aatataaaag cttccacgtt    360
tttgtataca tttctttcca tattagtagc tactactaaa tgattatctt ctttcatatc    420
ttgtagataa gatagactat ctttatcttt attagtagaa aatacttctg gccatacatc    480
gttaaatttt tttgttgttg ttagatataa tattaaaatat ctagaggatc ctattatttg    540
tggtaaaatg tttatagagt aaaatgatct ggctattaaa cataggccag ttaccataga    600
atgctgcttc ccgttacagt gttttaccat aaccatagat ctgcctgtat tgttgataca    660
tataacagct gtaaatccta aaaaattcct atcataatta ttaatattag gtaattcatt    720
tccatgtgaa agatagacta attttatatc ctttacctcc aaataattat ttacatctct    780
taaacaatct attttaatat cattaactgg tattttataa tatccagaaa ggtttgaagg    840
ggttgatgga ataagtctat taacatcgtt aagtaaatta ttaatatcat gaatctttat    900
tatattatac ccataagtta aatttatatt tactttctca tcatctgact tagttagttt    960
gtaataaggt gtgtctgaaa aaattaaaag gtaattcgtt gaatgaagct gtatttgctg   1020
tatcattttt atctaatttt ggagatttag cagtacttac ttcattagaa gaagaatctg   1080
ccagttcctg tctattactg atatttcgtt tcattattat atgatttata ttttacttttt  1140
tcaattatat atactcattt gactagttaa tcaataaaaa gaattctcaa aattgaaaat   1200
atataattac aatataaaa atg gga gct ggg caa tcc agc cca gca acc ggc    1251
                          Met Gly Ala Gly Gln Ser Ser Pro Ala Thr Gly
                            1               5                  10 tcg cag aac cag tct ggc aac act ggc agc ata atc aac aac tac tac      1299
Ser Gln Asn Gln Ser Gly Asn Thr Gly Ser Ile Ile Asn Asn Tyr Tyr
            15                  20                  25 atg caa cag tac cag aac tcc atg gac aca cag ttg gga gac aat gcc      1347
Met Gln Gln Tyr Gln Asn Ser Met Asp Thr Gln Leu Gly Asp Asn Ala
        30                  35                  40 atc agt gga ggc tcc aac gag ggc tcc acg gac aca act tca aca cac      1395
Ile Ser Gly Gly Ser Asn Glu Gly Ser Thr Asp Thr Thr Ser Thr His
    45                  50                  55 aca acc aac act caa aac aat gac tgg ttc tcg aag ctc gcc agt tca      1443
```

```
Thr Thr Asn Thr Gln Asn Asn Asp Trp Phe Ser Lys Leu Ala Ser Ser
 60              65                  70                  75 gct ttt acc ggt ctg ttc ggt gca ctg ctc gcc gac aag aag aca gag     1491
Ala Phe Thr Gly Leu Phe Gly Ala Leu Leu Ala Asp Lys Lys Thr Glu
                 80                  85                  90 gaa acg aca ctt ctt gag gac cgc atc ctc acc acc cgc aac ggg cac     1539
Glu Thr Thr Leu Leu Glu Asp Arg Ile Leu Thr Thr Arg Asn Gly His
             95                 100                 105 acc acc tcg acg acc caa tcg agt gtg ggt gtc aca cac ggg tac tcc     1587
Thr Thr Ser Thr Thr Gln Ser Ser Val Gly Val Thr His Gly Tyr Ser
            110                 115                 120 aca gag gag gac cac gtt gct ggg ccc aac aca tcg ggc ctg gag acg     1635
Thr Glu Glu Asp His Val Ala Gly Pro Asn Thr Ser Gly Leu Glu Thr
        125                 130                 135 cga gtg gtg cag gca gag aga ttc tac aaa aag tac ttg ttt gac tgg     1683
Arg Val Val Gln Ala Glu Arg Phe Tyr Lys Lys Tyr Leu Phe Asp Trp
140                 145                 150                 155 aca acg gac aag gca ttt gga cac ctg gaa aag ctg gag ctc ccg tcc     1731
Thr Thr Asp Lys Ala Phe Gly His Leu Glu Lys Leu Glu Leu Pro Ser
                160                 165                 170 gac cac cac ggt gtc ttt gga cac ttg gtg gac tcg tac gcc tat atg     1779
Asp His His Gly Val Phe Gly His Leu Val Asp Ser Tyr Ala Tyr Met
            175                 180                 185 aga aat ggc tgg gat gtt gag gtg tcc gct gtt ggc aac cag ttc aac     1827
Arg Asn Gly Trp Asp Val Glu Val Ser Ala Val Gly Asn Gln Phe Asn
        190                 195                 200 ggc ggg tgc ctc ctg gtg gcc atg gta cct gaa tgg aag gaa ttt gac     1875
Gly Gly Cys Leu Leu Val Ala Met Val Pro Glu Trp Lys Glu Phe Asp
205                 210                 215 aca cgg gag aaa tac caa ctc acc ctt ttc ccg cac cag ttt att agc     1923
Thr Arg Glu Lys Tyr Gln Leu Thr Leu Phe Pro His Gln Phe Ile Ser
220                 225                 230                 235 ccc aga act aac atg act gcc cac atc acg gtc ccc tac ctt ggt gtg     1971
Pro Arg Thr Asn Met Thr Ala His Ile Thr Val Pro Tyr Leu Gly Val
                240                 245                 250 aac agg tat gat cag tac aag aag cat aag ccc tgg aca ttg gtt gtc     2019
Asn Arg Tyr Asp Gln Tyr Lys Lys His Lys Pro Trp Thr Leu Val Val
            255                 260                 265 atg gtc gtg tcg cca ctt acg gtc aac aac act agt gcg gca caa atc     2067
Met Val Val Ser Pro Leu Thr Val Asn Asn Thr Ser Ala Ala Gln Ile
        270                 275                 280 aag gtc tac gcc aac ata gct ccg acc tat gtt cac gtg gcc ggt gaa     2115
Lys Val Tyr Ala Asn Ile Ala Pro Thr Tyr Val His Val Ala Gly Glu
285                 290                 295 ctc ccc tcg aaa gag ggg att ttc ccg gtt gca tgt gcg gac ggt tac     2163
Leu Pro Ser Lys Glu Gly Ile Phe Pro Val Ala Cys Ala Asp Gly Tyr
300                 305                 310                 315 gga gga ttg gtg acg aca gac ccg aag aca gct gac cct gct tat ggc     2211
Gly Gly Leu Val Thr Thr Asp Pro Lys Thr Ala Asp Pro Ala Tyr Gly
                320                 325                 330 aag gtg tac aac ccg cct agg act aac tac cct ggg cgc ttc acc aac     2259
Lys Val Tyr Asn Pro Pro Arg Thr Asn Tyr Pro Gly Arg Phe Thr Asn
            335                 340                 345 ctg ttg gac gtg gcc gaa gcg tgt ccc act ttc ctc tgc ttt gac gac     2307
Leu Leu Asp Val Ala Glu Ala Cys Pro Thr Phe Leu Cys Phe Asp Asp
        350                 355                 360 ggg aaa ccg tac gtc acc acg cgg acg gat gac acc cga ctt ttg gcc     2355
Gly Lys Pro Tyr Val Thr Thr Arg Thr Asp Asp Thr Arg Leu Leu Ala
365                 370                 375
```

```
aag ttt gac ctt tcc ctt gcc gca aaa cat atg tcc aac aca tac ctg      2403
Lys Phe Asp Leu Ser Leu Ala Ala Lys His Met Ser Asn Thr Tyr Leu
380                 385                 390                 395 tca ggg att gct cag tac tac aca cag tac tct ggc acc atc aat ttg      2451
Ser Gly Ile Ala Gln Tyr Tyr Thr Gln Tyr Ser Gly Thr Ile Asn Leu
                400                 405                 410 cat ttc atg ttt aca ggt tcc act gat tca aag gcc cga tac atg gtg      2499
His Phe Met Phe Thr Gly Ser Thr Asp Ser Lys Ala Arg Tyr Met Val
            415                 420                 425 gcc tac atc cca cct ggg gtg gag aca cca ccg gac aca cct gaa agg      2547
Ala Tyr Ile Pro Pro Gly Val Glu Thr Pro Pro Asp Thr Pro Glu Arg
        430                 435                 440 gct gcc cac tgc att cac gct gaa tgg gac act gga cta aac tcc aaa      2595
Ala Ala His Cys Ile His Ala Glu Trp Asp Thr Gly Leu Asn Ser Lys
    445                 450                 455 ttc act ttc tca atc ccg tac gta tcc gcc gcg gat tac gcg tac aca      2643
Phe Thr Phe Ser Ile Pro Tyr Val Ser Ala Ala Asp Tyr Ala Tyr Thr
460                 465                 470                 475 gcg tct gac acg gca gaa aca atc aac gta cag gga tgg gtc tgc atc      2691
Ala Ser Asp Thr Ala Glu Thr Ile Asn Val Gln Gly Trp Val Cys Ile
                480                 485                 490 tac caa att aca cac ggg aag gct gaa aat gac acc ttg gtc gtg tcg      2739
Tyr Gln Ile Thr His Gly Lys Ala Glu Asn Asp Thr Leu Val Val Ser
            495                 500                 505 gtt agc gcc ggc aaa gac ttt gag ttg cgc ctc ccg att gac ccc cgc      2787
Val Ser Ala Gly Lys Asp Phe Glu Leu Arg Leu Pro Ile Asp Pro Arg
        510                 515                 520 cag cag acc acc gct acc ggg gaa tca gca gac ccg gtc acc acc acc      2835
Gln Gln Thr Thr Ala Thr Gly Glu Ser Ala Asp Pro Val Thr Thr Thr
    525                 530                 535 gtg gag aac tac ggc ggt gag aca caa atc cag aga cgt cac cac acg      2883
Val Glu Asn Tyr Gly Gly Glu Thr Gln Ile Gln Arg Arg His His Thr
540                 545                 550                 555 gac att ggt ttc atc atg gac aga ttt gtg aag atc caa agc ttg agc      2931
Asp Ile Gly Phe Ile Met Asp Arg Phe Val Lys Ile Gln Ser Leu Ser
                560                 565                 570 cca aca cat gtc att gac ctc atg cag gct cac caa cac ggt ctg gtg      2979
Pro Thr His Val Ile Asp Leu Met Gln Ala His Gln His Gly Leu Val
            575                 580                 585 ggt gcc ttg ctg cgt gca gcc acg tac tac ttt tct gac ctg gaa att      3027
Gly Ala Leu Leu Arg Ala Ala Thr Tyr Tyr Phe Ser Asp Leu Glu Ile
        590                 595                 600 gtt gta cgg cac gaa ggc aat ctg acc tgg gtg ccc aac ggc gcc cct      3075
Val Val Arg His Glu Gly Asn Leu Thr Trp Val Pro Asn Gly Ala Pro
    605                 610                 615 gaa tca gcc ctg ttg aac acc agc aac ccc act gcc tac aac aag gca      3123
Glu Ser Ala Leu Leu Asn Thr Ser Asn Pro Thr Ala Tyr Asn Lys Ala
620                 625                 630                 635 cca ttc acg aga ctc gct ctc ccc tac act gcg ccg cac cgt gtg ctg      3171
Pro Phe Thr Arg Leu Ala Leu Pro Tyr Thr Ala Pro His Arg Val Leu
                640                 645                 650 gca aca gtg tac aac ggg acg agt aag tat gct gtg ggt ggt tca ggc      3219
Ala Thr Val Tyr Asn Gly Thr Ser Lys Tyr Ala Val Gly Gly Ser Gly
            655                 660                 665 aga aga ggc gac atg ggg tct ctc gcg gcg cga gtc gtg aaa cag ctt      3267
Arg Arg Gly Asp Met Gly Ser Leu Ala Ala Arg Val Val Lys Gln Leu
        670                 675                 680 cct gct tca ttt aac tac ggt gca atc aag gcc gac gcc atc cac gaa      3315
Pro Ala Ser Phe Asn Tyr Gly Ala Ile Lys Ala Asp Ala Ile His Glu
    685                 690                 695
```

-continued

| | |
|---|---|
| ctt ctc gtg cgc atg aaa cgg gcc gag ctc tac tgc ccc aga ccg ctg<br>Leu Leu Val Arg Met Lys Arg Ala Glu Leu Tyr Cys Pro Arg Pro Leu<br>700                         705               710                    715 | 3363 |
| ttg gca ata gag gtg tct tcg caa gac agg cac aag caa aag atc att<br>Leu Ala Ile Glu Val Ser Ser Gln Asp Arg His Lys Gln Lys Ile Ile<br>                 720                    725                    730 | 3411 |
| gca cca gca aag cag ctt ctg aat ttt gac ctg ctc aag ttg gcc gga<br>Ala Pro Ala Lys Gln Leu Leu Asn Phe Asp Leu Leu Lys Leu Ala Gly<br>735                                  740                    745 | 3459 |
| gac gtt gag tcc aac ccc ggg cca ttc ttc ttt gct gac gtt agg tca<br>Asp Val Glu Ser Asn Pro Gly Pro Phe Phe Phe Ala Asp Val Arg Ser<br>                 750                    755                    760 | 3507 |
| aac ttt tca aag ttg gta gac aca atc aac cag atg cag gag gac atg<br>Asn Phe Ser Lys Leu Val Asp Thr Ile Asn Gln Met Gln Glu Asp Met<br>765                         770               775 | 3555 |
| tcc aca aaa cac ggg ccc gac ttc aac cgg ttg gtg tcc gca ttt gag<br>Ser Thr Lys His Gly Pro Asp Phe Asn Arg Leu Val Ser Ala Phe Glu<br>780                         785                    790               795 | 3603 |
| gaa ttg gcc act gga gtt aaa gct atc agg acc ggt ctc gac gag gcc<br>Glu Leu Ala Thr Gly Val Lys Ala Ile Arg Thr Gly Leu Asp Glu Ala<br>                 800                    805                    810 | 3651 |
| aaa ccc tgg tac aag ctt atc aaa ctc cta agc cgc ctg tcg tgc atg<br>Lys Pro Trp Tyr Lys Leu Ile Lys Leu Leu Ser Arg Leu Ser Cys Met<br>                 815                    820                    825 | 3699 |
| gcc gct gtg gca gca cgg tcc aag gac cca gtc ctt gtg gcc atc atg<br>Ala Ala Val Ala Ala Arg Ser Lys Asp Pro Val Leu Val Ala Ile Met<br>830                         835                    840 | 3747 |
| ctg gcc gac acc ggt ctc gag cgt cag aga cct ctg aaa gtg aga gct<br>Leu Ala Asp Thr Gly Leu Glu Arg Gln Arg Pro Leu Lys Val Arg Ala<br>845                                  850                    855 | 3795 |
| aag ctc cca cag cag gaa gga cct tac gct ggc ccg ttg gag aga cag<br>Lys Leu Pro Gln Gln Glu Gly Pro Tyr Ala Gly Pro Leu Glu Arg Gln<br>860                         865                    870               875 | 3843 |
| aaa ccg ctg aaa gtg aaa gca aaa gcc ccg gtc gtc aag gaa gga cct<br>Lys Pro Leu Lys Val Lys Ala Lys Ala Pro Val Val Lys Glu Gly Pro<br>                 880                    885                    890 | 3891 |
| tac gag gga ccg gtg aag aag cct gtc gct ttg aaa gtg aaa gct aag<br>Tyr Glu Gly Pro Val Lys Lys Pro Val Ala Leu Lys Val Lys Ala Lys<br>                 895                    900                    905 | 3939 |
| aac ttg ata gtc act gag agt ggt gcc cca ccg acc gac ttg caa aag<br>Asn Leu Ile Val Thr Glu Ser Gly Ala Pro Pro Thr Asp Leu Gln Lys<br>910                         915                    920 | 3987 |
| atg gtc atg ggc aac aca aag cct gtt gag ctc atc ctt gac ggg aag<br>Met Val Met Gly Asn Thr Lys Pro Val Glu Leu Ile Leu Asp Gly Lys<br>925                         930                    935 | 4035 |
| aca gta gcc atc tgt tgt gct act gga gtg ttt ggc act gct tac ctc<br>Thr Val Ala Ile Cys Cys Ala Thr Gly Val Phe Gly Thr Ala Tyr Leu<br>940                         945                    950               955 | 4083 |
| gtg cct cgt cat ctt ttc gca gag aag tat gac aag atc atg ctg gat<br>Val Pro Arg His Leu Phe Ala Glu Lys Tyr Asp Lys Ile Met Leu Asp<br>                 960                    965                    970 | 4131 |
| ggc aga gcc atg aca gac agt gac tac aga gtg ttt gag ttt gag att<br>Gly Arg Ala Met Thr Asp Ser Asp Tyr Arg Val Phe Glu Phe Glu Ile<br>                 975                    980                    985 | 4179 |
| aaa gta aaa gga cag gac atg ctc tca gac gct gcg ctc atg gtg ctc<br>Lys Val Lys Gly Gln Asp Met Leu Ser Asp Ala Ala Leu Met Val Leu<br>                 990                    995                 1000 | 4227 |
| cac cgt ggg aac cgc gtg aga gat atc acg aaa cac ttt cgt gat aca<br>His Arg Gly Asn Arg Val Arg Asp Ile Thr Lys His Phe Arg Asp Thr | 4275 |

-continued

| | | |
|---|---|---|
| gca aga atg aag aaa ggc acc ccc gtc gtc ggt gtg gtc aac aac gcc<br>Ala Arg Met Lys Lys Gly Thr Pro Val Val Gly Val Val Asn Asn Ala<br>1020                   1025                   1030                   1035 | 4323 |
| gac gtt ggg aga ctg att ttc tct ggt gag gcc ctc acc tac aag gat<br>Asp Val Gly Arg Leu Ile Phe Ser Gly Glu Ala Leu Thr Tyr Lys Asp<br>                   1040                   1045                   1050 | 4371 |
| att gta gtg tgc atg gac gga gac acc atg cct ggc ctc ttt gcc tac<br>Ile Val Val Cys Met Asp Gly Asp Thr Met Pro Gly Leu Phe Ala Tyr<br>1055                   1060                   1065 | 4419 |
| aaa gcc gcc acc aag gca ggc tac tgt gga gga gcc gtt ctc gcc aag<br>Lys Ala Ala Thr Lys Ala Gly Tyr Cys Gly Gly Ala Val Leu Ala Lys<br>                   1070                   1075                   1080 | 4467 |
| gac ggg gcc gac act ttc atc gtc ggc act cac tcc gca gga ggc aat<br>Asp Gly Ala Asp Thr Phe Ile Val Gly Thr His Ser Ala Gly Gly Asn<br>                   1085                   1090                   1095 | 4515 |
| gga gtt gga tac tgc tca tgc gtt tcc agg tcc atg ctt ctc aga atg<br>Gly Val Gly Tyr Cys Ser Cys Val Ser Arg Ser Met Leu Leu Arg Met<br>1100                   1105                   1110                   1115 | 4563 |
| aag gca cac gtt gac cct gaa cca caa cac gag tagtaatttt tctgcagccc<br>Lys Ala His Val Asp Pro Glu Pro Gln His Glu<br>                   1120                   1125 | 4616 |
| gggttttat agctaattag tcattttttc gtaagtaagt attttattt aatactttt | 4676 |
| attgtactta tgttaaatat aactgatgat aacaaaatcc attatgtatt atttataact | 4736 |
| gtaatttctt tagcgtagtt agatgtccaa tctctctcaa atacatcggc tatctttta | 4796 |
| gtgagatttt gatctatgca gttgaaactt atgaacgcgt gatgattaaa atgtgaaccg | 4856 |
| tccaaatttg cagtcattat atgagcgtat ctattatcta ctatcatcat ctttgagtta | 4916 |
| ttaatatcat ctactttaga attgatagga aatatgaata cctttgtagt aatatctata | 4976 |
| ctatctacac ctaactcatt aagacttttg atag | 5010 |

<210> SEQ ID NO 47
<211> LENGTH: 1126
<212> TYPE: PRT
<213> ORGANISM: Foot-and-mouth disease virus

<400> SEQUENCE: 47

Met Gly Ala Gly Gln Ser Ser Pro Ala Thr Gly Ser Gln Asn Gln Ser
1               5                    10                   15

Gly Asn Thr Gly Ser Ile Ile Asn Asn Tyr Tyr Met Gln Gln Tyr Gln
               20                   25                   30

Asn Ser Met Asp Thr Gln Leu Gly Asp Asn Ala Ile Ser Gly Gly Ser
        35                   40                   45

Asn Glu Gly Ser Thr Asp Thr Thr Ser Thr His Thr Thr Asn Thr Gln
50                    55                   60

Asn Asn Asp Trp Phe Ser Lys Leu Ala Ser Ser Ala Phe Thr Gly Leu
65                   70                   75                   80

Phe Gly Ala Leu Leu Ala Asp Lys Lys Thr Glu Glu Thr Thr Leu Leu
               85                   90                   95

Glu Asp Arg Ile Leu Thr Thr Arg Asn Gly His Thr Thr Ser Thr Thr
        100                  105                  110

Gln Ser Ser Val Gly Val Thr His Gly Tyr Ser Thr Glu Glu Asp His
              115                  120                  125

Val Ala Gly Pro Asn Thr Ser Gly Leu Glu Thr Arg Val Val Gln Ala
    130                   135                   140

-continued

```
Glu Arg Phe Tyr Lys Lys Tyr Leu Phe Asp Trp Thr Thr Asp Lys Ala
145                 150                 155                 160

Phe Gly His Leu Glu Lys Leu Glu Leu Pro Ser Asp His His Gly Val
                165                 170                 175

Phe Gly His Leu Val Asp Ser Tyr Ala Tyr Met Arg Asn Gly Trp Asp
            180                 185                 190

Val Glu Val Ser Ala Val Gly Asn Gln Phe Asn Gly Gly Cys Leu Leu
        195                 200                 205

Val Ala Met Val Pro Glu Trp Lys Glu Phe Asp Thr Arg Glu Lys Tyr
    210                 215                 220

Gln Leu Thr Leu Phe Pro His Gln Phe Ile Ser Pro Arg Thr Asn Met
225                 230                 235                 240

Thr Ala His Ile Thr Val Pro Tyr Leu Gly Val Asn Arg Tyr Asp Gln
                245                 250                 255

Tyr Lys Lys His Lys Pro Trp Thr Leu Val Val Met Val Val Ser Pro
                260                 265                 270

Leu Thr Val Asn Asn Thr Ser Ala Ala Gln Ile Lys Val Tyr Ala Asn
            275                 280                 285

Ile Ala Pro Thr Tyr Val His Val Ala Gly Leu Pro Ser Lys Glu
        290                 295                 300

Gly Ile Phe Pro Val Ala Cys Ala Asp Gly Tyr Gly Gly Leu Val Thr
305                 310                 315                 320

Thr Asp Pro Lys Thr Ala Asp Pro Ala Tyr Gly Lys Val Tyr Asn Pro
                325                 330                 335

Pro Arg Thr Asn Tyr Pro Gly Arg Phe Thr Asn Leu Leu Asp Val Ala
                340                 345                 350

Glu Ala Cys Pro Thr Phe Leu Cys Phe Asp Gly Lys Pro Tyr Val
            355                 360                 365

Thr Thr Arg Thr Asp Asp Thr Arg Leu Leu Ala Lys Phe Asp Leu Ser
            370                 375                 380

Leu Ala Ala Lys His Met Ser Asn Thr Tyr Leu Ser Gly Ile Ala Gln
385                 390                 395                 400

Tyr Tyr Thr Gln Tyr Ser Gly Thr Ile Asn Leu His Phe Met Phe Thr
                405                 410                 415

Gly Ser Thr Asp Ser Lys Ala Arg Tyr Met Val Ala Tyr Ile Pro Pro
                420                 425                 430

Gly Val Glu Thr Pro Pro Asp Thr Pro Glu Arg Ala Ala His Cys Ile
            435                 440                 445

His Ala Glu Trp Asp Thr Gly Leu Asn Ser Lys Phe Thr Phe Ser Ile
    450                 455                 460

Pro Tyr Val Ser Ala Ala Asp Tyr Ala Tyr Thr Ala Ser Asp Thr Ala
465                 470                 475                 480

Glu Thr Ile Asn Val Gln Gly Trp Val Cys Ile Tyr Gln Ile Thr His
                485                 490                 495

Gly Lys Ala Glu Asn Asp Thr Leu Val Val Ser Val Ser Ala Gly Lys
                500                 505                 510

Asp Phe Glu Leu Arg Leu Pro Ile Asp Pro Arg Gln Thr Thr Ala
            515                 520                 525

Thr Gly Glu Ser Ala Asp Pro Val Thr Thr Val Glu Asn Tyr Gly
            530                 535                 540

Gly Glu Thr Gln Ile Gln Arg Arg His His Thr Asp Ile Gly Phe Ile
545                 550                 555                 560

Met Asp Arg Phe Val Lys Ile Gln Ser Leu Ser Pro Thr His Val Ile
```

-continued

```
                565                 570                 575
Asp Leu Met Gln Ala His Gln His Gly Leu Val Gly Ala Leu Leu Arg
            580                 585                 590
Ala Ala Thr Tyr Tyr Phe Ser Asp Leu Glu Ile Val Val Arg His Glu
            595                 600                 605
Gly Asn Leu Thr Trp Val Pro Asn Gly Ala Pro Glu Ser Ala Leu Leu
            610                 615                 620
Asn Thr Ser Asn Pro Thr Ala Tyr Asn Lys Ala Pro Phe Thr Arg Leu
625                 630                 635                 640
Ala Leu Pro Tyr Thr Ala Pro His Arg Val Leu Ala Thr Val Tyr Asn
            645                 650                 655
Gly Thr Ser Lys Tyr Ala Val Gly Gly Ser Gly Arg Arg Gly Asp Met
            660                 665                 670
Gly Ser Leu Ala Ala Arg Val Val Lys Gln Leu Pro Ala Ser Phe Asn
            675                 680                 685
Tyr Gly Ala Ile Lys Ala Asp Ala Ile His Glu Leu Leu Val Arg Met
            690                 695                 700
Lys Arg Ala Glu Leu Tyr Cys Pro Arg Pro Leu Leu Ala Ile Glu Val
705                 710                 715                 720
Ser Ser Gln Asp Arg His Lys Gln Lys Ile Ile Ala Pro Ala Lys Gln
            725                 730                 735
Leu Leu Asn Phe Asp Leu Leu Lys Leu Ala Gly Asp Val Glu Ser Asn
            740                 745                 750
Pro Gly Pro Phe Phe Ala Asp Val Arg Ser Asn Phe Ser Lys Leu
            755                 760                 765
Val Asp Thr Ile Asn Gln Met Gln Glu Asp Met Ser Thr Lys His Gly
            770                 775                 780
Pro Asp Phe Asn Arg Leu Val Ser Ala Phe Glu Glu Leu Ala Thr Gly
785                 790                 795                 800
Val Lys Ala Ile Arg Thr Gly Leu Asp Glu Ala Lys Pro Trp Tyr Lys
            805                 810                 815
Leu Ile Lys Leu Leu Ser Arg Leu Ser Cys Met Ala Ala Val Ala Ala
            820                 825                 830
Arg Ser Lys Asp Pro Val Leu Val Ala Ile Met Leu Ala Asp Thr Gly
            835                 840                 845
Leu Glu Arg Gln Arg Pro Leu Lys Val Arg Ala Lys Leu Pro Gln Gln
            850                 855                 860
Glu Gly Pro Tyr Ala Gly Pro Leu Glu Arg Gln Lys Pro Leu Lys Val
865                 870                 875                 880
Lys Ala Lys Ala Pro Val Val Lys Glu Gly Pro Tyr Glu Gly Pro Val
            885                 890                 895
Lys Lys Pro Val Ala Leu Lys Val Lys Ala Lys Asn Leu Ile Val Thr
            900                 905                 910
Glu Ser Gly Ala Pro Pro Thr Asp Leu Gln Lys Met Val Met Gly Asn
            915                 920                 925
Thr Lys Pro Val Glu Leu Ile Leu Asp Gly Lys Thr Val Ala Ile Cys
            930                 935                 940
Cys Ala Thr Gly Val Phe Gly Thr Ala Tyr Leu Val Pro Arg His Leu
945                 950                 955                 960
Phe Ala Glu Lys Tyr Asp Lys Ile Met Leu Asp Gly Arg Ala Met Thr
            965                 970                 975
Asp Ser Asp Tyr Arg Val Phe Glu Phe Glu Ile Lys Val Lys Gly Gln
            980                 985                 990
```

-continued

```
Asp Met Leu Ser Asp Ala Ala Leu Met Val Leu His Arg Gly Asn Arg
        995                 1000                1005

Val Arg Asp Ile Thr Lys His Phe Arg Asp Thr Ala Arg Met Lys Lys
    1010                1015                1020

Gly Thr Pro Val Val Gly Val Val Asn Asn Ala Asp Val Gly Arg Leu
1025                1030                1035                1040

Ile Phe Ser Gly Glu Ala Leu Thr Tyr Lys Asp Ile Val Val Cys Met
                1045                1050                1055

Asp Gly Asp Thr Met Pro Gly Leu Phe Ala Tyr Lys Ala Ala Thr Lys
            1060                1065                1070

Ala Gly Tyr Cys Gly Gly Ala Val Leu Ala Lys Asp Gly Ala Asp Thr
        1075                1080                1085

Phe Ile Val Gly Thr His Ser Ala Gly Gly Asn Gly Val Gly Tyr Cys
    1090                1095                1100

Ser Cys Val Ser Arg Ser Met Leu Leu Arg Met Lys Ala His Val Asp
1105                1110                1115                1120

Pro Glu Pro Gln His Glu
            1125

<210> SEQ ID NO 48
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gaattcaaaa gtagaaaata tattctaatt tattgcacgg atgggagctg ggcaatccag    60
ccca                                                                64

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cttgccgcaa aacatatgtc ca                                            22

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tggacatatg ttttgcggca ag                                            22

<210> SEQ ID NO 51
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
```
ctaatttatt gcacggatgg gagctgggca atcca            35

<210> SEQ ID NO 52
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ctggattgcc cagctcccat ccgtgcaata aattaga         37

<210> SEQ ID NO 53
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gaaaatatat tctaatttat tgcacgga              28

<210> SEQ ID NO 54
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tccgtgcaat aaattagaat atattttc              28

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Met Gly Ala Gly Gln Ser Ser Pro
 1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Leu Ala Ala Lys His Met Ser
 1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide -continued

<400> SEQUENCE: 57

Met Gly Ala Gly Gln Ser Ser
 1               5

<210> SEQ ID NO 58
<211> LENGTH: 5012
<212> TYPE: DNA
<213> ORGANISM: Foot-and-mouth disease virus
<220> FEATURE:
<221> NAME/KEY: CDS
<222> LOCATION: (1221)..(4598)

<400> SEQUENCE: 58

```
ttcataaata caagtttgat taaacttaag ttgttctaaa gttctttcct ccgaaggtat      60
agaacaaagt atttcttcta catccttact atttattgca gcttttaaca gcctatcacg     120
tatcctattt ttagtattgg tagaacgttt tagttctaaa gttaaaatat tagacataat     180
tggcatattg cttattcctt gcatagttga gtctgtagat cgtttcagta tatcactgat     240
taatgtacta ctgttatgat gaaatataga atcgatattg gcatttaact gttttgttat     300
actaagtcta gattttaaat cttctagtaa tatgctattt aatataaaag cttccacgtt     360
tttgtataca tttcttttcca tattagtagc tactactaaa tgattatctt ctttcatatc     420
ttgtagataa gatagactat cttttatcttt attagtagaa aatacttctg gccatacatc     480
gttaaatttt tttgttgttg ttagatataa tattaaatat ctagaggatc ctattatttg     540
tggtaaaatg tttatagagt aaaatgatct ggctattaaa cataggccag ttaccataga     600
atgctgcttc ccgttacagt gttttaccat aaccatagat ctgcctgtat tgttgataca     660
tataacagct gtaaatccta aaaaattcct atcataatta ttaatattag gtaattcatt     720
tccatgtgaa agatagacta attttatatc ctttacctcc aaataattat ttacatctct     780
taaacaatct attttaatat cattaactgg tattttataa tatccagaaa ggtttgaagg     840
ggttgatgga ataagtctat taacatcgtt aagtaaatta ttaatatcat gaatctttat     900
tatattatac ccataagtta aatttatatt tactttctca tcatctgact tagttagttt     960
gtaataaggt gtgtctgaaa aaattaaaag gtaattcgtt gaatgaagct gtatttgctg    1020
tatcattttt atctaatttt ggagatttag cagtacttac ttcattagaa gaagaatctg    1080
ccagttcctg tctattactg atatttcgtt tcattattat atgatttata ttttactttt    1140
tcaattatat atactcattt gactagttaa tcaataaaaa gaattcaaaa gtagaaaata    1200
tattctaatt tattgcacgg atg gga gct ggg caa tcc agc cca gca acc ggc   1253
                        Met Gly Ala Gly Gln Ser Ser Pro Ala Thr Gly
                         1               5                  10 tcg cag aac cag tct ggc aac act ggc agc ata atc aac aac tac tac     1301
Ser Gln Asn Gln Ser Gly Asn Thr Gly Ser Ile Ile Asn Asn Tyr Tyr
        15                  20                  25 atg caa cag tac cag aac tcc atg gac aca cag ttg gga gac aat gcc     1349
Met Gln Gln Tyr Gln Asn Ser Met Asp Thr Gln Leu Gly Asp Asn Ala
    30                  35                  40 atc agt gga ggc tcc aac gag ggc tcc acg gac aca act tca aca cac     1397
Ile Ser Gly Gly Ser Asn Glu Gly Ser Thr Asp Thr Thr Ser Thr His
45                  50                  55 aca acc aac act caa aac aat gac tgg ttc tcg aag ctc gcc agt tca     1445
Thr Thr Asn Thr Gln Asn Asn Asp Trp Phe Ser Lys Leu Ala Ser Ser
 60                  65                  70                  75 gct ttt acc ggt ctg ttc ggt gca ctg ctc gcc gac aag aag aca gag    1493
Ala Phe Thr Gly Leu Phe Gly Ala Leu Leu Ala Asp Lys Lys Thr Glu
                80                  85                  90
```

```
gaa acg aca ctt ctt gag gac cgc atc ctc acc acc cgc aac ggg cac    1541
Glu Thr Thr Leu Leu Glu Asp Arg Ile Leu Thr Thr Arg Asn Gly His
             95                 100                 105 acc acc tcg acg acc caa tcg agt gtg ggt gtc aca cac ggg tac tcc    1589
Thr Thr Ser Thr Thr Gln Ser Ser Val Gly Val Thr His Gly Tyr Ser
        110                 115                 120 aca gag gag gac cac gtt gct ggg ccc aac aca tcg ggc ctg gag acg    1637
Thr Glu Glu Asp His Val Ala Gly Pro Asn Thr Ser Gly Leu Glu Thr
    125                 130                 135 cga gtg gtg cag gca gag aga ttc tac aaa aag tac ttg ttt gac tgg    1685
Arg Val Val Gln Ala Glu Arg Phe Tyr Lys Lys Tyr Leu Phe Asp Trp
140                 145                 150                 155 aca acg gac aag gca ttt gga cac ctg gaa aag ctg gag ctc ccg tcc    1733
Thr Thr Asp Lys Ala Phe Gly His Leu Glu Lys Leu Glu Leu Pro Ser
                160                 165                 170 gac cac cac ggt gtc ttt gga cac ttg gtg gac tcg tac gcc tat atg    1781
Asp His His Gly Val Phe Gly His Leu Val Asp Ser Tyr Ala Tyr Met
            175                 180                 185 aga aat ggc tgg gat gtt gag gtg tcc gct gtt ggc aac cag ttc aac    1829
Arg Asn Gly Trp Asp Val Glu Val Ser Ala Val Gly Asn Gln Phe Asn
        190                 195                 200 ggc ggg tgc ctc ctg gtg gcc atg gta cct gaa tgg aag gaa ttt gac    1877
Gly Gly Cys Leu Leu Val Ala Met Val Pro Glu Trp Lys Glu Phe Asp
    205                 210                 215 aca cgg gag aaa tac caa ctc acc ctt ttc ccg cac cag ttt att agc    1925
Thr Arg Glu Lys Tyr Gln Leu Thr Leu Phe Pro His Gln Phe Ile Ser
220                 225                 230                 235 ccc aga act aac atg act gcc cac atc acg gtc ccc tac ctt ggt gtg    1973
Pro Arg Thr Asn Met Thr Ala His Ile Thr Val Pro Tyr Leu Gly Val
                240                 245                 250 aac agg tat gat cag tac aag aag cat aag ccc tgg aca ttg gtt gtc    2021
Asn Arg Tyr Asp Gln Tyr Lys Lys His Lys Pro Trp Thr Leu Val Val
            255                 260                 265 atg gtc gtg tcg cca ctt acg gtc aac aac act agt gcg gca caa atc    2069
Met Val Val Ser Pro Leu Thr Val Asn Asn Thr Ser Ala Ala Gln Ile
        270                 275                 280 aag gtc tac gcc aac ata gct ccg acc tat gtt cac gtg gcc ggt gaa    2117
Lys Val Tyr Ala Asn Ile Ala Pro Thr Tyr Val His Val Ala Gly Glu
    285                 290                 295 ctc ccc tcg aaa gag ggg att ttc ccg gtt gca tgt gcg gac ggt tac    2165
Leu Pro Ser Lys Glu Gly Ile Phe Pro Val Ala Cys Ala Asp Gly Tyr
300                 305                 310                 315 gga gga ttg gtg acg aca gac ccg aag aca gct gac cct gct tat ggc    2213
Gly Gly Leu Val Thr Thr Asp Pro Lys Thr Ala Asp Pro Ala Tyr Gly
                320                 325                 330 aag gtg tac aac ccg cct agg act aac tac cct ggg cgc ttc acc aac    2261
Lys Val Tyr Asn Pro Pro Arg Thr Asn Tyr Pro Gly Arg Phe Thr Asn
            335                 340                 345 ctg ttg gac gtg gcc gaa gcg tgt ccc act ttc ctc tgc ttt gac gac    2309
Leu Leu Asp Val Ala Glu Ala Cys Pro Thr Phe Leu Cys Phe Asp Asp
        350                 355                 360 ggg aaa ccg tac gtc acc acg cgg acg gat gac acc cga ctt ttg gcc    2357
Gly Lys Pro Tyr Val Thr Thr Arg Thr Asp Asp Thr Arg Leu Leu Ala
    365                 370                 375 aag ttt gac ctt tcc ctt gcc gca aaa cat atg tcc aac aca tac ctg    2405
Lys Phe Asp Leu Ser Leu Ala Ala Lys His Met Ser Asn Thr Tyr Leu
380                 385                 390                 395 tca ggg att gct cag tac tac aca cag tac tct ggc acc atc aat ttg    2453
Ser Gly Ile Ala Gln Tyr Tyr Thr Gln Tyr Ser Gly Thr Ile Asn Leu
```

-continued

```
                         400                      405                      410
cat ttc atg ttt aca ggt tcc act gat tca aag gcc cga tac atg gtg     2501
His Phe Met Phe Thr Gly Ser Thr Asp Ser Lys Ala Arg Tyr Met Val
            415                      420                      425 gcc tac atc cca cct ggg gtg gag aca cca ccg gac aca cct gaa agg     2549
Ala Tyr Ile Pro Pro Gly Val Glu Thr Pro Pro Asp Thr Pro Glu Arg
                430                      435                      440 gct gcc cac tgc att cac gct gaa tgg gac act gga cta aac tcc aaa     2597
Ala Ala His Cys Ile His Ala Glu Trp Asp Thr Gly Leu Asn Ser Lys
        445                      450                      455 ttc act ttc tca atc ccg tac gta tcc gcc gcg gat tac gcg tac aca     2645
Phe Thr Phe Ser Ile Pro Tyr Val Ser Ala Ala Asp Tyr Ala Tyr Thr
460                      465                      470                      475 gcg tct gac acg gca gaa aca atc aac gta cag gga tgg gtc tgc atc     2693
Ala Ser Asp Thr Ala Glu Thr Ile Asn Val Gln Gly Trp Val Cys Ile
                480                      485                      490 tac caa att aca cac ggg aag gct gaa aat gac acc ttg gtc gtg tcg     2741
Tyr Gln Ile Thr His Gly Lys Ala Glu Asn Asp Thr Leu Val Val Ser
        495                      500                      505 gtt agc gcc ggc aaa gac ttt gag ttg cgc ctc ccg att gac ccc cgc     2789
Val Ser Ala Gly Lys Asp Phe Glu Leu Arg Leu Pro Ile Asp Pro Arg
    510                      515                      520 cag cag acc acc gct acc ggg gaa tca gca gac ccg gtc acc acc acc     2837
Gln Gln Thr Thr Ala Thr Gly Glu Ser Ala Asp Pro Val Thr Thr Thr
        525                      530                      535 gtg gag aac tac ggc ggt gag aca caa atc cag aga cgt cac cac acg     2885
Val Glu Asn Tyr Gly Gly Glu Thr Gln Ile Gln Arg Arg His His Thr
540                      545                      550                      555 gac att ggt ttc atc atg gac aga ttt gtg aag atc caa agc ttg agc     2933
Asp Ile Gly Phe Ile Met Asp Arg Phe Val Lys Ile Gln Ser Leu Ser
                560                      565                      570 cca aca cat gtc att gac ctc atg cag gct cac caa cac ggt ctg gtg     2981
Pro Thr His Val Ile Asp Leu Met Gln Ala His Gln His Gly Leu Val
        575                      580                      585 ggt gcc ttg ctg cgt gca gcc acg tac tac ttt tct gac ctg gaa att     3029
Gly Ala Leu Leu Arg Ala Ala Thr Tyr Tyr Phe Ser Asp Leu Glu Ile
            590                      595                      600 gtt gta cgg cac gaa ggc aat ctg acc tgg gtg ccc aac ggc gcc cct     3077
Val Val Arg His Glu Gly Asn Leu Thr Trp Val Pro Asn Gly Ala Pro
605                      610                      615 gaa tca gcc ctg ttg aac acc agc aac ccc act gcc tac aac aag gca     3125
Glu Ser Ala Leu Leu Asn Thr Ser Asn Pro Thr Ala Tyr Asn Lys Ala
620                      625                      630                      635 cca ttc acg aga ctc gct ctc ccc tac act gcg ccg cac cgt gtg ctg     3173
Pro Phe Thr Arg Leu Ala Leu Pro Tyr Thr Ala Pro His Arg Val Leu
                640                      645                      650 gca aca gtg tac aac ggg acg agt aag tat gct gtg ggt ggt tca ggc     3221
Ala Thr Val Tyr Asn Gly Thr Ser Lys Tyr Ala Val Gly Gly Ser Gly
        655                      660                      665 aga aga ggc gac atg ggg tct ctc gcg gcg cga gtc gtg aaa cag ctt     3269
Arg Arg Gly Asp Met Gly Ser Leu Ala Ala Arg Val Val Lys Gln Leu
            670                      675                      680 cct gct tca ttt aac tac ggt gca atc aag gcc gac gcc atc cac gaa     3317
Pro Ala Ser Phe Asn Tyr Gly Ala Ile Lys Ala Asp Ala Ile His Glu
        685                      690                      695 ctt ctc gtg cgc atg aaa cgg gcc gag ctc tac tgc ccc aga ccg ctg     3365
Leu Leu Val Arg Met Lys Arg Ala Glu Leu Tyr Cys Pro Arg Pro Leu
700                      705                      710                      715 ttg gca ata gag gtg tct tcg caa gac agg cac aag caa aag atc att     3413
```

-continued

```
                Leu Ala Ile Glu Val Ser Ser Gln Asp Arg His Lys Gln Lys Ile Ile
                                720                 725                 730 gca cca gca aag cag ctt ctg aat ttt gac ctg ctc aag ttg gcc gga        3461
Ala Pro Ala Lys Gln Leu Leu Asn Phe Asp Leu Leu Lys Leu Ala Gly
                735                 740                 745 gac gtt gag tcc aac ccc ggg cca ttc ttc ttt gct gac gtt agg tca        3509
Asp Val Glu Ser Asn Pro Gly Pro Phe Phe Phe Ala Asp Val Arg Ser
            750                 755                 760 aac ttt tca aag ttg gta gac aca atc aac cag atg cag gag gac atg        3557
Asn Phe Ser Lys Leu Val Asp Thr Ile Asn Gln Met Gln Glu Asp Met
765                 770                 775 tcc aca aaa cac ggg ccc gac ttc aac cgg ttg gtg tcc gca ttt gag        3605
Ser Thr Lys His Gly Pro Asp Phe Asn Arg Leu Val Ser Ala Phe Glu
780                 785                 790                 795 gaa ttg gcc act gga gtt aaa gct atc agg acc ggt ctc gac gag gcc        3653
Glu Leu Ala Thr Gly Val Lys Ala Ile Arg Thr Gly Leu Asp Glu Ala
                800                 805                 810 aaa ccc tgg tac aag ctt atc aaa ctc cta agc cgc ctg tcg tgc atg        3701
Lys Pro Trp Tyr Lys Leu Ile Lys Leu Leu Ser Arg Leu Ser Cys Met
            815                 820                 825 gcc gct gtg gca gca cgg tcc aag gac cca gtc ctt gtg gcc atc atg        3749
Ala Ala Val Ala Ala Arg Ser Lys Asp Pro Val Leu Val Ala Ile Met
        830                 835                 840 ctg gcc gac acc ggt ctc gag cgt cag aga cct ctg aaa gtg aga gct        3797
Leu Ala Asp Thr Gly Leu Glu Arg Gln Arg Pro Leu Lys Val Arg Ala
845                 850                 855 aag ctc cca cag cag gaa gga cct tac gct ggc ccg ttg gag aga cag        3845
Lys Leu Pro Gln Gln Glu Gly Pro Tyr Ala Gly Pro Leu Glu Arg Gln
860                 865                 870                 875 aaa ccg ctg aaa gtg aaa gca aaa gcc ccg gtc gtc aag gaa gga cct        3893
Lys Pro Leu Lys Val Lys Ala Lys Ala Pro Val Val Lys Glu Gly Pro
                880                 885                 890 tac gag gga ccg gtg aag aag cct gtc gct ttg aaa gtg aaa gct aag        3941
Tyr Glu Gly Pro Val Lys Lys Pro Val Ala Leu Lys Val Lys Ala Lys
            895                 900                 905 aac ttg ata gtc act gag agt ggt gcc cca ccg acc gac ttg caa aag        3989
Asn Leu Ile Val Thr Glu Ser Gly Ala Pro Pro Thr Asp Leu Gln Lys
        910                 915                 920 atg gtc atg ggc aac aca aag cct gtt gag ctc atc ctt gac ggg aag        4037
Met Val Met Gly Asn Thr Lys Pro Val Glu Leu Ile Leu Asp Gly Lys
925                 930                 935 aca gta gcc atc tgt tgt gct act gga gtg ttt ggc act gct tac ctc        4085
Thr Val Ala Ile Cys Cys Ala Thr Gly Val Phe Gly Thr Ala Tyr Leu
940                 945                 950                 955 gtg cct cgt cat ctt ttc gca gag aag tat gac aag atc atg ctg gat        4133
Val Pro Arg His Leu Phe Ala Glu Lys Tyr Asp Lys Ile Met Leu Asp
                960                 965                 970 ggc aga gcc atg aca gac agt gac tac aga gtg ttt gag ttt gag att        4181
Gly Arg Ala Met Thr Asp Ser Asp Tyr Arg Val Phe Glu Phe Glu Ile
            975                 980                 985 aaa gta aaa gga cag gac atg ctc tca gac gct gcg ctc atg gtg ctc        4229
Lys Val Lys Gly Gln Asp Met Leu Ser Asp Ala Ala Leu Met Val Leu
        990                 995                 1000 cac cgt ggg aac cgc gtg aga gat atc acg aaa cac ttt cgt gat aca        4277
His Arg Gly Asn Arg Val Arg Asp Ile Thr Lys His Phe Arg Asp Thr
1005                1010                1015 gca aga atg aag aaa ggc acc ccc gtc gtc ggt gtg gtc aac aac gcc        4325
Ala Arg Met Lys Lys Gly Thr Pro Val Val Gly Val Val Asn Asn Ala
1020                1025                1030                1035
```

```
gac gtt ggg aga ctg att ttc tct ggt gag gcc ctc acc tac aag gat    4373
Asp Val Gly Arg Leu Ile Phe Ser Gly Glu Ala Leu Thr Tyr Lys Asp
            1040                1045                1050 att gta gtg tgc atg gac gga gac acc atg cct ggc ctc ttt gcc tac    4421
Ile Val Val Cys Met Asp Gly Asp Thr Met Pro Gly Leu Phe Ala Tyr
            1055                1060                1065 aaa gcc gcc acc aag gca ggc tac tgt gga gga gcc gtt ctc gcc aag    4469
Lys Ala Ala Thr Lys Ala Gly Tyr Cys Gly Gly Ala Val Leu Ala Lys
            1070                1075                1080 gac ggg gcc gac act ttc atc gtc ggc act cac tcc gca gga ggc aat    4517
Asp Gly Ala Asp Thr Phe Ile Val Gly Thr His Ser Ala Gly Gly Asn
            1085                1090                1095 gga gtt gga tac tgc tca tgc gtt tcc agg tcc atg ctt ctc aga atg    4565
Gly Val Gly Tyr Cys Ser Cys Val Ser Arg Ser Met Leu Leu Arg Met
1100                1105                1110                1115 aag gca cac gtt gac cct gaa cca caa cac gag tagtaatttt tctgcagccc  4618
Lys Ala His Val Asp Pro Glu Pro Gln His Glu
            1120                1125 gggttttat agctaattag tcattttttc gtaagtaagt attttattt aatactttt     4678 attgtactta tgttaaatat aactgatgat aacaaaatcc attatgtatt atttataact  4738
gtaatttctt tagcgtagtt agatgtccaa tctctctcaa atacatcggc tatctttta   4798 gtgagatttt gatctatgca gttgaaactt atgaacgcgt gatgattaaa atgtgaaccg  4858
tccaaatttg cagtcattat atgagcgtat ctattatcta ctatcatcat ctttgagtta  4918
ttaatatcat ctactttaga attgatagga aatatgaata cctttgtagt aatatctata  4978
ctatctacac ctaactcatt aagacttttg atag                              5012

<210> SEQ ID NO 59
<211> LENGTH: 1126
<212> TYPE: PRT
<213> ORGANISM: Foot-and-mouth disease virus

<400> SEQUENCE: 59

Met Gly Ala Gly Gln Ser Ser Pro Ala Thr Gly Ser Gln Asn Gln Ser
1               5                   10                  15

Gly Asn Thr Gly Ser Ile Ile Asn Asn Tyr Tyr Met Gln Gln Tyr Gln
            20                  25                  30

Asn Ser Met Asp Thr Gln Leu Gly Asp Asn Ala Ile Ser Gly Gly Ser
        35                  40                  45

Asn Glu Gly Ser Thr Asp Thr Thr Ser Thr His Thr Thr Asn Thr Gln
    50                  55                  60

Asn Asn Asp Trp Phe Ser Lys Leu Ala Ser Ser Ala Phe Thr Gly Leu
65                  70                  75                  80

Phe Gly Ala Leu Leu Ala Asp Lys Lys Thr Glu Glu Thr Thr Leu Leu
                85                  90                  95

Glu Asp Arg Ile Leu Thr Thr Arg Asn Gly His Thr Thr Ser Thr Thr
            100                 105                 110

Gln Ser Ser Val Gly Val Thr His Gly Tyr Ser Thr Glu Glu Asp His
        115                 120                 125

Val Ala Gly Pro Asn Thr Ser Gly Leu Glu Thr Arg Val Val Gln Ala
    130                 135                 140

Glu Arg Phe Tyr Lys Lys Tyr Leu Phe Asp Trp Thr Thr Asp Lys Ala
145                 150                 155                 160

Phe Gly His Leu Glu Lys Leu Glu Leu Pro Ser Asp His His Gly Val
                165                 170                 175
```

-continued

```
Phe Gly His Leu Val Asp Ser Tyr Ala Tyr Met Arg Asn Gly Trp Asp
            180                 185                 190

Val Glu Val Ser Ala Val Gly Asn Gln Phe Asn Gly Gly Cys Leu Leu
        195                 200                 205

Val Ala Met Val Pro Glu Trp Lys Glu Phe Asp Thr Arg Glu Lys Tyr
    210                 215                 220

Gln Leu Thr Leu Phe Pro His Gln Phe Ile Ser Pro Arg Thr Asn Met
225                 230                 235                 240

Thr Ala His Ile Thr Val Pro Tyr Leu Gly Val Asn Arg Tyr Asp Gln
                245                 250                 255

Tyr Lys Lys His Lys Pro Trp Thr Leu Val Val Met Val Val Ser Pro
            260                 265                 270

Leu Thr Val Asn Asn Thr Ser Ala Ala Gln Ile Lys Val Tyr Ala Asn
        275                 280                 285

Ile Ala Pro Thr Tyr Val His Val Ala Gly Glu Leu Pro Ser Lys Glu
    290                 295                 300

Gly Ile Phe Pro Val Ala Cys Ala Asp Gly Tyr Gly Gly Leu Val Thr
305                 310                 315                 320

Thr Asp Pro Lys Thr Ala Asp Pro Ala Tyr Gly Lys Val Tyr Asn Pro
                325                 330                 335

Pro Arg Thr Asn Tyr Pro Gly Arg Phe Thr Asn Leu Leu Asp Val Ala
            340                 345                 350

Glu Ala Cys Pro Thr Phe Leu Cys Phe Asp Asp Gly Lys Pro Tyr Val
        355                 360                 365

Thr Thr Arg Thr Asp Asp Thr Arg Leu Leu Ala Lys Phe Asp Leu Ser
    370                 375                 380

Leu Ala Ala Lys His Met Ser Asn Thr Tyr Leu Ser Gly Ile Ala Gln
385                 390                 395                 400

Tyr Tyr Thr Gln Tyr Ser Gly Thr Ile Asn Leu His Phe Met Phe Thr
                405                 410                 415

Gly Ser Thr Asp Ser Lys Ala Arg Tyr Met Val Ala Tyr Ile Pro Pro
            420                 425                 430

Gly Val Glu Thr Pro Pro Asp Thr Pro Glu Arg Ala Ala His Cys Ile
        435                 440                 445

His Ala Glu Trp Asp Thr Gly Leu Asn Ser Lys Phe Thr Phe Ser Ile
    450                 455                 460

Pro Tyr Val Ser Ala Ala Asp Tyr Ala Tyr Thr Ala Ser Asp Thr Ala
465                 470                 475                 480

Glu Thr Ile Asn Val Gln Gly Trp Val Cys Ile Tyr Gln Ile Thr His
                485                 490                 495

Gly Lys Ala Glu Asn Asp Thr Leu Val Val Ser Val Ser Ala Gly Lys
            500                 505                 510

Asp Phe Glu Leu Arg Leu Pro Ile Asp Pro Arg Gln Gln Thr Thr Ala
        515                 520                 525

Thr Gly Glu Ser Ala Asp Pro Val Thr Thr Val Glu Asn Tyr Gly
    530                 535                 540

Gly Glu Thr Gln Ile Gln Arg Arg His His Thr Asp Ile Gly Phe Ile
545                 550                 555                 560

Met Asp Arg Phe Val Lys Ile Gln Ser Leu Ser Pro Thr His Val Ile
                565                 570                 575

Asp Leu Met Gln Ala His Gln His Gly Leu Val Gly Ala Leu Leu Arg
            580                 585                 590

Ala Ala Thr Tyr Tyr Phe Ser Asp Leu Glu Ile Val Val Arg His Glu
```

-continued

```
            595                 600                 605
Gly Asn Leu Thr Trp Val Pro Asn Gly Ala Pro Glu Ser Ala Leu Leu
        610                 615                 620

Asn Thr Ser Asn Pro Thr Ala Tyr Asn Lys Ala Pro Phe Thr Arg Leu
625                 630                 635                 640

Ala Leu Pro Tyr Thr Ala Pro His Arg Val Leu Ala Thr Val Tyr Asn
                645                 650                 655

Gly Thr Ser Lys Tyr Ala Val Gly Gly Ser Gly Arg Arg Gly Asp Met
                660                 665                 670

Gly Ser Leu Ala Ala Arg Val Val Lys Gln Leu Pro Ala Ser Phe Asn
            675                 680                 685

Tyr Gly Ala Ile Lys Ala Asp Ala Ile His Glu Leu Leu Val Arg Met
        690                 695                 700

Lys Arg Ala Glu Leu Tyr Cys Pro Arg Pro Leu Leu Ala Ile Glu Val
705                 710                 715                 720

Ser Ser Gln Asp Arg His Lys Gln Lys Ile Ile Ala Pro Ala Lys Gln
                725                 730                 735

Leu Leu Asn Phe Asp Leu Leu Lys Leu Ala Gly Asp Val Glu Ser Asn
                740                 745                 750

Pro Gly Pro Phe Phe Ala Asp Val Arg Ser Asn Phe Ser Lys Leu
            755                 760                 765

Val Asp Thr Ile Asn Gln Met Gln Glu Asp Met Ser Thr Lys His Gly
        770                 775                 780

Pro Asp Phe Asn Arg Leu Val Ser Ala Phe Glu Glu Leu Ala Thr Gly
785                 790                 795                 800

Val Lys Ala Ile Arg Thr Gly Leu Asp Glu Ala Lys Pro Trp Tyr Lys
                805                 810                 815

Leu Ile Lys Leu Leu Ser Arg Leu Ser Cys Met Ala Val Ala Ala
                820                 825                 830

Arg Ser Lys Asp Pro Val Leu Val Ala Ile Met Leu Ala Asp Thr Gly
            835                 840                 845

Leu Glu Arg Gln Arg Pro Leu Lys Val Arg Ala Lys Leu Pro Gln Gln
        850                 855                 860

Glu Gly Pro Tyr Ala Gly Pro Leu Glu Arg Gln Lys Pro Leu Lys Val
865                 870                 875                 880

Lys Ala Lys Ala Pro Val Val Lys Glu Gly Pro Tyr Glu Gly Pro Val
                885                 890                 895

Lys Lys Pro Val Ala Leu Lys Val Lys Ala Lys Asn Leu Ile Val Thr
            900                 905                 910

Glu Ser Gly Ala Pro Pro Thr Asp Leu Gln Lys Met Val Met Gly Asn
        915                 920                 925

Thr Lys Pro Val Glu Leu Ile Leu Asp Gly Lys Thr Val Ala Ile Cys
930                 935                 940

Cys Ala Thr Gly Val Phe Gly Thr Ala Tyr Leu Val Pro Arg His Leu
945                 950                 955                 960

Phe Ala Glu Lys Tyr Asp Lys Ile Met Leu Asp Gly Arg Ala Met Thr
                965                 970                 975

Asp Ser Asp Tyr Arg Val Phe Glu Phe Glu Ile Lys Val Lys Gly Gln
                980                 985                 990

Asp Met Leu Ser Asp Ala Ala Leu Met Val Leu His Arg Gly Asn Arg
            995                 1000                1005

Val Arg Asp Ile Thr Lys His Phe Arg Asp Thr Ala Arg Met Lys Lys
        1010                1015                1020
```

```
Gly Thr Pro Val Val Gly Val Val Asn Asn Ala Asp Val Gly Arg Leu
1025                1030                1035                1040

Ile Phe Ser Gly Glu Ala Leu Thr Tyr Lys Asp Ile Val Val Cys Met
                1045                1050                1055

Asp Gly Asp Thr Met Pro Gly Leu Phe Ala Tyr Lys Ala Ala Thr Lys
            1060                1065                1070

Ala Gly Tyr Cys Gly Gly Ala Val Leu Ala Lys Asp Gly Ala Asp Thr
        1075                1080                1085

Phe Ile Val Gly Thr His Ser Ala Gly Gly Asn Gly Val Gly Tyr Cys
    1090                1095                1100

Ser Cys Val Ser Arg Ser Met Leu Leu Arg Met Lys Ala His Val Asp
1105                1110                1115                1120

Pro Glu Pro Gln His Glu
            1125

<210> SEQ ID NO 60
<211> LENGTH: 111
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gaattcactg taaaaataga aactataatc atataatagt gtaggttggt agtagggtac      60
tcgtgattaa ttttattgtt aaacttgatg ggagctgggc aatccagccc a             111

<210> SEQ ID NO 61
<211> LENGTH: 105
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
tgggctggat tgcccagctc ccatcaagtt taacaataaa attaatcacg agtaccctac      60
taccaaccta cactattata tgattatagt ttctattttt acagt                   105

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
cttgccgcaa aacatatgtc ca                                             22

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
tggacatatg ttttgcggca ag                                             22
```

<210> SEQ ID NO 64
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
actgtaaaaa tagaaactat aatcata                                         27

<210> SEQ ID NO 65
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
taatagtgta ggttggtagt agggtac                                         27

<210> SEQ ID NO 66
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tcgtgattaa ttttattgtt aaacttg                                         27

<210> SEQ ID NO 67
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
acctacacta ttatatgatt atagtttcta tttttacagt                           40

<210> SEQ ID NO 68
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
caagtttaac aataaaatta atcacgagta ccctactacc a                         41

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
actgtaaaaa tagaaactat aat                                             23

<210> SEQ ID NO 70

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
caagtttaac aataaaatta atca                                         24

<210> SEQ ID NO 71
<211> LENGTH: 111
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gaattcactg taaaaataga aactataatc atataatagt gtaggttggt agtagggtac   60
tcgtgattaa ttttattgtt aaacttgatg ggagctgggc aatccagccc a           111

<210> SEQ ID NO 72
<211> LENGTH: 105
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
tgggctggat tgcccagctc ccatcaagtt taacaataaa attaatcacg agtaccctac   60
taccaaccta cactattata tgattatagt ttctattttt acagt                  105

<210> SEQ ID NO 73
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
gaattcactg taaaaataga aactat                                       26

<210> SEQ ID NO 74
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
cagctcccat caagtttaac aataaaat                                     28

<210> SEQ ID NO 75
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gttaaacttg atgggagctg ggcaatcc                                     28
```

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
tgcctcctgg tggccatggt acc                                              23

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
ggtaccatgg ccaccaggag gca                                              23

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Met Gly Ala Gly Gln Ser Ser Pro
 1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Leu Ala Ala Lys His Met Ser
 1               5

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Cys Leu Leu Val Ala Met Val Pro
 1               5

<210> SEQ ID NO 81
<211> LENGTH: 5059
<212> TYPE: DNA
<213> ORGANISM: Foot-and-mouth disease virus
<220> FEATURE:
<221> NAME/KEY: CDS
<222> LOCATION: (1268)..(4645)

<400> SEQUENCE: 81

-continued

```
ttcataaata caagtttgat taaacttaag ttgttctaaa gttctttcct ccgaaggtat      60
agaacaaagt atttcttcta catccttact atttattgca gcttttaaca gcctatcacg     120
tatcctattt ttagtattgg tagaacgttt tagttctaaa gttaaaatat tagacataat     180
tggcatattg cttattcctt gcatagttga gtctgtagat cgtttcagta tatcactgat     240
taatgtacta ctgttatgat gaaatataga atcgatattg gcatttaact gttttgttat     300
actaagtcta gattttaaat cttctagtaa tatgctattt aatataaaag cttccacgtt     360
tttgtataca tttctttcca tattagtagc tactactaaa tgattatctt ctttcatatc     420
ttgtagataa gatagactat ctttatcttt attagtagaa aatacttctg gccatacatc     480
gttaaatttt tttgttgttg ttagatataa tattaaatat ctagaggatc ctattatttg     540
tggtaaaatg tttatagagt aaaatgatct ggctattaaa cataggccag ttaccataga     600
atgctgcttc ccgttacagt gttttaccat aaccatagat ctgcctgtat tgttgataca     660
tataacagct gtaaatccta aaaaattcct atcataatta ttaatattag gtaattcatt     720
tccatgtgaa agatagacta atttttatatc ctttacctcc aaataattat ttacatctct     780
taaacaatct attttaatat cattaactgg tattttataa tatccagaaa ggtttgaagg     840
ggttgatgga ataagtctat taacatcgtt aagtaaatta ttaatatcat gaatctttat     900
tatattatac ccataagtta aatttatatt tactttctca tcatctgact tagttagttt     960
gtaataaggt gtgtctgaaa aaattaaaag gtaattcgtt gaatgaagct gtatttgctg    1020 tatcatttttt atctaatttt ggagatttag cagtacttac ttcattagaa gaagaatctg    1080
ccagttcctg tctattactg atatttcgtt tcattattat atgatttata ttttactttt    1140
tcaattatat atactcattt gactagttaa tcaataaaaa gaattcactg taaaaataga    1200
aactataatc atataatagt gtaggttggt agtagggtac tcgtgattaa tttttattgtt    1260 aaacttg atg gga gct ggg caa tcc agc cca gca acc ggc tcg cag aac    1309
        Met Gly Ala Gly Gln Ser Ser Pro Ala Thr Gly Ser Gln Asn
          1               5                  10 cag tct ggc aac act ggc agc ata atc aac aac tac tac atg caa cag    1357
Gln Ser Gly Asn Thr Gly Ser Ile Ile Asn Asn Tyr Tyr Met Gln Gln
 15                  20                  25                  30 tac cag aac tcc atg gac aca cag ttg gga gac aat gcc atc agt gga    1405
Tyr Gln Asn Ser Met Asp Thr Gln Leu Gly Asp Asn Ala Ile Ser Gly
                 35                  40                  45 ggc tcc aac gag ggc tcc acg gac aca act tca aca cac aca acc aac    1453
Gly Ser Asn Glu Gly Ser Thr Asp Thr Thr Ser Thr His Thr Thr Asn
     50                  55                  60 act caa aac aat gac tgg ttc tcg aag ctc gcc agt tca gct ttt acc    1501
Thr Gln Asn Asn Asp Trp Phe Ser Lys Leu Ala Ser Ser Ala Phe Thr
 65                  70                  75 ggt ctg ttc ggt gca ctg ctc gcc gac aag aag aca gag gaa acg aca    1549
Gly Leu Phe Gly Ala Leu Leu Ala Asp Lys Lys Thr Glu Glu Thr Thr
             80                  85                  90 ctt ctt gag gac cgc atc ctc acc acc cgc aac ggg cac acc acc tcg    1597
Leu Leu Glu Asp Arg Ile Leu Thr Thr Arg Asn Gly His Thr Thr Ser
 95                 100                 105                 110 acg acc caa tcg agt gtg ggt gtc aca cac ggg tac tcc aca gag gag    1645
Thr Thr Gln Ser Ser Val Gly Val Thr His Gly Tyr Ser Thr Glu Glu
                115                 120                 125 gac cac gtt gct ggg ccc aac aca tcg ggc ctg gag acg cga gtg gtg    1693
Asp His Val Ala Gly Pro Asn Thr Ser Gly Leu Glu Thr Arg Val Val
            130                 135                 140
```

```
cag gca gag aga ttc tac aaa aag tac ttg ttt gac tgg aca acg gac    1741
Gln Ala Glu Arg Phe Tyr Lys Lys Tyr Leu Phe Asp Trp Thr Thr Asp
            145                 150                 155 aag gca ttt gga cac ctg gaa aag ctg gag ctc ccg tcc gac cac cac    1789
Lys Ala Phe Gly His Leu Glu Lys Leu Glu Leu Pro Ser Asp His His
        160                 165                 170 ggt gtc ttt gga cac ttg gtg gac tcg tac gcc tat atg aga aat ggc    1837
Gly Val Phe Gly His Leu Val Asp Ser Tyr Ala Tyr Met Arg Asn Gly
175                 180                 185                 190 tgg gat gtt gag gtg tcc gct gtt ggc aac cag ttc aac ggc ggg tgc    1885
Trp Asp Val Glu Val Ser Ala Val Gly Asn Gln Phe Asn Gly Gly Cys
                195                 200                 205 ctc ctg gtg gcc atg gta cct gaa tgg aag gaa ttt gac aca cgg gag    1933
Leu Leu Val Ala Met Val Pro Glu Trp Lys Glu Phe Asp Thr Arg Glu
        210                 215                 220 aaa tac caa ctc acc ctt ttc ccg cac cag ttt att agc ccc aga act    1981
Lys Tyr Gln Leu Thr Leu Phe Pro His Gln Phe Ile Ser Pro Arg Thr
    225                 230                 235 aac atg act gcc cac atc acg gtc ccc tac ctt ggt gtg aac agg tat    2029
Asn Met Thr Ala His Ile Thr Val Pro Tyr Leu Gly Val Asn Arg Tyr
240                 245                 250 gat cag tac aag aag cat aag ccc tgg aca ttg gtt gtc atg gtc gtg    2077
Asp Gln Tyr Lys Lys His Lys Pro Trp Thr Leu Val Val Met Val Val
255                 260                 265                 270 tcg cca ctt acg gtc aac aac act agt gcg gca caa atc aag gtc tac    2125
Ser Pro Leu Thr Val Asn Asn Thr Ser Ala Ala Gln Ile Lys Val Tyr
                275                 280                 285 gcc aac ata gct ccg acc tat gtt cac gtg gcc ggt gaa ctc ccc tcg    2173
Ala Asn Ile Ala Pro Thr Tyr Val His Val Ala Gly Glu Leu Pro Ser
            290                 295                 300 aaa gag ggg att ttc ccg gtt gca tgt gcg gac ggt tac gga gga ttg    2221
Lys Glu Gly Ile Phe Pro Val Ala Cys Ala Asp Gly Tyr Gly Gly Leu
        305                 310                 315 gtg acg aca gac ccg aag aca gct gac cct gct tat ggc aag gtg tac    2269
Val Thr Thr Asp Pro Lys Thr Ala Asp Pro Ala Tyr Gly Lys Val Tyr
    320                 325                 330 aac ccg cct agg act aac tac cct ggg cgc ttc acc aac ctg ttg gac    2317
Asn Pro Pro Arg Thr Asn Tyr Pro Gly Arg Phe Thr Asn Leu Leu Asp
335                 340                 345                 350 gtg gcc gaa gcg tgt ccc act ttc ctc tgc ttt gac gac ggg aaa ccg    2365
Val Ala Glu Ala Cys Pro Thr Phe Leu Cys Phe Asp Asp Gly Lys Pro
                355                 360                 365 tac gtc acc acg cgg acg gat gac acc cga ctt ttg gcc aag ttt gac    2413
Tyr Val Thr Thr Arg Thr Asp Asp Thr Arg Leu Leu Ala Lys Phe Asp
            370                 375                 380 ctt tcc ctt gcc gca aaa cat atg tcc aac aca tac ctg tca ggg att    2461
Leu Ser Leu Ala Ala Lys His Met Ser Asn Thr Tyr Leu Ser Gly Ile
        385                 390                 395 gct cag tac tac aca cag tac tct ggc acc atc aat ttg cat ttc atg    2509
Ala Gln Tyr Tyr Thr Gln Tyr Ser Gly Thr Ile Asn Leu His Phe Met
    400                 405                 410 ttt aca ggt tcc act gat tca aag gcc cga tac atg gtg gcc tac atc    2557
Phe Thr Gly Ser Thr Asp Ser Lys Ala Arg Tyr Met Val Ala Tyr Ile
415                 420                 425                 430 cca cct ggg gtg gag aca cca ccg gac aca cct gaa agg gct gcc cac    2605
Pro Pro Gly Val Glu Thr Pro Pro Asp Thr Pro Glu Arg Ala Ala His
                435                 440                 445 tgc att cac gct gaa tgg gac act gga cta aac tcc aaa ttc act ttc    2653
Cys Ile His Ala Glu Trp Asp Thr Gly Leu Asn Ser Lys Phe Thr Phe
            450                 455                 460
```

-continued

```
tca atc ccg tac gta tcc gcc gcg gat tac gcg tac aca gcg tct gac       2701
Ser Ile Pro Tyr Val Ser Ala Ala Asp Tyr Ala Tyr Thr Ala Ser Asp
        465                 470                 475 acg gca gaa aca atc aac gta cag gga tgg gtc tgc atc tac caa att       2749
Thr Ala Glu Thr Ile Asn Val Gln Gly Trp Val Cys Ile Tyr Gln Ile
480                 485                 490 aca cac ggg aag gct gaa aat gac acc ttg gtc gtg tcg gtt agc gcc       2797
Thr His Gly Lys Ala Glu Asn Asp Thr Leu Val Val Ser Val Ser Ala
495                 500                 505                 510 ggc aaa gac ttt gag ttg cgc ctc ccg att gac ccc cgc cag cag acc       2845
Gly Lys Asp Phe Glu Leu Arg Leu Pro Ile Asp Pro Arg Gln Gln Thr
            515                 520                 525 acc gct acc ggg gaa tca gca gac ccg gtc acc acc gtg gag aac           2893
Thr Ala Thr Gly Glu Ser Ala Asp Pro Val Thr Thr Val Glu Asn
        530                 535                 540 tac ggc ggt gag aca caa atc cag aga cgt cac cac acg gac att ggt       2941
Tyr Gly Gly Glu Thr Gln Ile Gln Arg Arg His His Thr Asp Ile Gly
            545                 550                 555 ttc atc atg gac aga ttt gtg aag atc caa agc ttg agc cca aca cat       2989
Phe Ile Met Asp Arg Phe Val Lys Ile Gln Ser Leu Ser Pro Thr His
560                 565                 570 gtc att gac ctc atg cag gct cac caa cac ggt ctg gtg ggt gcc ttg       3037
Val Ile Asp Leu Met Gln Ala His Gln His Gly Leu Val Gly Ala Leu
575                 580                 585                 590 ctg cgt gca gcc acg tac tac ttt tct gac ctg gaa att gtt gta cgg       3085
Leu Arg Ala Ala Thr Tyr Tyr Phe Ser Asp Leu Glu Ile Val Val Arg
            595                 600                 605 cac gaa ggc aat ctg acc tgg gtg ccc aac ggc gcc cct gaa tca gcc       3133
His Glu Gly Asn Leu Thr Trp Val Pro Asn Gly Ala Pro Glu Ser Ala
        610                 615                 620 ctg ttg aac acc agc aac ccc act gcc tac aac aag gca cca ttc acg       3181
Leu Leu Asn Thr Ser Asn Pro Thr Ala Tyr Asn Lys Ala Pro Phe Thr
            625                 630                 635 aga ctc gct ctc ccc tac act gcg ccg cac cgt gtg ctg gca aca gtg       3229
Arg Leu Ala Leu Pro Tyr Thr Ala Pro His Arg Val Leu Ala Thr Val
640                 645                 650 tac aac ggg acg agt aag tat gct gtg ggt ggt tca ggc aga aga ggc       3277
Tyr Asn Gly Thr Ser Lys Tyr Ala Val Gly Gly Ser Gly Arg Arg Gly
655                 660                 665                 670 gac atg ggg tct ctc gcg gcg cga gtc gtg aaa cag ctt cct gct tca       3325
Asp Met Gly Ser Leu Ala Ala Arg Val Val Lys Gln Leu Pro Ala Ser
            675                 680                 685 ttt aac tac ggt gca atc aag gcc gac gcc atc cac gaa ctt ctc gtg       3373
Phe Asn Tyr Gly Ala Ile Lys Ala Asp Ala Ile His Glu Leu Leu Val
            690                 695                 700 cgc atg aaa cgg gcc gag ctc tac tgc ccc aga ccg ctg ttg gca ata       3421
Arg Met Lys Arg Ala Glu Leu Tyr Cys Pro Arg Pro Leu Leu Ala Ile
705                 710                 715 gag gtg tct tcg caa gac agg cac aag caa aag atc att gca cca gca       3469
Glu Val Ser Ser Gln Asp Arg His Lys Gln Lys Ile Ile Ala Pro Ala
720                 725                 730 aag cag ctt ctg aat ttt gac ctg ctc aag ttg gcc gga gac gtt gag       3517
Lys Gln Leu Leu Asn Phe Asp Leu Leu Lys Leu Ala Gly Asp Val Glu
735                 740                 745                 750 tcc aac ccc ggg cca ttc ttc ttt gct gac gtt agg tca aac ttt tca       3565
Ser Asn Pro Gly Pro Phe Phe Phe Ala Asp Val Arg Ser Asn Phe Ser
            755                 760                 765 aag ttg gta gac aca atc aac cag atg cag gag gac atg tcc aca aaa       3613
Lys Leu Val Asp Thr Ile Asn Gln Met Gln Glu Asp Met Ser Thr Lys
```

-continued

```
              770                 775                 780
cac ggg ccc gac ttc aac cgg ttg gtg tcc gca ttt gag gaa ttg gcc     3661
His Gly Pro Asp Phe Asn Arg Leu Val Ser Ala Phe Glu Glu Leu Ala
            785                 790                 795 act gga gtt aaa gct atc agg acc ggt ctc gac gag gcc aaa ccc tgg     3709
Thr Gly Val Lys Ala Ile Arg Thr Gly Leu Asp Glu Ala Lys Pro Trp
    800                 805                 810 tac aag ctt atc aaa ctc cta agc cgc ctg tcg tgc atg gcc gct gtg     3757
Tyr Lys Leu Ile Lys Leu Leu Ser Arg Leu Ser Cys Met Ala Ala Val
815                 820                 825                 830 gca gca cgg tcc aag gac cca gtc ctt gtg gcc atc atg ctg gcc gac     3805
Ala Ala Arg Ser Lys Asp Pro Val Leu Val Ala Ile Met Leu Ala Asp
                835                 840                 845 acc ggt ctc gag cgt cag aga cct ctg aaa gtg aga gct aag ctc cca     3853
Thr Gly Leu Glu Arg Gln Arg Pro Leu Lys Val Arg Ala Lys Leu Pro
            850                 855                 860 cag cag gaa gga cct tac gct ggc ccg ttg gag aga cag aaa ccg ctg     3901
Gln Gln Glu Gly Pro Tyr Ala Gly Pro Leu Glu Arg Gln Lys Pro Leu
        865                 870                 875 aaa gtg aaa gca aaa gcc ccg gtc gtc aag gaa gga cct tac gag gga     3949
Lys Val Lys Ala Lys Ala Pro Val Val Lys Glu Gly Pro Tyr Glu Gly
    880                 885                 890 ccg gtg aag aag cct gtc gct ttg aaa gtg aaa gct aag aac ttg ata     3997
Pro Val Lys Lys Pro Val Ala Leu Lys Val Lys Ala Lys Asn Leu Ile
895                 900                 905                 910 gtc act gag agt ggt gcc cca ccg acc gac ttg caa aag atg gtc atg     4045
Val Thr Glu Ser Gly Ala Pro Pro Thr Asp Leu Gln Lys Met Val Met
                915                 920                 925 ggc aac aca aag cct gtt gag ctc atc ctt gac ggg aag aca gta gcc     4093
Gly Asn Thr Lys Pro Val Glu Leu Ile Leu Asp Gly Lys Thr Val Ala
            930                 935                 940 atc tgt tgt gct act gga gtg ttt ggc act gct tac ctc gtg cct cgt     4141
Ile Cys Cys Ala Thr Gly Val Phe Gly Thr Ala Tyr Leu Val Pro Arg
        945                 950                 955 cat ctt ttc gca gag aag tat gac aag atc atg ctg gat ggc aga gcc     4189
His Leu Phe Ala Glu Lys Tyr Asp Lys Ile Met Leu Asp Gly Arg Ala
    960                 965                 970 atg aca gac agt gac tac aga gtg ttt gag ttt gag att aaa gta aaa     4237
Met Thr Asp Ser Asp Tyr Arg Val Phe Glu Phe Glu Ile Lys Val Lys
975                 980                 985                 990 gga cag gac atg ctc tca gac gct gcg ctc atg gtg ctc cac cgt ggg     4285
Gly Gln Asp Met Leu Ser Asp Ala Ala Leu Met Val Leu His Arg Gly
                995                 1000                1005 aac cgc gtg aga gat atc acg aaa cac ttt cgt gat aca gca aga atg     4333
Asn Arg Val Arg Asp Ile Thr Lys His Phe Arg Asp Thr Ala Arg Met
            1010                1015                1020 aag aaa ggc acc ccc gtc gtc ggt gtg gtc aac aac gcc gac gtt ggg     4381
Lys Lys Gly Thr Pro Val Val Gly Val Val Asn Asn Ala Asp Val Gly
        1025                1030                1035 aga ctg att ttc tct ggt gag gcc ctc acc tac aag gat att gta gtg     4429
Arg Leu Ile Phe Ser Gly Glu Ala Leu Thr Tyr Lys Asp Ile Val Val
    1040                1045                1050 tgc atg gac gga gac acc atg cct ggc ctc ttt gcc tac aaa gcc gcc     4477
Cys Met Asp Gly Asp Thr Met Pro Gly Leu Phe Ala Tyr Lys Ala Ala
1055                1060                1065                1070 acc aag gca ggc tac tgt gga gga gcc gtt ctc gcc aag gac ggg gcc     4525
Thr Lys Ala Gly Tyr Cys Gly Gly Ala Val Leu Ala Lys Asp Gly Ala
                1075                1080                1085 gac act ttc atc gtc ggc act cac tcc gca gga ggc aat gga gtt gga     4573
Asp Thr Phe Ile Val Gly Thr His Ser Ala Gly Gly Asn Gly Val Gly
```

-continued

```
Asp Thr Phe Ile Val Gly Thr His Ser Ala Gly Gly Asn Gly Val Gly
        1090                1095                1100 tac tgc tca tgc gtt tcc agg tcc atg ctt ctc aga atg aag gca cac      4621
Tyr Cys Ser Cys Val Ser Arg Ser Met Leu Leu Arg Met Lys Ala His
        1105                1110                1115 gtt gac cct gaa cca caa cac gag tagtaatttt tctgcagccc gggtttttat     4675
Val Asp Pro Glu Pro Gln His Glu
    1120                1125 agctaattag tcattttttc gtaagtaagt attttattt aatactttt attgtactta      4735 tgttaaatat aactgatgat aacaaaatcc attatgtatt atttataact gtaatttctt    4795
tagcgtagtt agatgtccaa tctctctcaa atacatcggc tatcttttta gtgagatttt    4855
gatctatgca gttgaaactt atgaacgcgt gatgattaaa atgtgaaccg tccaaatttg    4915
cagtcattat atgagcgtat ctattatcta ctatcatcat ctttgagtta ttaatatcat    4975
ctactttaga attgatagga aatatgaata cctttgtagt aatatctata ctatctacac    5035
ctaactcatt aagactttg atag                                            5059
```

<210> SEQ ID NO 82
<211> LENGTH: 1126
<212> TYPE: PRT
<213> ORGANISM: Foot-and-mouth disease virus

<400> SEQUENCE: 82

```
Met Gly Ala Gly Gln Ser Ser Pro Ala Thr Gly Ser Gln Asn Gln Ser
 1               5                   10                  15

Gly Asn Thr Gly Ser Ile Ile Asn Asn Tyr Tyr Met Gln Gln Tyr Gln
            20                  25                  30

Asn Ser Met Asp Thr Gln Leu Gly Asp Asn Ala Ile Ser Gly Gly Ser
        35                  40                  45

Asn Glu Gly Ser Thr Asp Thr Thr Ser Thr His Thr Thr Asn Thr Gln
    50                  55                  60

Asn Asn Asp Trp Phe Ser Lys Leu Ala Ser Ser Ala Phe Thr Gly Leu
65                  70                  75                  80

Phe Gly Ala Leu Leu Ala Asp Lys Lys Thr Glu Glu Thr Thr Leu Leu
                85                  90                  95

Glu Asp Arg Ile Leu Thr Thr Arg Asn Gly His Thr Thr Ser Thr Thr
            100                 105                 110

Gln Ser Ser Val Gly Val Thr His Gly Tyr Ser Thr Glu Glu Asp His
        115                 120                 125

Val Ala Gly Pro Asn Thr Ser Gly Leu Glu Thr Arg Val Val Gln Ala
    130                 135                 140

Glu Arg Phe Tyr Lys Lys Tyr Leu Phe Asp Trp Thr Thr Asp Lys Ala
145                 150                 155                 160

Phe Gly His Leu Glu Lys Leu Glu Leu Pro Ser Asp His His Gly Val
                165                 170                 175

Phe Gly His Leu Val Asp Ser Tyr Ala Tyr Met Arg Asn Gly Trp Asp
            180                 185                 190

Val Glu Val Ser Ala Val Gly Asn Gln Phe Asn Gly Gly Cys Leu Leu
        195                 200                 205

Val Ala Met Val Pro Glu Trp Lys Glu Phe Asp Thr Arg Glu Lys Tyr
    210                 215                 220

Gln Leu Thr Leu Phe Pro His Gln Phe Ile Ser Pro Arg Thr Asn Met
225                 230                 235                 240

Thr Ala His Ile Thr Val Pro Tyr Leu Gly Val Asn Arg Tyr Asp Gln
```

-continued

```
                245                 250                 255
Tyr Lys Lys His Lys Pro Trp Thr Leu Val Val Met Val Val Ser Pro
            260                 265                 270

Leu Thr Val Asn Asn Thr Ser Ala Ala Gln Ile Lys Val Tyr Ala Asn
        275                 280                 285

Ile Ala Pro Thr Tyr Val His Val Ala Gly Glu Leu Pro Ser Lys Glu
    290                 295                 300

Gly Ile Phe Pro Val Ala Cys Ala Asp Gly Tyr Gly Gly Leu Val Thr
305                 310                 315                 320

Thr Asp Pro Lys Thr Ala Asp Pro Ala Tyr Gly Lys Val Tyr Asn Pro
                325                 330                 335

Pro Arg Thr Asn Tyr Pro Gly Arg Phe Thr Asn Leu Leu Asp Val Ala
            340                 345                 350

Glu Ala Cys Pro Thr Phe Leu Cys Phe Asp Asp Gly Lys Pro Tyr Val
        355                 360                 365

Thr Thr Arg Thr Asp Asp Thr Arg Leu Leu Ala Lys Phe Asp Leu Ser
    370                 375                 380

Leu Ala Ala Lys His Met Ser Asn Thr Tyr Leu Ser Gly Ile Ala Gln
385                 390                 395                 400

Tyr Tyr Thr Gln Tyr Ser Gly Thr Ile Asn Leu His Phe Met Phe Thr
                405                 410                 415

Gly Ser Thr Asp Ser Lys Ala Arg Tyr Met Val Ala Tyr Ile Pro Pro
            420                 425                 430

Gly Val Glu Thr Pro Pro Asp Thr Pro Glu Arg Ala Ala His Cys Ile
        435                 440                 445

His Ala Glu Trp Asp Thr Gly Leu Asn Ser Lys Phe Thr Phe Ser Ile
    450                 455                 460

Pro Tyr Val Ser Ala Ala Asp Tyr Ala Tyr Thr Ala Ser Asp Thr Ala
465                 470                 475                 480

Glu Thr Ile Asn Val Gln Gly Trp Val Cys Ile Tyr Gln Ile Thr His
                485                 490                 495

Gly Lys Ala Glu Asn Asp Thr Leu Val Val Ser Val Ser Ala Gly Lys
            500                 505                 510

Asp Phe Glu Leu Arg Leu Pro Ile Asp Pro Arg Gln Gln Thr Thr Ala
        515                 520                 525

Thr Gly Glu Ser Ala Asp Pro Val Thr Thr Val Glu Asn Tyr Gly
    530                 535                 540

Gly Glu Thr Gln Ile Gln Arg Arg His His Thr Asp Ile Gly Phe Ile
545                 550                 555                 560

Met Asp Arg Phe Val Lys Ile Gln Ser Leu Ser Pro Thr His Val Ile
                565                 570                 575

Asp Leu Met Gln Ala His Gln His Gly Leu Val Gly Ala Leu Leu Arg
            580                 585                 590

Ala Ala Thr Tyr Tyr Phe Ser Asp Leu Glu Ile Val Val Arg His Glu
        595                 600                 605

Gly Asn Leu Thr Trp Val Pro Asn Gly Ala Pro Glu Ser Ala Leu Leu
    610                 615                 620

Asn Thr Ser Asn Pro Thr Ala Tyr Asn Lys Ala Pro Phe Thr Arg Leu
625                 630                 635                 640

Ala Leu Pro Tyr Thr Ala Pro His Arg Val Leu Ala Thr Val Tyr Asn
                645                 650                 655

Gly Thr Ser Lys Tyr Ala Val Gly Gly Ser Gly Arg Arg Gly Asp Met
            660                 665                 670
```

```
Gly Ser Leu Ala Ala Arg Val Val Lys Gln Leu Pro Ala Ser Phe Asn
            675                 680                 685

Tyr Gly Ala Ile Lys Ala Asp Ala Ile His Glu Leu Leu Val Arg Met
        690                 695                 700

Lys Arg Ala Glu Leu Tyr Cys Pro Arg Pro Leu Leu Ala Ile Glu Val
705                 710                 715                 720

Ser Ser Gln Asp Arg His Lys Gln Lys Ile Ile Ala Pro Ala Lys Gln
                725                 730                 735

Leu Leu Asn Phe Asp Leu Leu Lys Leu Ala Gly Asp Val Glu Ser Asn
            740                 745                 750

Pro Gly Pro Phe Phe Ala Asp Val Arg Ser Asn Phe Ser Lys Leu
        755                 760                 765

Val Asp Thr Ile Asn Gln Met Gln Glu Asp Met Ser Thr Lys His Gly
        770                 775                 780

Pro Asp Phe Asn Arg Leu Val Ser Ala Phe Glu Glu Leu Ala Thr Gly
785                 790                 795                 800

Val Lys Ala Ile Arg Thr Gly Leu Asp Glu Ala Lys Pro Trp Tyr Lys
            805                 810                 815

Leu Ile Lys Leu Leu Ser Arg Leu Ser Cys Met Ala Ala Val Ala Ala
            820                 825                 830

Arg Ser Lys Asp Pro Val Leu Val Ala Ile Met Leu Ala Asp Thr Gly
            835                 840                 845

Leu Glu Arg Gln Arg Pro Leu Lys Val Arg Ala Lys Leu Pro Gln Gln
        850                 855                 860

Glu Gly Pro Tyr Ala Gly Pro Leu Glu Arg Gln Lys Pro Leu Lys Val
865                 870                 875                 880

Lys Ala Lys Ala Pro Val Val Lys Glu Gly Pro Tyr Glu Gly Pro Val
                885                 890                 895

Lys Lys Pro Val Ala Leu Lys Val Lys Ala Lys Asn Leu Ile Val Thr
            900                 905                 910

Glu Ser Gly Ala Pro Pro Thr Asp Leu Gln Lys Met Val Met Gly Asn
            915                 920                 925

Thr Lys Pro Val Glu Leu Ile Leu Asp Gly Lys Thr Val Ala Ile Cys
        930                 935                 940

Cys Ala Thr Gly Val Phe Gly Thr Ala Tyr Leu Val Pro Arg His Leu
945                 950                 955                 960

Phe Ala Glu Lys Tyr Asp Lys Ile Met Leu Asp Gly Arg Ala Met Thr
                965                 970                 975

Asp Ser Asp Tyr Arg Val Phe Glu Phe Glu Ile Lys Val Lys Gly Gln
                980                 985                 990

Asp Met Leu Ser Asp Ala Ala Leu Met Val Leu His Arg Gly Asn Arg
            995                 1000                1005

Val Arg Asp Ile Thr Lys His Phe Arg Asp Thr Ala Arg Met Lys Lys
            1010                1015                1020

Gly Thr Pro Val Val Gly Val Val Asn Asn Ala Asp Val Gly Arg Leu
1025                1030                1035                1040

Ile Phe Ser Gly Glu Ala Leu Thr Tyr Lys Asp Ile Val Val Cys Met
            1045                1050                1055

Asp Gly Asp Thr Met Pro Gly Leu Phe Ala Tyr Lys Ala Ala Thr Lys
            1060                1065                1070

Ala Gly Tyr Cys Gly Gly Ala Val Leu Ala Lys Asp Gly Ala Asp Thr
            1075                1080                1085
```

```
Phe Ile Val Gly Thr His Ser Ala Gly Gly Asn Gly Val Gly Tyr Cys
    1090                1095                1100

Ser Cys Val Ser Arg Ser Met Leu Leu Arg Met Lys Ala His Val Asp
1105                1110                1115                1120

Pro Glu Pro Gln His Glu
            1125

<210> SEQ ID NO 83
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
aagcttttct ttattctata cttaaaaag                                    29

<210> SEQ ID NO 84
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ggtggccatg gtacctgaat ggaag                                        25

<210> SEQ ID NO 85
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
cttccattca ggtaccatgg ccacc                                        25

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Val Ala Met Val Pro Glu Trp Lys
  1               5

<210> SEQ ID NO 87
<211> LENGTH: 6315
<212> TYPE: DNA
<213> ORGANISM: Foot-and-mouth disease virus
<220> FEATURE:
<221> NAME/KEY: CDS
<222> LOCATION: (1513)..(4890)

<400> SEQUENCE: 87 gacccttta c aagaataaaa gaagaaacaa ctgtgaaata gtttataaat gtaattcgta    60
tgcagaaaac gataatatat tttggtatga gaaatctaaa ggagacatag tttgtataga   120
catgcgctct tccgatgaga tattcgatgc ttttctaatg tatcatatag ctacaagata   180
```

```
tgcctatcat gatgatgata tatatctaca aatagtgtta tattattcta ataatcaaaa      240
tgttatatct tatattacga aaataaaata cgttaagtat ataagaaata aaactagaga      300
cgatattcat aaagtaaaaa tattagctct agaagacttt acaacggaag aaatatattg      360
ttggattagt aatatataac agcgtagctg cacggttttg atcattttcc aacaatataa      420
accaatgaag gaggacgact catcaaacat aaataacatt cacgaaaaat attcagtatc      480
agatttatca caagatgatt atgttattga atgtatagac ggatcttttg attcgatcaa      540
gtatagagat ataaaggtta taataatgaa gaataacggt tacgttaatt gtagtaaatt      600
atgtaaaatg cggaataaat acttttctag atggttgcgt ctttctactt ctaaagcatt      660
attagacatt tacaataata agtcagtaga taatgctatt gttaaagtct atggtaaagg      720
taagaaactt attataacag gatttttatct caaacaaaat atgatacgtt atgttattga      780
gtggataggg gatgatttta caaacgatat atacaaaatg attaatttct ataatgcgtt      840
attcggtaac gatgaattaa aaatagtatc ctgtgaaaac actctatgcc cgtttataga      900
acttggtaga tgctattatg gtaaaaaatg taagtatata cacggagatc aatgtgatat      960
ctgtggtcta tatatactac accctaccga tattaaccaa cgagtttctc acaagaaaac     1020
ttgtttagta gatagagatt ctttgattgt gtttaaaaga agtaccagta aaaagtgtgg     1080
catatgcata aagaaataa acaaaaaaca tatttccgaa cagtattttg gaattctccc     1140
aagttgtaaa catatttttt gcctatcatg tataagacgt tgggcagata ctaccagaaa     1200
tacagatact gaaaatacgt gtcctgaatg tagaatagtt tttccttttca taataccagc     1260 taggtattgg atagataata aatatgataa aaaaatatta tataatagat ataagaaaat     1320
gattttacca aaaaatacct a taagaacaat aaaaatataa ttacatttac ggaaaaatagc     1380 tggttttagt ttaccaactt agagtaatta tcatattgaa tctatattgc taattagcta     1440 ataaaaccc gggtcgcgaa agcttttctt tattctatac ttaaaaagtg caaataaata     1500
caaaggttct tg atg gga gct ggg caa tcc agc cca gca acc ggc tcg cag    1551
              Met Gly Ala Gly Gln Ser Ser Pro Ala Thr Gly Ser Gln
                1               5                  10 aac cag tct ggc aac act ggc agc ata atc aac aac tac tac atg caa       1599
Asn Gln Ser Gly Asn Thr Gly Ser Ile Ile Asn Asn Tyr Tyr Met Gln
 15                 20                  25 cag tac cag aac tcc atg gac aca cag ttg gga gac aat gcc atc agt       1647
Gln Tyr Gln Asn Ser Met Asp Thr Gln Leu Gly Asp Asn Ala Ile Ser
30                  35                  40                  45 gga ggc tcc aac gag ggc tcc acg gac aca act tca aca cac aca acc       1695
Gly Gly Ser Asn Glu Gly Ser Thr Asp Thr Thr Ser Thr His Thr Thr
                50                  55                  60 aac act caa aac aat gac tgg ttc tcg aag ctc gcc agt tca gct ttt       1743
Asn Thr Gln Asn Asn Asp Trp Phe Ser Lys Leu Ala Ser Ser Ala Phe
         65                  70                  75 acc ggt ctg ttc ggt gca ctg ctc gcc gac aag aag aca gag gaa acg       1791
Thr Gly Leu Phe Gly Ala Leu Leu Ala Asp Lys Lys Thr Glu Glu Thr
     80                  85                  90 aca ctt ctt gag gac cgc atc ctc acc acc cgc aac ggg cac acc acc       1839
Thr Leu Leu Glu Asp Arg Ile Leu Thr Thr Arg Asn Gly His Thr Thr
 95                 100                 105 tcg acg acc caa tcg agt gtg ggt gtc aca cac ggg tac tcc aca gag       1887
Ser Thr Thr Gln Ser Ser Val Gly Val Thr His Gly Tyr Ser Thr Glu
110                 115                 120                 125 gag gac cac gtt gct ggg ccc aac aca tcg ggc ctg gag acg cga gtg       1935
Glu Asp His Val Ala Gly Pro Asn Thr Ser Gly Leu Glu Thr Arg Val
                130                 135                 140
```

```
gtg cag gca gag aga ttc tac aaa aag tac ttg ttt gac tgg aca acg    1983
Val Gln Ala Glu Arg Phe Tyr Lys Lys Tyr Leu Phe Asp Trp Thr Thr
            145                 150                 155 gac aag gca ttt gga cac ctg gaa aag ctg gag ctc ccg tcc gac cac    2031
Asp Lys Ala Phe Gly His Leu Glu Lys Leu Glu Leu Pro Ser Asp His
        160                 165                 170 cac ggt gtc ttt gga cac ttg gtg gac tcg tac gcc tat atg aga aat    2079
His Gly Val Phe Gly His Leu Val Asp Ser Tyr Ala Tyr Met Arg Asn
    175                 180                 185 ggc tgg gat gtt gag gtg tcc gct gtt ggc aac cag ttc aac ggc ggg    2127
Gly Trp Asp Val Glu Val Ser Ala Val Gly Asn Gln Phe Asn Gly Gly
190                 195                 200                 205 tgc ctc ctg gtg gcc atg gta cct gaa tgg aag gaa ttt gac aca cgg    2175
Cys Leu Leu Val Ala Met Val Pro Glu Trp Lys Glu Phe Asp Thr Arg
                210                 215                 220 gag aaa tac caa ctc acc ctt ttc ccg cac cag ttt att agc ccc aga    2223
Glu Lys Tyr Gln Leu Thr Leu Phe Pro His Gln Phe Ile Ser Pro Arg
            225                 230                 235 act aac atg act gcc cac atc acg gtc ccc tac ctt ggt gtg aac agg    2271
Thr Asn Met Thr Ala His Ile Thr Val Pro Tyr Leu Gly Val Asn Arg
        240                 245                 250 tat gat cag tac aag aag cat aag ccc tgg aca ttg gtt gtc atg gtc    2319
Tyr Asp Gln Tyr Lys Lys His Lys Pro Trp Thr Leu Val Val Met Val
    255                 260                 265 gtg tcg cca ctt acg gtc aac aac act agt gcg gca caa atc aag gtc    2367
Val Ser Pro Leu Thr Val Asn Asn Thr Ser Ala Ala Gln Ile Lys Val
270                 275                 280                 285 tac gcc aac ata gct ccg acc tat gtt cac gtg gcc ggt gaa ctc ccc    2415
Tyr Ala Asn Ile Ala Pro Thr Tyr Val His Val Ala Gly Glu Leu Pro
                290                 295                 300 tcg aaa gag ggg att ttc ccg gtt gca tgt gcg gac ggt tac gga gga    2463
Ser Lys Glu Gly Ile Phe Pro Val Ala Cys Ala Asp Gly Tyr Gly Gly
            305                 310                 315 ttg gtg acg aca gac ccg aag aca gct gac cct gct tat ggc aag gtg    2511
Leu Val Thr Thr Asp Pro Lys Thr Ala Asp Pro Ala Tyr Gly Lys Val
        320                 325                 330 tac aac ccg cct agg act aac tac cct ggg cgc ttc acc aac ctg ttg    2559
Tyr Asn Pro Pro Arg Thr Asn Tyr Pro Gly Arg Phe Thr Asn Leu Leu
    335                 340                 345 gac gtg gcc gaa gcg tgt ccc act ttc ctc tgc ttt gac gac ggg aaa    2607
Asp Val Ala Glu Ala Cys Pro Thr Phe Leu Cys Phe Asp Asp Gly Lys
350                 355                 360                 365 ccg tac gtc acc acg cgg acg gat gac acc cga ctt ttg gcc aag ttt    2655
Pro Tyr Val Thr Thr Arg Thr Asp Asp Thr Arg Leu Leu Ala Lys Phe
                370                 375                 380 gac ctt tcc ctt gcc gca aaa cat atg tcc aac aca tac ctg tca ggg    2703
Asp Leu Ser Leu Ala Ala Lys His Met Ser Asn Thr Tyr Leu Ser Gly
            385                 390                 395 att gct cag tac tac aca cag tac tct ggc acc atc aat ttg cat ttc    2751
Ile Ala Gln Tyr Tyr Thr Gln Tyr Ser Gly Thr Ile Asn Leu His Phe
        400                 405                 410 atg ttt aca ggt tcc act gat tca aag gcc cga tac atg gtg gcc tac    2799
Met Phe Thr Gly Ser Thr Asp Ser Lys Ala Arg Tyr Met Val Ala Tyr
    415                 420                 425 atc cca cct ggg gtg gag aca cca ccg gac aca cct gaa agg gct gcc    2847
Ile Pro Pro Gly Val Glu Thr Pro Pro Asp Thr Pro Glu Arg Ala Ala
430                 435                 440                 445 cac tgc att cac gct gaa tgg gac act gga cta aac tcc aaa ttc act    2895
His Cys Ile His Ala Glu Trp Asp Thr Gly Leu Asn Ser Lys Phe Thr
```

-continued

```
                    450                 455                 460
ttc tca atc ccg tac gta tcc gcc gcg gat tac gcg tac aca gcg tct    2943
Phe Ser Ile Pro Tyr Val Ser Ala Ala Asp Tyr Ala Tyr Thr Ala Ser
            465                 470                 475 gac acg gca gaa aca atc aac gta cag gga tgg gtc tgc atc tac caa    2991
Asp Thr Ala Glu Thr Ile Asn Val Gln Gly Trp Val Cys Ile Tyr Gln
        480                 485                 490 att aca cac ggg aag gct gaa aat gac acc ttg gtc gtg tcg gtt agc    3039
Ile Thr His Gly Lys Ala Glu Asn Asp Thr Leu Val Val Ser Val Ser
    495                 500                 505 gcc ggc aaa gac ttt gag ttg cgc ctc ccg att gac ccc cgc cag cag    3087
Ala Gly Lys Asp Phe Glu Leu Arg Leu Pro Ile Asp Pro Arg Gln Gln
510                 515                 520                 525 acc acc gct acc ggg gaa tca gca gac ccg gtc acc acc gtg gag        3135
Thr Thr Ala Thr Gly Glu Ser Ala Asp Pro Val Thr Thr Val Glu
                530                 535                 540 aac tac ggc ggt gag aca caa atc cag aga cgt cac cac acg gac att    3183
Asn Tyr Gly Gly Glu Thr Gln Ile Gln Arg Arg His His Thr Asp Ile
            545                 550                 555 ggt ttc atc atg gac aga ttt gtg aag atc caa agc ttg agc cca aca    3231
Gly Phe Ile Met Asp Arg Phe Val Lys Ile Gln Ser Leu Ser Pro Thr
        560                 565                 570 cat gtc att gac ctc atg cag gct cac caa cac ggt ctg gtg ggt gcc    3279
His Val Ile Asp Leu Met Gln Ala His Gln His Gly Leu Val Gly Ala
    575                 580                 585 ttg ctg cgt gca gcc acg tac tac ttt tct gac ctg gaa att gtt gta    3327
Leu Leu Arg Ala Ala Thr Tyr Tyr Phe Ser Asp Leu Glu Ile Val Val
590                 595                 600                 605 cgg cac gaa ggc aat ctg acc tgg gtg ccc aac ggc gcc cct gaa tca    3375
Arg His Glu Gly Asn Leu Thr Trp Val Pro Asn Gly Ala Pro Glu Ser
                610                 615                 620 gcc ctg ttg aac acc agc aac ccc act gcc tac aac aag gca cca ttc    3423
Ala Leu Leu Asn Thr Ser Asn Pro Thr Ala Tyr Asn Lys Ala Pro Phe
            625                 630                 635 acg aga ctc gct ctc ccc tac act gcg ccg cac cgt gtg ctg gca aca    3471
Thr Arg Leu Ala Leu Pro Tyr Thr Ala Pro His Arg Val Leu Ala Thr
        640                 645                 650 gtg tac aac ggg acg agt aag tat gct gtg ggt ggt tca ggc aga aga    3519
Val Tyr Asn Gly Thr Ser Lys Tyr Ala Val Gly Gly Ser Gly Arg Arg
    655                 660                 665 ggc gac atg ggg tct ctc gcg gcg cga gtc gtg aaa cag ctt cct gct    3567
Gly Asp Met Gly Ser Leu Ala Ala Arg Val Val Lys Gln Leu Pro Ala
670                 675                 680                 685 tca ttt aac tac ggt gca atc aag gcc gac gcc atc cac gaa ctt ctc    3615
Ser Phe Asn Tyr Gly Ala Ile Lys Ala Asp Ala Ile His Glu Leu Leu
                690                 695                 700 gtg cgc atg aaa cgg gcc gag ctc tac tgc ccc aga ccg ctg ttg gca    3663
Val Arg Met Lys Arg Ala Glu Leu Tyr Cys Pro Arg Pro Leu Leu Ala
            705                 710                 715 ata gag gtg tct tcg caa gac agg cac aag caa aag atc att gca cca    3711
Ile Glu Val Ser Ser Gln Asp Arg His Lys Gln Lys Ile Ile Ala Pro
        720                 725                 730 gca aag cag ctt ctg aat ttt gac ctg ctc aag ttg gcc gga gac gtt    3759
Ala Lys Gln Leu Leu Asn Phe Asp Leu Leu Lys Leu Ala Gly Asp Val
    735                 740                 745 gag tcc aac ccc ggg cca ttc ttc ttt gct gac gtt agg tca aac ttt    3807
Glu Ser Asn Pro Gly Pro Phe Phe Phe Ala Asp Val Arg Ser Asn Phe
750                 755                 760                 765 tca aag ttg gta gac aca atc aac cag atg cag gag gac atg tcc aca    3855
```

| | | | | | | | | | | | | | |
|---|---|---|---|---|---|---|---|---|---|---|---|---|---|
|Ser|Lys|Leu|Val|Asp|Thr|Ile|Asn|Gln|Met|Gln|Glu|Asp|Met|Ser|Thr|
| | | |770| | | |775| | | |780| | | |

```
aaa cac ggg ccc gac ttc aac cgg ttg gtg tcc gca ttt gag gaa ttg    3903
Lys His Gly Pro Asp Phe Asn Arg Leu Val Ser Ala Phe Glu Glu Leu
            785                 790                 795 gcc act gga gtt aaa gct atc agg acc ggt ctc gac gag gcc aaa ccc    3951
Ala Thr Gly Val Lys Ala Ile Arg Thr Gly Leu Asp Glu Ala Lys Pro
        800                 805                 810 tgg tac aag ctt atc aaa ctc cta agc cgc ctg tcg tgc atg gcc gct    3999
Trp Tyr Lys Leu Ile Lys Leu Leu Ser Arg Leu Ser Cys Met Ala Ala
    815                 820                 825 gtg gca gca cgg tcc aag gac cca gtc ctt gtg gcc atc atg ctg gcc    4047
Val Ala Ala Arg Ser Lys Asp Pro Val Leu Val Ala Ile Met Leu Ala
830                 835                 840                 845 gac acc ggt ctc gag cgt cag aga cct ctg aaa gtg aga gct aag ctc    4095
Asp Thr Gly Leu Glu Arg Gln Arg Pro Leu Lys Val Arg Ala Lys Leu
                850                 855                 860 cca cag cag gaa gga cct tac gct ggc ccg ttg gag aga cag aaa ccg    4143
Pro Gln Gln Glu Gly Pro Tyr Ala Gly Pro Leu Glu Arg Gln Lys Pro
            865                 870                 875 ctg aaa gtg aaa gca aaa gcc ccg gtc gtc aag gaa gga cct tac gag    4191
Leu Lys Val Lys Ala Lys Ala Pro Val Val Lys Glu Gly Pro Tyr Glu
        880                 885                 890 gga ccg gtg aag aag cct gtc gct ttg aaa gtg aaa gct aag aac ttg    4239
Gly Pro Val Lys Lys Pro Val Ala Leu Lys Val Lys Ala Lys Asn Leu
    895                 900                 905 ata gtc act gag agt ggt gcc cca ccg acc gac ttg caa aag atg gtc    4287
Ile Val Thr Glu Ser Gly Ala Pro Pro Thr Asp Leu Gln Lys Met Val
910                 915                 920                 925 atg ggc aac aca aag cct gtt gag ctc atc ctt gac ggg aag aca gta    4335
Met Gly Asn Thr Lys Pro Val Glu Leu Ile Leu Asp Gly Lys Thr Val
                930                 935                 940 gcc atc tgt tgt gct act gga gtg ttt ggc act gct tac ctc gtg cct    4383
Ala Ile Cys Cys Ala Thr Gly Val Phe Gly Thr Ala Tyr Leu Val Pro
            945                 950                 955 cgt cat ctt ttc gca gag aag tat gac aag atc atg ctg gat ggc aga    4431
Arg His Leu Phe Ala Glu Lys Tyr Asp Lys Ile Met Leu Asp Gly Arg
        960                 965                 970 gcc atg aca gac agt gac tac aga gtg ttt gag ttt gag att aaa gta    4479
Ala Met Thr Asp Ser Asp Tyr Arg Val Phe Glu Phe Glu Ile Lys Val
    975                 980                 985 aaa gga cag gac atg ctc tca gac gct gcg ctc atg gtg ctc cac cgt    4527
Lys Gly Gln Asp Met Leu Ser Asp Ala Ala Leu Met Val Leu His Arg
990                 995                 1000                1005 ggg aac cgc gtg aga gat atc acg aaa cac ttt cgt gat aca gca aga    4575
Gly Asn Arg Val Arg Asp Ile Thr Lys His Phe Arg Asp Thr Ala Arg
                1010                1015                1020 atg aag aaa ggc acc ccc gtc gtc ggt gtg gtc aac aac gcc gac gtt    4623
Met Lys Lys Gly Thr Pro Val Val Gly Val Val Asn Asn Ala Asp Val
            1025                1030                1035 ggg aga ctg att ttc tct ggt gag gcc ctc acc tac aag gat att gta    4671
Gly Arg Leu Ile Phe Ser Gly Glu Ala Leu Thr Tyr Lys Asp Ile Val
        1040                1045                1050 gtg tgc atg gac gga gac acc atg cct ggc ctc ttt gcc tac aaa gcc    4719
Val Cys Met Asp Gly Asp Thr Met Pro Gly Leu Phe Ala Tyr Lys Ala
    1055                1060                1065 gcc acc aag gca ggc tac tgt gga gga gcc gtt ctc gcc aag gac ggg    4767
Ala Thr Lys Ala Gly Tyr Cys Gly Gly Ala Val Leu Ala Lys Asp Gly
1070                1075                1080                1085
```

-continued

| | | |
|---|---|---|
| gcc gac act ttc atc gtc ggc act cac tcc gca gga ggc aat gga gtt<br>Ala Asp Thr Phe Ile Val Gly Thr His Ser Ala Gly Gly Asn Gly Val<br>                1090                          1095                      1100 | 4815 |
| gga tac tgc tca tgc gtt tcc agg tcc atg ctt ctc aga atg aag gca<br>Gly Tyr Cys Ser Cys Val Ser Arg Ser Met Leu Leu Arg Met Lys Ala<br>                1105                          1110                      1115 | 4863 |
| cac gtt gac cct gaa cca caa cac gag tagtaatttt tctagaggat<br>His Val Asp Pro Glu Pro Gln His Glu<br>                1120                          1125 | 4910 |
| ccctcgagtt tttattgact agttaatcat aagataaata atatacagca ttgtaaccat | 4970 |
| cgtcatccgt tatacgggga ataatattac catacagtat tattaaattt tcttacgaag | 5030 |
| aatatagatc ggtatttatc gttagtttat tttacattta ttaattaaac atgtctacta | 5090 |
| ttacctgtta tggaaatgac aaatttagtt atataattta tgataaaatt aagataataa | 5150 |
| taatgaaatc aaataattat gtaaatgcta ctagattatg tgaattacga ggaagaaagt | 5210 |
| ttacgaactg gaaaaaatta agtgaatcta aatatattagt cgataatgta aaaaaaataa | 5270 |
| atgataaaac taaccagtta aaaacggata tgattatata cgttaaggat attgatcata | 5330 |
| aaggaagaga tacttgcggt tactatgtac accaagatct ggtatcttct atatcaaatt | 5390 |
| ggatatctcc gttattcgcc gttaaggtaa ataaaattat taactattat atatgtaatg | 5450 |
| aatatgatat acgacttagc gaaatggaat ctgatatgac agaagtaata gatgtagttg | 5510 |
| ataaattagt aggaggatac aatgatgaaa tagcagaaat aatatatttg tttaataaat | 5570 |
| ttatagaaaa atatattgct aacatatcgt tatcaactga attatctagt atattaaata | 5630 |
| atttttataaa ttttaataaa aaatacaata acgacataaa agatattaaa tctttaattc | 5690 |
| ttgatctgaa aaacacatct ataaaactag ataaaaagtt attcgataaa gataataatg | 5750 |
| aatcgaacga tgaaaaattg gaaacagaag ttgataagct aattttttc atctaaatag | 5810 |
| tattatttta ttgaagtacg aagttttacg ttagataaat aataaaggtc gattttatt | 5870 |
| ttgttaaata tcaaatatgt cattatctga taaagataca aaaacacacg gtgattatca | 5930 |
| accatctaac gaacagatat tacaaaaaat acgtcggact atggaaaacg aagctgatag | 5990 |
| cctcaataga agaagcatta aagaaattgt tgtagatgtt atgaagaatt gggatcatcc | 6050 |
| tctcaacgaa gaaatagata aagttctaaa ctggaaaaat gatacattaa acgatttaga | 6110 |
| tcatctaaat acagatgata atattaagga aatcatacaa tgtctgatta gagaatttgc | 6170 |
| gtttaaaaag atcaattcta ttatgtatag ttatgctatg gtaaaactca attcagataa | 6230 |
| cgaaacattg aaagataaaa ttaaggatta ttttatagaa actattctta aagacaaacg | 6290 |
| tggttataaa caaaagccat taccc | 6315 |

<210> SEQ ID NO 88
<211> LENGTH: 1126
<212> TYPE: PRT
<213> ORGANISM: Foot-and-mouth disease virus

<400> SEQUENCE: 88

Met Gly Ala Gly Gln Ser Ser Pro Ala Thr Gly Ser Gln Asn Gln Ser
 1               5                  10                  15

Gly Asn Thr Gly Ser Ile Ile Asn Asn Tyr Tyr Met Gln Gln Tyr Gln
            20                  25                  30

Asn Ser Met Asp Thr Gln Leu Gly Asp Asn Ala Ile Ser Gly Gly Ser
        35                  40                  45

Asn Glu Gly Ser Thr Asp Thr Thr Ser Thr His Thr Thr Asn Thr Gln
    50                  55                  60

-continued

```
Asn Asn Asp Trp Phe Ser Lys Leu Ala Ser Ser Ala Phe Thr Gly Leu
 65                  70                  75                  80

Phe Gly Ala Leu Leu Ala Asp Lys Lys Thr Glu Glu Thr Thr Leu Leu
                 85                  90                  95

Glu Asp Arg Ile Leu Thr Thr Arg Asn Gly His Thr Thr Ser Thr Thr
            100                 105                 110

Gln Ser Ser Val Gly Val Thr His Gly Tyr Ser Thr Glu Glu Asp His
        115                 120                 125

Val Ala Gly Pro Asn Thr Ser Gly Leu Glu Thr Arg Val Val Gln Ala
    130                 135                 140

Glu Arg Phe Tyr Lys Lys Tyr Leu Phe Asp Trp Thr Thr Asp Lys Ala
145                 150                 155                 160

Phe Gly His Leu Glu Lys Leu Glu Leu Pro Ser Asp His His Gly Val
                165                 170                 175

Phe Gly His Leu Val Asp Ser Tyr Ala Tyr Met Arg Asn Gly Trp Asp
                180                 185                 190

Val Glu Val Ser Ala Val Gly Asn Gln Phe Asn Gly Gly Cys Leu Leu
                195                 200                 205

Val Ala Met Val Pro Glu Trp Lys Glu Phe Asp Thr Arg Glu Lys Tyr
    210                 215                 220

Gln Leu Thr Leu Phe Pro His Gln Phe Ile Ser Pro Arg Thr Asn Met
225                 230                 235                 240

Thr Ala His Ile Thr Val Pro Tyr Leu Gly Val Asn Arg Tyr Asp Gln
                245                 250                 255

Tyr Lys Lys His Lys Pro Trp Thr Leu Val Val Met Val Val Ser Pro
                260                 265                 270

Leu Thr Val Asn Asn Thr Ser Ala Ala Gln Ile Lys Val Tyr Ala Asn
                275                 280                 285

Ile Ala Pro Thr Tyr Val His Val Ala Gly Glu Leu Pro Ser Lys Glu
                290                 295                 300

Gly Ile Phe Pro Val Ala Cys Ala Asp Gly Tyr Gly Gly Leu Val Thr
305                 310                 315                 320

Thr Asp Pro Lys Thr Ala Asp Pro Ala Tyr Gly Lys Val Tyr Asn Pro
                325                 330                 335

Pro Arg Thr Asn Tyr Pro Gly Arg Phe Thr Asn Leu Leu Asp Val Ala
                340                 345                 350

Glu Ala Cys Pro Thr Phe Leu Cys Phe Asp Asp Gly Lys Pro Tyr Val
                355                 360                 365

Thr Thr Arg Thr Asp Asp Thr Arg Leu Leu Ala Lys Phe Asp Leu Ser
370                 375                 380

Leu Ala Ala Lys His Met Ser Asn Thr Tyr Leu Ser Gly Ile Ala Gln
385                 390                 395                 400

Tyr Tyr Thr Gln Tyr Ser Gly Thr Ile Asn Leu His Phe Met Phe Thr
                405                 410                 415

Gly Ser Thr Asp Ser Lys Ala Arg Tyr Met Val Ala Tyr Ile Pro Pro
                420                 425                 430

Gly Val Glu Thr Pro Pro Asp Thr Pro Glu Arg Ala Ala His Cys Ile
                435                 440                 445

His Ala Glu Trp Asp Thr Gly Leu Asn Ser Lys Phe Thr Phe Ser Ile
                450                 455                 460

Pro Tyr Val Ser Ala Ala Asp Tyr Ala Tyr Thr Ala Ser Asp Thr Ala
465                 470                 475                 480
```

-continued

```
Glu Thr Ile Asn Val Gln Gly Trp Val Cys Ile Tyr Gln Ile Thr His
                485                 490                 495
Gly Lys Ala Glu Asn Asp Thr Leu Val Val Ser Val Ser Ala Gly Lys
                500                 505                 510
Asp Phe Glu Leu Arg Leu Pro Ile Asp Pro Arg Gln Gln Thr Thr Ala
                515                 520                 525
Thr Gly Glu Ser Ala Asp Pro Val Thr Thr Thr Val Glu Asn Tyr Gly
                530                 535                 540
Gly Glu Thr Gln Ile Gln Arg His His Thr Asp Ile Gly Phe Ile
545                 550                 555                 560
Met Asp Arg Phe Val Lys Ile Gln Ser Leu Ser Pro Thr His Val Ile
                565                 570                 575
Asp Leu Met Gln Ala His Gln His Gly Leu Val Gly Ala Leu Leu Arg
                580                 585                 590
Ala Ala Thr Tyr Tyr Phe Ser Asp Leu Glu Ile Val Val Arg His Glu
                595                 600                 605
Gly Asn Leu Thr Trp Val Pro Asn Gly Ala Pro Glu Ser Ala Leu Leu
                610                 615                 620
Asn Thr Ser Asn Pro Thr Ala Tyr Asn Lys Ala Pro Phe Thr Arg Leu
625                 630                 635                 640
Ala Leu Pro Tyr Thr Ala Pro His Arg Val Leu Ala Thr Val Tyr Asn
                645                 650                 655
Gly Thr Ser Lys Tyr Ala Val Gly Gly Ser Gly Arg Arg Gly Asp Met
                660                 665                 670
Gly Ser Leu Ala Ala Arg Val Val Lys Gln Leu Pro Ala Ser Phe Asn
                675                 680                 685
Tyr Gly Ala Ile Lys Ala Asp Ala Ile His Glu Leu Leu Val Arg Met
                690                 695                 700
Lys Arg Ala Glu Leu Tyr Cys Pro Arg Pro Leu Leu Ala Ile Glu Val
705                 710                 715                 720
Ser Ser Gln Asp Arg His Lys Gln Lys Ile Ile Ala Pro Ala Lys Gln
                725                 730                 735
Leu Leu Asn Phe Asp Leu Leu Lys Leu Ala Gly Asp Val Glu Ser Asn
                740                 745                 750
Pro Gly Pro Phe Phe Phe Ala Asp Val Arg Ser Asn Phe Ser Lys Leu
                755                 760                 765
Val Asp Thr Ile Asn Gln Met Gln Glu Asp Met Ser Thr Lys His Gly
                770                 775                 780
Pro Asp Phe Asn Arg Leu Val Ser Ala Phe Glu Glu Leu Ala Thr Gly
785                 790                 795                 800
Val Lys Ala Ile Arg Thr Gly Leu Asp Glu Ala Lys Pro Trp Tyr Lys
                805                 810                 815
Leu Ile Lys Leu Leu Ser Arg Leu Ser Cys Met Ala Ala Val Ala Ala
                820                 825                 830
Arg Ser Lys Asp Pro Val Leu Val Ala Ile Met Leu Ala Asp Thr Gly
                835                 840                 845
Leu Glu Arg Gln Arg Pro Leu Lys Val Arg Ala Lys Leu Pro Gln Gln
                850                 855                 860
Glu Gly Pro Tyr Ala Gly Pro Leu Glu Arg Gln Lys Pro Leu Lys Val
865                 870                 875                 880
Lys Ala Lys Ala Pro Val Val Lys Glu Gly Pro Tyr Glu Gly Pro Val
                885                 890                 895
Lys Lys Pro Val Ala Leu Lys Val Lys Ala Lys Asn Leu Ile Val Thr
```

-continued

```
                900                 905                 910
Glu Ser Gly Ala Pro Pro Thr Asp Leu Gln Lys Met Val Met Gly Asn
        915                     920                 925

Thr Lys Pro Val Glu Leu Ile Leu Asp Gly Lys Thr Val Ala Ile Cys
        930                     935             940

Cys Ala Thr Gly Val Phe Gly Thr Ala Tyr Leu Val Pro Arg His Leu
945                 950                 955                 960

Phe Ala Glu Lys Tyr Asp Lys Ile Met Leu Asp Gly Arg Ala Met Thr
                965                 970             975

Asp Ser Asp Tyr Arg Val Phe Glu Phe Glu Ile Lys Val Lys Gly Gln
            980                 985                 990

Asp Met Leu Ser Asp Ala Ala Leu Met Val Leu His Arg Gly Asn Arg
        995                 1000                1005

Val Arg Asp Ile Thr Lys His Phe Arg Asp Thr Ala Arg Met Lys Lys
        1010                1015                1020

Gly Thr Pro Val Val Gly Val Val Asn Asn Ala Asp Val Gly Arg Leu
1025                1030                1035                1040

Ile Phe Ser Gly Glu Ala Leu Thr Tyr Lys Asp Ile Val Val Cys Met
                1045                1050                1055

Asp Gly Asp Thr Met Pro Gly Leu Phe Ala Tyr Lys Ala Ala Thr Lys
            1060                1065                1070

Ala Gly Tyr Cys Gly Gly Ala Val Leu Ala Lys Asp Gly Ala Asp Thr
        1075                1080                1085

Phe Ile Val Gly Thr His Ser Ala Gly Gly Asn Gly Val Gly Tyr Cys
        1090                1095                1100

Ser Cys Val Ser Arg Ser Met Leu Leu Arg Met Lys Ala His Val Asp
1105                1110                1115                1120

Pro Glu Pro Gln His Glu
                1125
```